US010174013B2

(12) United States Patent
Czardybon et al.

(10) Patent No.: US 10,174,013 B2
(45) **Date of Patent: *Jan. 8, 2019**

(54) BENZIMIDAZOLE DERIVATIVES AS KINASE INHIBITORS

(71) Applicant: SELVITA S.A., Kraków (PL)

(72) Inventors: Wojciech Czardybon, Mikolów (PL); Krzysztof Brzózka, Kraków (PL); Michal Galezowski, Skierniewice (PL); Renata Windak, Kraków (PL); Mariusz Milik, Kraków (PL); Magdalena Zawadzka, Gdansk (PL); Pawel Guzik, Kraków (PL); Ewelina Wincza, Wroclaw (PL); Marta Prokop, Gdynia (PL); Katarzyna Wiklik, Kraków (PL); Aleksandra Sabiniarz, Brzeg (PL); Wieslaw Marek Cholody, Frederick, MD (US); Raymond Horvath, Montreal (CA); Tomasz Rzymski, Elblag (PL)

(73) Assignee: SELVITA S.A., Kraków (PL)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,601

(22) Filed: Jun. 10, 2016

(65) Prior Publication Data

US 2017/0152249 A1 Jun. 1, 2017

Related U.S. Application Data

(63) Continuation of application No. 14/654,779, filed as application No. PCT/EP2013/077754 on Dec. 20, 2013, now Pat. No. 9,388,192.

(30) Foreign Application Priority Data

Dec. 21, 2012 (GB) .................................. 1223265.8

(51) Int. Cl.

| | |
|---|---|
| ***C07D 235/24*** | (2006.01) |
| ***C07D 235/30*** | (2006.01) |
| ***C07D 235/06*** | (2006.01) |
| ***C07D 235/14*** | (2006.01) |
| ***C07D 401/14*** | (2006.01) |
| ***C07D 401/12*** | (2006.01) |
| ***C07D 403/04*** | (2006.01) |
| ***C07D 403/12*** | (2006.01) |
| ***C07D 413/04*** | (2006.01) |
| ***C07D 413/12*** | (2006.01) |
| ***C07D 487/08*** | (2006.01) |
| ***C07D 401/04*** | (2006.01) |
| ***C07D 403/14*** | (2006.01) |
| ***C07D 405/12*** | (2006.01) |

(52) U.S. Cl.

CPC ......... *C07D 413/12* (2013.01); *C07D 235/06* (2013.01); *C07D 235/14* (2013.01); *C07D 235/24* (2013.01); *C07D 235/30* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 413/04* (2013.01); *C07D 487/08* (2013.01)

(58) Field of Classification Search

CPC .. C07D 235/24; C07D 235/30; C07D 235/06; C07D 235/14; C07D 401/04; C07D 401/12; C07D 403/04; C07D 403/12; C07D 413/04; C07D 413/12

See application file for complete search history.

(56) References Cited

U.S. PATENT DOCUMENTS

| | | | |
|---|---|---|---|
| 3,418,318 | A | 12/1968 | Lambie et al. |
| 3,531,495 | A | 9/1970 | Lambie et al. |
| 4,670,402 | A | 6/1987 | Flegler |
| 6,448,271 | B1 | 9/2002 | Lubisch et al. |
| 9,388,192 | B2 | 7/2016 | Czardybon et al. |
| 2015/0216168 | A1 | 8/2015 | Frackenpohl et al. |

FOREIGN PATENT DOCUMENTS

| | | | |
|---|---|---|---|
| FR | 1469504 | A | 2/1967 |
| GB | A-01122988 | | 8/1968 |
| JP | A-2000-503017 | | 3/2000 |
| JP | 2001-518470 | A | 10/2001 |
| JP | A-2008-545776 | | 12/2008 |
| WO | WO-97/25316 | | 7/1997 |
| WO | WO-99/16755 | A1 | 4/1999 |
| WO | WO-03020698 | A2 | 3/2003 |
| WO | WO-06/134318 | | 12/2006 |
| WO | WO-10/107739 | | 9/2010 |
| WO | WO-11/058139 | | 5/2011 |
| WO | WO-2014037340 | A1 | 3/2014 |

OTHER PUBLICATIONS

Handbook of Pharmaceutical Excipients, Fourth Edition, Raymond C. Rowe, Ed., Pharmaceutical Press and American Pharmaceutical Association, 2003. (Year: 2003).*

Adam, M., et al., "Targeting PIM Kinases Impairs Survival of Hematopoietic Cells Transformed by Kinase Inhibitor-sensitive and Kinase Inhibitor-resistant Forms of Fms-like Tyrosine Kinase 3 and BCR/ABL," Cancer Research 66(7):3828-3835, American Association for Cancer Research, United States (2006).

Adayev, T., et al., "MNB/DYRK1A Phosphorylation Regulates the Interactions of Synaptojanin 1 with Endocytic Accessory Proteins," Biochemical and Biophysical Research Communications 351(4):1060-1065, Elsevier Inc., The Netherlands (2006).

(Continued)

*Primary Examiner* — Laura L Stockton

(74) *Attorney, Agent, or Firm* — Sterne, Kessler, Goldstein & Fox P.L.L.C.

(57) ABSTRACT

The present invention relates to derivatives of benzimidazoles of formula (I) as disclosed herein as well as pharmaceutical compositions comprising said derivatives. The derivates according to the present invention are serine/threonine and tyrosine kinase-inhibitors, particularly of PIM1-3- and DYRK1A-kinases and may particularly be used in the treatment of diseases linked to these kinases, such as e.g. leukemias, lymphomas, solid tumors and autoimmune disorders.

13 Claims, 6 Drawing Sheets

(56) References Cited

OTHER PUBLICATIONS

Aho, T.L.T., et al., "Pim-1 Kinase Promotes Inactivation of the Pro-apoptotic Bad Protein by Phosphorylating it on the $Ser^{112}$ Gatekeeper Site," FEBS Letters 571(1-3):43-49, Elsevier Science B.V., Netherlands (2004).
Allen, J.D., et al., "Pim-2 Transgene Induces Lymphoid Tumors, Exhibiting Potent Synergy with c-myc," Oncogene 15(10):1133-1141, Nature Publishing Group, England (1997).
Becker, W., "Recent insights into the Function of DYRK1A," The FEBS Journal 278(2):222, Blackwell in Publishing Ltd., England (2011).
Beier, U.H., et al., "Overexpression of Pim-1 in Head and Neck Squamous Cell Carcinomas," International Journal of Oncology 30(6):1381-1387, Spandidos, Greece (2007).
Blanco-Aparicio, C. and Carnero, A., "Pim Kinases in Cancer: Diagnostic, Prognostic and Treatment Opportunities," Biochemical Pharmacology 85(5):629-643, Elsevier Science, England (2013, available online Oct. 12, 2012).
Chen, J.L., et al., "Pim-1 and Pim-2 Kinases are Required for Efficient pre-B-Cell Transformation by v-Abl Oncogene," Blood 111(3):1677-1685, American Society of Hematology, United States (2008).
Chen, W.W., et al., "Pim Family Kinases Enhance Tumor Growth of Prostate Cancer Cells," Molecular Cancer Research 3(8):443-451, American Association for Cancer Research, United States (2005).
Cibull, T.L., et al., "Overexpression of Pim-1 During Progression of Prostatic Adenocarcinoma," Journal of Clinical Pathology 59(3):285-288, BMJ Publishing Group, England (2006).
Dai, H., et al., "Pim-2 Upregulation: Biological Implications Associated with Disease Progression and Perinueral Invasion in Prostate Cancer," The Prostate 65(3):276-286, Wiley-Liss, United States (2005).
Deutsch, A.J., et al., "MALT Lymphoma and Extranodal Diffuse Large B-cell Lymphoma are Targeted by Aberrant Somatic Hypermutation," Blood 109(8)1500-3504, American Society of Hematology, United States (2007).
Deutsch, A.J., et al., "Primary Cutaneous Marginal Zone B-cell Lymphomas are Targeted by Aberrant Somatic Hypermutation," The Journal of Investigative Dermatology 129(2):476-479, The Society for Investigative Dermatology, United States (2009).
Dhanasekaran, S.M., et al., "Delineation of Prognostic Biomarkers in Prostate Cancer," Nature 412(6849):822-826, Nature Publishing Group, England (2001).
Ferrer, I., et al., "Constitutive Dyrk1A is Abnormally Expressed in Alzheimer Disease, Down Syndrome, Pick Disease, and Related Transgenic Models," Neurobiology of Disease 20(2):392-400, Elsevier Inc., The Netherlands (2005).
Fox, C.J., et al., "The Serine/threonine Kinase Pim-2 is a Transcriptionally Regulated Apoptotic Inhibitor," Genes and Development 17(15):1841-1854, Cold Spring Harbor Laboratory Press, United States (2003).
Gaidano, G., et al., "Aberrant Somatic Hypermutation in Multiple Subtypes of AIDS-associated Non-Hodgkin Lymphoma," Blood 102(5):1833-1841, American Society of Hematology, United States (2003).
Gong, J., et al., "Serine/threonine Kinase Pim-2 Promotes Liver Tumorigenesis Induction Through Mediating Survival and Preventing Apoptosis of Liver Cell," The Journal of Surgical Research 153(1):17-22, Elsevier Inc., The Netherlands (2009).
Guedj, F., et al., "DYRK1A: A Master Regulatory Protein Controlling Brain Growth," Neurobiology of Disease 46(1):190-203, Elsevier Inc., The Netherlands (2012).
Hammerman, P.S., et al., "Lymphocyte Transformation by Pim-2 is Dependent on Nuclear Factor-kappaB Activation," Cancer Research 64(22):8341-8348, American Association for Cancer Research, United States (2004).
Himpel, S., et al., "Identification of the Autophosphorylation Sites and Characterization of their Effects in the Protein Kinase DYRK1A," The Biochemical Journal 359(Pt 3):497-505, Portland Press, England (2001).
International Search Report and Written Opinion for International Application No. PCT/EP2013/077754, European Patent Office, Netherlands, dated Jul. 2, 2014, 10 pages.
Jones, E.L., et al., "A Pilot Study Examining Associations Between DYRK1A and alpha-synuclein Dementias," Neuro-degenerative Diseases 10(1-4):229-231, Karger, Switzerland (Jan. 21, 2012).
Kane, L.P., et al., "Akt-dependent Phosphorylation Specifically Regulates Cot Induction of NF-kappa, B-dependent Transcription," Molecular and Cellular Biology 22(16):5962-5974, American Society for Microbiology, United States (2002).
Kentrup, H., et al., "Dyrk, A Dual Specificity Protein Kinase with Unique Structural Features Whose Activity is Dependent on Tyrosine Residues Between Subdomains VII and VIII," The Journal of Biological Chemistry 271(7):3488-3495, American Society for Biochemistry and Molecular Biology, United States (1996).
Kim, E.J., et al., "Dyrk1A Phosphorylates alpha-synuclein and Enhances Intracellular Inclusion Formation," The Journal of Biological Chemistry 281(44):33250-33257, American Society for Biochemistry and Molecular Biology, United States (2006).
Kim, K.T., et al., "Constitutively Activated FLT3 Phosphorylates BAD Partially Through pim-1," British Journal of Haematology 134(5):500-509, Blackwell Publishing Ltd., England (2006).
Kim, K.T., et al., "Pim-1 is Up-regulated by Constitutively Activated FLT3 and Plays a Role in FLT3-mediated Cell Survival," Blood 105(4):1759-1767, American Society of Hematology, United States (2005).
Kimura, R., et al., "The DYRK1A Gene, Encoded in Chromosome 21 Down Syndrome Critical Region, Bridges Between beta-amyloid Production and tau Phosphorylation in Alzheimer Disease," Human Molecular Genetics 16(1):15-23, Oxford University Press, England (2007).
Klejman, A., et al., "The Src Family Kinase Hck Couples BCR/ABL to STAT5 Activation in Myeloid Leukemia Cells," The EMBO Journal 21(21):5766-5774, Eurpean Molecular Biology Organization, Germany (2002).
Li, Y.Y., et al., "Essential Contribution of Ets-1 to Constitutive Pim-3 Expression in Human Pancreatic Cancer Cells," Cancer Science 100(3):396-404, Japanese Cancer Association, Japan (2009).
Li, Y.Y., et al., "Pim-3, A Proto-oncogene with Serine/threonine Kinase Activity, is Aberrantly Expressed in Human Pancreatic Cancer and Phosphorylates Bad to Block Bad-mediated Apoptosis in Human Pancreatic Cancer Cell Lines," Cancer Research 66(13):6741-6747, American Association for Cancer Research, United States (2006).
Libra, M., et al., "Analysis of Aberrant Somatic Hypermutation (SHM) in Non-Hodgkin's Lymphomas of Patients with Chronic HCV Infection," The Journal of Pathology 206(1):87-91, John Wiley and Sons, England (2005).
Liu, Y., et al., "STAT3 as a Therapeutic Target for Glioblastoma," Anti-cancer Agents in Medicinal Chemistry 10(7):512-519, Bentham Science Publishers, UAE (2010).
MacDonald A., et al., "Pim Kinases Phosphorylate Multiple Sites on Bad and Promote 14-3-3 Binding and Dissociation from Bcl-XL," BMC Cell Biology 7:1, 14 pages, BioMed Central, England (2006).
Mahindroo N., et al., "Hedgehog-Gli Signaling Pathway Inhibitors as Anticancer Agents," Journal of Medicinal Chemistry 52(13):3829-3845, American Chemical Society, United States (2009).
Martelli, M., et al., "Primary Mediastinal Large B-cell Lymphoma." Critical Reviews in Oncology/hematology 68(3):256-263, Elsevier Ireland Ltd., Ireland (2008).
Masuda, M., et al., "Stat3 Orchestrates Tumor Development and Progression: The Achilles' Heel of Head and Neck Cancers?," Current Cancer Drug Targets 10(1):117-126, Bentham Science Publishers, United Arab Emirates (2010).
Montesinos-Rongen, M., et al., "Primary Diffuse Large B-cell Lymphomas of the Central Nervous System are Targeted by Aberrant Somatic Hypermutation," Blood 103(5):1869-1875, American Society of Hematology, United States (2004).

(56) References Cited

OTHER PUBLICATIONS

Murakami, N., et al., "Phosphorylation by Dyrk1A of Clathrin Coated Vesicle-associated Proteins: identification of the Substrate Proteins and the Effects of Phosphorylation," PLoS One 7(4):e34845, 170 pages, Public Library of Science, United States (Apr. 13, 2012).
Murakami N., et al.. "Phosphorylation of Amphiphysin I by Minibrain Kinase/dual-specificity Tyrosine Phosphorylation-regulated Kinase, a Kinase Implicated in Down Syndrome," The Journal of Biological Chemistry 281(33):23712-23724, American Society for Biochemistry and Molecular Biology, United States (2006).
Nawijn, M.C., et al., "For Better or for Worse: The Role of Pim Oncogenes in Tumorigenesis," Nature Reviews. Cancer 11(1):23-34, MacMillan Publishers Ltd., England (2011).
Nieborowska-Skorska M., et al., "Complementary Functions of the Antiapoptotic Protein A1 and Serine/threonine Kinase pim-1 in the BCR/ABL-mediated Leukemogenesis," Blood 99(12):4531-4539, American Society of Hematology, United States (2002).
Nosaka, T. and Kitamura, T., "Pim-1 Expression is Sufficient to Induce Cytokine Independence in Murine Hematopoietic Cells, But is Dispensable for BCR-ABL-mediated Transformation," Experimental Hematology 30(7):697-702, Elsevier Science Inc., Netherlands (2002).
Park, J., et al., "Function and Regulation of Dyrk1A: Towards Understanding Down Syndrome," Cellular and Molecular Life Sciences 66(20):3235-3240, Springer, Switzerland (2009).
Popivanova, B.K., et al., "Proto-oncogene, Pim-3 with Serine/threonine Kinase Activity, is Aberrantly Expressed in Human Colon Cancer Cells and can Prevent Bad-mediated Apoptosis," Cancer Science 98(3):321-328, Japanese Cancer Association, Japan (2007).
Rainio, E.M., et al., "Pim Kinases are Upregulated During Epstein-Barr Virus Infection and Enhance EBNA2 Activity," Virology 333(2):201-206, Elsevier Inc., The Netherlands (2005).
Roh, M., et al., "A Role for Polyploidy in the Tumorigenicity of Pim-1-expressing Human Prostate and Mammary Epithelial Cells," PLoS One 3(7):e2572, 11 pages, Public Library of Science, United States (2008).
Roh, M., et al., "Overexpression of the Oncogenic Kinase Pim-1 Leads to Genomic Instability," Cancer Research 63(23):8079-8084, American Association for Cancer Research, United States (2003).
Rossi D., et al., "Aberrant Somatic Hypermutation in Transformation of Follicular Lymphoma and Chronic Lymphocytic Leukemia to Diffuse Large B-cell Lymphoma," Haematologica 91(10):1405-1409, Ferrata Storti Foundation, Italy (2006).
Seifert, A., et al., "DYRK1A Phosphotylates Caspase 9 at an Inhibitory Site and is Potently Inhibited in Human Cells by Harmine," The FEBS Journal 275(24):6268-6280, Blackwell Publishing Ltd., England (2008).
Tamburini J., et al., "Protein Synthesis is Resistant to Rapamycin and Constitutes a Promising Therapeutic Target in Acute Myeloid Leukemia," Blood 114(8):1618-1627, American Society of Hematology, United States (2009).
Tejedor, F.J. and Hammerle, B., "MNB/DYRK1A as a Multiple Regulator of Neuronal Development," The FEBS Journal 278(2):223-235, Blackwell Publishing Ltd., England (2011).
Thompson, J., et al., "Attenuation of Androgen Receptor-dependent Transcription by the Serine/threonine Kinase Pim-1," Laboratory Investigation 83(9):1301-1309, Nature Publishing Group, United States (2003).
Valdman, A., et al., "Pim-1 Expression in Prostatic Intraepithelial Neoplasia and Human Prostate Cancer," The Prostate 60(4):367-371, Wiley-Liss, United States (2004).
Vu, H.A., et al., "The Juxtamembrane Domain in ETV6/FLT3 is Critical for PIM-1 Uup-regulation and Cell Proliferation," Biochemical and Biophysical Research Communications 383(3):308-313, Elsevier Inc., The Netherlands (2009).
Wegiel, J., et al., "Link Between DYRK1A Overexpression and Several-fold Enhancement of Neurofibrillary Degeneration with 3-repeat tau Protein in Down Syndrome," Journal of Neuropathology and Experimental Neurology 70(1):36-50, American Association of Neuropathologists, United States (2011).
Wegiel, J., et al., "The Role of DYRK1A in Neurodegenerative Diseases," The FEBS Journal 278(2):236-245, Blackwell Publishing Ltd., England (2011).
Xu, Y., et al., "Overexpression of PIM-1 is a Potential Biomarker in Prostate Carcinoma," Journal of Surgical Oncology 92(4):326-330, Wiley-Liss, United States (2005).
Yan, B., et al., "The PIM-2 Kinase Phosphorylates BAD on Serine 112 and Reverses BAD-induced Cell Death," The Journal of Biological Chemistry 278(46):45358-45367, American Society for Biochemistry and Molecular Biology, United States (2003).
Zemskova, M., et al., "The PIM1 Kinase is a Critical Component of a Survival Pathway Activated by Docetaxel and Promotes Survival of Docetaxel-treated Prostate Cancer Cells," The Journal of Biological Chemistry 283(30):20635-20644, American Society for Biochemistry and Molecular Biology, United States (2008).
Zhang, P., et al., "Pim-3 is Expressed in Endothelial Cells and Promotes Vascular Tube formation," Journal of Cellular Physiology 220(1):82-90, Wiley-Liss, United States (2009).
Zheng, H.C., et al., "Aberrant Pim-3 Expression is Involved in Gastric Adenoma-adenocarcinoma Sequence and Cancer Progression," Journal of Cancer Research and Clinical Oncology 134(4):481-488, Springer-Verlag, Germany (2008).
Zippo, A., et al., "Identification of Flk-1 Target Genes in Vasculogenesis: Pim-1 is Required for Endothelial and Mural Cell Differentiation in vitro," Blood 103(12):4536-4544, American Society of Hematology, United States (2004).
Ahn, CM., et al., "Synthesis and in vitro Antitumor Activity of 2-Alkyl, 2-Aryl, and 2-Piperazinyl Benzimidazole-4,7-dione Derivatives," Arch. Pharm. Res. 23(4):288-301, Springer Publishing, United States (2000).
Ahn, CM., et al., "Synthesis of 6-Aziridnylbenzimidazole derivative and Their in Vitro Antitumor Activities," Arch. Pharm. Res. 21(5):599-609, Springer Publishing, United States (1998).
Golub, T.R, et al., "Molecular Classification of Cancer: Class Discovery and Class Prediction by Gene Expression Monitoring," Science 286:531-537, American Association for the Advancement of Science, United States (1999).
Skibo, E., et al., "Structure-Activity Studies of Benzimidazole-Based DNA-Cleaving Agents, Comparison of Benzimidazole, Pyrrolobenzimidazole, and Tetrahydropyridobenzimidazole Analogues," Journal of Medicinal Chemistry 37:78-92, American Chemistry Society, United States (1994).
Office Action dated Oct. 2, 2015, in U.S. Appl. No. 14/654,779 (now U.S. Pat. No. 9,388,192), Czardybon, W., et al., filed Jun. 22, 2015, 64 pages.
Notice of Allowance dated Mar. 10, 2016, in U.S. Appl. No. 14/654,779 (now U.S. Pat. No. 9,388,192), Czardybon, W., et al., filed Jun. 22, 2015, 7 pages.

* cited by examiner

BENZIMIDAZOLE DERIVATIVES AS KINASE INHIBITORS

FIELD OF THE INVENTION

The present invention relates to novel benzimidazole derivatives and pharmaceutically acceptable salts thereof. Such derivatives are potent inhibitors of certain serine/threonine and tyrosine kinases and in particular of PIM1-3- and DYRK1A-kinases. The present invention further relates to pharmaceutical compositions comprising such derivatives, wherein the pharmaceutical compositions are particularly useful in the treatment of PIM1-3-kinase- and DYRK1A-kinase-related disorders such as cancers (in particular leukemias, lymphomas and solid tumors), autoimmune diseases, inflammatory diseases and neurodegenerative disorders.

BACKGROUND OF THE INVENTION

Kinases are enzymes that modify other proteins by chemically adding phosphate groups to them (a process called phosphorylation). Phosphorylation of the targeted proteins results in a functional change of their activity but also can modify association with other proteins, trafficking and subcellular localization. It is estimated that up to 30% of all proteins can be modified by kinases. For this reason kinases are key regulators of majority of cellular pathways, especially those involved in signal transduction. Kinases are currently one of the most interesting and most extensively investigated drug targets. Among the new kinase targets for therapeutic inhibition pursued currently, PIM kinases are one of the most interesting emerging molecular targets. The PIM family of serine-threonine kinases is composed of three highly homologous proteins PIM-1, -2 and -3 which play an important role in intracellular signaling and contribute to pathways involved in cell survival, inflammation, cell movement and stress response (recent reviews please refer to Blanco-Aparicio Biochem Pharmacol. 2012 Oct. 5, Nawijn, Nat Rev Cancer. 2011 January; 11(1):23-34).

With regard to molecular mechanisms of PIM-1 involvement in oncogenic transformation and cancer development, one can point out several processes that are regulated by the PIM-1 kinase like stimulation of cell cycle progression, coactivation of mTOR pathway, inhibition of apoptosis, transcriptional coactivation of c-Myc, promotion of drug resistance and cell migration and metastasis. PIM kinases overexpression has been reported in a variety of cancer types, ranging from hematopoietic malignancies such as diffuse B cell lymphoma, chronic lymphocytic leukemia and acute myelogenous leukemia to solid tumors such as prostate and pancreatic cancer. Acquisition of mutations in the PIM-1 gene can be one of the molecular mechanisms involved in histological transformation of follicular lymphoma (FL) and B-chronic lymphocytic leukemia (B-CLL) to diffuse large B-cell lymphoma (DLBCL)(Rossi et al., Heamatologica, 2006, vol 91, no 10, pp 1405-9). Mutations of the PIM-1 gene have also been detected in cases of AIDS-associated non-Hodgkin lymphoma (Gaidano et al., Blood, 2003, vol 102, no 5, pp 1833-1841), HCV-infected B-cell NHL patients (Libra et al., J. Pathology, 2005, vol 206, Iss 1, pp 87-91), primary central nervous system lymphomas (PCNSLs) (Montesinos-Rongen et al., Blood, Mar. 1, 2004 vol. 103 no. 5 1869-1875), extranodal DLBCL cases and primary cutaneous marginal zone B-cell lymphoma (PCMZL) (Deutsch et al., J Invest Dermatol. 2009 February; 129(2):476-9; Deutsch et al., Blood Apr. 15, 2007 vol. 109 no. 8 3500-3504), primary mediastinal large B-cell lymphoma (PMLBCL) (Martelli et al., Crit Rev Oncol Hematol. 2008 December; 68(3):256-63.). PIM1 kinase is upregulated in Epstein Barr virus infected B-cells where it enhances transcriptional activity of EBNA2 protein, essential for the growth transformation and immortalization of infected B-cells. This mechanism of action of PIM-1 kinases may predispose immortalized B-cell to undergo malignant transformation (Rainio et al., Virology. 2005 Mar. 15; 333 (2):201-6.).

PIM-1 seems to play also a crucial role in development of acute myeloid leukemias (AML). Several reports pointed out a role of PIM-1 kinase in downstream signaling by FLT3 (Fms-like tyrosine kinase 3) kinase. Constitutively activating internal tandem duplication (ITD) mutations of the receptor tyrosine kinase FLT3 play an important role in leukemogenesis, and their presence is associated with poor prognosis in AML. Constitutive FLT3 signaling upregulates PIM-1 levels in leukemia cells and the juxtamembrane domain of FLT3 is a critical domain required for this upregulation (Kim et al., Blood. 2005 Feb. 15; 105(4):1759-67; Vu et al., Biochem Biophys Res Commun. 2009 Jun. 5; 383(3):308-13). Interestingly, this downstream signaling seems to be independent of STAT5, Akt and MAPK signaling. Up-regulation of PIM-1 kinase contributes to the proliferative and antiapoptotic pathways induced by FLT3 signaling, and the major antiapoptotic mechanism of action is PIM-1 dependent Bad phosphorylation (Kim et al., Br J Haematol. 2006 September; 134(5):500-9). Similarly to FLT3, PIM-1 kinase is also upregulated by the Bcr-Abl fusion protein, a major cause of the chronic myelogenous leukemia. A SH3/SH2 mediated interaction of Bcr/Abl kinase with Hck kinase (hematopoietic cell kinase) lead to activation of Hck and phosphorylation of STAT5B on the critical Tyr699 residue. Activated STAT5B stimulates expression of downstream effectors like PIM1 kinase and the A1 protein, key factors essential for in vitro transformation and in vivo leukemogenesis mediated by Bcr/Abl. (Klejman et al., EMBO J. 2002 Nov. 1; 21(21):5766-74; Nieborowska-Skorska et al., Blood. 2002 Jun. 15; 99(12): 4531-9). Whereas inhibition of PIM-1 seems not to be sufficient to overcome Bcr/Abl mediated transformation in cancer cells, an elegant study by Adam et al., showed that PIM-1 and PIM-2 play here redundant roles and simultaneous targeting of the two kinases may be an exciting therapeutic alternative to overcome resistance against small-molecule tyrosine kinase inhibitors (Nosaka and Kitamura, Exp Hematol. 2002 July; 30(7):697-702; Adam et al., Cancer Res. 2006 Apr. 1; 66(7):3828-35.). Involvement of PIM-1 kinase in development of prostate cancer has been extensively studied over the past years and provided several examples of clinical importance and rationale for therapeutic indication. Already in 2001 in a microarrays screen PIM-1 expression was shown to correlate with clinical outcome of the disease and was suggested to be a better marker than the standard diagnostic test for PSA levels in serum (Dhanasekaran et al., Nature. 2001 Aug. 23; 412(6849):822-6). This was further confirmed in studies performed by other groups (Cibull et al., J Clin Pathol. 2006 March; 59(3):285-8; Xu et al., J Surg Oncol. 2005 Dec. 15; 92(4):326-30; Thompson et al., Lab Invest. 2003 September; 83(9):1301-9; Valdman et al., Prostate. 2004 Sep. 1; 60(4):367-71). Overexpression of PIM-1 in human prostate cancer cells induces genomic instability by subverting the mitotic spindle checkpoint, centrosome amplification, chromosome misaggregation and polyploidy. When the PIM-1kinase is overexpressed in immortalized, non-tumorigenic human cells, these cells became tumorigenic (Roh et al., PLoS One. 2008 Jul. 2; 3(7):e2572; Roh et al., Cancer Res. 2003 Dec. 1; 63(23): 8079-84). A very interesting finding by Zemskova and colleagues support additionally use of PIM-1 kinase inhibitors in prostate cancer treatment. Surprisingly, treatment of prostate cancer cells with docetaxel, a standard of care induces STAT3 phosphorylation and transcriptional upregulation of the PIM-1 gene. Expression of PIM-1 kinase was crucial for survival of these cells after docetaxel treatment, as shown by knock down and inhibitor experiments. This data supports further testing of novel, small molecule kinase inhibitors in combination therapies with patients with docetaxel resistance (Zemskova et al., J Biol Chem. 2008 Jul. 25; 283(30):20635-44). In an extensive study by Beier et al., immunohistochemistry experiment performed on cells compared to non-neoplastic tissue showed overexpression of the PIM-1 protein in 98% (41/42) of invasive head and neck squamous cell carcinomas (HNSCC). This study was repeated using primary tumors and metastasis biopsies showing nearly significant correlation of PIM-1 expression with histological tumor, underlining role of PIM-1 in HNSCC developments (Beier et al., Int J Oncol. 2007 June; 30(6):1381-7).

PIM-2 is a second member of the PIM kinase family. Functionally, it has been noticed that PIM-2 overlaps with the Akt/mTOR pathway, but is regulated independently. Both PIM-2 and Akt1 kinase regulate NFκB-dependent transcription by phosphorylation of the Cot kinase (Kane et al., Mol Cell Biol. 2002 August; 22(16):5962-74; Hammerman et al., Cancer Res. 2004 Nov. 15; 64(22):8341-8). It has been indicated that PIM-2 expression maintains high levels of NF-κB activity and NF-κB activation by PIM-2 is required for its antiapoptotic function. Moreover, the data has suggested that Cot-dependent activation of NFκB can occur via the transcriptional induction of PIM-2 rather than as a direct result of a receptor-initiated kinase cascade. Several reports showed that PIM-2 can to some extent substitute or cooperate with PIM-1 in driving tumorigenesis. As both kinases share some of the targets, like the Bad protein, they act both as prosurvival kinases preventing induction of apoptosis (Yan et al., J Biol Chem. 2003 Nov. 14; 278(46):45358-67; Aho et al., FEBS Lett. 2004 Jul. 30; 571(1-3):43-9). As both PIM-1 and 2 are transcriptionally induced by upstream signaling (like FLT3 or Bcr-Abl signaling), they can cooperate and are essential in neoplastic transformation of B-cells by v-Abl oncogene (Chen et al., Blood. 2008 Feb. 1; 111(3):1677-85). Similarly to PIM-1, coexpression of PIM-2 and c-Myc transgene induces malignant transformation (Allen et al., Oncogene. 1997 Sep. 4; 15(10):1133-41). Also the effect on the cell cycle inhibition for both PIM-1 and PIM-2 seem to synergize in accelerating cell proliferation and cell cycle progression as shown in the literature, although the molecular mechanism of cell cycle regulation are described in detail only for PIM-1 kinase (Dai et al., Prostate. 2005 Nov. 1; 65(3):276-86; Chen et al., Mol Cancer Res. 2005 August; 3(8):443-51) There seem however also to be differences between the two kinases. Whereas recent publications on hypoxia point out its emerging role in solid tumor formation and chemoresistance, no similar reports are known for PIM-2 kinase and this role needs to be explored. On the other hand, in the publication by Tamburini, a special emphasis was put on the role of PIM-2 in phosphorylation of crucial 4EBP1 transcription factor (on serine S65)(Tamburini et al., Blood. 2009 Aug. 20; 114(8): 1618-27). As shown in this publication, expression of PIM-1 in clinical samples did not correlate with the above finding, providing a proof for non-overlapping role of PIM-1 and PIM-2 in regulation of 4EBP1 phosphorylation, regulation of protein synthesis and promotion of neoplastic transformation. Similar finding were already reported in by Fox and colleagues, stressing out a crucial role of PIM-2 kinase in controlling translation independently from the Akt/mTOR pathway and pointing towards inhibition of PIM-1 kinase as an attractive option for development of new therapies, especially in acute myelogenous leukemia (Fox et al., Genes Dev. 2003 Aug. 1; 17(15):1841-54).

Similarly to PIM-1, overexpression of PIM-2 has been documented in several human tumors types. One of the distinguishing reports is involvement of PIM-2 in tumorigenesis of hepatocellular carcinoma (HCC) (Gong et al., J Surg Res. 2009 May 1; 153(1):17-22). PIM-2 gene expression and its protein levels were investigated in human liver cancer tissues and HepG2 cells (human hepatocellular liver carcinoma cell line). In both cases the expression of PIM-2 gene and protein was higher than in immortalized liver cell line L02, indicating its role as a tumor biomarker. Further experiments indicated that PIM-2 expression and its kinase activity are IL-3 dependent; however its apoptotic inhibition role is IL-3-independent. It was also found that protection against apoptosis by PIM-2 is glucose-dependent, so liver cells growing in vivo, surrounded by high glucose and growth factors concentration have favorable conditions to express PIM-2, however PIM-2 was unable to prevent apoptosis upon glucose deprivation. So once overexpressed in hepatic cells PIM-2 can be an important factor in tumorigenesis.

PIM-3 is the third member of the PIM kinase family. Similarly to PIM-2 and PIM-1, PIM-3 acts in a prosurvival way preventing apoptosis by phosphorylation of Bad. However, in contrast to PIM-1/2, PIM-3 seems to be less specific to Ser112 residue, preferably phosphorylating Ser136, Ser155 and Ser170 (Macdonald et al., BMC Cell Biol. 2006 Jan. 10; 7:1). PIM-3 was the most effective kinase in phosphorylating Ser136 residue, which seems to be crucial for subsequent phosphorylation steps and interaction with the anti-apoptotic Bcl-XL protein. PIM phosphorylation of Bad was therefore found to promote the 14-3-3 binding and inhibition of Bcl-XL binding. Similarly to PIM-1, PIM-3 seems to be also involved in promoting vessel formation and angiogenesis (Zippo et al., Blood. 2004 Jun. 15; 103(12): 4536-44; Zhang et al., J Cell Physiol. 2009 July; 220(1):82-90). Angiogenesis is a physiological process involving the growth of new blood vessels from pre-existing vessels. This feature play significant role in tumorigenesis because angiogenesis usually precede metastasis. Although angiogenesis is a normal process in growth and development it is also a fundamental step in the transition of tumors from a dormant state to a malignant one. It was found that PIM-3 is highly expressed both at mRNA and protein levels in endothelial cells and the protein is co-localized at the cellular lamelliopodia focal kinase (FAK), a kinase involved in cellular adhesion and spreading processes. FAK is typically located at structures known as focal adhesions; these are multi-protein structures that link the extracellular matrix to the cytoplasmic cytoskeleton. It is recruited as a participant in focal adhesion dynamics between cells and has a role in motility and cell survival. FAK have also tyrosine kinase activity and originally identified as a substrate for the oncogene protein. After treatment with cytochalasin D which disrupts actin microfilaments, PIM-3 was dispersed from lamelliopodia suggesting strong interaction of PIM-3 with cytoskeleton. Furthermore knockdown of PIM-3 by siRNA had significant effects on endothelial cells migration, proliferation and formation of sprouts. In light of this finding PIM-3 kinase seems to be a new and promising target for novel inhibitors of angiogenesis.

PIM-3 overexpression has been observed in several human cancers, mainly solid tumors like gastrointestinal, colon or liver cancers where expression of PIM-3 seems to be also a poor prognostic marker, however its role in development of pancreatic adenocarcinoma has been studies in more detail (Popivanova et al., Cancer Sci. 2007 March; 98(3):321-8; Zheng et al., J Cancer Res Clin Oncol. 2008 April; 134(4):481-8). PIM-3 was found to be expressed in malignant lesions of the pancreas but not in normal pancreatic tissue (Li et al., Cancer Res. 2006 Jul. 1; 66(13):6741-7). In line with this finding, PIM-3 mRNA and protein were constitutively expressed in all examined human pancreatic cancer cell lines. Knock down of the PIM-1 mRNA levels resulted in apoptosis of the cells, proving essential role of PIM-3 in inhibition of apoptosis in pancreatic cancer cell lines. Further experiments showed that expression of PIM-3 in pancreatic cell lines is controlled by binding of the Ets-1 protein to the 5'-flanking region of human PIM-3 gene between −249 and −183 bp (Li et al., Cancer Sci. 2009 March; 100(3):396-404). Overexpression of Ets-1 transcription factor was able to stimulate transcription and translation of the PIM-3 kinase. These observations indicate that the transcription factor Ets-1 can induce aberrant PIM-3 expression and subsequently prevent apoptosis in human pancreatic cancer cells. Despite the fact that PIM-3 is a kinase of emerging role in cancer development, presented above results implicate how important and diversified roles PIM-3 may play in tumorigenesis and provide rationale for further development of PIM-3 inhibitors for cancer treatment.

DYRK1A/MNB kinase is a member of the dual-specificity tyrosine phosphorylation-regulated kinase (DYRK) family, that catalyses the phosphorylation of serine and threonine residues in its substrates as well as the autophosphorylation on a tyrosine residue in the activation loop (Himpel et al, Biochem J. 2001 Nov. 1; 359(Pt 3):497-505, Kentrup et al, J Biol Chem. 1996 Feb. 16; 271(7):3488-95). DYRK1A plays different roles during development, with an important role in controlling brain growth through neuronal proliferation and neurogenesis (Becker FEBS J. 2011 January; 278(2):222, Tejedor FEBS J. 2011 January; 278(2):223-35). Higher than normal levels of DYRK1A are associated with the pathology of neurodegenerative diseases. Especially the trisomy 21-linked Dyrk1A overexpression have been implicated in some neurobiological alterations of Down syndrome, such as mental retardation (Park Cell Mol Life Sci. 2009 October; 66(20):3235-40). Apart from its role in development, it is being increasingly recognised that overexpression of DYRK1A in the adult may contribute to cognitive deficits and Alzheimer-like neurodegeneration in Down syndrome (Wegiel FEBS J. 2011 January; 278(2):236-45). Enhanced phosphorylation of proteins involved in vesicle transport (dynamin, amphiphysin, synaptojanin) might contribute to synaptic dysregulation observed in DYRK1A-overexpressing mice (Murakami J Biol Chem. 2006 Aug. 18; 281(33):23712-24, Adayev Biochem Biophys Res Commun. 2006 Dec. 29; 351(4):1060-5, Xie PLoS One. 2012; 7(4):e34845). Moreover, overexpression of DYRK1A causes hyperphosphorylation of the microtubule-associated protein tau and subsequent formation of neurofibrillary tangles, one of the main pathological hallmarks of Alzheimer's disease or senile dementia (Wegiel FEBS J. 2011 January; 278(2):236-45). Other substrates of DYRK1A have also been identified as components of protein aggregates that are hallmarks of neurodegencrative diseases, such as amyloid plaques in Alzheimer's disease and Lewy bodies in Parkinson's disease and Lewy Body dementia (Kim J Biol Chem. 2006 Nov. 3; 281(44):33250-7). Dyrk1 phosphorylates the human microtubule-associated protein tau at Thr212 in vitro, a residue that is phosphorylated in fetal tau and hyper-phosphorylated in Alzheimer disease (AD) and tauopathies, including Pick disease (Ferrer Neurobiol Dis. 2005 November; 20(2):392-400). DYRK1A polymorphism was recently demonstrated to alter the risk of developing an alpha-synuclein-associated dementia (Jones Neurodegener Dis. 2012; 10(1-4):229-31). The expression of Dyrk1A is elevated in AD brains, when compared with non-diseased human brains (Ferrer Neurobiol Dis. 2005 November; 20(2):392-400; Kimura Hum Mol Genet. 2007 Jan. 1; 16(1):15-23).

OBJECTS AND SUMMARY OF THE INVENTION

The inventors of the present invention inter alia surprisingly found that compounds of formula (I) as defined herein exhibit a strong inhibitory activity against PIM1-3- and DYRK-kinases.

In a first aspect, the present invention relates to a compound of formula (I):

(I)

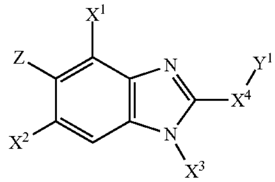

wherein $X^1$ is selected from the group consisting of nitro, cyano, methyl, trifluoromethyl, —C(═O)$T^1$, —C(═O)O$T^4$ and —S(═O)$_2T^4$;

Z and $X^2$ are each independently selected from the group consisting of F, Cl, Br, I, —$C_{1-3}$alkyl and trifluoromethyl, with the proviso that Z and $X^2$ are not both —$C_{1-3}$alkyl; $X^3$ is selected from the group consisting of H, —$C_{1-6}$alkyl, —$C_{1-6}$alkenyl, —$C_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —O$T^1$, —N($T^2$)($T^3$), —C(═O)N($T^2$)($T^3$), —C(═O)O$T^1$, —ST, —S(═O)$_2T^1$ and —S(═O)$_2$N($T^2$)($T^3$), and wherein said —$C_{1-6}$alkyl, —$C_{1-6}$alkenyl and —$C_{1-6}$alkynyl is optionally substituted with one or more substituents independently selected from F, —O$T^1$, —N($T^2$)($T^3$), —C(═O)N($T^2$)($T^3$), —C(═O)O$T^1$, —S$T^1$, —S(═O)$_2T^1$, —S(═O)$_2$N($T^2$)($T^3$) and a 3- to 6-membered carbocycle or heterocycle, wherein said 3- to 6-membered carbocycle or heterocycle is optionally substituted with one or more substituents independently selected from F, —O$T^1$, —N($T^2$)($T^3$), —C(═O)N($T^2$)($T^3$), —C(═O)O$T^1$, —ST, —S(═O)$_2T^1$ and —S(═O)$_2$N($T^2$)($T^3$);

$X^4$ is either absent or selected from —N$R^4$— and —N($R^4$)($CH_2$)—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —N$R^4$— or —N($R^4$)($CH_2$)—, wherein said —$C_{1-6}$alkyl is optionally substituted with one or more substituents independently selected from F, —$OT^1$, —N($T^2$)($T^3$), —C(═O)N($T^2$)($T^3$), —C(═O)$OT^1$, —ST, —S(═O)$_2T^1$, —S(═O)$_2$N($T^2$)($T^3$) and a 5- to 6-membered saturated heterocycle, and wherein said 4- to 7-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$), oxo and —$C_{1-3}$alkyl, wherein said —$C_{1-3}$alkyl is optionally substituted with one or more substituents independently selected from —$OT^7$, —N($T^2$)($T^3$) and a 6-membered saturated heterocycle;

$T^1$, $T^2$ and $T^3$ are each independently selected from H and —$C_{1-6}$alkyl optionally substituted with one or more substituents independently selected from F, —N($T^5$)($T^6$), —$OT^7$, —$ST^7$, cyano, —C(═O)$OT^7$, —C(═O)N($T^5$)($T^6$), —OC(═O)N($T^5$)($T^6$), —S(═O)$_2T^7$, —S(═O)$_2OT^8$ and —S(═O)$_2$N($T^5$)($T^6$);

$T^4$ is —$C_{1-6}$alkyl optionally substituted with one or more substituents independently selected from F, —N($T^5$)($T^6$), —$OT^7$, —$ST^7$, cyano, —C(═O)$OT^7$, —C(═O)N($T^5$)($T^6$), —OC(═O)N($T^5$)($T^6$), —S(═O)$_2T^8$, —S(═O)$_2OT^7$ and —S(═O)$_2$N($T^5$)($T^6$);

$T^5$, $T^6$ and $T^7$ are each independently selected from H and —$C_{1-6}$alkyl optionally substituted with one or more substituents independently selected from F, amino, hydroxyl, thiol and cyano; and $T^8$ is selected from —$C_{1-6}$alkyl optionally substituted with one or more substituents independently selected from F, amino, hydroxyl, thiol and cyano; or a pharmaceutically acceptable salt thereof.

In a preferred embodiment, $X^1$ is selected from the group consisting of nitro, cyano, methyl and trifluoromethyl. In an even more preferred embodiment, $X^1$ is selected from the group consisting of nitro, cyano and trifluoromethyl. It can be particularly preferred that $X^1$ is nitro.

In another preferred embodiment, Z and $X^2$ are each independently selected from the group consisting of F, Cl, Br, T, methyl and trifluoromethyl, with the proviso that Z and $X^2$ are not both methyl.

In another preferred embodiment, Z and $X^2$ are each independently selected from the group consisting of F, Cl, Br, I and trifluoromethyl.

In still another preferred embodiment, Z and $X^2$ are each independently selected from the group consisting of F, Cl, Br and I. In yet another preferred embodiment, Z and $X^2$ are each Br.

With respect to the definition of $X^3$, it can be preferred that said 3- to 6-membered saturated carbocycle or heterocycle as defined for $X^3$ is selected from the group consisting of cyclopropyl, cyclobutyl, cyclopentyl, cyclohexyl, aziridine, oxirane, thiirane, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine and thiomorpholine.

In yet another preferred embodiment, $X^3$ is selected from the group consisting of —$C_{2-6}$alkyl, —$C_{2-6}$alkenyl, —$C_{2-6}$ alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —ST, —S(═O)$_2T^1$ and —S(═O)$_2$N($T^2$)($T^3$), and wherein said —$C_{2-6}$alkyl, —$C_{2-6}$alkenyl and —$C_{2-6}$alkynyl is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$) and a 3- to 6-membered saturated carbocycle or heterocycle, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$). It can be particularly preferred that $X^3$ is selected from —$C_{2-6}$alkyl optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$). In an even more preferred embodiment, $X^3$ is selected from the group consisting of ethyl, propyl, isopropyl, butyl, isobutyl, secbutyl, wherein said ethyl, propyl, isopropyl, butyl, isobutyl, secbutyl is optionally substituted with one or more substituents independently selected from —OT, —N($T^2$)($T^3$), —C(═O)N($T^2$)($T^3$), —$ST^1$ and —S(═O)$_2$N($T^2$)($T^3$).

In still another preferred embodiment, $X^3$ is selected from the group consisting of H, —$C_{1-6}$alkyl, —$C_{1-6}$alkenyl, —$C_{1-6}$alkynyl, wherein said —$C_{1-6}$alkyl, —$C_{1-6}$alkenyl and —$C_{1-6}$alkynyl is optionally substituted with one or more substituents independently selected from F, —$OT^1$, —N($T^2$)($T^3$), —C(═O)N($T^2$)($T^3$), —C(═O)OT, —ST, —S(═O)$_2T^1$ and —S(═O)$_2$N($T^2$)($T^3$). It can be particularly preferred that $X^3$ is selected from the group consisting of H and —$C_{1-4}$alkyl optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$). In an even more preferred embodiment, $X^3$ is selected from the group consisting of H, methyl, ethyl, propyl, isopropyl, butyl, isobutyl, secbutyl, wherein said methyl, ethyl, propyl, isopropyl, butyl, isobutyl, secbutyl is optionally substituted with one or more substituents independently selected from —$OT^1$, —N($T^2$)($T^3$), —C(═O)N($T^2$)($T^3$), —$ST^1$ and —S(═O)$_2$N($T^2$)($T^3$).

In yet another preferred embodiment, $X^3$ is selected from the group consisting of —$C_{1-6}$alkyl, —$C_{1-6}$alkenyl, —$C_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —ST, —S(═O)$_2T^1$ and —S(═O)$_2$N($T^2$)($T^3$), and wherein said —$C_{1-6}$alkyl, —$C_{1-6}$alkenyl and —$C_{1-6}$alkynyl is substituted with a 3- to 6-membered carbocycle or heterocycle, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$). It can be particularly preferred that $X^3$ is selected from the group consisting of —$C_{1-3}$alkyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$), and wherein said —$C_{1-3}$alkyl is substituted with a 3- to 6-membered carbocycle or heterocycle, wherein said 3- to 6-membered carbocycle or heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$ and —$S(=O)_2N(T^2)(T^3)$.

In yet another preferred embodiment, $X^3$ is a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$ and —$S(=O)_2N(T^2)(T^3)$. It can further be preferred that $X^3$ is a 3- to 6-membered saturated heterocycle, with the proviso that the point of attachment on said heterocycle is carbon, wherein said 3- to 6-membered heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$ and —$S(=O)_2N(T^2)(T^3)$. It can be preferred that said 3- to 6-membered heterocycle is selected from the group consisting of aziridine, oxirane, thiirane, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine and thiomorpholine. It can also be preferred that said 3- to 6-membered heterocycle is selected from the group consisting of pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine and thiomorpholine.

In yet another preferred embodiment, $X^4$ is either absent or —$NR^4$— with $R^4$ being preferably H.

With respect to the definition of $Y^1$, it can be preferred that said 4- to 7-membered saturated or unsaturated aromatic carbocycle or heterocycle as defined for $Y^1$ is selected from the group consisting of cyclobutyl, cyclopentyl, cyclohexyl, cycloheptyl, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane, homopiperazine, phenyl, pyrrole, furan, thiophene, imidazole, pyrazole, oxazole, isoxazole, thiazole, isothiazole, pyridine, pyrazine, pyrimidine and pyridazine.

In yet another preferred embodiment, $X^4$ is —$NR^4$— and $Y^1$ is selected from the group consisting of H and —$C_{1-6}$alkyl, wherein said —$C_{1-6}$alkyl is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$, —$S(=O)_2N(T^2)(T^3)$. It can be particularly preferred that $X^4$ is —$NR^4$— and $Y^1$ is —$C_{1-4}$alkyl, wherein said —$C_{1-4}$alkyl is optionally substituted with one or more substituents independently selected from —$OT^1$, —$N(T^2)(T^3)$, —$C(=O)N(T^2)(T^3)$, —$ST^1$, —$S(=O)_2T^1$ and —$S(=O)_2N(T^2)(T^3)$. Before this background, it can be preferred that $R^4$, $T^1$, $T^2$ and $T^3$ are selected from H.

In still another preferred embodiment, $Y^1$ is a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$, —$S(=O)_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle. In such an embodiment, it can particularly be preferred that $X^4$ is absent.

In another preferred embodiment, $Y^1$ is a 4- to 7-membered saturated carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocycle is optionally substituted with one or more substituents independently selected from F, —$OT^1$, —$N(T^2)(T^3)$, —$C(=O)N(T^2)(T^3)$, —$C(=O)OT$, —$ST^1$, —$S(=O)_2T^1$, —$S(=O)_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle. It can be preferred that said 4- to 7-membered saturated carbocycle or heterocycle is selected from the group consisting of cyclobutyl, cyclopentyl, cyclohexyl, cycloheptyl, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane and homopiperazine. In such an embodiment, it can particularly be preferred that $X^4$ is absent.

In yet another preferred embodiment, $Y^1$ is a 4- to 7-membered saturated heterocycle, with the proviso that the point of attachment on said heterocycle is carbon if $X^4$ is —$NR^4$— or —$N(R^4)(CH_2)$—, wherein said 4- to 7-membered heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T'$, —$S(=O)_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle. It can be preferred that said 4- to 7-membered saturated heterocycle is selected from the group consisting of azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane and homopiperazine. In such an embodiment, it can particularly be preferred that $X^4$ is absent.

In a particularly preferred embodiment, $X^4$ is absent and $Y^1$ is a 4- to 7-membered saturated nitrogen-containing heterocycle, preferably selected from the group consisting of azetidine, pyrrolidine, imidazolidine, pyrazolidine, oxazolidine, isoxazolidine, thiazolidine, isothiazolidine, piperidine, piperazine, morpholine, thiomorpholine, azepane and homopiperazine, more preferably selected from the group consisting of azetidine, pyrrolidine, piperidine, piperazine, morpholine, azepane and homopiperazine, and most preferably being piperazine, with the proviso that the point of attachment on said heterocycle is nitrogen, wherein said 4- to 7-membered heterocycle is optionally substituted with one or more substituents independently selected from F, —$OT^1$, —$N(T^2)(T^3)$, —$C(=O)N(T^2)(T^3)$, —$C(=O)OT^1$, —ST, —$S(=O)_2T^1$, —$S(=O)_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle.

In still another preferred embodiment, $X^4$ is selected from —$NR^4$— and —$N(R^4)(CH_2)$— and $Y^1$ is a 4- to 7-membered saturated or unsaturated aromatic carbocycle or heterocycle, with the proviso that the point of attachment on said heterocycle is carbon, wherein said 4- to 7-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$ and oxo.

In another preferred embodiment, $T^1$, $T^2$ and $T^3$ are each independently selected from H and —$C_{1-3}$alkyl optionally substituted with one or more substituents independently selected from —$N(T^5)(T^6)$ and —$OT^7$, wherein $T^5$, $T^6$ and $T^7$ are preferably independently selected from the H and —$C_{1-3}$alkyl.

In still another preferred embodiment, $T^4$ is —$C_{1-3}$alkyl optionally substituted with one or more substituents independently selected from —$N(T^5)(T^6)$ and —$OT^7$, wherein $T^5$, $T^6$ and $T^7$ are preferably independently selected from the H and —$C_{1-3}$alkyl.

In yet another preferred embodiment, $T^5$, $T^6$ and $T^7$ are each independently selected from H and —$C_{1-3}$alkyl optionally substituted with one or more substituents independently selected from amino and hydroxyl.

In another preferred embodiment, $T^8$ is selected from —$C_{1-3}$alkyl optionally substituted with one or more substituents independently selected from amino and hydroxyl.

In a particularly preferred embodiment, $X^1$ is selected from the group consisting of nitro, cyano, methyl, trifluoromethyl, —C(═O)$T^1$, —C(═O)$OT^4$ and —S(═O)$_2T^4$; Z and $X^2$ are each independently selected from the group consisting of F, Cl, Br, I and trifluoromethyl; $X^3$ is selected from the group consisting of H, —$C_{1-6}$alkyl, —$C_{1-6}$alkenyl, —$C_{1-6}$alkynyl, wherein said —$C_{1-6}$alkyl, —$C_{1-6}$alkenyl and —$C_{1-6}$alkynyl is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$ and —S(═O)$_2N(T^2)(T^3)$; and $Y^1$ is a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl, wherein said —$C_{1-3}$alkyl is optionally substituted with one or more substituents independently selected from —$OT^7$ and —$N(T^2)(T^3)$.

In yet another particularly preferred embodiment, $X^1$ is selected from the group consisting of nitro, cyano, methyl, trifluoromethyl, —C(═O)$T^1$, —C(═O)$OT^4$ and —S(═O)$_2T^4$; Z and $X^2$ are each independently selected from the group consisting of F, Cl, Br, I and trifluoromethyl; $X^3$ is selected from the group consisting of —$C_{1-6}$alkyl, —$C_{1-6}$alkenyl, —$C_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$ and —S(═O)$_2N(T^2)(T^3)$, and wherein said —$C_{1-6}$alkyl, —$C_{1-6}$alkenyl and —$C_{1-6}$alkynyl is substituted with a 3- to 6-membered carbocycle or heterocycle, wherein said 3- to 6-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$ and —S(═O)$_2N(T^2)(T^3)$; and $Y^1$ is a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl, wherein said —$C_{1-3}$alkyl is optionally substituted with one or more substituents independently selected from —$OT^7$ and —$N(T^2)(T^3)$.

In preferred embodiments (A) of the first aspect, the present invention relates to:

(A)1. A compound of formula (I):

(I)

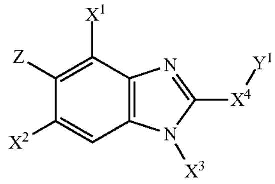

wherein $X^1$ is selected from the group consisting of nitro, cyano, methyl, trifluoromethyl, —C(═O)$T^1$, —C(═O)$OT^4$ and —S(═O)$_2T^4$;

Z and $X^2$ are each independently selected from the group consisting of F, Cl, Br, I, —$C_{1-3}$alkyl and trifluoromethyl, with the proviso that Z and $X^2$ are not both —$C_{1-3}$alkyl;

$X^3$ is selected from the group consisting of —$C_{1-6}$alkyl, —$C_{1-6}$alkenyl, —$C_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —$N(T^2)(T^3)$, —C(═O)$N(T^2)(T^3)$, —C(═O)$OT^1$, —$ST^1$, —S(═O)$_2T^1$ and —S(═O)$_2N(T^2)(T^3)$, and wherein said —$C_{1-6}$alkyl, —$C_{1-6}$alkenyl and —$C_{1-6}$alkynyl is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$ and a 3- to 6-membered saturated carbocycle or heterocycle, wherein said 3- to 6-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$ and —S(═O)$_2N(T^2)(T^3)$;

$X^4$ is either absent or selected from —$NR^4$— and —$N(R^4)(CH_2)$—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said —$C_{1-6}$alkyl is optionally substituted with one or more substituents independently selected from F, —$OT^1$, —$N(T^2)(T^3)$, —C(═O)$N(T^2)(T^3)$, —C(═O)OT, —ST, —S(═O)$_2T^1$, —S(═O)$_2N(T^2)(T^3)$ and a 5- to 6-membered saturated heterocycle, and wherein said 4- to 7-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle;

$T^1$, $T^2$ and $T^3$ are each independently selected from H and —$C_{1-6}$alkyl optionally substituted with one or more substituents independently selected from F, —$N(T^5)(T^6)$, —$OT^7$, —$ST^7$, cyano, —C(═O)$OT^7$, —C(═O)$N(T^5)(T^6)$, —OC(═O)$N(T^5)(T^6)$, —S(═O)$_2T^7$, —S(═O)$_2OT^8$ and —S(═O)$_2N(T^5)(T^6)$;

$T^4$ is —$C_{1-6}$alkyl optionally substituted with one or more substituents independently selected from F, —$N(T^5)(T^6)$, —$OT^7$, —$ST^7$, cyano, —C(═O)$OT^7$, —C(═O)$N(T^5)(T^6)$, —OC(═O)$N(T^5)(T^6)$, —S(═O)$_2T^8$, —S(═O)$_2OT^7$ and —S(═O)$_2N(T^5)(T^6)$;

$T^5$, $T^6$ and $T^7$ are each independently selected from H and —$C_{1-6}$alkyl optionally substituted with one or more substituents independently selected from F, amino, hydroxyl, thiol and cyano; and $T^8$ is selected from —$C_{1-6}$alkyl optionally substituted with one or more substituents independently selected from F, amino, hydroxyl, thiol and cyano; or a pharmaceutically acceptable salt thereof.

(A)2. A compound according to (A)1, wherein $X^1$ is selected from the group consisting of nitro, cyano, trifluoromethyl, —C(═O)$T^1$, and —S(═O)$_2T^4$.

(A)3. A compound according to (A)1 or (A)2, wherein $X^1$ is selected from the group consisting of nitro, cyano and trifluoromethyl.

(A)4. A compound according to any one of (A)1 to (A)3, wherein $X^1$ is nitro.

(A)5. A compound according to any one of (A)1 to (A)4, wherein Z and $X^2$ are each independently selected from the group consisting of F, Cl, Br, I, and trifluoromethyl.

(A)6. A compound according to any one of (A)1 to (A)5, wherein Z and $X^2$ are each independently selected from the group consisting of F, Cl, Br, and I.

(A)7. A compound according to any one of (A)1 to (A)6, wherein Z and $X^2$ are Br.

(A)8. A compound according to any one of (A)1 to (A)7, wherein $X^3$ is selected from the group consisting of —$C_{1-6}$alkyl, —$C_{1-6}$alkenyl, —$C_{1-6}$alkynyl, wherein said —$C_{1-6}$alkyl, —$C_{1-6}$alkenyl and —$C_{1-6}$alkynyl is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$ and —S(═O)$_2N(T^2)$($T^3$).

(A)9. A compound according to any one of (A)1 to (A)8, wherein $X^3$ is selected from the group consisting of —$C_{1-6}$alkyl, —$C_{1-6}$alkenyl, —$C_{1-6}$alkynyl.

(A)10. A compound according to any one of (A)1 to (A)9, wherein $X^3$ is a —$C_{1-6}$alkyl, preferably a —$C_{1-3}$alkyl or a —$C_{1-2}$alkyl, more preferably isopropyl or ethyl.

(A)11. A compound according to any one of (A)1 to (A)10, wherein $Y^1$ is a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —ST, —S(═O)$_2T^1$, —S(═O)$_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle.

(A)12. A compound according to any one of (A)1 to (A)11, wherein $Y^1$ is a 4- to 7-membered saturated carbocycle or heterocycle, with the proviso that the point of attachment on said heterocycle is carbon if $X^4$ is —$NR^4$— or —$N(R^4)(CH_2)$—, wherein said 4- to 7-membered carbocycle or heterocyclic is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle.

(A)13. A compound according to (A)11 or (A)12, wherein $X^4$ is absent.

(A)14. A compound according to any one of (A)1 to (A)13, wherein $X^4$ is absent and $Y^1$ is a 6-membered saturated carbocycle or heterocycle, wherein said 6-membered carbocycle or heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl.

(A)15. A compound according to any one of (A)1 to (A)14, wherein $X^4$ is absent and $Y^1$ is a 6-membered saturated heterocycle, wherein said 6-membered heterocycle is optionally substituted with one or more substituents independently selected from F, —$OT^1$, —$N(T^2)(T^3)$, —C(═O)$N(T^2)(T^3)$, —C(═O)$OT^1$, —$ST^1$, —S(═O)$_2T^1$, —S(═O)$_2N(T^2)(T^3)$, oxo and —$C_{1-3}$alkyl.

(A)16. A compound according to any one of (A)1 to (A)15, wherein $X^4$ is absent and $Y^1$ is piperidin or piperazine.

(A)17. A compound according to (A)1, wherein said compound is selected from the group consisting of 5,6-dibromo-1-ethyl-4-nitro-2-(piperazin-1-yl)-1H-1,3-benzodiazole;

5,6-dibromo-4-nitro-2-(piperazin-1-yl)-1-(propan-2-yl)-1H-1,3-benzodiazole;

(3S)-1-(5,6-dibromo-1-ethyl-4-nitro-1H-1,3-benzodiazol-2-yl)piperidin-3-amine;

5,6-dibromo-2-[(2S)-2-methylpiperazin-1-yl]-4-nitro-1-(propan-2-yl)-1H-1,3-benzodiazole; and 5,6-dibromo-4-nitro-2-(piperidin-4-yl)-1-(propan-2-yl)-1H-1,3-benzodiazole.

(A)18. A compound according to A(17), wherein said compound is selected from the group consisting of 5,6-dibromo-1-ethyl-4-nitro-2-(piperazin-1-yl)-1H-1,3-benzodiazole;

5,6-dibromo-4-nitro-2-(piperazin-1-yl)-1-(propan-2-yl)-1H-1,3-benzodiazole; and 5,6-dibromo-4-nitro-2-(piperidin-4-yl)-1-(propan-2-yl)-1H-1,3-benzodiazole.

In another preferred embodiment, the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate. The hydrochloride salt can be particularly preferred.

In a second aspect, the present invention is concerned with a pharmaceutical composition comprising the compound according to the first aspect as outlined above, including all preferred embodiments as mentioned above. Preferred embodiments of the second aspect are referred to when describing the present invention in more detail.

In a third aspect, the present invention is concerned with a pharmaceutical composition according to the present invention for use in the treatment of specific diseases, particularly in the treatment of cancer, an autoimmune disease and an inflammatory disease as will also be set out below in more detail.

As regards the third aspect and the compounds outlined above in embodiments (A), the compounds of embodiments (A) are in a preferred embodiment of the third aspect for use in the treatment of leukemias such as acute myelogenous leukemia (AML), Hodgkin's and Non-Hodgkin's lypmhomas such as diffuse large B-cell lymphoma (DLBCL) and multiple myeloma (MM).

In a fourth aspect, the present invention is concerned with a method for modulating or regulating and preferably inhibiting serine/threonine or tyrosine kinases, preferably selected from the group consisting of PIM1-3, FLT3 and DYRK1A and more preferably selected from the group consisting of PIM1-3 and DYRK1A or selected from the group consisting of PIM1-3 and FLT3 including FLT3 wildtype and FLT3 mutant kinases, wherein said serine/threonine or tyrosine kinases are exposed to at least one compound of formula (I) as defined above (including all preferred embodiments as defined above) or a pharmaceutically acceptable salt thereof, wherein said method is preferably performed outside the human or animal body.

In a fifth aspect, the present invention relates to the use of a compound of formula (I) as defined above (including all preferred embodiments as defined above) or a pharmaceutically acceptable salt thereof as serine/threonine or tyrosine kinase modulating and preferably inhibiting agent, wherein said kinase is preferably selected from the group consisting of PIM1-3, FLT3 and DYRK1A and more preferably selected from the group consisting of PIM1-3 and DYRK1A.

DETAILED DESCRIPTION OF THE INVENTION

Figure 1:
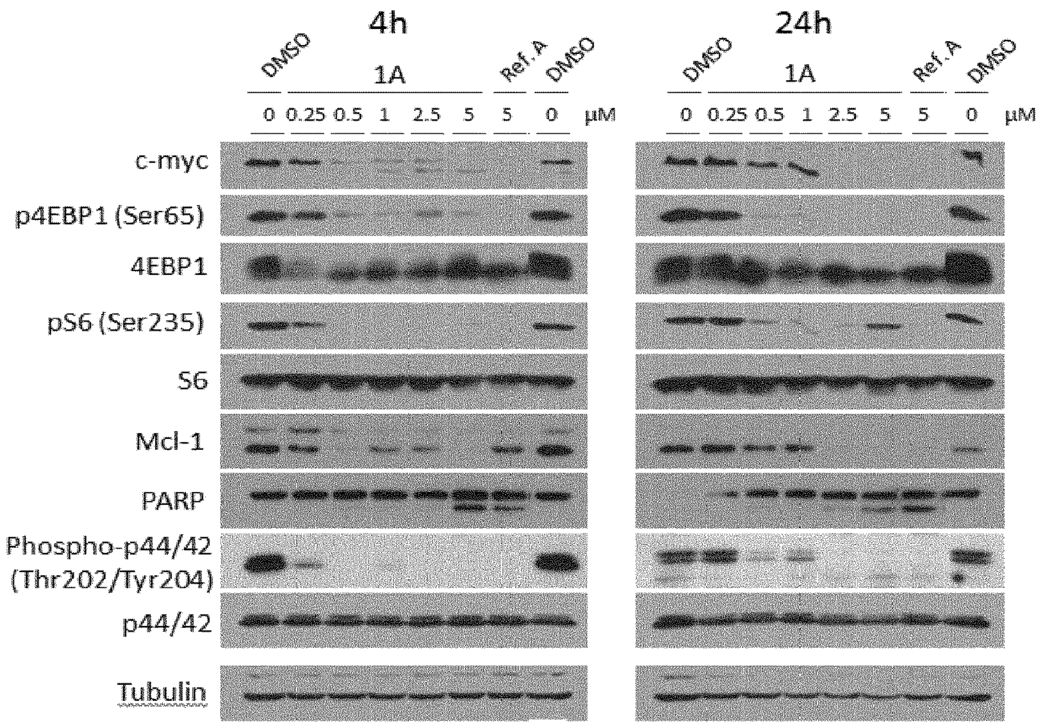
FIG. 1: PIM-kinase biomarkers in MV4-11 cells upon incubation of the cells with compound 1A of the present invention (see example 3.14 for further details).

The inventors of the present invention inter alia succeeded in identifying new compounds which efficiently inhibit PIM1-3- and DYRK1A-kinases. The compounds of the present invention may thus be particularly used in the treatment of cancer, autoimmune diseases and inflammatory diseases. Before some of the embodiments of the present invention are described in more detail, the following definitions are introduced.

1. DEFINITIONS

General Definitions

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "alkyl" refers to a hydrocarbon chain that may be a straight chain or branched chain, containing the indicated number of carbon atoms. For example, $C_{1-6}$ indicates that the group can have from 1 to 6 (inclusive) carbon atoms in it. If there is no indication of carbon atoms of the alkyl, the term "alkyl" refers to a $C_{1-15}$alkyl, preferably a $C_{1-10}$alkyl, and more preferably to a $C_{1-4}$alkyl.

In general, the number of carbon atoms present in a given group is designated "$C_{x-y}$" where x and y are the lower and upper limits, respectively. For example, a group designated as "$C_{1-5}$" contains from 1 to 5 (inclusive) carbon atoms. The carbon number as used in the definitions herein refers to carbon backbone and carbon branching, but does not include carbon atoms of the substituents. General examples of alkyl groups include methyl, ethyl, propyl, isopropyl, butyl, n-butyl, isobutyl, secbutyl, tert-butyl, and pentyl. For example, the term "$C_{1-3}$alkyl" refers to a straight or branched chain saturated hydrocarbon containing 1-3 carbon atoms. Examples of a $C_{1-3}$alkyl group include, but are not limited to, methyl, ethyl, propyl and isopropyl. For example, the term "$C_{6-10}$alkyl" refers to a straight or branched chain saturated hydrocarbon containing 6-10 carbon atoms. Examples of a $C_{6-10}$alkyl group include, but are not limited to, hexyl, octyl and decyl.

"Alkenyl" is a hydrocarbon chain having at least one (preferably only one) carbon-carbon double bond. "Alkynyl" is a hydrocarbon chain having at least one (preferably only one) carbon-carbon triple bond.

The term "heterocycle" refers to a cyclic structure comprising carbon atoms and at least one heteroatom. The term "heteroatom" as used herein preferably refers to nitrogen, sulfur and oxygen atoms. A heterocycle may generally contain different heteroatoms. For the present invention, nitrogen as heteroatom may be preferred. Further, for the present invention, it can be preferred that a heterocycle comprises one or two heteroatoms. If reference to a specific heterocycle is made herein (such as e.g. to piperazine), this reference has to be understood as relating to the commonly used and defined structure of said heterocycle in the field of chemistry.

If e.g. reference to a "4- to 7-membered saturated or unsaturated aromatic carbocycle or heterocycle" is made herein, it needs to be understood that the term "aromatic" is used in combination with the term "unsaturated" only; thus, the above definition may also be regarded as short definition of a "4- to 7-membered saturated non-aromatic or a 4- to 7-membered unsaturated aromatic carbocycle or heterocycle". Of course, the term "aromatic" as used in the short definition is not to be read in combination with the term "saturated" since reference would otherwise be made to a non-existing "saturated aromatic carbocycle or heterocycle".

The term "halogen" includes fluorine, bromine, chlorine or iodine. The term "amino" represents $—NH_2$, the term "hydroxyl" is —OH, the term "thiol" is —SH, the term "nitro" is $—NO_2—$, the term "cyano" is —CN and "oxo" is =O. "Carbon branching" or "branched alkyl" means that one or more alkyl groups such as methyl, ethyl or propyl, replace one or both hydrogens in a $—CH_2—$ group of a linear alkyl chain.

If a substituent is not defined as the final substituent but rather as a bridging substituent (such as e.g. the $X^4$ definition of "$—NR^4(CH_2)—$"), the definition is preferably used in terms of the orientation in a compound of the present invention as from left to right in the overall structure. This means e.g. for "$—NR^4(CH_2)—$" that the nitrogen is attached to the benzimidazole-moiety, whereas the $—CH_2—$ is attached to substituent $Y^1$.

If a point of attachment on a heterocycle is referred to herein, this refers to an atom in the heterocycle, to which the remaining moiety of the compound is attached to. In some cases of the present invention, this may refer to the attachment of $X^4$ to a heterocycle in the $Y^1$-position or, alternatively, if $X^4$ is not present, to the attachment of the benzimidazole-moiety at position 2 to the heterocycle in the $Y^1$-position (direct bond). In other cases of the present invention, this may refer to the attachment of a heterocycle in the $X^3$-position to the nitrogen-atom of the benzimidazole-moiety.

The invention disclosed herein is meant to encompass all pharmaceutically acceptable salts of the disclosed compounds, particularly the salts referred to above. Further, the pharmaceutically acceptable salts include metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, fumarate, tartrate and the like; sulfonates such as methanesulfonate, benzenesulfonate, p-toluenesulfonate, and the like; amino acid salts such as arginate, asparginate, glutamate and the like. A particularly preferred pharmaceutically acceptable salt may be selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate. The hydrochloride salt is particularly preferred for compounds of the present invention.

The compounds disclosed herein may contain one or more asymmetric centers and may thus lead to enantiomers, diastereomers, and other stereoisomeric forms. The present invention is also meant to encompass all such possible forms as well as their racemic and resolved forms and mixtures thereof, unless specified otherwise. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers). The term "chiral center" refers to an atom to which four different groups are attached. The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction. The term "racemic" refers to a mixture of equal parts of enantiomers and which is optically inactive. The term "resolution" refers to the separation or concentration or depletion of one of the two enantiomeric forms of a molecule.

"Pharmaceutically active agent" as used herein means that a compound is potent of modulating a response in a human or animal being in vivo. When reference is made to a compound as "the only pharmaceutically active agent", this is meant to describe that the activity of a corresponding pharmaceutical composition is due to said active agent only.

The term "pharmaceutically acceptable excipient" as used herein refers to compounds commonly comprised in pharmaceutical compositions, which are known to the skilled person. Such compounds or excipients are exemplary listed below. In view of the definition "pharmaceutically active agent" as given above, a pharmaceutically acceptable excipient can be defined as being pharmaceutically inactive.

Description of Pharmaceutical Compositions According to the Present Invention

A pharmaceutical composition according to the present invention may be formulated for oral, buccal, nasal, rectal, topical, transdermal or parenteral application. Oral application may be preferred. Parenteral application can also be preferred and includes intravenous, intramuscular or subcutaneous administration. The compound according to formula (I) should be applied in pharmaceutically effective amounts, for example in the amounts as set out herein below.

A pharmaceutical composition of the present invention may also be designated as formulation or dosage form. A compound of formula (I) may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, salt solutions, alcohols, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethylcellulose, polyvinylpyrrolidone and the like. The pharmaceutical compositions can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compounds of formula (I) in water-soluble form. Additionally, suspensions of the compounds of formula (I) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a compound of formula (I). Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluant or solvent. Among the acceptable vehicles and solvents that can be used are water and isotonic sodium chloride solution. Sterile oils are also conventionally used as solvent or suspending medium.

Suppositories for rectal administration of a compound of formula (I) can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the compound according to formula (I) from said suppositories.

For administration by inhalation, the compounds according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the compound of formula (I) or a sustained release of the compound of formula (I).

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

As regards human patients, the compound of formula (I) may be administered to a patient in an amount of about 0.001 mg to about 5000 mg per day, preferably of about 0.01 mg to about 100 mg per day, more preferably of about 0.1 mg to about 50 mg per day.

Indications, for which the Compounds of the Present Invention May be Used

The compounds according to the present invention may be used for the treatment of a disease selected from the group consisting of myeloid leukemia (both acute and chronic), acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma [pinealoma], glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformians of the skull, meningioma, meningiosarcoma, gliomatosis of the meninges; undifferentiated small cell squamous cell, undifferentiated large cell squamous cell, adenocarcinoma, alveolar carcinoma, bronchial adenoma, sarcoma, lymphoma, chondromatous hanlartoma, mesothelioma of the bronchus; lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, leiomyosarcoma, lymphoma of the esophagus, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pretumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

Since the compounds of the present invention are PIM-kinase inhibitors, they may particularly be used for the treatment of PIM-kinase linked diseases. Thus, the compounds of the present invention may be used for the treatment of cancer, in particular hematopoietic malignancies such as diffuse B cell lymphoma, chronic lymphocytic leukemia and acute myelogenous leukemia, follicular lymphoma (FL) and B-chronic lymphocytic leukemia (B-CLL), diffuse large B-cell lymphoma (DLBCL), AIDS-associated non-Hodgkin lymphoma, HCV-infected B-cell NHL, primary central nervous system lymphomas (PCNSLs), extranodal DLBCL, primary cutaneous marginal zone B-cell lymphoma (PCMZL), primary mediastinal large B-cell lymphoma (PMLBCL); acute myeloid leukemias (AML); chronic myelogenous leukemia; invasive head and neck squamous cell carcinomas (HNSCC); solid tumors such as prostate cancer, pancreatic cancer, gastrointestinal cancer, colon cancer, liver cancer; and hepatocellular carcinoma (HCC). Further, the compounds may be used for the treatment of an inflammatory disease, in particular rheumatoid arthritis, lupus, multiple sclerosis and inflammatory bowel disease.

Some compounds of the present invention not only inhibit PIM-kinases but also the FLT3-kinase. When reference is made in the present application to the FLT3-kinase, this is meant to include mutant versions thereof. FLT3 (FMS-like tyrosine kinase) plays a crucial role in pathogenesis of acute myeloid leukemia (AML) which is most common type of acute leukemias in adults and in 20% of childhood leukemia cases. Inhibition of FLT3 kinase, which is frequently overexpressed and mutated (e.g. ITD mutation which is usually associated with poor prognosis) in AML patients is a promising target for the therapy. In addition to inhibition FLT3 itself which should be beneficial in AML treatment, combination of inhibitory activity against FLT3 and PIM which are on the same signaling pathway should be an especially desired way of acting against hematological malignancies helping e.g. overcoming drug resistance. Thus, compounds according to the present invention inhibiting PIM-kinases and the FLT3-kinase may particularly be used in the treatment of AML; it can be especially preferred to treat AML patients harbouring an ITD mutation, D835H, D835Y or N8411 in FLT3 with such compounds.

A role of DYRK1 in cancer is described. DYRK1A potentiates the transcriptional activity Gli1 (glioma-associated oncogene homologue 1), a transcription factor being a terminal effector of hedgehog signaling, which is a key pathway for embryogenesis, stem cell maintenance and tumorigenesis (J. Med. Chem., 2009, 52(13), 3829-3845). DYRK1A acts as a negative regulator of apoptosis. (FEBS J., 2008, 275(24), 6268-6280) Therefore inhibiting DYRK1A activity in cancer cells was proposed as a new strategy to combat the dismal prognosis associated with cancers that display resistance to pro-apoptotic stimuli. STAT3, that is overexpressed in various cancers and represents an interesting target to impede cancer progression, is also activated by DYRK1A (Curr Cancer Drug Targets. 2010 February; 10(1):117-26; Anticancer Agents Med Chem. 2010 September; 10(7):512-9.). The compounds of the present invention may thus be used in order to treat cancer, in particular glioblastoma, breast cancer, gliomas, melanomas, esophageal cancer, pancreas cancer and non-small-cell lung cancers.

DYRK1A is also believed to be implicated in neural differentiation. (Neurobiol Dis. 2012 April; 46(1):190-203) The role of DYRK1A kinase in neurodegeneration is well established, therefore Alzheimer's disease, Down syndrome and other taupathies such as progressive supranuclear palsy, Pick's disease, chronic traumatic encephalopathy and frontotemporal dementia may also be treated with the compounds according to the present application. (FEBS J. 2011 January; 278(2):236-45; J Neuropathol Exp Neurol. 2011 January; 70(1):36-50). DYRK1A kinase was also associated with development of pathology in α-synuclein dementias such as dementia with Lewy bodies and Parkinson's disease dementia (J Biol Chem. 2006 Nov. 3; 281(44):33250-7; Neurodegener Dis. 2012; 10(1-4):229-31).

Most preferably, the compounds of the present invention may be used for the treatment of a disease selected from the group consisting of leukemias including acute lymphoblastic leukemia, acute myelogenous leukemia and chronic lymphocytic leukemia, lymphoma, myeloma, myloproliferative disorder, allograft rejection, inflammatory bowel disease, multiple sclerosis, psoriasis, rheumatoid arthritis, systemic lupus erythematosus, Alzheimer disease and Down syndrome.

In a preferred embodiment relating to the pharmaceutical compositions of the present invention, said pharmaceutical composition comprises said compound as the only pharmaceutically active agent.

Alternatively, said pharmaceutical composition comprises at least one further independent pharmaceutically active agent in addition to said compound. As outlined above, the pharmaceutical composition according to the present invention may particularly be used in the treatment of cancer, an autoimmune or an inflammatory disease or neurodegenerative disorders such that at least one further independent pharmaceutically active agents directed to the treatment of such a particular disease may be additionally present.

Further, the compounds of the present invention may be useful as adjuvants to e.g. cancer treatment. They may be used in combination with one or more additional drugs, for example a chemotherapeutic agent which acts by the same or by a different mechanism of action. Such drugs are listed in the example section of the present application and comprise both targeted agents such as kinase inhibitors of the PI3K/Akt/mTOR pathway or the JAK/STAT pathway, but also standard chemotherapy agents such as cytarabine, and vosaroxin. In particular, the compounds of preferred embodiments (A) stated above may be used in cancer therapy (e.g. for use in treating acute myelogenous leukemia (AML), diffuse large B-cell lymphoma (DLBCL) and multiple myeloma (MM)) in combination with a chemotherapeutic agent such as a PI3K inhibitor, a JAK kinase inhibitor, cytarabine, vosaroxin and combinations thereof. Other targeted cancer therapy agents such as e.g. kinase inhibitors may, however, also be used in combination with compounds of the present invention.

2. ALTERNATIVE FORMULATIONS

The subject matter of the present invention may also be referred to as follows:

Method of administering to a subject in need thereof an effective amount of a compound according to formula (I) or a pharmaceutically acceptable salt thereof as defined above (including the preferred embodiments).

Method of treating a disease selected from the disease as disclosed herein by administering to a subject in need thereof an effective amount of a compound according to formula (I) or a pharmaceutically acceptable salt thereof as defined above (including the preferred embodiments).

Method for treating a PIM1-3- and/or FLT3- and/or DYRK1A-related disorder, said method comprising the step of administering to a patient in need thereof a therapeutic amount of a compound according to formula (I) or a pharmaceutically acceptable salt thereof as defined above (including the preferred embodiments).

Method for treating a PIM1-3- and/or FLT3- and/or DYRK1A-related cancer, said method comprising the step of administering to a patient in need thereof a therapeutic amount of a compound according to formula (I) or a pharmaceutically acceptable salt thereof as defined above (including the preferred embodiments).

Method for treating a PIM1-3- and/or FLT3- and/or DYRK1A-related inflammatory disorder, said method comprising the step of administering to a patient in need thereof a therapeutic amount of a compound according to formula (I) or a pharmaceutically acceptable salt thereof as defined above (including the preferred embodiments).

Method for treating a PIM1-3- and/or FLT3- and/or DYRK1A-related autoimmune disorder, said method comprising the step of administering to a patient in need thereof a therapeutic amount of a compound according to formula (I) or a pharmaceutically acceptable salt thereof as defined above (including the preferred embodiments).

Method for treating a PIM1-3- and/or FLT3- and/or DYRK1A-related neurodegenerative disorder, said method comprising the step of administering to a patient in need thereof a therapeutic amount of a compound according to formula (I) or a pharmaceutically acceptable salt thereof as defined above (including the preferred embodiments).

In the following, examples of embodiments of the present invention are outlined. However, said examples should not be construed as limiting the scope of the present invention.

3. EXAMPLES

3.1. Compounds of Example 1

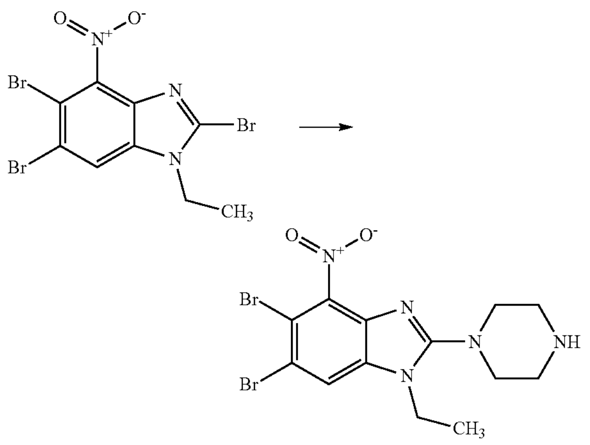

5,6-dibromo-1-ethyl-4-nitro-2-(piperazin-1-yl)-1H-1,3-benzodiazole hydrochloride (Example 1A)

2,5,6-tribromo-1-ethyl-4-nitro-1H-1,3-benzodiazole (150 mg, 0.35 mmol) and BOC piperazine (260 mg, 1.4 mmol) was dissolved in EtOH (3.0 ml). The resulting mixture was stirred at temperature 170° C. under microwave conditions until the reaction was completed (20 min) by LC/MS. The mixture was allowed to cool to RT and concentrated in-vacuo. The product was purified on silica gel using EA/hex (1:1). The product was dissolved in 1,4-dioxane (3.0 ml) and 4M HCl in dioxane (1.0 ml) was added. The mixture was stirred at room temperature until the reaction was complete (18 hrs) by LC/MS. Diethyl ether (5.0 ml) was added, product was filtered off, washed with diethyl ether and dried to afford 5,6-dibromo-1-ethyl-4-nitro-2-(piperazin-1-yl)-1H-1,3-benzodiazole hydrochloride (41 mg, 0.087 mmol). 1H NMR (600 MHz, DMSO) δ 9.59 (s, 1H), 8.21 (s, 1H), 4.18 (q, J=7.2 Hz, 2H), 3.60-3.58 (m, 4H), 3.25 (s, 4H), 1.33 (t, J=7.2 Hz, 3H); m/z 433.8; rt 2.4 min.

The following compounds were prepared by the procedure of Example 1A, using the appropriate starting materials (SM):

| Ex. | Name and structure | 1HNMR (400 MHz) | m/z | rt | SM |
|---|---|---|---|---|---|
| 1C | N-(3-aminopropyl)-5,6-dibromo-1-ethyl-4-nitro-1H-1,3-benzodiazol-2-amine hydrochloride 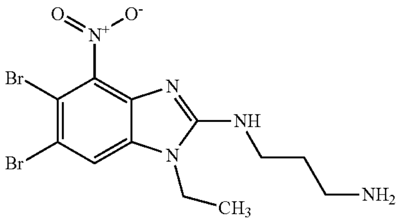 | 1H NMR (600 MHz, DMSO) δ 8.17 (s, 4H), 8.04 (s, 2H), 7.93 (s, 1H), 4.16 (q, J = 7.1 Hz, 2H), 3.46 (dd, J = 11.6, 6.0 Hz, 2H), 2.88 (tt, J = 13.3, 6.5 Hz, 2H), 1.95-1.87 (m, 2H), 1.19 (t, J = 7.1 Hz, 3H). | 421.8 | 2.5 | 2,5,6-tribromo-1-ethyl-4-nitro-1H-1,3-benzodiazole 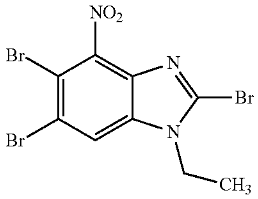 Method 3A and tert-butyl N-(3-aminopropyl)carbamate (commercial) |
| 1D | N-(3-aminopropyl)-5,6-dibromo-4-nitro-1H-1,3-benzodiazol-2-amine hydrochloride 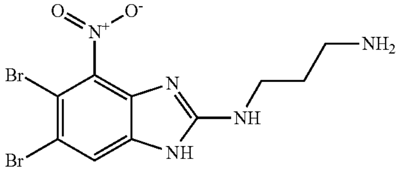 | 1H NMR (600 MHz, DMSO) δ 8.43 (s, 1H), 7.56 (s, 1H), 3.38 (t, J = 6.5 Hz, 2H), 2.84 (t, J = 7.1 Hz, 2H), 1.81 (p, J = 6.8 Hz, 2H). | 393.8 | 2.2 | 2,5,6-tribromo-4-nitro-1H-1,3-benzodiazole 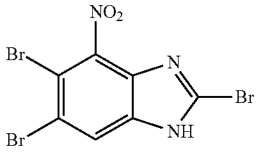 Method 2A and tert-butyl N-(3-aminopropyl)carbamate (commerical) |
| 1E | 5,6-dibromo-4-nitro-2-(piperazin-1-yl)-1H-1,3-benzodiazole hydrochloride 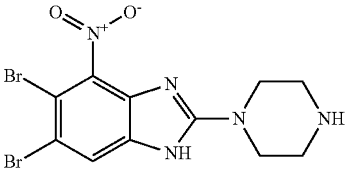 | 1H NMR (600 MHz, DMSO) δ 9.41 (bs, 1H), 7.72 (s, 1H), 3.84 (dd, J = 15.7, 10.4 Hz, 4H), 3.22 (bs, 4H). | 405.8 | 2.4 | 2,5,6-tribromo-4-nitro-1H-1,3-benzodiazole 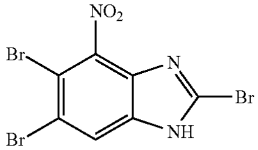 Method 2A and tert-butyl piperazine-1-carboxylate (Commerical) |

-continued

| Ex. | Name and structure | 1HNMR (400 MHz) | m/z | rt | SM |
|---|---|---|---|---|---|
| 1F | 1-(5,6-dibromo-1-ethyl-4-nitro-1H-1,3-benzodiazol-2-yl)piperidin-3-amine hydrochloride 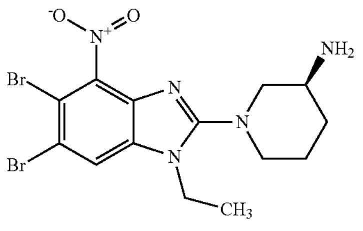 | $^{1}$H NMR (600 MHz, DMSO) δ 8.42 (bs, 3H), 8.17 (s, 1H), 4.17 (tt, J = 13.8, 7.0 Hz, 2H), 3.79 (dd, J = 12.4, 3.4 Hz, 1H), 3.51-3.46 (m, 1H), 3.36 (d, J = 4.4 Hz, 1H), 3.18 (dd, J = 12.5, 9.0 Hz, 1H), 3.10-3.04 (m, 1H), 2.04 (dd, J = 8.8, 3.9 Hz, 1H), 1.91 (dd, J = 8.8, 4.3 Hz, 1H), 1.73-1.61 (m, 2H), 1.35 (t, J = 7.2 Hz, 3H). | 447.9 | 2.4 | 2,5,6-tribromo-1-ethyl-4-nitro-1H-1,3-benzodiazole 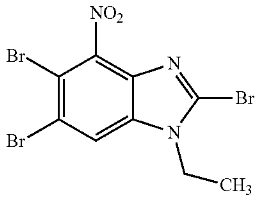 Method 3A and tert-butyl N-(piperidin-3-yl)carbamate (commerical) |
| 1G | 1-amino-3-[(5,6-dibromo-1-ethyl-4-nitro-1H-1,3-benzodiazol-2-yl)amino]propan-2-ol hydrochloride 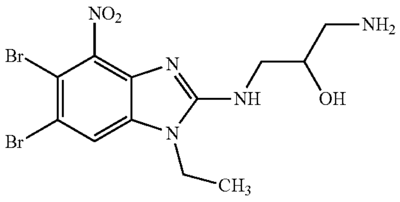 | 1H NMR (600 MHz, DMSO) δ 7.89 (s, 1H), 4.15-4.07 (m, 3H), 3.84-3.78 (m, 1H), 3.44-3.36 (m, 4H), 2.78 (dd, J = 12.9, 3.8 Hz, 1H), 2.63-2.58 (m, 1H), 1.19 (t, J = 7.1 Hz, 3H), 1.07 (s, 1H). | 437.9 | 2.4 | 2,5,6-tribromo-1-ethyl-4-nitro-1H-1,3-benzodiazole 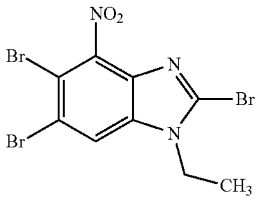 Method 3A and tert-butyl N-(3-amino-2-hydroxypropyl)carbamate (commercial) |
| 1H | 1-N-(5,6-dibromo-1-ethyl-4-nitro-1H-1,3-benzodiazol-2-yl)cyclohexane-1,4-diamine hydrochloride 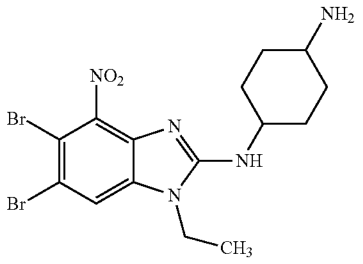 | — | 461.9 | 2.7 | 2,5,6-tribromo-1-ethyl-4-nitro-1H-1,3-benzodiazole 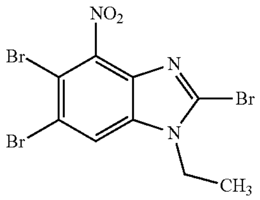 Method 3A and tert-butyl N-(4-aminocyclohexyl)carbamate |

-continued

| Ex. | Name and structure | 1HNMR (400 MHz) | m/z | rt | SM |
|---|---|---|---|---|---|
| 1I | 1-(5,6-dibromo-1-ethyl-4-nitro-1H-1,3-benzodiazol-2-yl)piperidin-4-amine hydrochloride 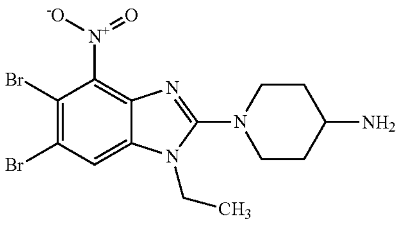 | — | 447.9 | 2.6 | 2,5,6-tribromo-1-ethyl-4-nitro-1H-1,3-benzodiazole 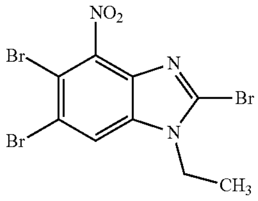 Method 3A and tert-butyl N-(piperidin-4-yl)carbamate (commercial) |
| 1L | N-(3-aminopropyl)-5,6-dibromo-4-nitro-1-(propan-2-yl)-1H-1,3-benzodiazol-2-amine hydrochloride 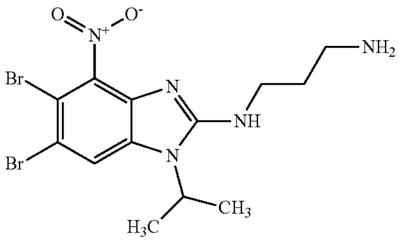 | $^1$H NMR (600 MHz, DMSO) δ 8.05 (bs, 3H), 7.94 (s, 1H), 7.86 (bs, 1H), 4.79 (hept, J = 6.9 Hz, 1H), 3.46 (bs, 2H), 2.89-2.83 (m, 2H), 1.94-1.88 (m, 2H), 1.49 (d, J = 6.9 Hz, 6H). | 435.9 | 2.6 | 2,5,6-tribromo-1-(2-propyl)-4-nitro-1H-1,3-benzodiazole 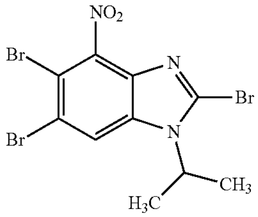 Method 3B and tert-butyl N-(3-aminopropyl)carbamate |
| 1M | 5,6-dibromo-4-nitro-2-(piperazin-1-yl)-1-propyl-1H-1,3-benzodiazole hydrochloride 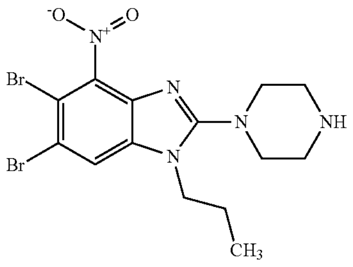 | $^1$H NMR (600 MHz, DMSO) δ 9.62 (s, 2H), 8.26 (s, 1H), 4.13-4.08 (m, 2H), 3.60-3.57 (m, 4H), 3.24 (s, 4H), 1.78-1.70 (m, 2H), 0.85 (t, J = 7.4 Hz, 3H). | 447.9 | 2.5 | 2,5,6-tribromo-4-nitro-1-propyl-1H-1,3-benzodiazole 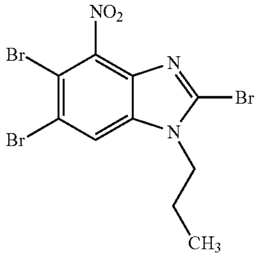 Method 3F and tert-butyl piperazine-1-carboxylate (Commercial) |

-continued

| Ex. | Name and structure | 1HNMR (400 MHz) | m/z | rt | SM |
|---|---|---|---|---|---|
| 1N | 5,6-dibromo-1-(2-methylpropyl)-4-nitro-2-(piperazin-1-yl)-1H-1,3-benzodiazole hydrochloride 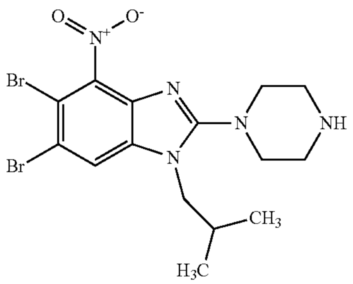 | $^1$H NMR (600 MHz, DMSO) δ 9.55 (bs, 2H), 8.32 (s, 1H), 4.02 (d, J = 7.6 Hz, 2H), 3.59-3.54 (m, 4H), 3.23 (bs, 4H), 2.22-2.12 (m, 1H), 0.78 (d, J = 6.6 Hz, 6H). | 461.9 | 2.8 | 2,5,6-tribromo-1-(2-methylpropyl)-4-nitro-1H-1,3-benzodiazole 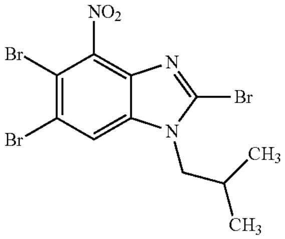 Method 3D and tert-butyl piperazine-1-carboxylate (Commerical) |
| 1P | N-(3-aminopropyl)-5,6-dibromo-4-nitro-1-propyl-1H-1,3-benzodiazol-2-amine hydrochloride 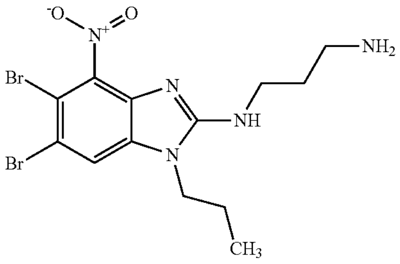 | $^1$H NMR (600 MHz, DMSO) δ 8.10 (bs, 1H), 8.05 (bs, 2H), 7.95 (s, 1H), 6.74 (bs, 1H), 4.08 (t, J = 7.4 Hz, 2H), 3.47 (dd, J = 11.8, 6.1 Hz, 2H), 2.89-2.83 (m, 2H), 1.93-1.87 (m, 2H), 1.67-1.60 (m, 2H), 0.89 (t, J = 7.3 Hz, 3H). | 418.9 | 3.6 | 2,5,6-tribromo-4-nitro-1-propyl-1H-1,3-benzodiazole 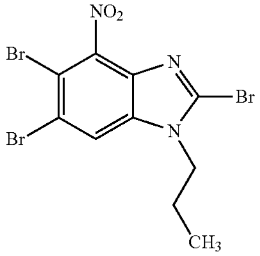 Method 3F And tert-butyl N-(3-aminopropyl)carbamate (Commerical) |
| 1Q | N-(azepan-4-yl)-5,6-dibromo-1-ethyl-4-nitro-1H-1,3-benzodiazol-2-amine hydrochloride 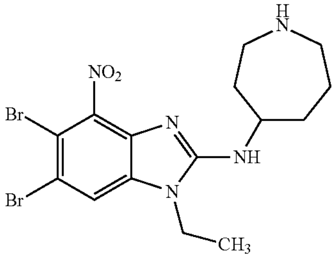 | — | 440.9 | 3.8 | 2,5,6-tribromo-1-ethyl-4-nitro-1H-1,3-benzodiazole 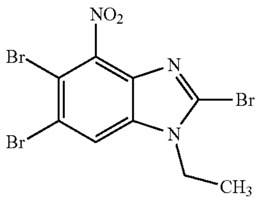 Method 3A And tert-butyl 4-aminoazepane-1-carboxylate (commercial) |

-continued

| Ex. | Name and structure | 1HNMR (400 MHz) | m/z | rt | SM |
| --- | --- | --- | --- | --- | --- |
| 1R | 5,6-dibromo-1-(cyclopropylmethyl)-4-nitro-2-(piperazin-1-yl)-1H-1,3-benzodiazole hydrochloride 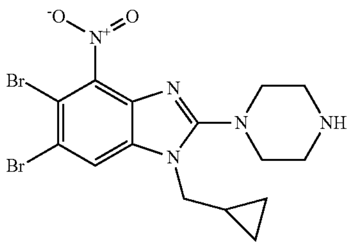 | 1H NMR (600 MHz, DMSO) δ 9.42 (s, 1H), 8.30 (s, 1H), 4.09 (d, J = 7.0 Hz, 2H), 3.56 (dd, J = 16.8, 11.6 Hz, 4H), 3.28-3.21 (m, 4H), 1.30-1.24 (m, 1H), 0.51-0.44 (m, 2H), 0.41-0.37 (m, 2H). | 445.9 | 2.7 | 2,5,6-tribromo-1-(cyclopropylmethyl)-4-nitro-1H-1,3-benzodiazole 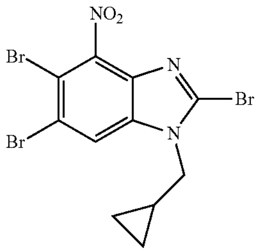 Method 3C and tert-butyl piperazine-1-carboxylate (Commerical) |
| 1S | 1-(5,6-dibromo-4-nitro-1H-1,3-benzodiazol-2-yl)piperidin-3-amine hydrochloride 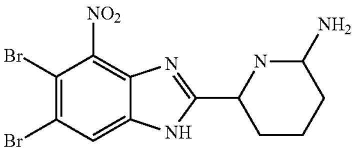 | 1H NMR (600 MHz, DMSO) δ 8.28 (s, 3H), 7.67 (s, 1H), 4.19 (dd, J = 12.7, 3.3 Hz, 1H), 3.79 (dt, J = 12.7, 4.2 Hz, 1H), 3.39-3.25 (m, 3H), 2.05-1.99 (m, 1H), 1.85 (dd, J = 9.3, 3.9 Hz, 1H), 1.70-1.57 (m, 2H). | 461.9 | 2.8 | 2,5,6-tribromo-4-nitro-1H-1,3-benzodiazole 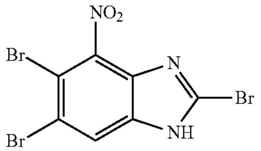 Method 2A and tert-butyl N-(piperidin-3-yl)carbamate (commercial) |
| 1T | 1-[5,6-dibromo-4-nitro-1-(propan-2-yl)-1H-1,3-benzodiazol-2-yl]piperidin-3-amine hydrochloride 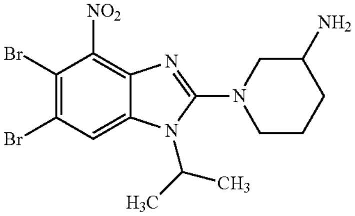 | $^{1}$H NMR (600 MHz, DMSO) δ 8.40 (bs, 3H), 8.25 (s, 1H), 4.60 (hept, J = 6.8 Hz, 1H), 3.59 (dd, J = 12.3, 3.2 Hz, 1H), 3.39 (d, J = 2.7 Hz, 1H), 3.27 (dd, J = 8.5, 4.4 Hz, 1H), 3.15 (dd, J = 12.3, 8.7 Hz, 1H), 3.01 (dd, J = 15.8, 6.3 Hz, 1H), 2.02 (dd, J = 9.1, 3.6 Hz, 1H), 1.92 (dd, J = 9.6, 3.9 Hz, 1H), 1.74-1.61 (m, 2H), 1.55 (dd, J = 10.8, 6.9 Hz, 6H). | 461.9 | 2.5 | 2,5,6-tribromo-1-(2-propyl)-4-nitro-1H-1,3-benzodiazole 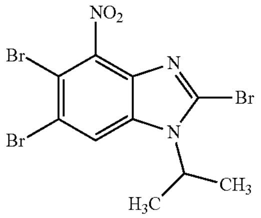 Method 3B and tert-butyl N-(piperidin-3-yl)carbamate (commercial) |

-continued

| Ex. | Name and structure | 1HNMR (400 MHz) | m/z | rt | SM |
|---|---|---|---|---|---|
| IU | 1-(5,6-dibromo-4-nitro-1-propyl-1H-1,3-benzodiazol-2-yl)piperidin-3-amine hydrochloride 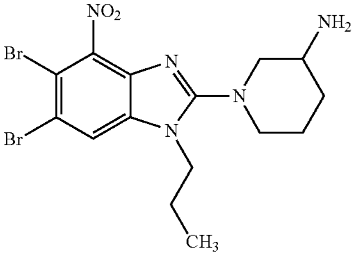 | — | 475.9 | 2.9 | 2,5,6-tribromo-4-nitro-1-propyl-1H-1,3-benzodiazole 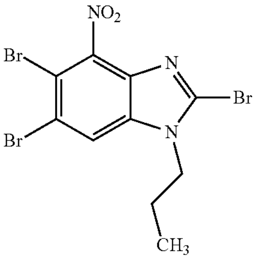 Method 3F and tert-butyl N-(piperidin-3-yl)carbamate (commercial) |
| IV | 1-[5,6-dibromo-1-(2-methylpropyl)-4-nitro-1H-1,3-benzodiazol-2-yl]piperidin-3-amine hydrochloride 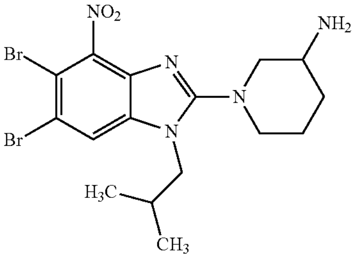 | 1H NMR (600 MHz, DMSO) δ 8.37 (d, J = 3.6 Hz, 3H), 8.29 (s, 1H), 4.05-3.96 (m, J = 22.2, 14.6, 7.2 Hz, 2H), 3.89-3.80 (m, 1H), 3.54 (d, J = 12.9 Hz, 1H), 3.36-3.23 (m, 1H), 3.07 (dd, J = 12.3, 9.8 Hz, 1H), 3.00-2.93 (m, 1H), 2.18 (dp, J = 13.9, 6.8 Hz, 1H), 2.11-2.03 (m, 1H), 1.93-1.83 (m, 1H), 1.70-1.54 (m, 2H), 0.77 (dd, J = 6.3 Hz, 5H). | 427.8 | 2.8 | 2,5,6-tribromo-1-(2-methylpropyl)-4-nitro-1H-1,3-benzodiazole 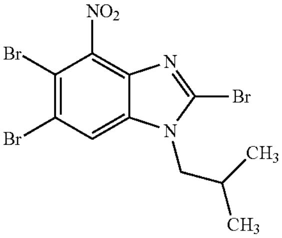 Method 3D and tert-butyl N-(piperidin-3-yl)carbamate (commercial) |
| IW | 1-amino-3-{[5,6-dibromo-4-nitro-1-(propan-2-yl)-1H-1,3-benzodiazol-2-yl]amino}propan-2-ol hydrochloride 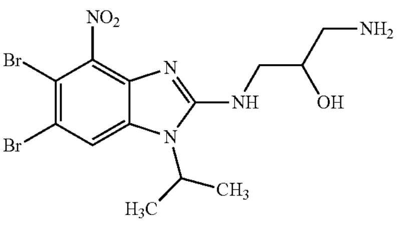 | — | 451.8 | 5.2 | 2,5,6-tribromo-1-(2-propyl)-4-nitro-1H-1,3-benzodiazole 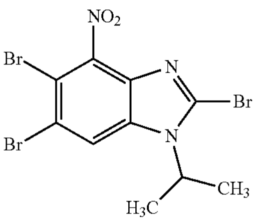 Method 3B and tert-butyl N-(3-amino-2-hydroxypropyl)carbamate (commercial) |

-continued

| Ex. | Name and structure | 1HNMR (400 MHz) | m/z | rt | SM |
|---|---|---|---|---|---|
| IX | 1-amino-3-[(5,6-dibromo-4-nitro-1-propyl-1H-1,3-benzodiazol-2-yl)amino]propan-2-ol hydrochloride 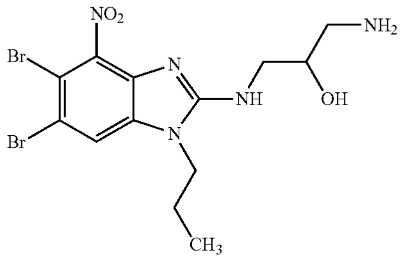 | — | 465.9 | 6.3 | 2,5,6-tribromo-4-nitro-1-propyl-1H-1,3-benzodiazole 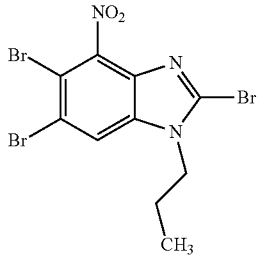 Method 3F and tert-butyl N-(3-aminno-2-hydroxypropyl)carbamate (commercial) |
| IY | 1-amino-3-{[5,6-dibromo-1-(2-methylpropyl)-4-nitro-1H-1,3-benzodiazol-2-yl]amino}propan-2-ol hydrochloride 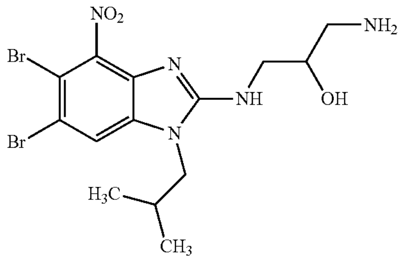 | 1H NMR (600 MHz, DMSO) δ 7.97 (s, 1H), 4.03-3.99 (m, 1H), 3.99-3.95 (m, 2H), 3.49 (dt, J = 13.5, 5.9 Hz, 1H), 3.42-3.36 (m, 1H), 2.95 (ddd, J = 12.8, 5.9, 3.3 Hz, 1H), 2.78-2.70 (m, 1H), 2.11 (dp, J = 14.1, 6.9 Hz, 1H), 0.88 (dd, J = 6.6, 2.8 Hz, 6H). | 447.9 | 2.7 | 2,5,6-tribromo-1-(2-methylpropyl)-4-nitro-1H-1,3-benzodiazole 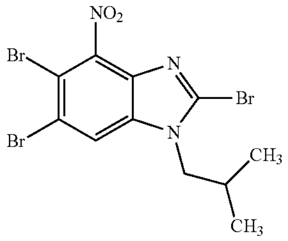 Method 3D and tert-butyl N-(3-amino-2-hydroxypropyl)carbamate (commercial) |
| 1Z | [1-(5,6-dibromo-1-ethyl-4-nitro-1H-1,3-benzodiazol-2-yl)pyrrolidin-2-yl]methanamine hydrochloride 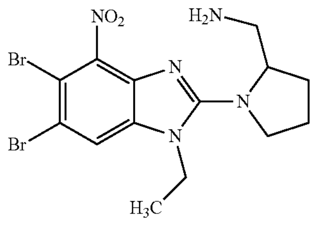 | 1H NMR (600 MHz, DMSO) δ 8.14 (s, 3H), 8.05 (s, 1H), 4.39 (dd, J = 11.4, 6.0 Hz, 1H), 4.31 (dq, J = 14.4, 7.1 Hz, 1H), 4.15 (dq, J = 14.3, 7.0 Hz, 1H), 3.88 (dd, J = 15.4, 7.2 Hz, 1H), 3.65 (dd, J = 9.8, 6.3 Hz, 1H), 3.10-3.01 (m, 2H), 2.10-1.99 (m, 2H), 1.96-1.88 (m, 2H), 1.34 (t, J = 7.1 Hz, 3H). | 457.9 | 2.2 | 2,5,6-tribromo-1-ethyl-4-nitro-1H-1,3-benzodiazole 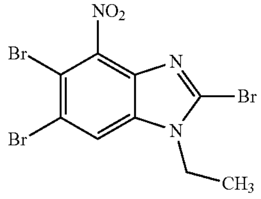 Method 3A and tert-butyl N-(pyrrolidin-2-ylmethyl)carbamate |

-continued

| Ex. | Name and structure | 1HNMR (400 MHz) | m/z | rt | SM |
|---|---|---|---|---|---|
| 1AA | 5,6-dibromo-1-ethyl-4-nitro-N-[(3S)-piperidin-3-yl]-1H-1,3-benzodiazol-2-amine hydrochloride 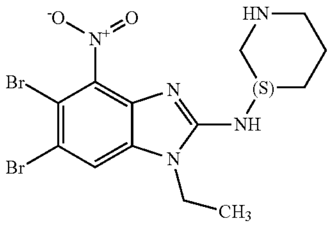 | — | 481.9 | 2.2 | 2,5,6-tribromo-1-ethyl-4-nitro-1H-1,3-benzodiazole 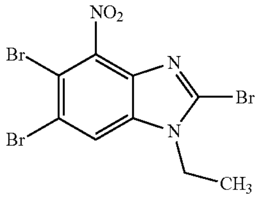 Method 3A And tert-butyl (3S)-3-aminopiperidine-1-carboxylate |
| 1AB | N-(3-aminopropyl)-5,6-dibromo-1-(cyclopropylmethyl)-4-nitro-1H-1,3-benzodiazol-2-amine hydrochloride 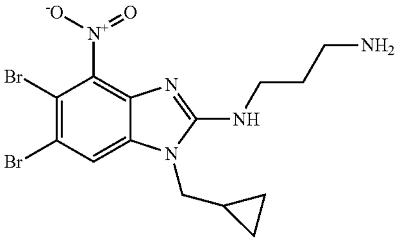 | 1H NMR (600 MHz, DMSO) δ 8.03 (bs, 3H), 7.97 (s, 1H), 4.07 (d, J = 7.1 Hz, 2H), 3.49-3.44 (m, 2H), 2.90-2.83 (m, 2H), 1.91 (p, 2H), 1.26-1.18 (m, 1H), 0.48-0.42 (m, 4H). | 430 | 2.1 | 2,5,6-tribromo-1-(cyclopropylmethyl)-4-nitro-1H-1,3-benzodiazole 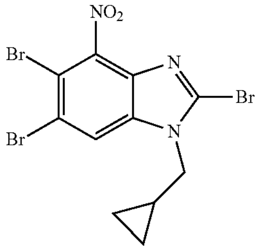 Method 3C and -butyl N-(3-aminopropyl)carbamate |
| 1AC | N-(azepan-4-yl)-5,6-dibromo-1-(2-methylpropyl)-4-nitro-1H-1,3-benzodiazol-2-amine hydrochloride 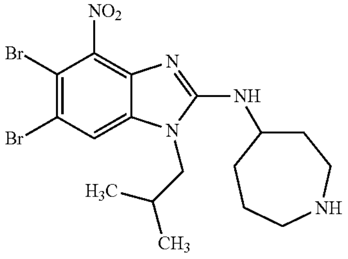 | — | 447.9 | 2.6 | 2,5,6-tribromo-1-(2-methylpropyl)-4-nitro-1H-1,3-benzodiazole 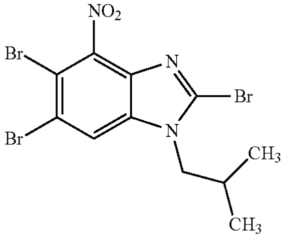 Method 3D And tert-butyl 4-aminoazepane-1-carboxylate |

-continued

| Ex. | Name and structure | 1HNMR (400 MHz) | m/z | rt | SM |
|---|---|---|---|---|---|
| 1AD | 5,6-dibromo-1-ethyl-2-(2-methylpiperazin-1-yl)-4-nitro-1H-1,3-benzodiazole hydrochloride 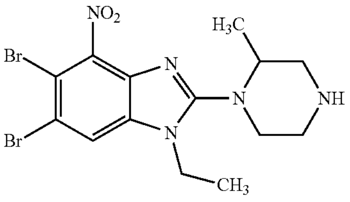 | 1H NMR (600 MHz, DMSO) δ 9.57 (bs, 1H), 9.36 (bs, 1H), 8.30 (s, 1H), 4.27-4.13 (m, 2H), 3.87 (td, J = 6.6, 3.6 Hz, 1H), 3.47 (dt, J = 13.6, 5.1 Hz, 1H), 3.38 (dt, J = 13.6, 5.2 Hz, 1H), 3.36-3.31 (m, 1H), 3.24-3.19 (m, 2H), 3.06 (dt, J = 10.5, 6.5 Hz, 1H), 1.31 (t, J = 7.2 Hz, 3H), 1.16 (d, J = 6.6 Hz, 3H). | 448.8 | 3.2 | 2,5,6-tribromo-1-ethyl-4-nitro-1H-1,3-benzodiazole 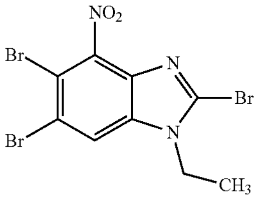 Method 3A and tert-butyl 3-methylpiperazine-1-carboxylate (commercial) |
| 1AE | 1-(5,6-dibromo-1-ethyl-4-nitro-1H-1,3-benzodiazol-2-yl)azepan-3-amine hydrochloride 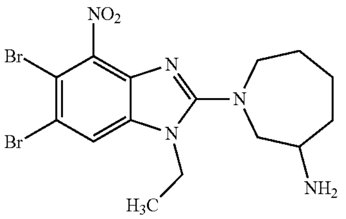 | — | 433.8 | 2.7 | 2,5,6-tribromo-1-ethyl-4-nitro-1H-1,3-benzodiazole 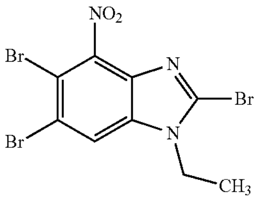 Method 3A And tert-butyl N-(azepan-3-yl)carbamate |
| 1AF | 5,6-dibromo-1-ethyl-4-nitro-N-(pyrrolidin-3-yl)-1H-1,3-benzodiazol-2-amine hydrochloride 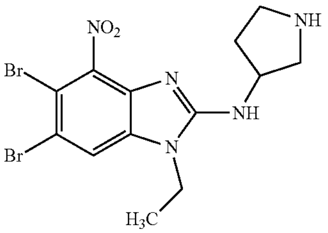 | 1H NMR (600 MHz, DMSO) δ 7.96 (s, 1H), 4.57 (s, 1H), 4.20 (q, J = 7.2 Hz, 2H), 3.46-3.37 (m, 2H), 3.31-3.21 (m, 2H), 2.25 (dt, J = 15.1, 7.3 Hz, 1H), 2.08 (td, J = 13.2, 5.8 Hz, 1H), 1.20 (t, J = 7.1 Hz, 3H). | 434.8 | 3 | 2,5,6-tribromo-1-ethyl-4-nitro-1H-1,3-benzodiazole 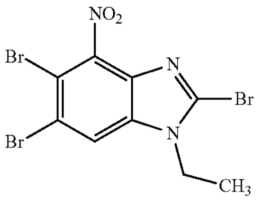 Method 3A and tert-butyl 3-aminopyrrolidine-1-carboxylate |

-continued

| Ex. | Name and structure | 1HNMR (400 MHz) | m/z | rt | SM |
| --- | --- | --- | --- | --- | --- |
| 1AG | (3R)-1-(5,6-dibromo-1-ethyl-4-nitro-1H-1,3-benzodiazol-2-yl)pyrrolidin-3-amine hydrochloride 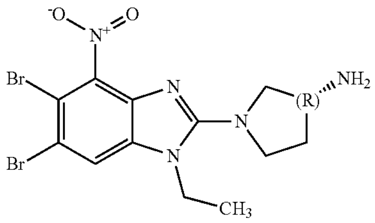 | 1H NMR (600 MHz, DMSO) δ 8.56 (s, 1H), 8.03 (s, 1H), 4.35-4.20 (m, 1H), 3.95 (dd, J = 9.6, 7.8 Hz, 1H), 3.93-3.88 (m, 1H), 3.85-3.75 (m, 1H), 2.32 (td, J = 13.7, 8.2 Hz, 1H), 2.17 (ddd, J = 16.3, 7.6, 4.3 Hz, 1H), 1.33 (t, J = 7.2 Hz, 1H). | 447.8 | 2.7 | 2,5,6-tribromo-1-ethyl-4-nitro-1H-1,3-benzodiazole 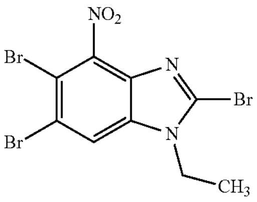 Method 3A and tert-butyl N-[(3R)-pyrrolidin-3-yl]carbamate |
| 1AH | (3S)-1-(5,6-dibromo-1-ethyl-4-nitro-1H-1,3-benzodiazol-2-yl)piperidin-3-amine hydrochloride 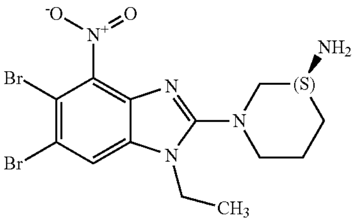 | — | 447.9 | 2.6 | 2,5,6-tribromo-1-ethyl-4-nitro-1H-1,3-benzodiazole 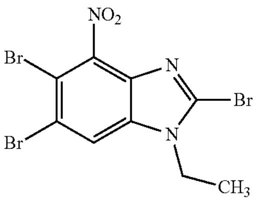 Method 3A and tert-butyl N-[(3R)-piperidin-3-yl]carbamate |
| 1AI | (3R)-1-(5,6-dibromo-1-ethyl-4-nitro-1H-1,3-benzodiazol-2-yl)piperidin-3-amine hydrochloride 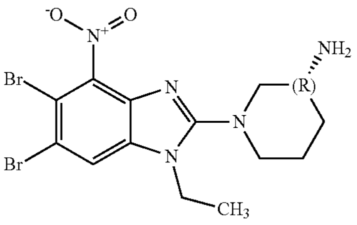 | $^1$H NMR (600 MHz, DMSO) δ 8.36 (bs, 3H), 8.17 (s, 1H), 4.21-4.13 (m, 2H), 3.78 (dd, J = 12.4, 3.3 Hz, 1H), 3.51-3.45 (m, 1H), 3.40-3.33 (m, 1H), 3.20-3.15 (m, 1H), 3.10-3.05 (m, 1H), 2.04 (dd, J = 8.9, 3.4 Hz, 1H), 1.91 (dd, J = 9.3, 4.0 Hz, 1H), 1.73-1.61 (m, 2H), 1.35 (t, J = 7.2 Hz, 3H). | 433.8 | 2.5 | 2,5,6-tribromo-1-ethyl-4-nitro-1H-1,3-benzodiazole 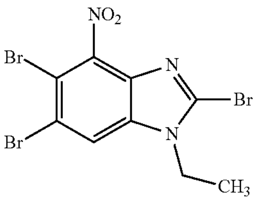 Method 3A and tert-butyl N-[(3R)-piperidin-3-yl]carbamate |

-continued

| Ex. | Name and structure | 1HNMR (400 MHz) | m/z | rt | SM |
| --- | --- | --- | --- | --- | --- |
| 1AJ | (3S)-1-(5,6-dibromo-1-ethyl-4-nitro-1H-1,3-benzodiazol-2-yl)pyrrolidin-3-amine hydrochloride 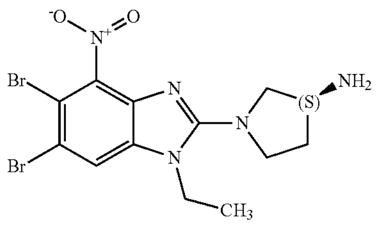 | 1H NMR (600 MHz, DMSO) δ 8.45 (bs, 3H), 8.02 (s, 1H), 4.33-4.22 (m, 2H), 3.95-3.87 (m, 3H), 3.79 (dt, J = 9.1, 4.9 Hz, 2H), 2.32 (td, J = 13.9, 8.3 Hz, 1H), 2.15 (ddd, J = 12.2, 7.6, 4.1 Hz, 1H), 1.32 (t, J = 7.2 Hz, 3H). | 434.8 | 2.9 | 2,5,6-tribromo-1-ethyl-4-nitro-1H-1,3-benzodiazole 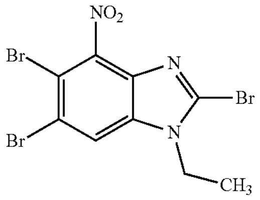 Method 3A And tert-butyl N-[(3R)-pyrrolidyn-3-yl]carbamate |
| 1AK | N-(2-aminoethyl)-5,6-dibromo-4-nitro-1H-1,3-benzodiazol-2-amine hydrochloride 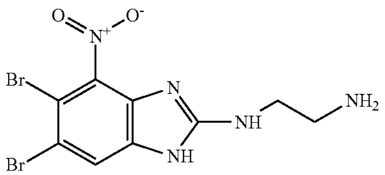 | — | 407.9 | 2.5 | 2,5,6-tribromo-4-nitro-1H-1,3-benzodiazole 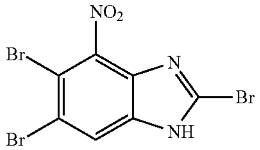 Method 2A and tert-butyl N-(2-aminoethyl)carbamate |
| 1AL | N-(2-aminoethyl)-5,6-dibromo-1-ethyl-4-nitro-1H-1,3-benzodiazol-2-amine hydrochloride 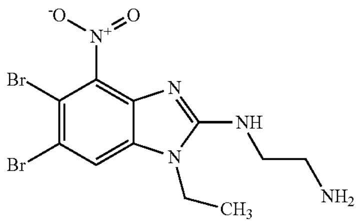 | 1H NMR (600 MHz, DMSO) δ 8.15 (s, 3H), 8.06 (t, J = 5.2 Hz, 1H), 7.95 (s, 1H), 4.18 (q, J = 7.1 Hz, 2H), 3.63 (q, J = 5.8 Hz, 2H), 3.11-3.04 (m, 2H), 1.22 (t, J = 7.1 Hz, 3H). | 447.9 | 2.8 | 2,5,6-tribromo-1-ethyl-4-nitro-1H-1,3-benzodiazole 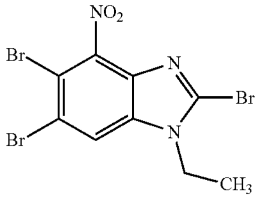 Method 3A and tert-butyl N-(2-aminoethyl)carbamate |

-continued

| Ex. | Name and structure | 1HNMR (400 MHz) | m/z | rt | SM |
|---|---|---|---|---|---|
| 1AM | 5,6-dibromo-1-ethyl-4-nitro-N-(pyrrolidin-2-ylmethyl)-1H-1,3-benzodiazol-2-amine hydrochloride 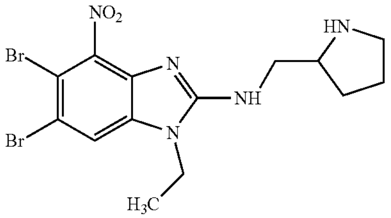 | $^1$H NMR (600 MHz, DMSO) δ 9.43 (bs, 1H), 9.15 (bs, 1H), 8.17 (t, J = 5.6 Hz, 1H), 7.97 (s, 1H), 4.19 (q, J = 7.1 Hz, 2H), 3.80 (td, J = 13.5, 6.6 Hz, 1H), 3.25-3.19 (m, 1H), 3.19-3.13 (m, 1H), 2.04 (td, J = 12.6, 7.6 Hz, 1H), 1.97-1.90 (m, 1H), 1.90-1.82 (m, 1H), 1.72 (dq, J = 12.9, 8.1 Hz, 1H), 1.23 (t, J = 7.1 Hz, 3H). | 462.8 | 3.3 | 2,5,6-tribromo-1-ethyl-4-nitro-1H-1,3-benzodiazole 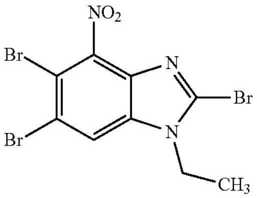 Method 3A and tert-butyl 2-(aminomethyl)pyrrol-idine-1-carboxylate |
| 1AN | 5,6-dibromo-2-(1,4-diazepan-1-yl)-1-ethyl-4-nitro-1H-1,3-benzodiazole hydrochloride 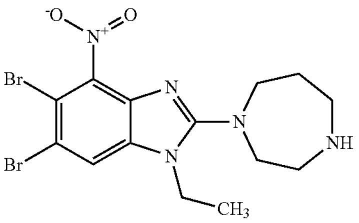 | 1H NMR (600 MHz, DMSO) δ 8.02 (s, 1H), 4.18 (q, J = 7.1 Hz, 2H), 3.70-3.66 (m, 4H), 3.08-3.05 (m, 2H), 2.93-2.90 (m, 2H), 1.91 (dt, J = 11.5, 5.9 Hz, 2H), 1.29 (t, J = 7.2 Hz, 3H). | 461.9 | 3.1 | 2,5,6-tribromo-1-ethyl-4-nitro-1H-1,3-benzodiazole 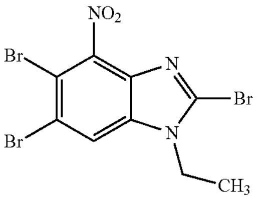 Method 3A and tert-butyl 1,4-diazepane-1-carboxylate |
| 1AO | 5,6-dibromo-2-[(2R)-2-methylpiperazin-1-yl]-4-nitro-1-(propan-2-yl)-1H-1,3-benzodiazole hydrochloride 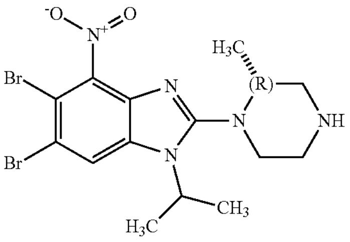 | 1H NMR (600 MHz, DMSO) δ 8.95 (bs, 2H), 8.39 (s, 1H), 4.80 (hept, J = 6.8 Hz, 1H), 3.69-3.63 (m, 1H), 3.53 (d, J = 14.4 Hz, 1H), 3.30 (d, J = 13.1 Hz, 2H), 3.27-3.17 (m, 2H), 3.05 (dd, J = 12.6, 8.5 Hz, 1H), 1.58 (d, J = 7.0 Hz, 3H), 1.51 (d, J = 6.9 Hz, 3H), 1.05 (d, J = 6.5 Hz, 3H). | 461.9 | 2.8 | 2,5,6-tribromo-1-(2-propyl)-4-nitro-1H-1,3-benzodiazole 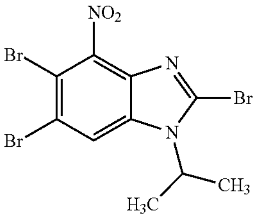 Method 3B And tert-butyl (3R)-3-methylpiperazine-1-carboxylate |

-continued

| Ex. | Name and structure | 1HNMR (400 MHz) | m/z | rt | SM |
|---|---|---|---|---|---|
| 1AP | (3S)-1-[5,6-dibromo-4-nitro-1-(propan-2-yl)-1H-1,3-benzodiazol-2-yl]piperidin-3-amine hydrochloride 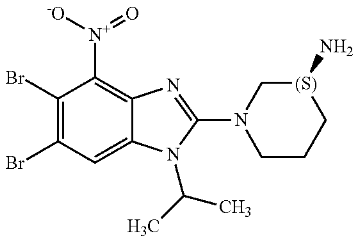 | 1H NMR (300 MHz, dmso) δ 8.35 (s, 3H), 8.24 (s, 1H), 4.57 (dt, J = 13.8, 6.9 Hz, 1H), 3.61-3.51 (m, 1H), 3.37 (s, 1H), 3.25 (d, J = 13.0 Hz, 1H), 3.12 (dd, J = 12.2, 8.6 Hz, 1H), 3.04-2.92 (m, 1H), 1.99 (d, J = 11.6 Hz, 1H), 1.89 (s, 1H), 1.65 (d, J = 8.5 Hz, 1H), 1.53 (dd, J = 6.8, 5.4 Hz, 6H). | 461.9 | 2.8 | 2,5,6-tribromo-1-(2-propyl)-4-nitro-1H-1,3-benzodiazole 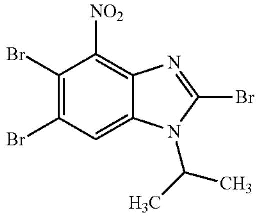 Method 3B and tert-butyl N-[(3S)-piperidin-3-yl]carbamate |
| 1AQ | {4-[5,6-dibromo-4-nitro-1-(propan-2-yl)-1H-1,3-benzodiazol-2-yl]morpholin-2-yl}methanamine hydrochloride 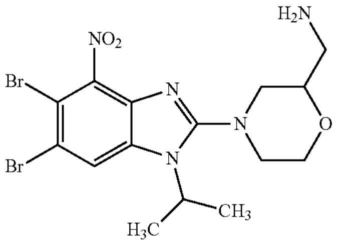 | 1H NMR (600 MHz, DMSO) δ 8.28 (s, 1H), 8.15 (s, 3H), 4.66-4.60 (m, 1H), 4.00-3.97 (m, 1H), 3.96-3.91 (m, 1H), 3.79 (td, J = 11.5, 2.3 Hz, 1H), 3.44 (d, J = 12.4 Hz, 1H), 3.34 (d, J = 11.3 Hz, 1H), 3.09 (ddd, J = 11.3, 8.1, 3.6 Hz, 2H), 2.94 (dd, J = 12.5, 10.4 Hz, 1H), 2.92-2.86 (m, 1H), 1.58 (d, J = 6.9 Hz, 3H), 1.53 (d, J = 6.9 Hz, 3H). | 477.8 | 5.7 | 2,5,6-tribromo-1-(2-propyl)-4-nitro-1H-1,3-benzodiazole 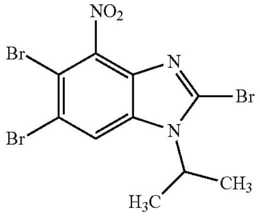 Method 3B And tert-butyl N-(morpholin-2-ylmethyl)carbamate |
| 1AR | 5,6-dibromo-N-(morpholin-2-ylmethyl)-4-nitro-1-(propan-2-yl)-1H-1,3-benzodiazol-2-amine hydrochloride 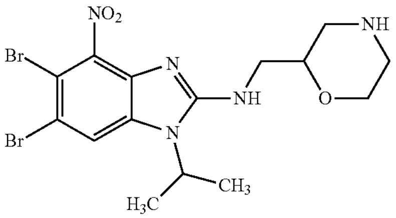 | — | 461.9 | 3 | 2,5,6-tribromo-1-(2-propyl)-4-nitro-1H-1,3-benzodiazole 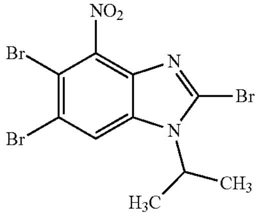 Method 3B and tert-butyl 2-(aminomethyl)morpholine-4-carboxylate |

-continued

| Ex. | Name and structure | 1HNMR (400 MHz) | m/z | rt | SM |
| --- | --- | --- | --- | --- | --- |
| 1AS | 5,6-dibromo-4-nitro-N-[(3S)-piperidin-3-yl]-1-(propan-2-yl)-1H-1,3-benzodiazol-2-amine hydrochloride 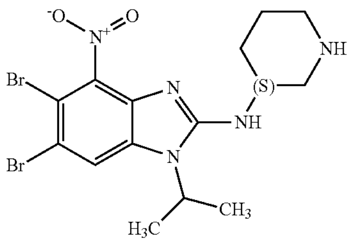 | $^1$H NMR (600 MHz, DMSO) δ 8.76 (bs, 1H), 8.70 (bs, 1H), 7.98 (s, 1H), 7.33 (d, J = 7.2 Hz, 1H), 4.69 (hept, J = 6.9 Hz, 1H), 4.13 (qd, J = 10.5, 5.4 Hz, 1H), 3.43 (d, J = 11.2 Hz, 1H), 3.20 (d, J = 12.5 Hz, 1H), 2.89-2.79 (m, 2H), 2.04-1.97 (m, 1H), 1.91 (dd, J = 14.2, 3.6 Hz, 1H), 1.74-1.61 (m, 2H), 1.50 (dd, J = 6.9, 1.0 Hz, 6H). | 461.8 | 2.9 | 2,5,6-tribromo-1-(2-propyl)-4-nitro-1H-1,3-benzodiazole 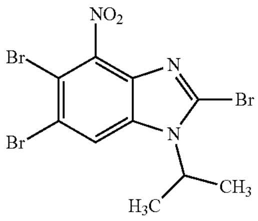 Method 3B And tert-butyl (3S)-3-aminopiperidine-1-carboxylate |
| 1AT | (3R)-1-[5,6-dibromo-4-nitro-1-(propan-2-yl)-1H-1,3-benzodiazol-2-yl]piperidin-3-amine hydrochloride 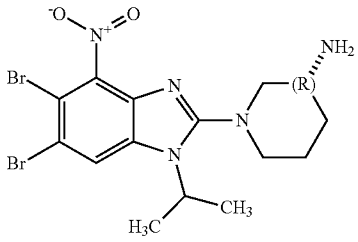 | 1H NMR (600 MHz, DMSO) δ 8.38 (d, J = 3.5 Hz, 3H), 8.26 (s, 1H), 4.64-4.56 (m, 1H), 3.59 (dd, J = 12.3, 3.2 Hz, 1H), 3.39 (d, J = 4.5 Hz, 1H), 3.27 (dd, J = 8.3, 4.5 Hz, 1H), 3.14 (dd, J = 12.4, 8.7 Hz, 1H), 3.01 (dd, J = 15.8, 6.3 Hz, 1H), 2.02 (dd, J = 8.9, 3.5 Hz, 1H), 1.92 (dd, J = 9.5, 3.9 Hz, 1H), 1.75-1.61 (m, 2H), 1.55 (dd, J = 10.7, 6.9 Hz, 6H). | 475.9 | 3 | 2,5,6-tribromo-1-(2-propyl)-4-nitro-1H-1,3-benzodiazole 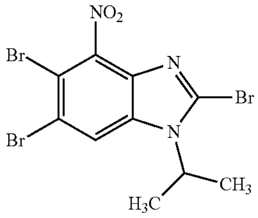 Method 3B And tert-butyl N-[(3R)-piperidin-3-yl]carbamate |

-continued

| Ex. | Name and structure | 1HNMR (400 MHz) | m/z | rt | SM |
|---|---|---|---|---|---|
| 1AU | (3R)-1-[5,6-dibromo-1-(2-methylpropyl)-4-nitro-1H-1,3-benzodiazol-2-yl]piperidin-3-amine hydrochloride 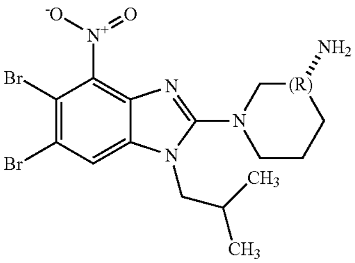 | 1H NMR (600 MHz, DMSO) δ 8.31 (d, J = 3.6 Hz, 3H), 8.29 (s, 1H), 4.02 (d, J = 2.7 Hz, 2H), 3.84 (d, J = 3.5 Hz, 1H), 3.82 (d, J = 3.5 Hz, 1H), 3.54 (d, J = 12.9 Hz, 1H), 3.31 (dd, J = 9.4, 4.4 Hz, 1H), 3.06 (dd, J = 12.3, 9.8 Hz, 1H), 3.00-2.92 (m, 1H), 2.18 (dt, J = 13.9, 7.1 Hz, 1H), 2.09-2.04 (m, 1H), 1.88 (dd, J = 9.8, 3.7 Hz, 1H), 1.70-1.62 (m, 1H), 1.61-1.54 (m, 1H), 0.77 (t, J = 6.4 Hz, 6H). | 473.9 | 3.1 | 2,5,6-tribromo-1-(2-methylpropyl)-4-nitro-1H-1,3-benzodiazole 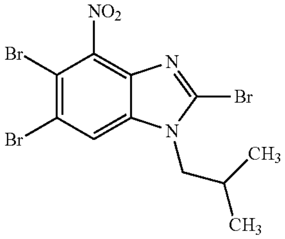 Method 3D And tert-butyl N-[(3R)-piperidin-3-yl]carbamate |
| 1AV | (3S)-1-[5,6-dibromo-1-(cyclopropylmethyl)-4-nitro-1H-1,3-benzodiazol-2-yl]piperidin-3-amine hydrochloride 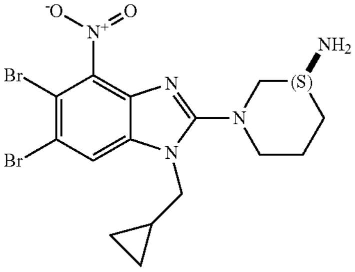 | $^1$H NMR (600 MHz, DMSO) δ 8.28 (d, J = 3.2 Hz, 3H), 8.25 (s, 1H), 4.08 (d, J = 7.0 Hz, 2H), 3.80 (dd, J = 12.3, 3.4 Hz, 1H), 3.56-3.50 (m, 1H), 3.35 (ddd, J = 14.2, 9.1, 4.9 Hz, 1H), 3.11 (dd, J = 12.4, 9.5 Hz, 1H), 3.06-2.99 (m, 1H), 2.09-2.02 (m, 1H), 1.89 (dd, J = 9.0, 4.5 Hz, 1H), 1.72-1.63 (m, 1H), 1.59 (dt, J = 10.8, 6.6 Hz, 1H), 1.30-1.22 (m, 1H), 0.51-0.47 (m, 2H), 0.41-0.36 (m, 2H). | 473.9 | 3 | 2,5,6-tribromo-1-(cyclopropylmethyl)-4-nitro-1H-1,3-benzodiazole 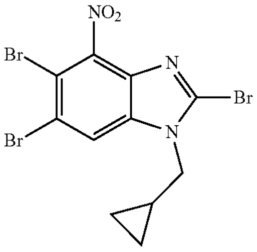 Method 3C And tert-butyl N-[(3S)-piperidin-3-yl]carbamate |

-continued

| Ex. | Name and structure | 1HNMR (400 MHz) | m/z | rt | SM |
|---|---|---|---|---|---|
| 1AW | (3R)-1-[5,6-dibromo-1-(cyclopropylmethyl)-4-nitro-1H-1,3-benzodiazol-2-yl]piperidin-3-amine hydrochloride 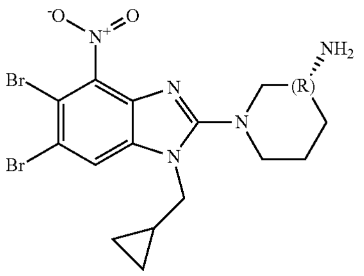 | $^1$H NMR (600 MHz, DMSO) δ 8.25 (bs, 4H), 4.08 (d, J = 7.0 Hz, 2H), 3.80 (dd, J = 12.3, 3.4 Hz, 1H), 3.56-3.50 (m, 1H), 3.35 (dd, J = 9.2, 4.3 Hz, 1H), 3.11 (dd, J = 12.4, 9.5 Hz, 1H), 3.06-3.00 (m, 1H), 2.08-2.02 (m, 1H), 1.88 (dd, J = 9.1, 4.5 Hz, 1H), 1.67 (ddd, J = 13.7, 10.5, 5.5 Hz, 1H), 1.59 (dt, J = 11.0, 6.8 Hz, 1H), 1.30-1.21 (m, 1H), 0.51-0.47 (m, 2H), 0.41-0.36 (m, 2H). | 461.8 | 2.9 | 2,5,6-tribromo-1-(cyclopropylmethyl)-4-nitro-1H-1,3-benzodiazole 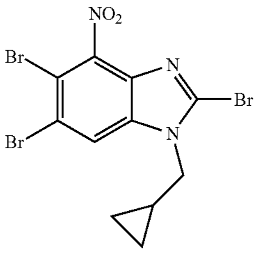 Method 3C And tert-butyl N-[(3R)-piperidin-3-yl]carbamate |
| 1AX | 5,6-dibromo-2-[(2S)-2-methylpiperazin-1-yl]-4-nitro-1-(propan-2-yl)-1H-1,3-benzodiazole hydrochloride 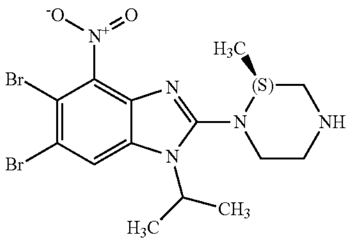 | 1H NMR (600 MHz, DMSO) δ 8.91 (bs, 2H), 8.39 (s, 1H), 4.81 (hept, J = 7.0 Hz, 1H), 3.70-3.62 (m, 1H), 3.31-3.17 (m, 4H), 3.05 (dd, J = 12.7, 8.5 Hz, 1H), 1.58 (d, J = 7.0 Hz, 3H), 1.51 (d, J = 6.9 Hz, 3H), 1.05 (d, J = 6.5 Hz, 1H). | 447.8 | 2.7 | 2,5,6-tribromo-1-(2-propyl)-4-nitro-1H-1,3-benzodiazole 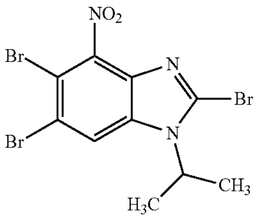 Method 3B And tert-butyl (3S)-3-methylpiperazine-1-carboxylate |
| 1AY | (3R)-1-[5,6-dibromo-4-nitro-1-(propan-2-yl)-1H-1,3-benzodiazol-2-yl]pyrrolidin-3-amine hydrochloride 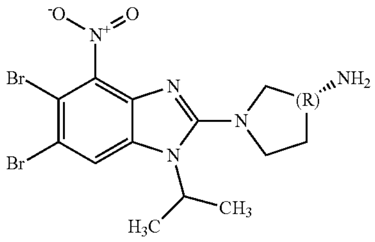 | 1H NMR (600 MHz, DMSO) δ 8.43 (s, 1H), 8.09 (s, 1H), 4.78 (hept, J = 6.8 Hz, 1H), 3.92-3.82 (m, 1H), 3.70-3.64 (m, 1H), 2.29 (td, J = 13.5, 7.2 Hz, 1H), 2.14-2.04 (m, 1H), 1.55 (dd, J = 16.1, 6.9 Hz, 2H). | 447.8 | 5.5 | 2,5,6-tribromo-1-(2-propyl)-4-nitro-1H-1,3-benzodiazole 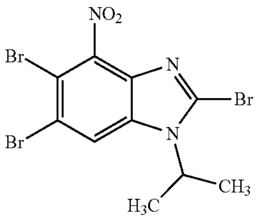 Method 3B and tert-butyl N-[(3R)-pyrrolidin-3-yl]carbamate |

-continued

| Ex. | Name and structure | 1HNMR (400 MHz) | m/z | rt | SM |
|---|---|---|---|---|---|
| 1AZ | (3S)-1-[5,6-dibromo-4-nitro-1-(propan-2-yl)-1H-1,3-benzodiazol-2-yl]pyrrolidin-3-amine hydrochloride 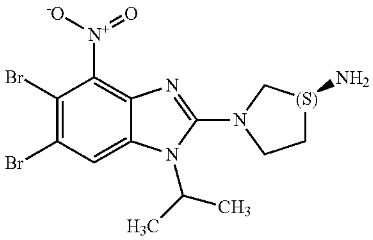 | 1H NMR (300 MHz, dmso) δ 8.39 (s, 3H), 8.08 (s, 1H), 4.76 (dt, J = 13.8, 6.9 Hz, 1H), 3.83 (dd, J = 17.1, 6.9 Hz, 3H), 3.71-3.58 (m, 2H), 2.25 (dt, J = 13.5, 6.6 Hz, 1H), 2.13-1.98 (m, 1H), 1.53 (dd, J = 7.8, 7.1 Hz, 6H | 447.9 | 2.9 | 2,5,6-tribromo-1-(2-propyl)-4-nitro-1H-1,3-benzodiazole 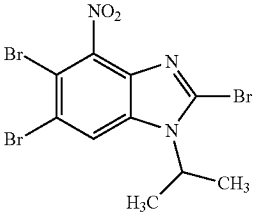 Method 3B And tert-butyl N-[(3S)-pyrrolidin-3-yl]carbamate |
| 1BA | 5,6-dibromo-4-nitro-1-(propan-2-yl)-N-(pyrrolidin-3-yl)-1H-1,3-benzodiazol-2-amine hydrochloride 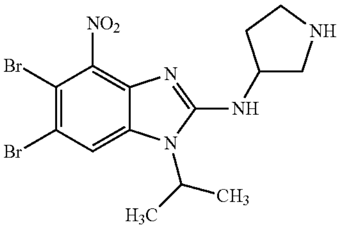 | 1H NMR (600 MHz, DMSO) δ 7.98 (s, 1H), 4.83 (hept, J = 6.8 Hz, 1H), 4.57-4.51 (m, 1H), 3.45-3.35 (m, 2H), 3.31-3.19 (m, 2H), 2.30-2.18 (m, 1H), 2.08 (td, J = 13.2, 5.9 Hz, 1H), 1.50 (dd, J = 6.9, 2.0 Hz, 6H). | 462.8 | 3.4 | 2,5,6-tribromo-1-(2-propyl)-4-nitro-1H-1,3-benzodiazole 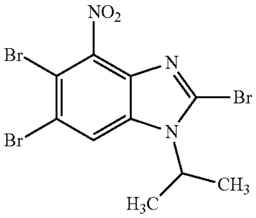 Method 3B And tert-butyl 3-aminopyrrolidine-1-carboxylate |
| 1BB | 5,6-dibromo-1-(2-methoxyethyl)-4-nitro-2-(piperazin-1-yl)-1H-1,3-benzodiazole hydrochloride 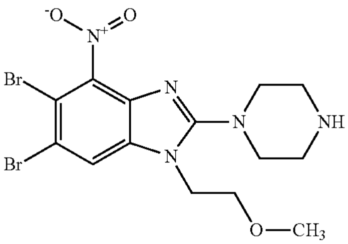 | — | 463.8 | 2.6 | 2,5,6-tribromo-1-(2-methoxyethyl)-4-nitro-1H-1,3-benzodiazole 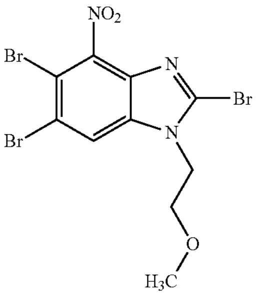 Method 3E and tert-butyl piperazine-1-carboxylate (Commercial) |

-continued

| Ex. | Name and structure | 1HNMR (400 MHz) | m/z | rt | SM |
|---|---|---|---|---|---|
| 1BC | trans-1-N-[5,6-dibromo-4-nitro-1-(propan-2-yl)-1H-1,3-benzodiazol-2-yl]cyclohexane-1,4-diamine hydrochloride 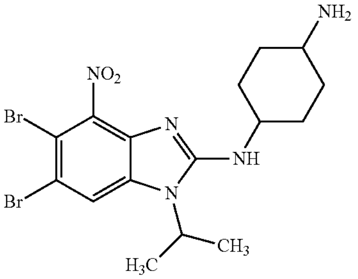 | — | 475.9 | 3.3 | 2,5,6-tribromo-1-(2-propyl)-4-nitro-1H-1,3-benzodiazole 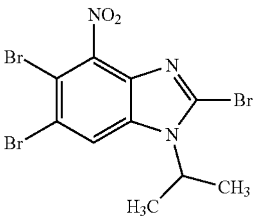 Method 3B And tert-butyl N-[trans-4-aminocyclohexyl]carbamate |
| 1BD | 5,6-dibromo-4-nitro-1-(propan-2-yl)-N-[(3S)-pyrrolidin-3-yl]-1H-1,3-benzodiazol-2-amine hydrochloride 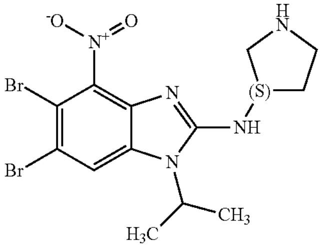 | 1H NMR (600 MHz, DMSO) δ 9.43 (bs, 1H), 9.12 (bs, 1H), 7.98 (s, 1H), 7.79 (d, J = 6.3 Hz, 1H), 4.81 (hept, J = 6.8 Hz, 1H), 4.56-4.49 (m, 1H), 3.44-3.35 (m, 2H), 3.25 (tt, J = 13.1, 6.4 Hz, 2H), 2.28-2.20 (m, 1H), 2.10-2.04 (m, 1H), 1.50 (dd, J = 6.8, 1.3 Hz, 6H). | 447.8 | 2.9 | 2,5,6-tribromo-1-(2-propyl)-4-nitro-1H-1,3-benzodiazole 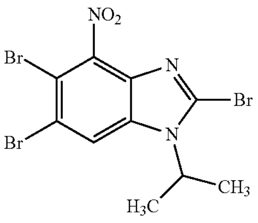 Method 3B and tert-butyl (3S)-3-aminopyrrolidine-1-carboxylate |
| 1BF | 5,6-dibromo-4-nitro-1-(propan-2-yl)-N-[(3R)-pyrrolidin-3-yl]-1H-1,3-benzodiazol-2-amine hydrochloride 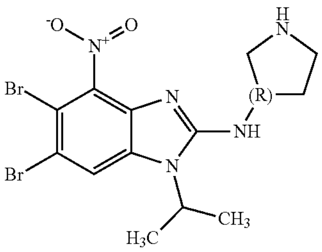 | 1H NMR (600 MHz, DMSO) δ 9.47 (bs, 1H), 9.16 (bs, 1H), 7.98 (s, 1H), 7.82 (d, J = 6.4 Hz, 1H), 4.82 (hept, J = 6.9 Hz, 1H), 4.53 (dt, J = 11.4, 5.6 Hz, 1H), 3.45-3.35 (m, 2H), 3.29-3.20 (m, 2H), 2.28-2.21 (m, 1H), 2.08 (td, J = 13.3, 5.9 Hz, 1H), 1.50 (dd, J = 6.9, 1.7 Hz, 6H). | 447.8 | 2.7 | 2,5,6-tribromo-1-(2-propyl)-4-nitro-1H-1,3-benzodiazole 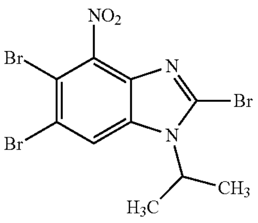 Method 3B And tert-butyl (3R)-3-aminopyrrolidine-1-carboxylate |

-continued

| Ex. | Name and structure | 1HNMR (400 MHz) | m/z | rt | SM |
|---|---|---|---|---|---|
| 1BG | (3R)-1-[5,6-dibromo-1-(cyclopropylmethyl)-4-nitro-1H-1,3-benzodiazol-2-yl]pyrrolidin-3-amine hydrochloride 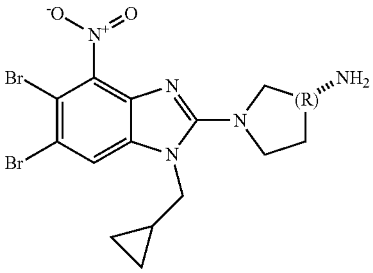 | 1H NMR (600 MHz, DMSO) δ 8.32 (s, 3H), 8.07 (s, 1H), 4.22-4.13 (m, 2H), 3.94-3.88 (m, 3H), 3.83-3.76 (m, 2H), 2.33 (td, J = 13.7, 8.1 Hz, 1H), 2.13 (ddd, J = 12.3, 7.8, 4.1 Hz, 1H), 1.30-1.23 (m, 1H), 0.47 (d, J = 8.1 Hz, 2H), 0.40-0.37 (m, 2H). | 459.9 | 2.9 | 2,5,6-tribromo-1-(cyclopropylmethyl)-4-nitro-1H-1,3-benzodiazole 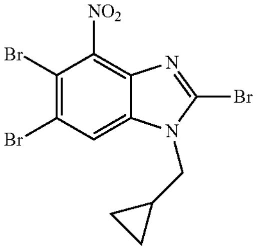 Method 3C and tert-butyl N-[(3R)-pyrrolidin-3-yl]carbamate |
| 1BH | 5,6-dibromo-1-(propan-2-yl)-2-{[(3R)-pyrrolidin-3-yl]amino}-1H-1,3-benzodiazole-4-carbonitrile hydrochloride 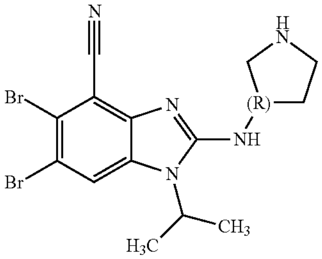 | 1H NMR (600 MHz, DMSO) δ 8.02 (s, 1H), 7.51 (d, J = 5.8 Hz, 1H), 4.68-4.64 (m, J = 13.8, 6.9 Hz, 1H), 4.63-4.57 (m, J = 12.2, 6.1 Hz, 1H), 3.55 (dd, J = 12.0, 6.7 Hz, 1H), 3.41-3.40 (m, 1H), 3.32-3.28 (m, 2H), 3.24 (dd, J = 11.9, 5.4 Hz, 1H), 2.31 (td, J = 14.8, 7.2 Hz, 1H), 2.10 (td, J = 13.4, 6.5 Hz, 1H), 1.49 (dd, J = 6.8, 2.3 Hz, 6H). | 427.8 | 2.7 | 2,5,6-tribromo-1-(propan-2-yl)-1H-1,3-benzodiazole-4-carbonitrile 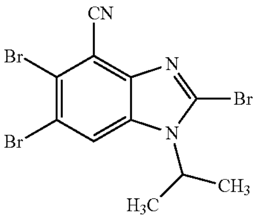 Method 8B and tert-butyl (3R)-3-aminopyrrolidine-1-carboxylate |
| 1BI | 2-[(3R)-3-aminopyrrolidin-1-yl]-5,6-dibromo-1-(propan-2-yl)-1H-1,3-benzodiazole-4-carbonitrile hydrochloride 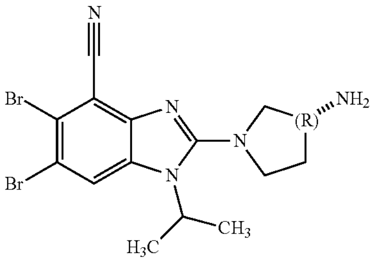 | $^{1}$H NMR (600 MHz, DMSO) δ 8.54 (bs, 3H), 8.11 (s, 1H), 4.79 (hept, J = 6.9 Hz, 1H), 3.94-3.90 (m, 3H), 3.79-3.70 (m, 2H), 2.35-2.28 (m, 1H), 2.17-2.10 (m, 1H), 1.54 (dd, J = 19.0, 6.9 Hz, 6H). | 427.8 | 2.6 | 2,5,6-tribromo-1-(propan-2-yl)-1H-1,3-benzodiazole-4-carbonitrile 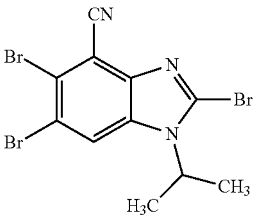 Method 8B And tert-butyl N-[(3S)-pyrrolidin-3-yl]carbamate |

-continued

| Ex. | Name and structure | 1HNMR (400 MHz) | m/z | rt | SM |
|---|---|---|---|---|---|
| 1BJ | 2-[(3S)-3-aminopiperidin-1-yl]-5,6-dibromo-1-(propan-2-yl)-1H-1,3-benzodiazole-4-carbonitrile hydrochloride 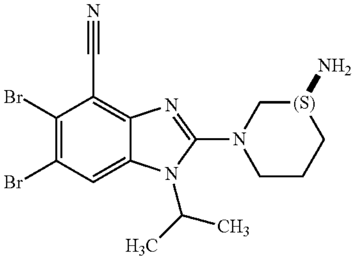 | $^{1}$H NMR (600 MHz, DMSO) δ 8.30 (s, 1H), 8.06 (bs, 2H), 4.55 (hept, J = 7.0 Hz, 1H), 3.65 (dd, J = 12.3, 3.3 Hz, 1H), 3.50-3.44 (m, 2H), 3.16 (dd, J = 12.4, 8.8 Hz, 1H), 3.09-3.03 (m, 1H), 2.04 (dd, J = 13.0, 4.5 Hz, 1H), 1.91 (dd, J = 9.4, 4.5 Hz, 1H), 1.77-1.70 (m, 1H), 1.64-1.56 (m, 1H), 1.53 (dd, J = 7.3, 1.3 Hz, 6H). | 441.9 | 2.8 | 2,5,6-tribromo-1-(propan-2-yl)-1H-1,3-benzodiazole-4-carbonitrile 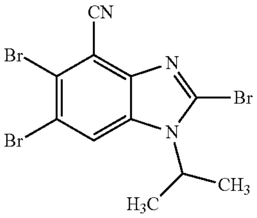 Method 8B And tert-butyl N-[(3S)-piperidin-3-yl]carbamate |
| 1BK | 5,6-dibromo-1-(propan-2-yl)-2-{[(3S)-pyrrolidin-3-yl]amino}-1H-1,3-benzodiazole-4-carbonitrile hydrochloride 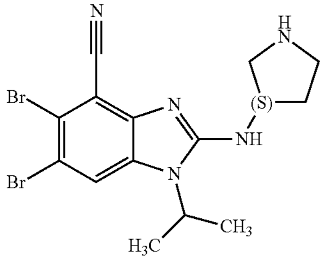 | $^{1}$H NMR (600 MHz, DMSO) δ 9.25 (bs, 1H), 8.99 (bs, 1H), 8.01 (s, 1H), 7.72 (d, J = 6.2 Hz, 1H), 4.75 (hept, J = 6.9 Hz, 1H), 4.66-4.60 (m, 1H), 3.54-3.47 (m, 2H), 3.29 (td, J = 11.9, 6.9 Hz, 2H), 2.30 (dt, J = 15.1, 7.1 Hz, 1H), 2.11 (dt, J = 13.3, 6.0 Hz, 1H), 1.49 (d, J = 6.9 Hz, 6H). | 427.9 | 2.8 | 2,5,6-tribromo-1-(propan-2-yl)-1H-1,3-benzodiazole-4-carbonitrile 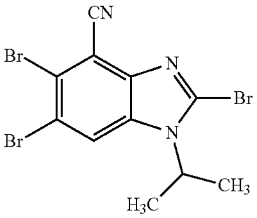 Method 8B And tert-butyl (3S)-3-aminopyrrolidine-1-carboxylate |
| 1BL | 5,6-dibromo-2-(piperazin-1-yl)-1-(propan-2-yl)-1H-1,3-benzodiazole-4-carbonitrile hydrochloride 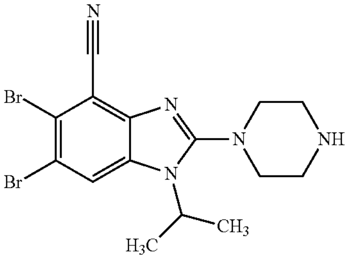 | 1H NMR (600 MHz, DMSO) δ 9.51 (bs, 2H), 8.32 (s, 1H), 4.61 (hept, J = 6.8 Hz, 1H), 3.54-3.50 (m, 4H), 3.29 (bs, 4H), 1.53 (d, J = 6.9 Hz, 6H). | 427.8 | 2.7 | 2,5,6-tribromo-1-(propan-2-yl)-1H-1,3-benzodiazole-4-carbonitrile 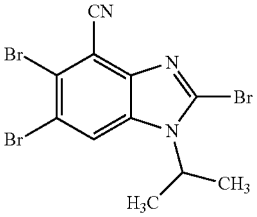 Method 8B tert-butyl piperazine-1-carboxylate (Commercial) |

-continued

| Ex. | Name and structure | 1HNMR (400 MHz) | m/z | rt | SM |
|---|---|---|---|---|---|
| 1BM | 2-[2-(aminomethyl)morpholin-4-yl]-5,6-dibromo-1-(propan-2-yl)-1H-1,3-benzodiazole-4-carbonitrile hydrochloride 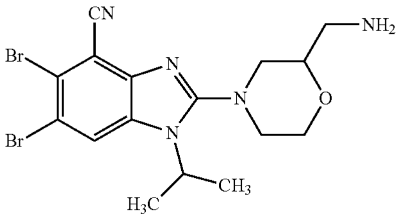 | 1H NMR (600 MHz, DMSO) δ 8.31 (s, 1H), 8.16 (s, 3H), 4.62 (hept, J = 6.9 Hz, 1H), 4.03-3.94 (m, 2H), 3.81 (td, J = 11.5, 2.4 Hz, 1H), 3.51 (d, J = 12.4 Hz, 1H), 3.39 (d, J = 11.3 Hz, 1H), 3.17-3.07 (m, 2H), 3.01 (dd, J = 12.6, 10.4 Hz, 1H), 2.95-2.88 (m, 1H), 1.56 (d, J = 6.9 Hz, 3H), 1.52 (d, J = 6.9 Hz, 3H). | 457.9 | 2.7 | 2,5,6-tribromo-1-(propan-2-yl)-1H-1,3-benzodiazole-4-carbonitrile 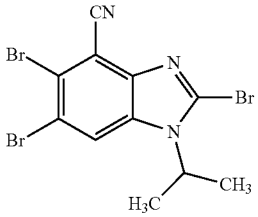 Method 8B And tert-butyl N-(morpholin-2-ylmethyl)carbamate |
| 1BN | 5,6-dibromo-2-[(morpholin-2-ylmethyl)amino]-1-(propan-2-yl)-1H-1,3-benzodiazole-4-carbonitrile hydrochloride 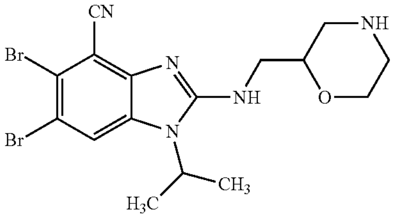 | $^1$H NMR (600 MHz, DMSO) δ 9.16 (bs, 1H), 9.12 (bs, 1H), 7.96 (s, 1H), 7.66 (t, J = 5.7 Hz, 1H), 4.70 (hept, J = 6.9 Hz, 1H), 4.03-3.97 (m, 2H), 3.61-3.55 (m, 2H), 3.54-3.49 (m, 2H), 3.17 (d, J = 12.8 Hz, 1H), 3.04-2.97 (m, 1H), 2.88-2.82 (m, 1H), 1.47 (d, J = 6.7 Hz, 6H). | 457.9 | 2.8 | 2,5,6-tribromo-1-(propan-2-yl)-1H-1,3-benzodiazole-4-carbonitrile 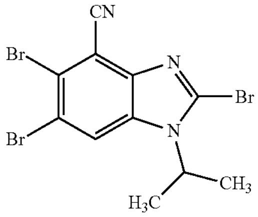 Method 8B and tert-butyl 2-(aminomethyl)morpholine-4-carboxylate |
| 1BS | 1-[5,6-dibromo-4-nitro-2-(piperazin-1-yl)-1H-1,3-benzodiazol-1-yl]propan-2-ol hydrochloride 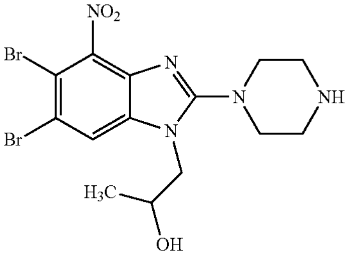 | — | 463.8 | 2.3 | 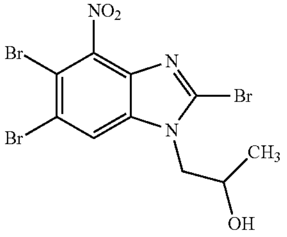 Method 5A And tert-butyl piperazine-1-carboxylate (Commerical) |

-continued

| Ex. | Name and structure | 1HNMR (400 MHz) | m/z | rt | SM |
|---|---|---|---|---|---|
| 1BT | 5,6-dibromo-2-{[(3R)-piperidin-3-yl]amino}-1-(propan-2-yl)-1H-1,3-benzodiazole-4-carbonitrile hydrochloride 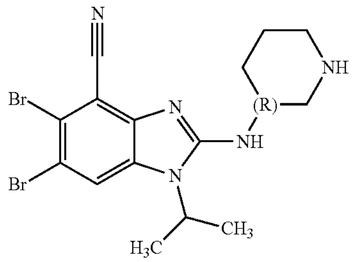 | $^1$H NMR (600 MHz, DMSO) δ 9.19 (bs, 1H), 8.87 (bs, 1H), 7.99 (s, 1H), 7.60 (d, J = 7.5 Hz, 1H), 4.81 (hept, J = 6.8 Hz, 1H), 4.31-4.24 (m, 1H), 3.43 (d, J = 12.5 Hz, 1H), 3.17 (d, J = 12.6 Hz, 1H), 2.95 (dd, J = 19.0, 9.5 Hz, 1H), 2.88 (dd, J = 19.1, 9.3 Hz, 1H), 2.01 (dd, J = 9.5, 3.7 Hz, 1H), 1.95 (dd, J = 9.5, 4.9 Hz, 1H), 1.78-1.68 (m, 2H), 1.48 (dd, J = 6.8, 3.4 Hz, 6H). | 441.8 | 2.8 | 2,5,6-tribromo-1-(propan-2-yl)-1H-1,3-benzodiazole-4-carbonitrile 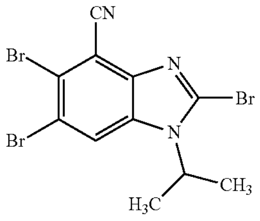 Method 8B And tert-butyl (3R)-3-aminopyrrolidine-1-carboxylate |
| 1BV | 2-[(3R)-3-aminopiperidin-1-yl]-5,6-dibromo-1-(propan-2-yl)-1H-1,3-benzodiazole-4-carbonitrile hydrochloride 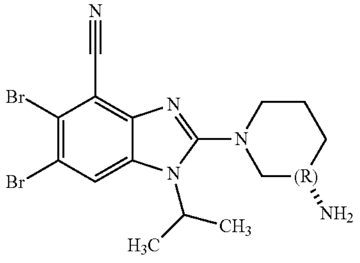 | — | 441.9 | 2.7 | 2,5,6-tribromo-1-(propan-2-yl)-1H-1,3-benzodiazole-4-carbonitrile 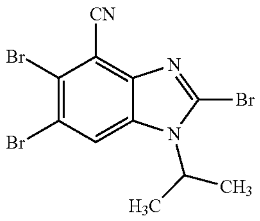 Method 8B And tert-butyl N-[(3R)-piperidin-3-yl]carbamate |
| 1CA | 5,6-dibromo-4-nitro-N-[(3R)-piperidin-3-yl]-1-(propan-2-yl)-1H-1,3-benzodiazol-2-amine hydrochloride 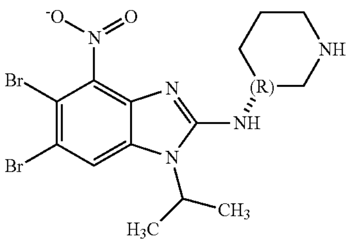 | 1H NMR (300 MHz, dmso) δ 9.02 (bs, 1H), 8.79 (bs, 1H), 7.96 (s, 1H), 7.49 (d, J = 7.4 Hz, 1H), 4.76 (dt, J = 13.8, 6.9 Hz, 1H), 4.20-4.05 (m, 1H), 3.42-3.31 (m, 1H), 3.19-3.07 (m, 1H), 2.93-2.78 (m, 2H), 2.01-1.84 (m, 2H), 1.72-1.59 (m, 2H), 1.47 (d, J = 6.8 Hz, 6H). | 461.8 | 2.8 | 2,5,6-tribromo-1-(2-propyl)-4-nitro-1H-1,3-benzodiazole 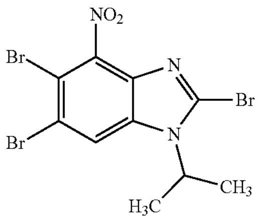 Method 3B And tert-butyl (3R)-3-aminopiperidine-1-carboxylate |

-continued

| Ex. | Name and structure | 1HNMR (400 MHz) | m/z | rt | SM |
|---|---|---|---|---|---|
| 1CD | 5,6-dibromo-N-[(3S,4S)-4-methoxypyrrolidin-3-yl]-4-nitro-1-(propan-2-yl)-1H-1,3-benzodiazol-2-amine hydrochloride<br>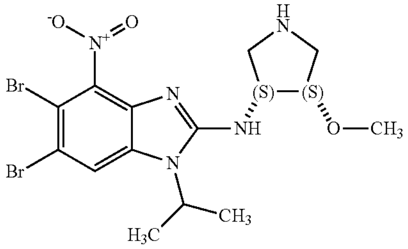 | | 477.8 | 3.2 | 2,5,6-tribromo-1-(2-propyl)-4-nitro-1H-1,3-benzodiazole<br>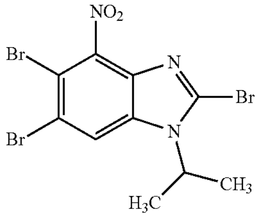<br>Method 3B And tert-butyl (3S,4S)-3-amino-4-methoxypyrrolidine-1-carboxylate |
| 1CE | (3S,4S)-4-{[5,6-dibromo-4-nitro-1-(propan-2-yl)-1H-1,3-benzodiazol-2-yl]amino}pyrrolidin-3-ol hydrochloride<br>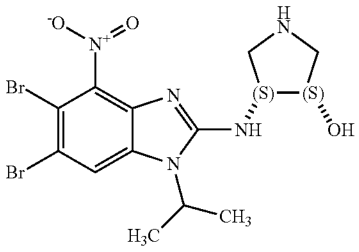 | 1H NMR (600 MHz, DMSO) δ 9.35 (bs, 1H), 9.27 (bs, 1H), 7.99 (s, 1H), 7.63 (d, J = 5.9 Hz, 1H), 4.82 (hept, J = 6.9 Hz, 1H), 4.42-4.40 (m, 1H), 4.29 (dt, J = 5.7, 3.0 Hz, 1H), 3.55 (td, J = 12.7, 6.5 Hz, 2H), 3.50-3.46 (m, 2H), 1.50 (d, J = 6.9 Hz, 6H). | 463.8 | 2.8 | 2,5,6-tribromo-1-(2-propyl)-4-nitro-1H-1,3-benzodiazole<br>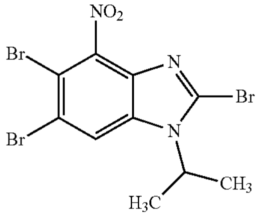<br>Method 3B And tert-butyl (3S,4S)-3-amino-4-hydroxypyrrolidine-1-carboxylate |
| 1CH | 5,6-dibromo-1-(cyclopropylmethyl)-4-nitro-N-[(3R)-piperidin-3-yl]-1H-1,3-benzodiazol-2-amine hydrochloride<br>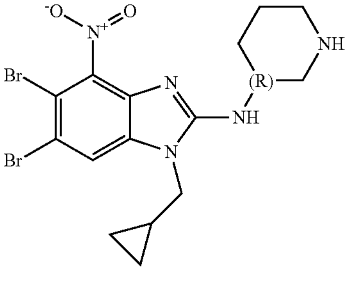 | | 473.9 | 6.4 | 2,5,6-tribromo-1-(cyclopropylmethyl)-4-nitro-1H-1,3-benzodiazole<br>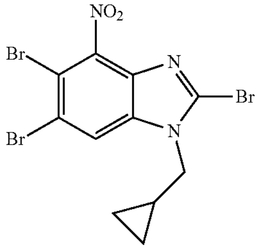<br>Method 3C And tert-butyl (3R)-3-aminopiperidine-1-carboxylate |

-continued

| Ex. | Name and structure | 1HNMR (400 MHz) | m/z | rt | SM |
|---|---|---|---|---|---|
| 1CI | 5,6-dibromo-1-(cyclopropylmethyl)-4-nitro-N-[(3S)-pyrrolidin-3-yl]-1H-1,3-benzodiazol-2-amine hydrochloride 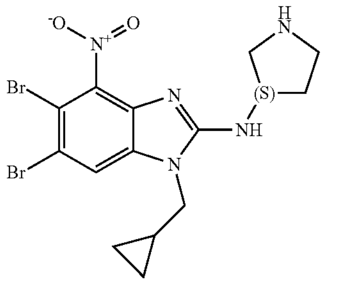 | | 459.8 | 6.2 | 2,5,6-tribromo-1-(cyclopropylmethyl)-4-nitro-1H-1,3-benzodiazole 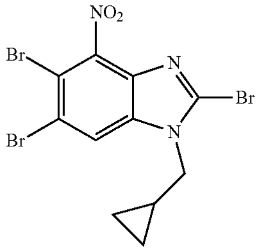 Method 3C And tert-butyl (3S)-3-aminopyrrolidine-1-carboxylate |
| 1CJ | 5,6-dibromo-1-(cyclopropylmethyl)-4-nitro-N-[(3R)-pyrrolidin-3-yl]-1H-1,3-benzodiazol-2-amine hydrochloride 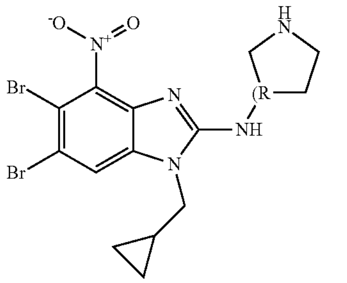 | | 459.8 | 2.9 | 2,5,6-tribromo-1-(cyclopropylmethyl)-4-nitro-1H-1,3-benzodiazole 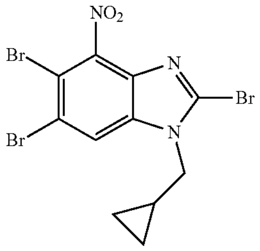 Method 3C And tert-butyl (3R)-3-aminopiperidine-1-carboxylate |
| 1CK | (3S)-1-[5,6-dibromo-1-(cyclopropylmethyl)-4-nitro-1H-1,3-benzodiazol-2-yl]pyrrolidin-3-amine hydrochloride 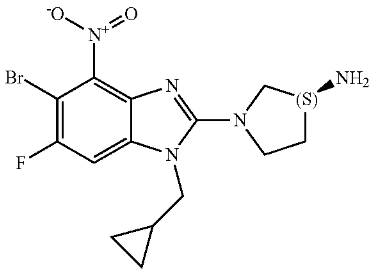 | | 459.8 | 2.7 | 2,5,6-tribromo-1-(cyclopropylmethyl)-4-nitro-1H-1,3-benzodiazole 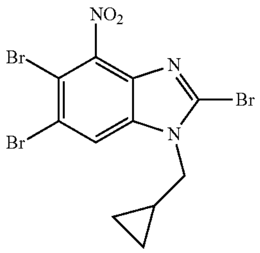 Method 3C And tert-butyl N-[(3S)-pyrrolidin-3-yl]carbamate |

-continued

| Ex. | Name and structure | 1HNMR (400 MHz) | m/z | rt | SM |
|---|---|---|---|---|---|
| 1CL | 5-bromo-6-fluoro-4-nitro-2-(piperazin-1-yl)-1-(propan-2-yl)-1H-1,3-benzodiazole hydrochloride 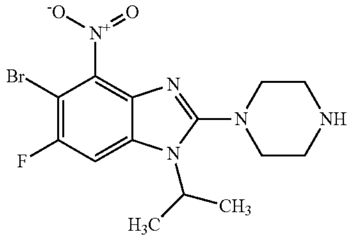 | | 387.9 | 2.5 | 2,5-dibromo-6-fluoro-4-nitro-1-(propan-2-yl)-1H-1,3-benzodiazole 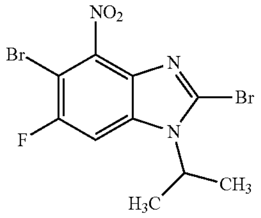 Method 13 and tert-butyl piperazine-1-carboxylate |
| 1CM | (3R)-1-(5,6-dibromo-4-nitro-1-propyl-1H-1,3-benzodiazol-2-yl)pyrrolidin-3-amine hydrochloride 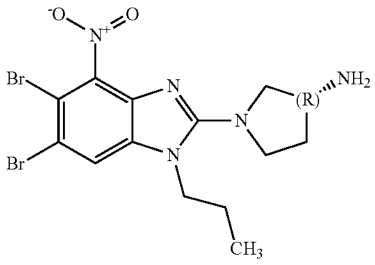 | 1H NMR (600 MHz, DMSO) δ 8.43 (bs, 3H), 8.07 (s, 1H), 4.17 (t, J = 7.8 Hz, 2H), 3.93-3.86 (m, 3H), 3.81-3.74 (m, 2H), 2.35-2.27 (m, 1H), 2.14 (dd, J = 8.9, 4.5 Hz, 1H), 1.80-1.67 (m, 2H), 0.89 (t, J = 7.3 Hz, 3H). | 447.9 | 2.6 | 2,5,6-tribromo-4-nitro-1-propyl-1H-1,3-benzodiazole 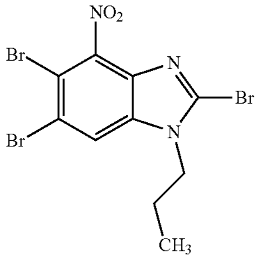 Method 3F And tert-butyl N-[(3R)-pyrrolidin-3-yl]carbamate |
| 1CN | 5,6-dichloro-1-ethyl-4-nitro-2-(piperazin-1-yl)-1H-1,3-benzodiazole hydrochloride 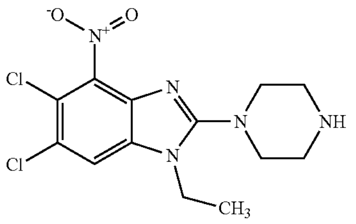 | | 343.9 | 2.5 | 2-bromo-5,6-dichloro-1-ethyl-4-nitro-1H-1,3-benzodiazole 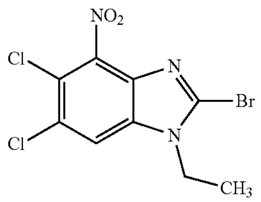 Method 2B And tert-butyl piperazine-1-carboxylate |

-continued

| Ex. | Name and structure | 1HNMR (400 MHz) | m/z | rt | SM |
|---|---|---|---|---|---|
| 1CO | (3R)-1-(5,6-dichloro-1-ehtyl-4-nitro-1H-1,3-benzodiazol-2-yl)pyrrolidin-3-amine hydrochloride 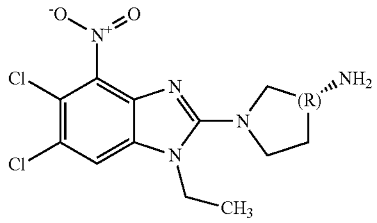 | | 343.9 | 2.5 | 2-bromo-5,6-dichloro-1-ethyl-4-nitro-1H-1,3-benzodiazole 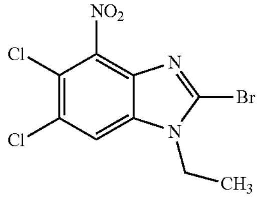 Method 2B And tert-butyl N-[(3R)-pyrrolidin-3-yl]carbamate |
| 1CP | 1-[5,6-dibromo-4-nitro-1-(propan-2-yl)-1H-1,3-benzodiazol-2-yl]piperidin-4-amine hydrochloride 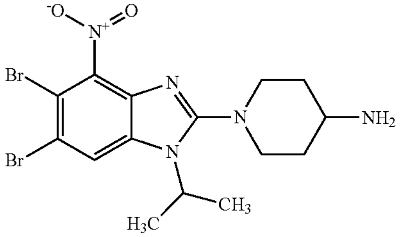 | 1H NMR (300 MHz, dmso) δ 8.22 (s, 1H), 8.21-8.09 (m, 3H), 4.47 (dt, J = 13.8, 6.8 Hz, 1H), 3.51 (d, J = 12.8 Hz, 2H), 3.32-3.16 (m, 1H), 3.12-2.99 (m, 2H), 2.05-1.94 (m, 2H), 1.79-1.63 (m, 2H), 1.52 (d, J = 6.9 Hz, 6H). | 461.9 | 2.6 | 2,5,6-tribromo-1-(2-propyl)-4-nitro-1H-1,3-benzodiazole 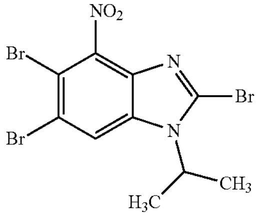 Method 3B And tert-butyl N-(piperidin-4-yl)carbamate |
| 1CQ | cis-1-N-[5,6-dibromo-4-nitro-1-(propan-2-yl)-1H-1,3-benzodiazol-2-yl]cyclohexane-1,4-diamine hydrochloride hydrochloride 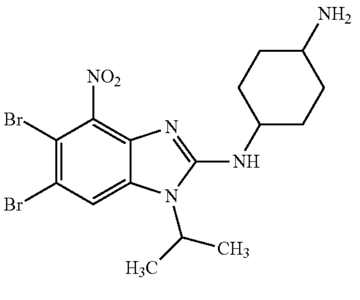 | 1H NMR (300 MHz, dmso) δ 8.02 (bs, 3H), 7.92 (s, 1H), 6.96 (d, J = 4.1 Hz, 1H), 4.87 (dd, J = 13.6, 6.8 Hz, 1H), 3.18-3.02 (m, 1H), 2.04-1.91 (m, J = 9.8 Hz, 2H), 1.78-1.68 (m, 4H), 1.67-1.55 (m, 2H), 1.47 (d, J = 6.8 Hz, 6H). | 475.9 | 3.0 | 2,5,6-tribromo-1-(2-propyl)-4-nitro-1H-1,3-benzodiazole 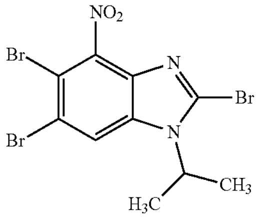 Method 3B And cis-tert-butyl N-(4-aminocyclohexyl)carbamate |

-continued

| Ex. | Name and structure | 1HNMR (400 MHz) | m/z | rt | SM |
|---|---|---|---|---|---|
| 1CR | N-(azetidin-3-yl)-5,6-dibromo-4-nitro-1-(propan-2-yl)-1H-1,3-benzodiazol-2-amine hydrochloride<br>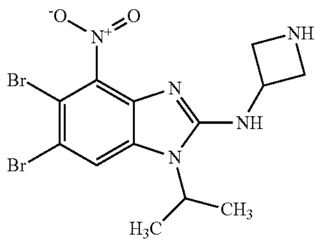 | | 433.8 | 2.8 | 2,5,6-tribromo-1-(2-propyl)-4-nitro-1H-1,3-benzodiazole<br>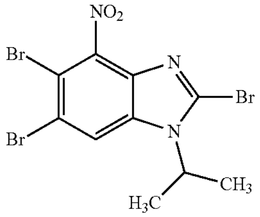<br>Method 3B<br>And tert-butyl 3-aminoazetidine-1-carboxylate |
| 1CS | (3R)-1-[5,6-dibromo-1-(2-methoxyethyl)-4-nitro-1H-1,3-benzodiazol-2-yl]pyrrolidin-3-amine hydrochloride<br>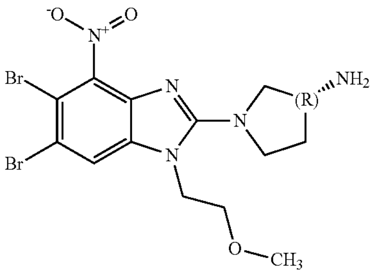 | | 463.8 | 2.5 | 2,5,6-tribromo-1-(2-methoxyethyl)-4-nitro-1H-1,3-benzodiazole<br>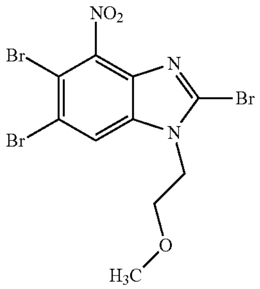<br>Method 3E<br>and tert-butyl N-[(3R)-pyrrolidin-3-yl]carbamate |
| 1CT | (3S)-1-(5,6-dichloro-1-ethyl-4-nitro-1H-1,3-benzodiazol-2-yl)piperidin-3-amine hydrochloride<br>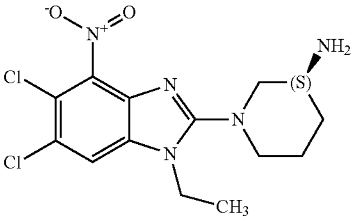 | | 357.9 | 2.6 | 2-bromo-5,6-dichloro-1-ehtyl-4-nitro-1H-1,3-benzodiazole<br>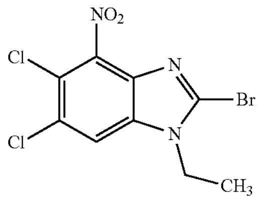<br>Method 2B<br>And tert-butyl N-[(3S)-piperidin-3-yl]carbamate |

-continued

| Ex. | Name and structure | 1HNMR (400 MHz) | m/z | rt | SM |
|---|---|---|---|---|---|
| 1CX | 1-[5-bromo-6-methyl-4-nitro-1-(propan-2-yl)-1H-1,3-benzodiazol-2-yl]azetidin-3-amine hydrochloride 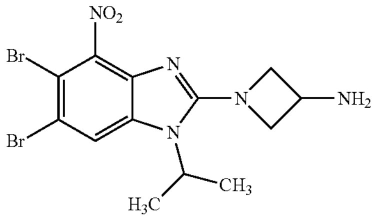 | 1H NMR (300 MHz, dmso) δ 8.51 (bs, 3H), 8.11 (s, 1H), 4.50 (dd, J = 9.1, 8.7 Hz, 2H), 4.39 (dt, J = 13.9, 6.9 Hz, 1H), 4.25 (d, J = 9.1 Hz, 2H), 4.19-4.08 (m, 1H), 1.50 (d, J = 6.9 Hz, 6H). | 433.8 | 2.5 | 2,5,6-tribromo-1-(2-propyl)-4-nitro-1H-1,3-benzodiazole 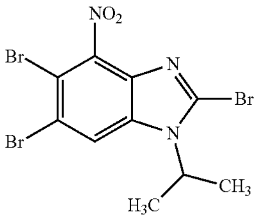 Method 3B And tert-butyl N-(azetidin-3-yl)carbamate |
| 1CY | (3R)-1-[5-bromo-6-fluoro-4-nitro-1-(propan-2-yl)-1H-1,3-benzodiazol-2-yl]pyrrolidin-3-amine hydrochloride 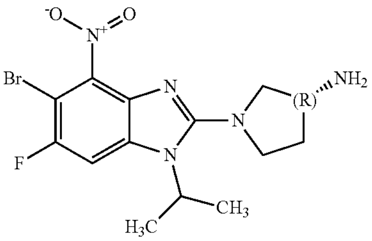 | | 387.9 | 2.5 | 2,5-dibromo-6-fluoro-4-nitro-1-(propan-2-yl)-1H-1,3-benzodiazole 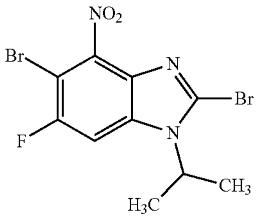 Method 13 and tert-butyl N-[(3R)-pyrrolidin-3-yl]carbamate |
| 1DA | 5,6-dichloro-1-ethyl-2-[(2S)-2-methylpiperazin-1-yl]-4-nitro-1H-1,3-benzodiazole hydrochloride 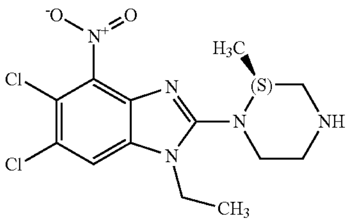 | | 358.0 | 2.6 | 2-bromo-5,6-dichloro-1-ethyl-4-nitro-1H-1,3-benzodiazole 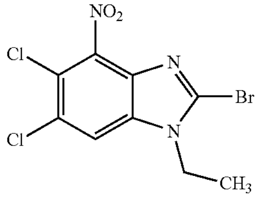 Method 2B And tert-butyl (3S)-3-methylpiperazine-1-carboxylate |

-continued

| Ex. | Name and structure | 1HNMR (400 MHz) | m/z | rt | SM |
|---|---|---|---|---|---|
| 1DC | (3R)-1-(5,6-dibromo-1-cyclobutyl-4-nitro-1H-1,3-benzodiazol-2-yl)pyrrolidin-3-amine hydrochloride 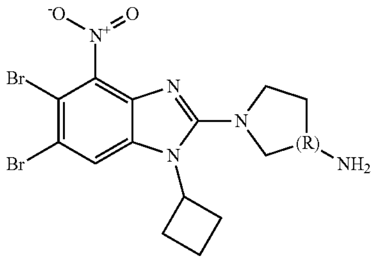 | 1H NMR (300 MHz, dmso) δ 8.37 (bs, 3H), 8.10 (s, 1H), 5.00-4.86 (m, 1H), 3.84-3.72 (m, 3H), 3.62 (dd, J = 11.1, 7.5 Hz, 2H), 2.79-2.60 (m, 2H), 2.44-2.32 (m, 2H), 2.30-2.17 (m, 1H), 2.09-1.99 (m, 1H), 1.97-1.85 (m, 1H), 1.83-1.70 (m, 1H). | 459.8 | 2.6 | 2,5,6-tribromo-1-cyclobutyl-4-nitro-1H-1,3-benzodiazole 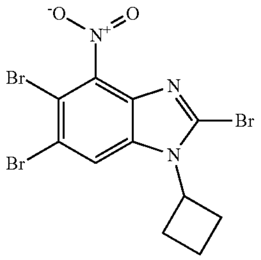 Method 5C and tert-butyl N-[(3R)-pyrrolidin-3-yl]carbamate |
| 1DF | 3-{2-[(3R)-3-aminopyrrolidin-1-yl]-5,6-dibromo-4-nitro-1H-1,3-benzodiazol-1-yl}propan-1-ol hydrochloride 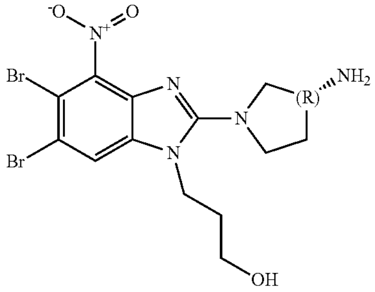 | | 463.8 | 2.2 | 2,5,6-tribromo-4-nitro-1-[3-(oxan-2-yloxy)propyl]-1H-1,3-benzodiazole 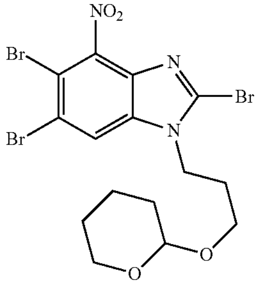 Method 3K And tert-butyl N-[(3R)-pyrrolidin-3-yl]carbamate |
| 1DG | 5,6-dibromo-1-cyclobutyl-4-nitro-2-(piperazin-1-yl)-1H-1,3-benzodiazole hydrochloride 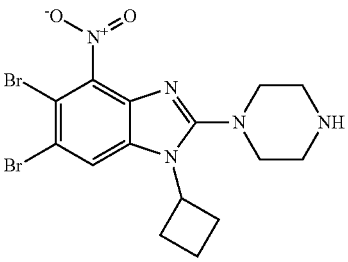 | 1H NMR (600 MHz, DMSO) δ 9.34 (bs, 2H), 8.11 (s, 1H), 4.81 (p, J = 8.8 Hz, 1H), 3.45 (d, J = 4.8 Hz, 2H), 3.44 (s, 1H), 3.44-3.42 (m, 1H), 3.25-3.19 (m, 4H), 2.61-2.54 (m, 2H), 2.54-2.49 (m, 2H), 1.91-1.84 (m, 1H), 1.84-1.75 (m, 1H). | 459.8 | 2.8 | 2,5,6-tribromo-1-cyclobutyl-4-nitro-1H-1,3-benzodiazole 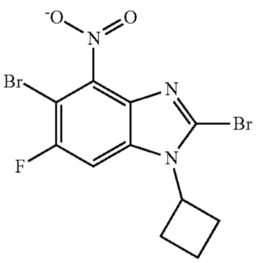 Method 5C and tert-butyl piperazine-1-carboxylate |

-continued

| Ex. | Name and structure | 1HNMR<br>(400 MHz) | m/z | rt | SM |
|---|---|---|---|---|---|
| 1DJ | 2-[5,6-dibromo-4-nitro-2-(piperazin-1-yl)-1H-1,3-benzodiazol-1-yl]ethan-1-ol hydrochloride<br>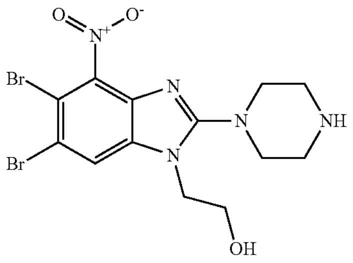 | | 449.8 | 2.2 | 2,5,6-tribromo-4-nitro-1-[2-(oxan-2-yloxy)ethyl]-1H-1,3-benzodiazole<br>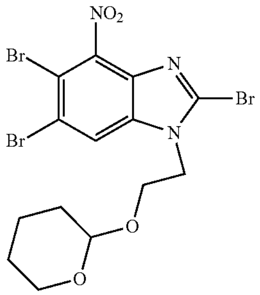<br>Method 3L<br>And tert-butyl piperazine-1-carboxylate |
| 1DK | 5,6-dibromo-4-nitro-N-(piperidin-4-yl)-1-(propan-2-yl)-1H-1,3-benzodiazol-2-amine hydrochloride<br>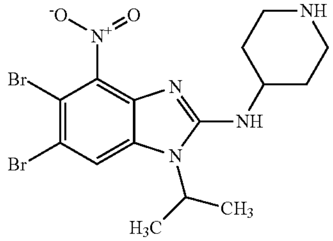 | 1H NMR (600 MHz, DMSO) δ 9.08-8.99 (m, 1H), 8.87-8.80 (m, 1H), 7.91 (s, 1H), 7.48 (d, J = 7.2 Hz, 1H), 4.78 (sept., J = 6.8 Hz, 1H), 3.31-3.24 (m, 2H), 3.04-2.96 (m, 2H), 2.07-2.00 (m, 2H), 1.85-1.76 (m, 2H), 1.46 (d, J = 6.9 Hz, 6H). | 461.8 | 2.8 | 2,5,6-tribromo-1-(2-propyl)-4-nitro-1H-1,3-benzodiazole<br>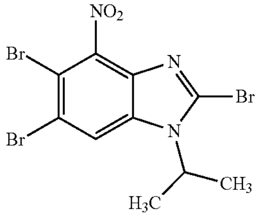<br>Method 3B<br>And tert-butyl 4-aminopiperidine-1-carboxylate |
| 1DN | [1-(5,6-dibromo-1-isopropyl-4-nitro-1,3-benzodiazol-2-yl)piperazin-2-yl]methanol hydrochloride<br>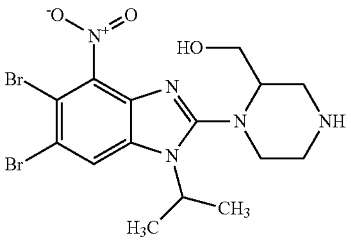 | | 477.9 | 5.4 | 2,5,6-tribromo-1-(2-propyl)-4-nitro-1H-1,3-benzodiazole<br>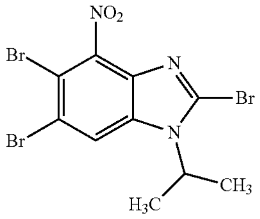<br>Method 3B<br>And tert-butyl 3-(hydroxymethyl)pipe-razine-1-carboxylate |

-continued

| Ex. | Name and structure | 1HNMR (400 MHz) | m/z | rt | SM |
|---|---|---|---|---|---|
| 1DO | cis-1-N-(5,6-dibromo-1-ethyl-4-nitro-1,3-benzodiazol-2-yl)cyclohexane-1,4-diamine hydrochloride 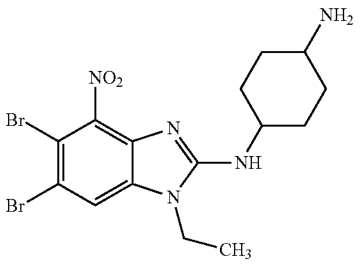 | 1H NMR (300 MHz, dmso) δ 8.05 (bs, 3H), 7.90 (s, 1H), 7.09 (d, J = 1.8 Hz, 1H), 4.22 (q, J = 6.9 Hz, 2H), 3.10 (s, 1H), 2.05-1.92 (m, 2H), 1.81-1.69 (m, 4H), 1.69-1.59 (m, 2H), 1.17 (t, J = 7.0 Hz, 3H). | 461.9 | 2.8 | 2,5,6-tribromo-1-ethyl-4-nitro-1H-1,3-benzodiazole 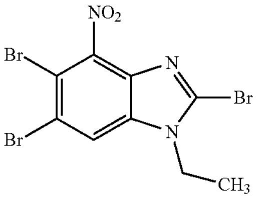 Method 3A And cis-tert-butyl N-(4-aminocyclohexyl)carbamate |
| 1DP | 5,6-dibromo-1-ethyl-2-[(2S)-2-methylpiperazin-1-yl]-1,3-benzodiazole-4-carbonitrile hydrochloride 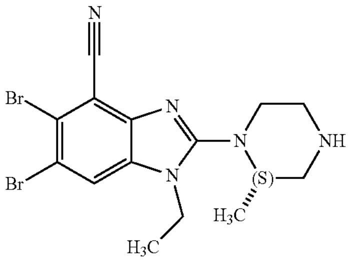 | 1H NMR (300 MHz, dmso) δ 8.97 (bs, 2H), 8.33 (s, 1H), 4.17 (dt, J = 12.3, 7.3 Hz, 2H), 3.95-3.86 (m, 1H), 3.42 (dd, J = 10.6, 4.9 Hz, 2H), 3.36 (d, J = 3.6 Hz, 1H), 3.26 (t, J = 5.1 Hz, 2H), 3.11 (dd, J = 12.8, 6.4 Hz, 1H), 1.27 (t, J = 7.1 Hz, 3H), 1.16 (d, J = 6.7 Hz, 3H). | 427.9 | 2.3 | 2,5,6-tribromo-1-ethyl-1,3-benzodiazole-4-carbonitrile 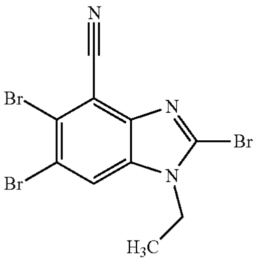 Method 8C And tert-butyl (3S)-3-methylpiperazine-1-carboxylate |
| 1DQ | 2-[(3S)-3-aminopiperidin-1-yl]-5,6-dibromo-1-ethyl-1,3-benzodiazole-4-carbonitrile hydrochloride 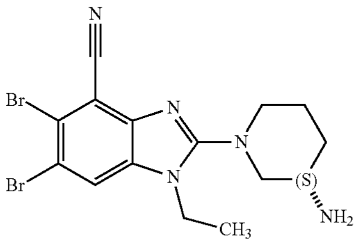 | 1H NMR (300 MHz, dmso) δ 8.24 (bs, 3H), 8.19 (s, 1H), 4.13 (q, J = 7.3 Hz, 2H), 3.53 (d, J = 13.1 Hz, 1H), 3.44-3.31 (m, 1H), 3.24-3.04 (m, 3H), 2.08-1.97 (m, 1H), 1.95-1.84 (m, 1H), 1.65 (dd, J = 21.5, 13.9 Hz, 2H), 1.32 (t, J = 7.1 Hz, 3H). | 427.8 | 2.5 | 2,5,6-tribromo-1-ethyl-1,3-benzodiazole-4-carbonitrile 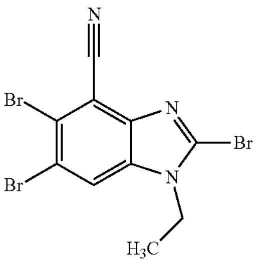 Method 8C And tert-butyl N-[(3S)-piperidin-3-yl]carbamate |

-continued

| Ex. | Name and structure | 1HNMR (400 MHz) | m/z | rt | SM |
|---|---|---|---|---|---|
| 1DR | 2-[(3R)-3-aminopyrrolidin-1-yl]-5,6-dibromo-1-ehtyl-1,3-benzodiazole-4-carbonitrile hydrochloride 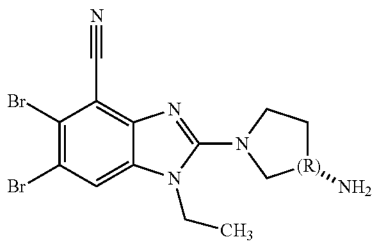 | 1H NMR (300 MHz, dmso) δ 8.38 (bs, 3H), 8.03 (s, 1H), 4.24 (q, J = 7.3 Hz, 4H), 3.99-3.89 (m, 3H), 3.87-3.77 (m, 2H), 2.29 (dd, J = 13.6, 7.8 Hz, 1H), 2.15 (d, J = 4.5 Hz, 2H), 1.29 (t, J = 7.1 Hz, 3H). | 413.8 | 2.4 | 2,5,6-tribromo-1-ethyl-1,3-benzodiazole-4-carbonitrile 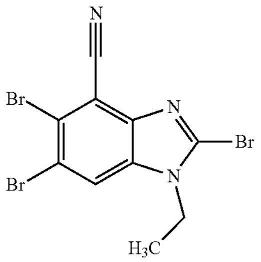 Method 8C And and tert-butyl N-[(3R)-pyrrolidin-3-yl]carbamate |
| 1DS | 2-(4-aminopiperidin-1-yl)-5,6-dibromo-1-ethyl-1H-1,3-benzodiazole-4-carbonitrile 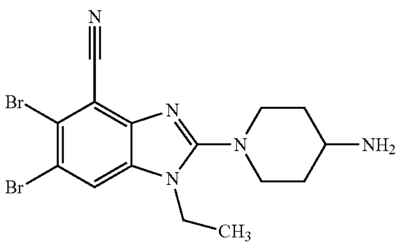 | | 427.9 | 4.9 | 2,5,6-tribromo-1-ethyl-1,3-benzodiazole-4-carbonitrile 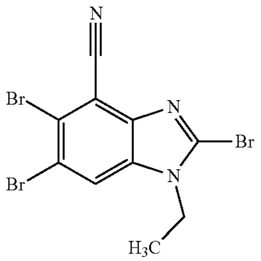 Method 8C And tert-butyl N-(piperidin-4-yl)carbamate |
| 1DT | 2-(4-aminopiperidin-1-yl)-5,6-dibromo-1-(propan-2-yl)-1H-1,3-benzodiazole-4-carbonitrile 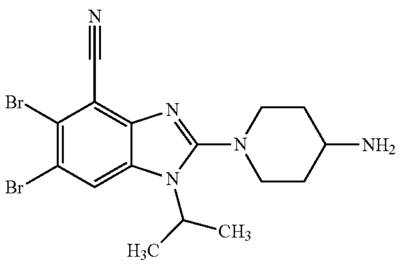 | | 441.9 | 5.6 | 2,5,6-tribromo-1-(propan-2-yl)-1H-1,3-benzodiazole-4-carbonitrile 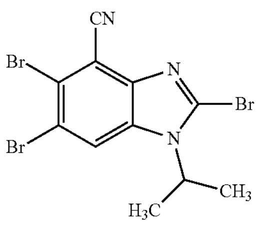 And tert-butyl N-(piperidin-4-yl)carbamate |

-continued

| Ex. | Name and structure | 1HNMR (400 MHz) | m/z | rt | SM |
|---|---|---|---|---|---|
| 1DU | 1-N-(5,6-dibromo-1-ethyl-4-nitro-1H-1,3-benzodiazol-2-yl)trans-cyclohexane-1,4-diamine 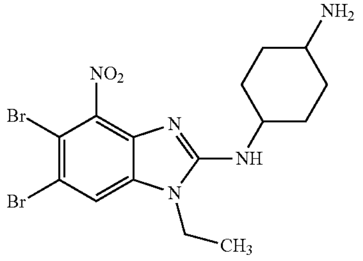 | 1H NMR (600 MHz, DMSO) δ 7.88 (s, 1H), 7.85-7.79 (m, 3H), 7.28 (d, J = 7.8 Hz, 1H), 4.09 (q, J = 7.1 Hz, 2H), 3.74-3.66 (m, 1H), 3.05-2.97 (m, 1H), 2.04-2.00 (m, 2H), 2.00-1.95 (m, 2H), 1.48-1.37 (m, 4H), 1.16 (t, J = 7.1 Hz, 3H). | 461.9 | 2.3 | 2,5,6-tribromo-1-ethyl-4-nitro-1H-1,3-benzodiazole 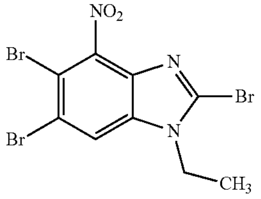 And trans-tert-butyl N-(4-aminocyclohexyl) carbamate |
| 1DV | 5,6-dibromo-1-ethyl-2-{[trans-4-aminocyclohexyl]amino}-1H-1,3-benzodiazole-4-carbonitrile 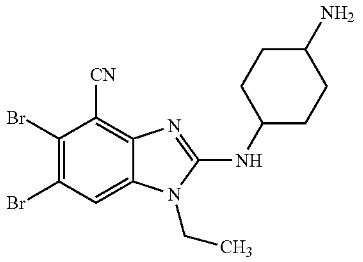 | | 441.9 | 2.3 | 2,5,6-tribromo-1-ethyl-1,3-benzodiazole-4-carbonitrile 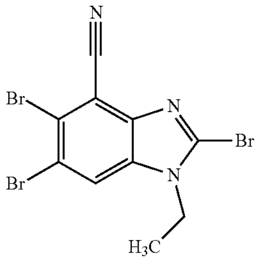 Method 8C And trans-tert-butyl N-(4-aminocyclohexyl) carbamate |
| 1DW | 5,6-dibromo-2-[(3R)-3-(methylamino)pyrrolidin-1-yl]-1-(propan-2-yl)-1H-1,3-benzodiazole-4-carbonitrile 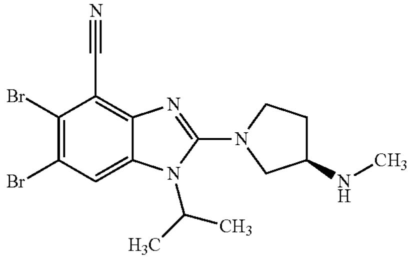 | | | | 2,5,6-tribromo-1-(propan-2-yl)-1H-1,3-benzodiazole-4-carbonitrile 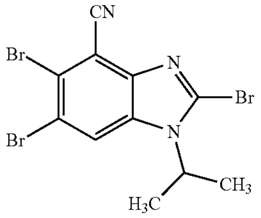 And tert-butyl N-methyl-N-[(3R)-pyrrolidin-3-yl]carbamate |

-continued

| Ex. | Name and structure | 1HNMR (400 MHz) | m/z | rt | SM |
| --- | --- | --- | --- | --- | --- |
| 1DY | 5,6-dibromo-1-(propan-2-yl)-2-{[trans-4-aminocyclohexyl]amino}-1H-1,3-benzodiazole-4-carbonitrile 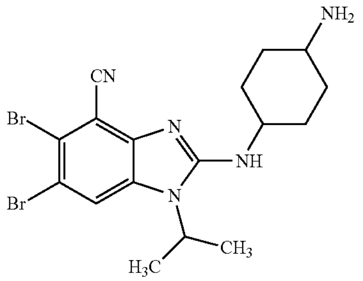 | | | | 2,5,6-tribromo-1-(propan-2-yl)-1H-1,3-benzodiazole-4-carbonitrile 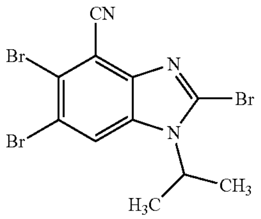 And trans-tert-butyl N-(4-aminocyclohexyl) carbamate |
| 1DZ | (3S)-1-(5,6-dibromo-1-ethyl-4-nitro-1H-1,3-benzodiazol-2-yl)-N-methylpiperidin-3-amine 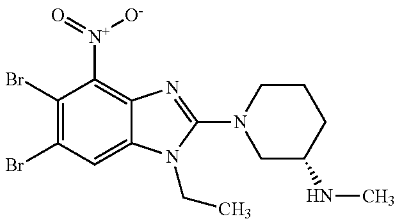 | | | | 2,5,6-tribromo-1-ethyl-4-nitro-1H-1,3-benzodiazole 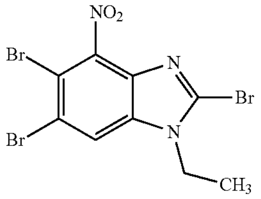 And (3S)-tert-butyl N-methyl-N-(piperidin-3-yl)carbamate |
| 1EA | 5,6-dibromo-2-[(2S)-2-ethylpiperazin-1-yl]-4-nitro-1-(propan-2-yl)-1H-1,3-benzodiazole 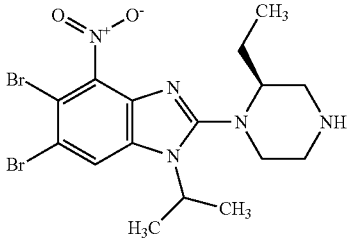 | | | | 2,5,6-tribromo-1-(2-propyl)-4-nitro-1H-1,3-benzodiazole 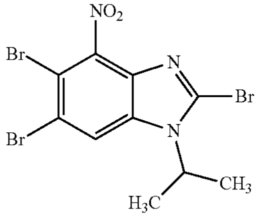 Method 3B And (3S)-tert-butyl 3-ethylpiperazine-1-carboxylate |

-continued

| Ex. | Name and structure | 1HNMR (400 MHz) | m/z | rt | SM |
|---|---|---|---|---|---|
| 1EB | 1-[5,6-dibromo-4-nitro-1-(propan-2-yl)-1H-1,3-benzodiazol-2-yl]-trans-4-methoxypyrrolidin-3-amine 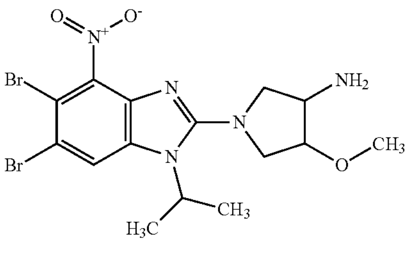 | | | | 2,5,6-tribromo-1-(2-propyl)-4-nitro-1H-1,3-benzodiazole 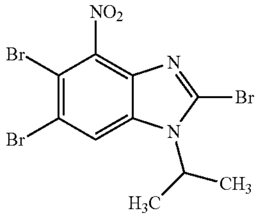 Method 3B And trans-4-methoxypyrrolidin-3-amine |

3.2. Compounds of Example 2

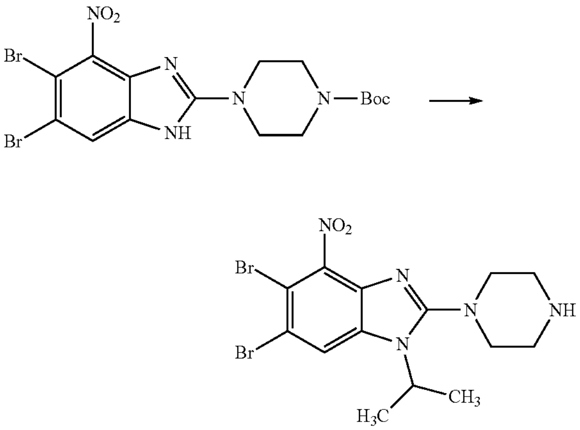

5,6-dibromo-4-nitro-2-(piperazin-1-yl)-1-(propan-2-yl)-1H-1,3-benzodiazole hydrochloride (Example 2A)

Tert-butyl 4-(5,6-dibromo-4-nitro-1H-1,3-benzodiazol-2-yl)piperazine-1-carboxylate (Method 4A)(0.4 mmol, 200 mg) was dissolved in acetonitrile (5 ml). Next, NaOH (0.5 mmol, 19 mg) was added. The mixture was stirred at RT for 0.5 h. Then 2-Iodopropane (32 mmol, 538 mg) was added dropwise. The resulting mixture was stirred at 85° C. in a sealed tube until the reaction was complete (18 hours) by LC/MS. The mixture was allowed to cool to RT and concentrated in-vacuo. The product was taken up into ethyl acetate and washed with water. The organic extract was dried over MgSO4, filtered and concentrated. The product was purified on silica gel using EA/hex (1:4). The obtained product (0.3 mmol, 180 mg) was dissolved in MeOH (3 ml), then hydrogen chloride, (4M in 1,4-dioxane, 1 ml) was added dropwise. The resulting mixture was stirred at RT overnight. Solid was filtered and washed with $Et_2O$ to afford 5,6-dibromo-4-nitro-2-(piperazin-1-yl)-1-(propan-2-yl)-1H-1,3-benzodiazole hydrochloride (130 mg). $^1H$ NMR (600 MHz, DMSO) δ 9.37 (s, 2H), 8.28 (s, 1H), 4.62 (hept, J=6.9 Hz, 1H), 3.47-3.44 (m, 4H), 3.28-3.26 (m, 4H), 1.54 (d, J=6.9 Hz, 6H); m/z 472; rt 2.4.

The following compounds were prepared by the procedure of Example 2A, using the appropriate starting materials.

| Ex. | Compound | 1HNMR (400 MHz) | m/z | RT | SM |
|---|---|---|---|---|---|
| 2B | 5,6-dibromo-4-nitro-2-(piperazin-1-yl)-1-(prop-2-yn-1-yl)-1H-1,3-benzodiazole hydrochloride 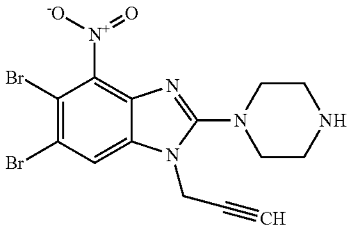 | 1H NMR (600 MHz, DMSO) δ 9.52 (s, 2H), 8.17 (s, 1H), 5.10 (d, J = 2.4 Hz, 2H), 3.65-3.62 (m, 4H), 3.61 (t, J = 2.4 Hz, 1H), 3.28 (s, 4H). | 443.9 | 2.5 | tert-butyl 4-(5,6-dibromo-4-nitro-1H-1,3-benzodiazol-2-yl)piperazine-1-carboxylate Method 4A 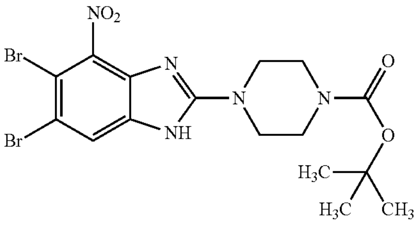 and propargyl bromide (commercial) |
| 2C | 5,6-dibromo-4-nitro-2-(piperazin-1-yl)-1-[2-(piperazin-1-yl)ethyl]-1H-1,3-benzodiazole hydrochloride 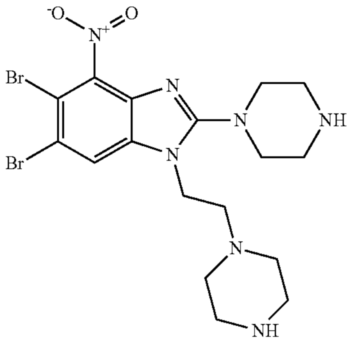 | 1H NMR (600 MHz, DMSO) δ 9.92 (bs, 2H), 9.44 (bs, 2H), 8.45 (s, 1H), 4.68-4.56(m, 2H), 3.66-3.55 (m, 8H), 3.56-3.49 (m, 8H). | 473.9 | 3.0 | tert-butyl 4-(5,6-dibromo-4-nitro-1H-1,3-benzodiazol-2-yl)piperazine-1-carboxylate Method 4A 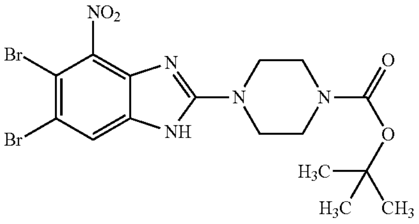 and tert-butyl 4-(2-chloroethyl)piperazine-1-Carboxylate (commercial) |
| 2D | 5,6-dibromo-1-cyclopentyl-4-nitro-2-(piperazin-1-yl)-1H-1,3-benzodiazole hydrochloride 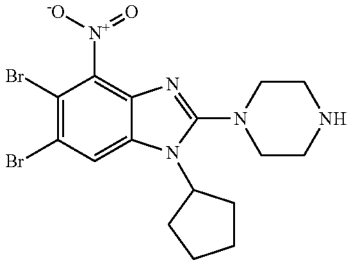 | $^1$H NMR (600 MHz, DMSO) δ 9.41 (bs, 2H), 7.99 (s, 1H), 4.72 (p, J = 9.0 Hz, 1H), 3.51-3.42 (m, 4H), 3.31-3.22 (m, 4H), 2.12-2.00 (m, 4H), 1.99-1.91 (m, 2H), 1.73 (dt, J = 11.2, 4.6 Hz, 2H). | 473.9 | 6.6 | tert-butyl 4-(5,6-dibromo-4-nitro-1H-1,3-benzodiazol-2-yl)piperazine-1-carboxylate Method 4A 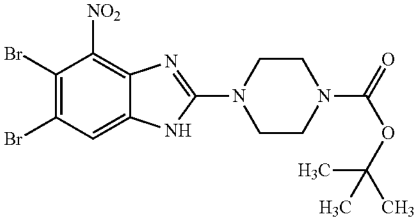 and cyclopentyl iodide (commercial) |

-continued

| Ex. | Compound | 1HNMR (400 MHz) | m/z | RT | SM |
|---|---|---|---|---|---|
| 2E | 5,6-dibromo-1-(3-methylbut-2-en-1-yl)-4-nitro-2-(piperazin-1-yl)-1H-1,3-benzodiazole hydrochloride 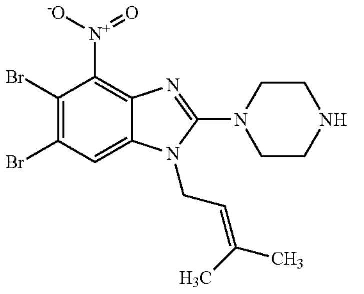 | — | 473.9 | 3.3 | tert-butyl 4-(5,6-dibromo-4-nitro-1H-1,3-benzodiazol-2-yl)piperazine-1-carboxylate Method 4A 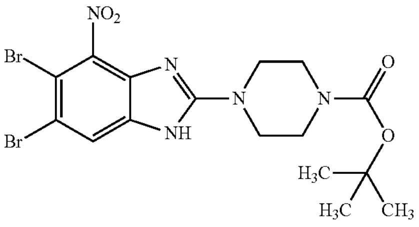 and 1-bromo-3-methyl-but-2-en (commercial) |
| 2F | 5,6-dibromo-1-(cyclobutylmethyl)-4-nitro-2-(piperazin-1-yl)-1H-1,3-benzodiazole hydrochloride 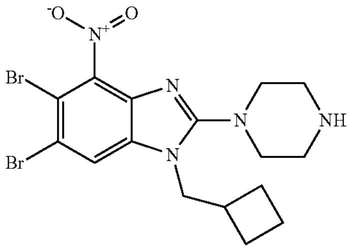 | 1H NMR (600 MHz, DMSO) δ 8.20 (s, 1H), 4.21 (d, J = 7.4 Hz, 2H), 3.26 (dd, J = 5.9, 3.9 Hz, 4H), 2.89-2.85 (m, 4H), 2.79-2.70 (m, 1H), 1.91-1.77 (m, 4H), 1.75-1.68 (m, 2H). | 459.9 | 2.9 | tert-butyl 4-(5,6-dibromo-4-nitro-1H-1,3-benzodiazol-2-yl)piperazine-1-carboxylate Method 4A 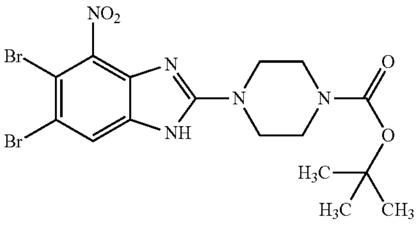 and methylcyclobutyl bromide |
| 2G | N-(3-aminopropyl)-5,6-dibromo-4-nitro-1-(prop-2-yn-1-yl)-1H-1,3-benzodiazol-2-amine hydrochloride 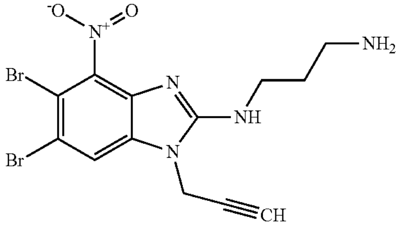 | — | 461.9 | 3.2 | tert-butyl N-{3-[(5,6-dibromo-4-nitro-1H-1,3-benzodiazol-2-yl)amino]propyl}carbamate 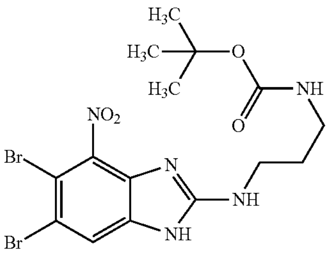 Method 4C and propargyl bromide |

-continued

| Ex. | Compound | 1HNMR (400 MHz) | m/z | RT | SM |
|---|---|---|---|---|---|
| 2H | N-(3-aminopropyl)-5,6-dibromo-1-cyclopentyl-4-nitro-1H-1,3-benzodiazol-2-amine hydrochloride<br>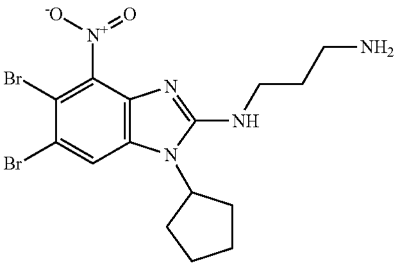 | — | 463 | 2.3 | tert-butyl N-{3-[(5,6-dibromo-4-nitro-1H-1,3-benzodiazol-2-yl)amino]propyl}carbamate<br>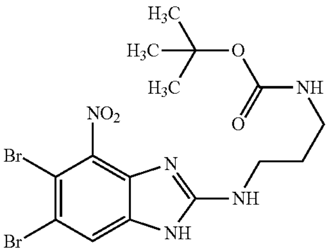<br>Method 4C<br>And cyclopentyl iodide |
| 2I | 5,6-dibromo-1-(butan-2-yl)-4-nitro-2-(piperazin-1-yl)-1H-1,3-benzodiazole hydrochloride<br>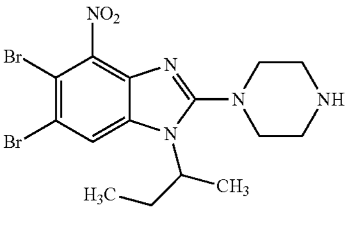 [SMILES: CCC(C)n1c(N2CCNCC2)nc2c([N+](=O)[O-])c(Br)c(Br)cc21] | — | 486.9 | 3.4 | tert-butyl 4-(5,6-dibromo-4-nitro-1H-1,3-benzodiazol-2-yl)piperazine-1-carboxylate<br>Method 4A<br>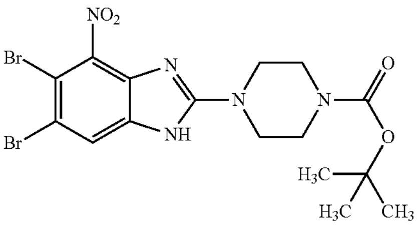<br>and 2-butyl bromide |
| 2J | 3-[5,6-dibromo-4-nitro-2-(piperazin-1-yl)-1H-1,3-benzodiazol-1-yl]propan-1-aminehydrochloride<br>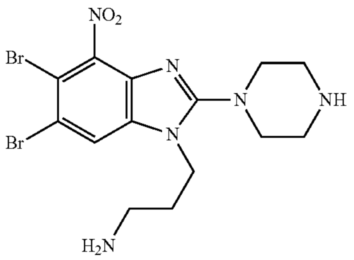 [SMILES: NCCCn1c(N2CCNCC2)nc2c([N+](=O)[O-])c(Br)c(Br)cc21] | — | 462.9 | 1.9 | tert-butyl 4-(5,6-dibromo-4-nitro-1H-1,3-benzodiazol-2-yl)piperazine-1-carboxylate<br>Method 4A<br>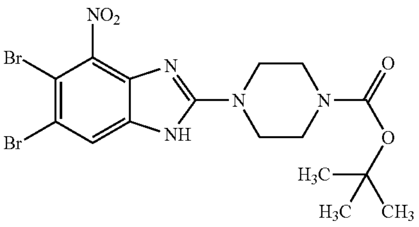<br>and tert-butyl N-(3-bromopropyl)carbamate |

-continued

| Ex. | Compound | 1HNMR (400 MHz) | m/z | RT | SM |
|---|---|---|---|---|---|
| 2L | 2-[5,6-dibromo-4-nitro-2-(piperazin-1-yl)-1H-1,3-benzodiazol-1-yl]acetamide 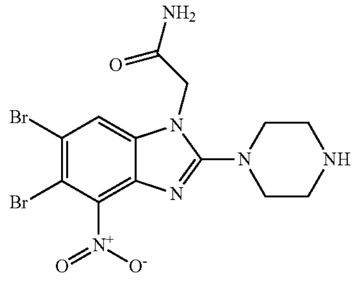 [SMILES: NC(=O)Cn1c(N2CCNCC2)nc2c([N+](=O)[O-])c(Br)c(Br)cc21] | | | | tert-butyl 4-(5,6-dibromo-4-nitro-1H-1,3-benzodiazol-2-yl)piperazine-1-carboxylate Method 4A 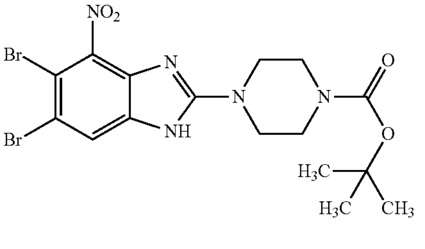 and 2-bromoacetamide |

3.3. Compounds of Example 3

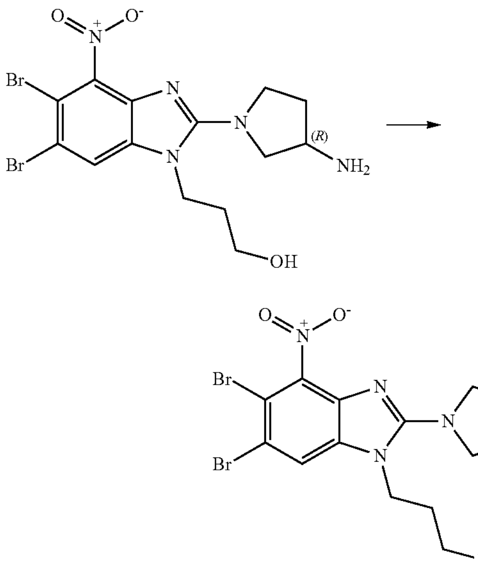

(3R)-1-[1-(3-aminopropyl)-5,6-dibromo-4-nitro-1H-1,3-benzodiazol-2-yl]pyrrolidin-3-amine (Example 3A)

A suspension of 3-{2-[(3R)-3-aminopyrrolidin-1-yl]-5,6-dibromo-4-nitro-1H-1,3-benzodiazol-1-yl}propan-1-ol (53.2 mg, 0.115 mmol) in MeOH/triethylamine (7:1 v/v, 3.1 mL) was stirred at 0° C. for 10 min. Di-tert-butyl dicarbonate (67.8 mg, 0.264 mmol) in MeOH (1.3 mL) was added slowly over 10 min under an argon atmosphere. The mixture was stirred at 0° C. for 1 h and then at room temperature for 16 h to completion (checked by TLC, AcOEt-Hex: 4-1). The solvent was removed under reduced pressure. The solid obtained was dissolved in CH2Cl2 (4 mL) and the resulting solution was washed with water (3 mL×3). The organic layer was separated, dried over anhydrous Na2SO4 and evaporated to give tert-butyl N-[(3R)-1-[5,6-dibromo-1-(3-hydroxypropyl)-4-nitro-1H-1,3-benzodiazol-2-yl]pyrrolidin-3-yl]carbamate as a yellow solid (62.9 mg, 0.108 mmol, 97%). It was dissolved without any further purification in dry tetrahydrofuran (1.1 mL) with triphenylphosphine (32.3 mg, 2.0 mmol) and phtalimide (58.0 mg, 2.0 mmol. A solution of diisopropyl azodicarboxylate (48 uL, 2.2 mmol) in tetrahydrofuran (0.4 mL) was added dropwise with stirring overnight at room temperature. Thus, the solvent was removed by evaporation and the residue taken into CH2Cl2 (4 mL), washed with a solution of sodium bicarbonate and water, dried over magnesium sulfate, filtered ad evaporated to dryness. The residue was chromatographed on a silica gel column eluted with ethyl acetate-hexane mixture (4:1) to obtain tert-butyl N-[(3R)-1-{5,6-dibromo-1-[3-(1,3-dioxo-2,3-dihydro-1H-isoindol-2-yl)propyl]-4-nitro-1H-1,3-benzodiazol-2-yl}pyrrolidin-3-yl]carbamate (72.6 mg, 0.102 mmol, 99%). m/z=693.0, rt=3.7 min. It was suspended in absolute ethanol (3.0 mL) and a solution of monohydrate hydrazine (50.4 μL, 1.017 mmol) in absolute ethanol (1.0 mL) was slowly added. The mixture was refluxed for 2.0 h. evaporation of the solvent gave solid which was dissolved 4.4 M HCl in ethanol (4.0 mL) is added. The mixture is stirred at room temperature until the reaction is complete (18 h) by LCMS. Diethyl ether (5.0 ml) is added, product is filtered off, washed with diethyl ether, dried and purified by preparative HPLC to afford (3R)-1-[1-(3-aminopropyl)-5,6-dibromo-4-nitro-1H-1,3-benzodiazol-2-yl]pyrrolidin-3-amine. m/z 462.9; rt 1.8 min.

The following compound was prepared by the procedure of Example 3A, using the appropriate starting materials.

| Ex. | Compound | 1HNMR (400 MHz) | m/z | rt | SM |
|---|---|---|---|---|---|
| 3B | (3S)-1-[1-(2-aminoethyl)-5,6-dibromo-4-nitro-1H-1,3-benzodiazol-2-yl]pyrrolidin-3-amine 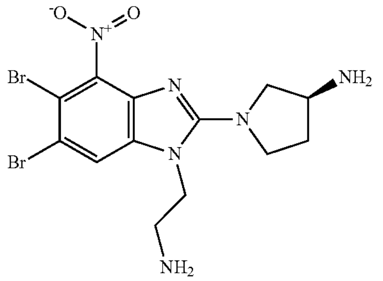 | | | | 2-{2-[(3S)-3-aminopyrrolidin-1-yl]-5,6-dibromo-4-nitro-1H-1,3-benzodiazol-1-yl}ethan-1-ol 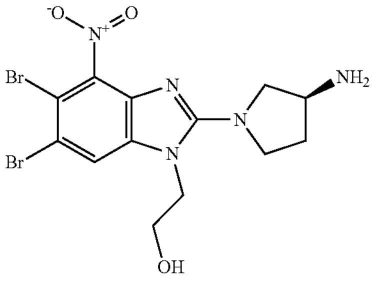 |

3.4. Compounds of Example 4

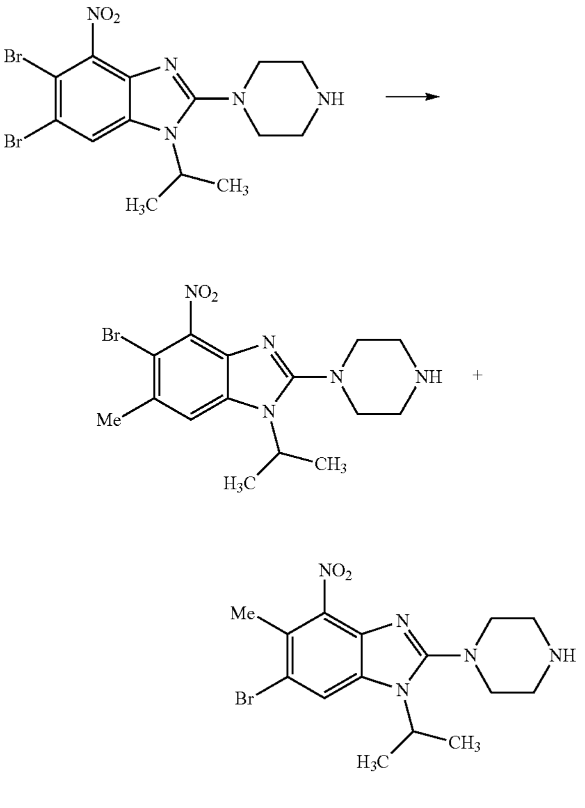

5-methyl-6-bromo-4-nitro-2-(piperazin-1-yl)-1-(propan-2-yl)-1H-1,3-benzodiazole (Example 4A) and 5-bromo-6-methyl-4-nitro-2-(piperazin-1-yl)-1-(propan-2-yl)-1H-1,3-benzodiazole (Example 4B)

5,6-dibromo-4-nitro-2-(piperazin-1-yl)-1-(propan-2-yl)-1H-1,3-benzodiazole (Example 2A) (0.08 mmol, 50 mg) was suspended in a mixture of 1,4-dioxane/H2O (10:1) (1.5 ml). methyl boronic acid (0.2 mmol, 39.5 mg) and Cs2CO3 (0.16 mmol, 34.5 mg) were added. The reaction mixture was flushed with argon for 5 min. Then [1,1'-Bis(diphenylphosphino)ferrocene]dichloropalladium(II) was added. The resulting mixture was stirred at 130° C. until the reaction was complete (16 hours) by LC/MS. The mixture was allowed to cool to RT and filtered through Celite. Solvent was evaporated in-vacuo. The product was dissolved in ethyl acetate and washed with water. The organic extract was dried over MgSO4, filtered and concentrated.

The products were purified on HPLC to afford 5-bromo-6-methyl-4-nitro-2-(piperazin-1-yl)-1-(propan-2-yl)-1H-1,3-benzodiazole trifluoroacetate (10 mg). m/z 383.9; rt 2.5; 5-methyl-6-bromo-4-nitro-2-(piperazin-1-yl)-1-(propan-2-yl)-1H-1,3-benzodiazole (5 mg) m/z 383.9, rt 2.6; 1H NMR (300 MHz, dmso) δ 9.19 (bs, 2H), 8.13 (s, 1H), 4.59 (sept, J=6.9 Hz, 1H), 3.42-3.35 (m, 4H), 3.31-3.21 (m, 4H), 2.34 (s, 3H), 1.51 (d, J=6.9 Hz, 6H).

3.5. Compounds of Example 8

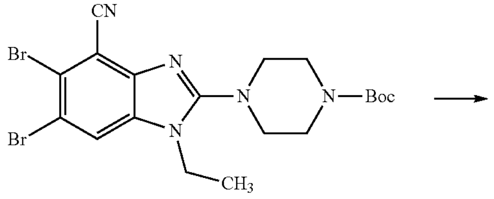

-continued

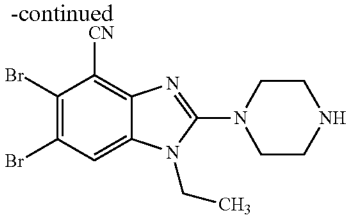

5,6-dibromo-1-ethyl-2-(piperazin-1-yl)-1H-1,3-benzodiazole-4-carbonitrilehydrochloride (Example 8A)

tert-butyl 4-(5,6-dibromo-4-cyano-1-ethyl-1H-1,3-benzodiazol-2-yl)piperazine-1-carboxylate (Method 8A) (900 mg, 2.18 mmol) was dissolved in 1,4-dioxane (5.0 ml) and 4M HCl in dioxane (2.0 ml) was added. The mixture was stirred at room temperature until the reaction was complete (18 hrs) by LC/MS. Diethyl ether (10.0 ml) was added, product was filtered off, washed with diethyl ether and dried to afford 5,6-dibromo-1-ethyl-2-(piperazin-1-yl)-1H-1,3-benzodiazole-4-carbonitrile hydrochloride (820 mg, 1.8 mmol) 1H NMR (600 MHz, DMSO) δ 9.47 (s, 2H), 8.24 (s, 1H), 4.17 (q, J=7.2 Hz, 2H), 3.67-3.62 (m, 4H), 3.29 (s, 4H), 1.32 (t, J=7.2 Hz, 3H), m/z 413.9; rt 2.2.

The following example was prepared by the procedure of Examples 8A, using the appropriate starting materials:

-continued

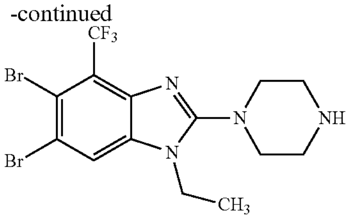

5,6-dibromo-1-ethyl-2-(piperazin-1-yl)-4-(trifluoromethyl)-1H-1,3-benzodiazolehydrochloride (Example 9A)

tert-butyl 4-(5,6-dibromo-1-ethyl-4-iodo-1H-1,3-benzodiazol-2-yl)piperazine-1-carboxylate (150 mg, 0.24 mmol) methyl 2,2-difluoro-2-(fluorosulfonyl)acetate (0.092 ml, 0.73 mmol) and copper (I) iodide (4.7 mg, 0.024 mmol) were dissolved in DMF (3.0 ml). The resulting mixture was stirred at 150° C. under microwave conditions until the reaction was complete (10 min) by LC/MS. The mixture was allowed to cool to RT and concentrated in-vacuo. The residue was dissolved in ethyl acetate and washed with water. The organic extract was dried over MgSO4, filtered and concentrated. The product was purified on silica gel

| Ex. | Compound | 1HNMR (400 MHz) | m/z | RT | SM |
|---|---|---|---|---|---|
| 8G | 2-[(3R)-3-aminopyrrolidin-1-yl]-5,6-dibromo-1-[(3S)-pyrrolidin-3-yl]-1H-1,3-benzodiazole-4-carbonitrile 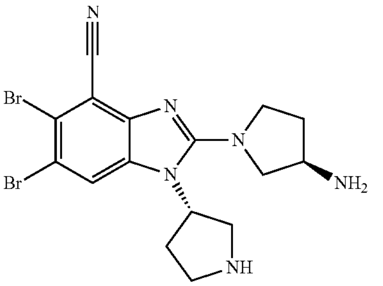 [SMILES: N#Cc1c(Br)c(Br)cc2c1nc(N1CC[C@@H](N)C1)n2[C@H]1CCNC1] | | 454.9 | 1.6 | tert-butyl (3S)-3-{5,6-dibromo-2-[(3R)-3-{[(tert-butoxy)carbonyl]amino}pyrrolidin-1-yl]-4-cyano-1H-1,3-benzodiazol-1-yl}pyrrolidine-1-carboxylate 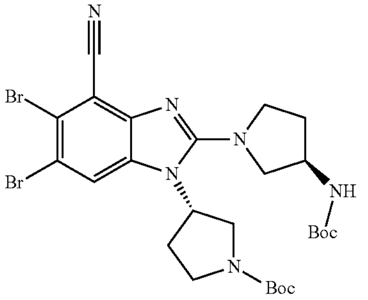 |

3.6. Compounds of Example 9

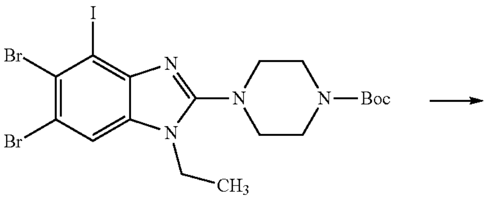

using EA/hex (1:1). The product was dissolved in 1,4-dioxane (1.0 ml) and 4M HCl in dioxane (1.0 ml) was added. The mixture was stirred at room temperature until the reaction was complete (18 hrs) by LC/MS. The mixture was concentrated in-vacuo and purified on HPLC to afford 5,6-dibromo-1-ethyl-2-(piperazin-1-yl)-4-(trifluoromethyl)-1H-1,3-benzodiazole hydrochloride (22 mg, 0.05 mmol). 1H NMR (600 MHz, DMSO) δ 9.21 (bs, 2H), 8.23 (s, 1H), 4.16 (t, J=7.2 Hz, 2H), 3.59-3.55 (m, 4H), 3.29 (bs, 4H), 1.31 (t, J=7.1 Hz, 3H); m/z 456.8; rt 3.1.

The following example was prepared by the procedure of Example 9A, using the appropriate starting materials:

| Ex. | Compound | 1HNMR (400 MHz) | m/z | RT | SM |
|---|---|---|---|---|---|
| 9B | 6-bromo-4-nitro-2-(piperazin-1-yl)-1-(propan-2-yl)-5-(trifluoromethyl)-1H-1,3-benzodiazole 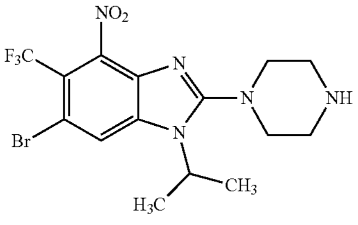 [SMILES: CC(C)n1c(N2CCNCC2)nc2c([N+](=O)[O-])c(C(F)(F)F)c(Br)cc21] | 1H NMR (300 MHz, dmso) δ 8.94 (s, 2H), 8.29 (s, 1H), 4.21 (q, J = 7.1 Hz, 2H), 3.58-3.45 (m, 4H), 3.27 (s, 4H), 1.33(t, J = 7.1 Hz, 3H). | 421.9 | 2.7 | tert-butyl N-[1-(4-amino-5,6-dibromo-1-ethyl-1H-1,3-benzodiazol-2-yl)piperidin-3-yl]carbamate: 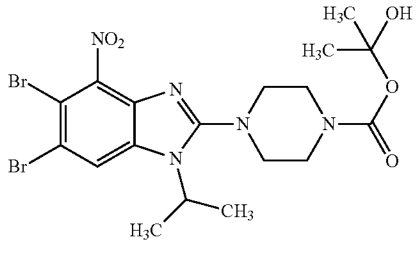 Method 12A |

3.7. Compounds of Example 21

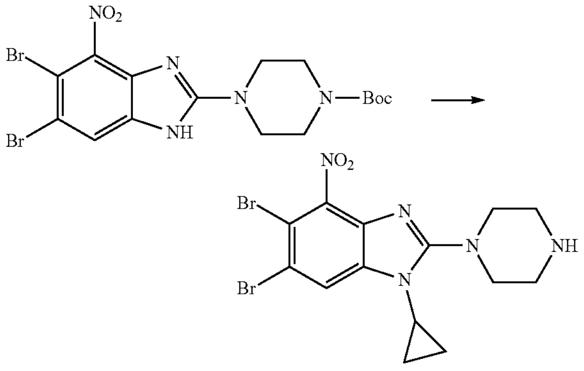

5,6-dibromo-1-cyclopropyl-4-nitro-2-(piperazin-1-yl)-1H-1,3-benzodiazole trifluoroacetate (Example 21A)

tert-butyl 4-(5,6-dibromo-1H-1,3-benzodiazol-2-yl)piperazine-1-carboxylate (150 mg, 0.33 mmol) was dissolved in dichloroethane (5.0 ml). Cyclopropylboronic acid (56 mg, 0.65 mmol), copper (II) acetate (59 mg, 0.33 mol), 2,2'-bipyridine (51 mg, 0.65 mmols) and sodium carbonate (70 mg, 0.65 mmol) were added. The resulting mixture was stirred at 60° C. until the reaction was complete (3 days) by LC/MS. The mixture was allowed to cool to RT and concentrated in-vacuo. The product was taken up into DMC and washed with water. The organic extract was dried over MgSO4, filtered and concentrated. The product was purified on silica gel using EA/hex (1:4). The product was dissolved in sulfuric acid (conc.) (2.0 ml) and stirred 0° C. for 30 min, then potassium nitrate (12 mg, 0.12 mmol) was added in one portion and stirred at 0° C. for additional 3 hrs. The reaction mixture was left to warm to room temperature and was stirred until the reaction was complete (16 hrs). The mixture was poured onto ice. The product was taken up into DCM, dried over $MgSO_4$, filtered and concentrated. The product was purified on HPLC to afford 5,6-dibromo-1-cyclopropyl-4-nitro-2-(piperazin-1-yl)-1H-1,3-benzodiazole trifluoroacetate (3.2 mg, 0.007 mmol); m/z 455.9; rt 3 min.

3.8. Compounds of Example 22

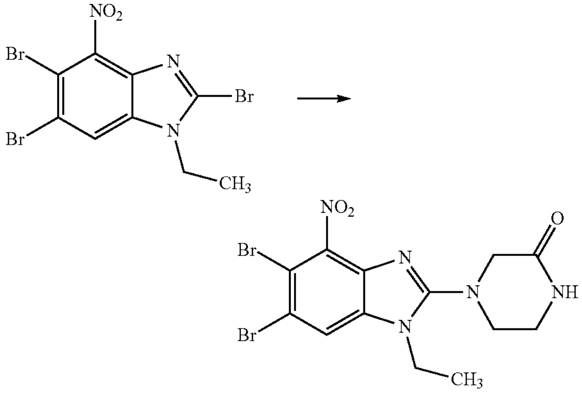

4-(5,6-dibromo-1-ethyl-4-nitro-1H-1,3-benzodiazol-2-yl)piperazin-2-one (Example 22A)

2,5,6-tribromo-1-ethyl-4-nitro-1H-1,3-benzodiazole (100 mg, 0.23 mmol) and 2-piperazinone (117 mg, 1.17 mmol) were dissolved in EtOH (3.0 ml). The resulting mixture was stirred at temperature 170° C. under microwave conditions until the reaction was complete (20 min) by LC/MS. The mixture was allowed to cool to RT and concentrated in-vacuo. The product was filtered off, washed with EtOH and dried to afford-(5,6-dibromo-1-ethyl-4-nitro-1H-1,3-benzodiazol-2-yl)piperazin-2-one (97 mg, 0.22 mmol); m/z 462.9; rt 3.1 min.

The following examples were prepared by the procedure of Example 22A, using the appropriate starting materials:

| Ex. | Compound | 1HNMR (400 MHz) | m/z | RT | SM |
|---|---|---|---|---|---|
| 22B | 4-[(5,6-dibromo-1-ethyl-4-nitro-1H-1,3-benzodiazol-2-yl)amino]cyclohexan-1-ol 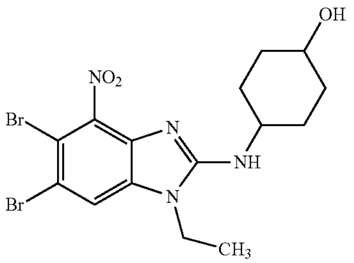 [SMILES: CCn1c(NC2CCC(O)CC2)nc2c([N+](=O)[O-])c(Br)c(Br)cc21] | 1H NMR (600 MHz, DMSO) δ 7.85 (s, 1H), 7.16 (d, J = 7.8 Hz, 1H), 4.56 (d, J = 3.3 Hz, 1H), 4.08 (q, J = 7.1 Hz, 2H), 3.68 (dtd, J = 15.2, 7.7, 4.0 Hz, 1H), 3.40 (ddd, J = 21.1, 13.6, 7.2 Hz, 1H), 1.92 (d, J = 11.4 Hz, 2H), 1.85 (d, J = 10.9 Hz, 2H), 1.44-1.34 (m, 2H), 1.29-1.21 (m, 2H), 1.15 (t, J = 7.1 Hz, 3H). | 447.9 | 2.6 | 2,5,6-tribromo-1-ethyl-4-nitro-1H-1,3-benzodiazole 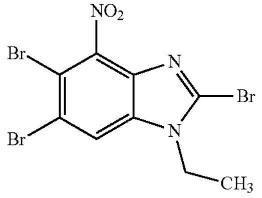 Method 3A And4-aminocyclohexan-1-ol |
| 22F | (3S)-1-(5,6-dibromo-1-ethyl-4-nitro-1H-1,3-benzodiazol-2-yl)pyrrolidin-3-ol 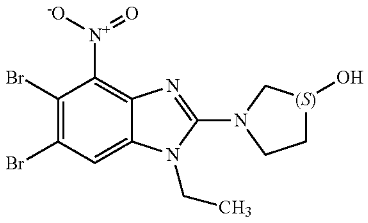 | 1H NMR (600 MHz, DMSO) δ 7.96 (s, 1H), 5.05 (d, J = 3.6 Hz, 1H), 4.38 (t, J = 6.1 Hz, 1H), 4.32-4.19 (m, 2H), 3.80-3.75 (m, 2H), 3.72-3.67 (m, 1H), 3.50 (d, J = 10.6 Hz, 1H), 2.00 (dtd, J = 12.9, 8.8, 4.4 Hz, 1H), 1.91-1.86 (m, 1H), 1.27 (t, J = 7.1 Hz, 3H). | 379.8 | 2.2 | 2,5,6-tribromo-1-ethyl-4-nitro-1H-1,3-benzodiazole 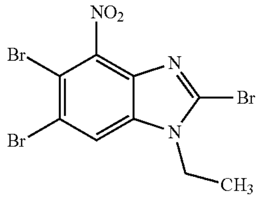 Method 3A And(3S)-pyrrolidin-3-ol |
| 22G | 1-[5,6-dibromo-4-nitro-1-(propan-2-yl)-1H-1,3-benzodiazol-2-yl]piperidin-3- 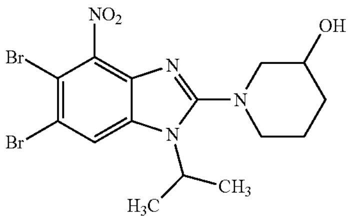 [SMILES: CC(C)n1c(N2CCCC(O)C2)nc2c([N+](=O)[O-])c(Br)c(Br)cc21] | $^{1}$H NMR (600 MHz, DMSO) δ 8.18 (s, 1H), 4.93 (d, J = 4.5 Hz, 1H), 4.55 (hept, J = 6.9 Hz, 1H), 3.74-3.68 (m, 1H), 3.42 (dd, J = 12.2, 3.6 Hz, = 1H), 3.28 (dd, J = 11.2, 4.2 Hz, 1H), 3.02 (ddd, J = 12.5, 10.0, 2.8 Hz, 1H), 2.84 (dd, J = 12.2, 8.4 Hz, 1H), 1.90-1.85 (m, 1H), 1.82 (dd, J = 9.1, 4.2 Hz, 1H), 1.64-1.55 (m, 1H), 1.53 (dd, J = 7.3, 1.2 Hz, 6H), 1.44-1.34 (m, 1H). | 476.9 | 3.5 | 2,5,6-tribromo-1-(2-propyl)-4-nitro-1H-1,3-benzodiazole 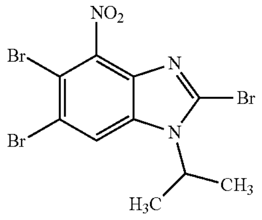 Method 3B And piperidin-3-ol |

-continued

| Ex. | Compound | 1HNMR (400 MHz) | m/z | RT | SM |
|---|---|---|---|---|---|
| 22H | {1-[5,6-dibromo-4-nitro-1-(propan-2-yl)-1H-1,3-benzodiazol-2-yl]piperidin-3-yl}methanol 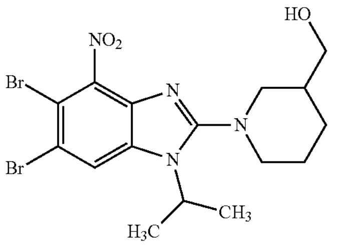 [SMILES: CC(C)n1c(N2CCCC(CO)C2)nc2c([N+](=O)[O-])c(Br)c(Br)cc21] | 1H NMR (600 MHz, DMSO) δ 8.19 (s, 1H), 4.56-4.49 (m, 1H), 3.54-3.50 (m, 1H), 3.40-3.36 (m, 2H), 3.29 (dd, J = 10.6, 8.1 Hz, 1H), 2.97-2.90 (m, 1H), 2.77 (dd, J = 12.4, 10.0 Hz, 1H), 1.83-1.61 (m, 4H), 1.54 (dd, J = 20.4, 6.9 Hz, 6H), 1.21-1.13 (m, 1H). | 428.9 | 3 | 2,5,6-tribromo-1-(2-propyl)-4-nitro-1H-1,3-benzodiazole 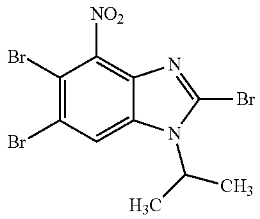 Method 3B And piperidin-3-yl-methanol |
| 22I | (3S)-1-[5,6-dibromo-4-nitro-1-(propan-2-yl)-1H-1,3-benzodiazol-2-yl]piperidin-3-ol 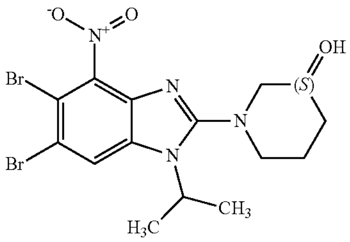 | — | 465.9 | 2.8 | 2,5,6-tribromo-1-(2-propyl)-4-nitro-1H-1,3-benzodiazole 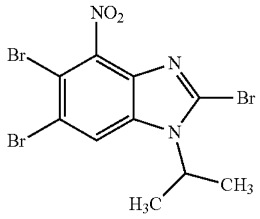 Method 3B (3S)-piperidin-3-ol |
| 22J | N-[2-(2-aminoethoxy)ethyl]-5,6-dibromo-4-nitro-1-(propan-2-yl)-1H-1,3-benzodiazol-2-amine 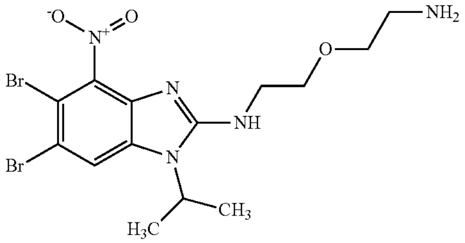 | $^{1}$H NMR (600 MHz, DMSO) δ 8.04 (bs, 2H), 7.90 (s, 1H), 7.63 (t, J = 5.4 Hz, 1H), 4.84 (hept, J = 6.8 Hz, (m, 4H), 3.56 (q, J = 5.6 Hz, 2H), 2.97 (bs, 2H), 1.48 (d, J = 6.9 Hz, 6H). | 448.8 | 3.8 | 2,5,6-tribromo-1-(2-propyl)-4-nitro-1H-1,3-benzodiazole 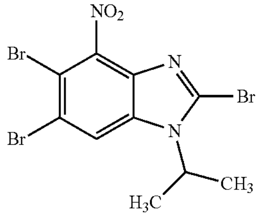 Method 3B And 2-(2-aminoethoxy)ethanamine |

-continued

| Ex. | Compound | 1HNMR (400 MHz) | m/z | RT | SM |
| --- | --- | --- | --- | --- | --- |
| 22K | 5,6-dibromo-2-(morpholin-4-yl)-4-nitro-1-(propan-2-yl)-1H-1,3-benzodiazole<br>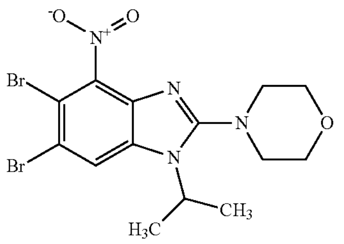 | 1H NMR (600 MHz, DMSO) δ 8.23 (s, 1H), 4.61 (hept, J = 6.9 Hz, 1H), 3.78-3.74 (m, 5H), 3.23-3.20 (m, 4H), 1.54 (d, J = 6.9 Hz, 6H). | 427.9 | 5.8 | 2,5,6-tribromo-1-(2-propyl)-4-nitro-1H-1,3-benzodiazole<br>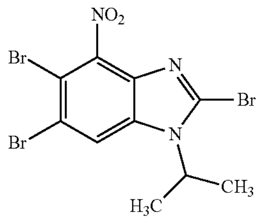<br>Method 3B And morpholine |
| 22L | 1-N-(5,6-dibromo-1-ethyl-4-nitro-1H-1,3-benzodiazol-2-yl)cyclohexane-1,2-diamine<br>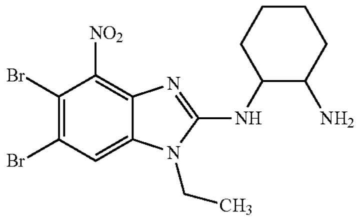 [SMILES: CCn1c(NC2CCCCC2N)nc2c([N+](=O)[O-])c(Br)c(Br)cc21] | — | 461.9 | 2.9 | 2,5,6-tribromo-1-ethyl-4-nitro-1H-1,3-benzodiazole<br>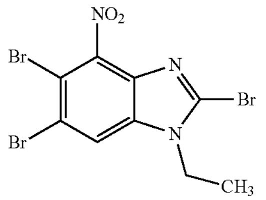<br>Method 3A And 1,2-cyclohexanediamine |
| 22M | 5,6-dibromo-1-ethyl-2-(4-methyl-1,4-diazepan-1-yl)-4-nitro-1H-1,3-benzodiazole<br>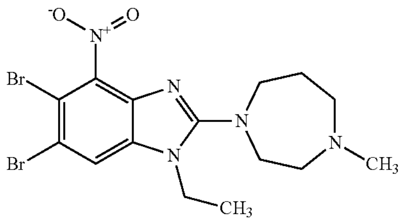 | $^1$H NMR (600 MHz, DMSO) δ 8.01 (s, 1H), 4.18 (q, J = 7.1 Hz, 2H), 3.69-3.64 (m, 4H), 2.70 (dd, J = 6.2, 3.4 Hz, 2H), 2.56-2.54 (m, 2H), 2.28 (s, 3H), 1.95-1.90 (m, 2H), 1.27 (t, J = 7.1 Hz, 3H). | 461.9 | 2.5 | 2,5,6-tribromo-1-ethyl-4-nitro-1H-1,3-benzodiazole<br>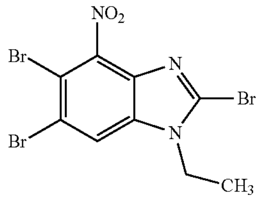<br>Method 3A And N-methylhomopiperazine |
| 22N | 1-N-(5,6-dibromo-1-ethyl-4-nitro-1H-1,3-benzodiazol-2-yl)benzene-1,2-diamine<br>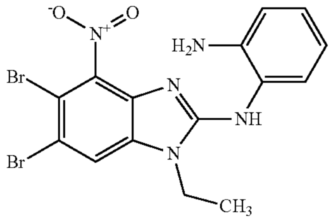 | — | 455.8 | 3.2 | 2,5,6-tribromo-1-ethyl-4-nitro-1H-1,3-benzodiazole<br>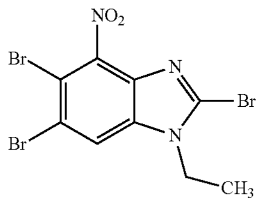<br>Method 3A And ortho-phenylenediamine |

-continued

| Ex. | Compound | 1HNMR (400 MHz) | m/z | RT | SM |
| --- | --- | --- | --- | --- | --- |
| 22O | 5,6-dibromo-N-({1-[2-(dimethylamino)ethyl]pyrrolidin-3-yl}methyl)-1-ethyl-4-nitro-1H-1,3-benzodiazol-2-amine<br>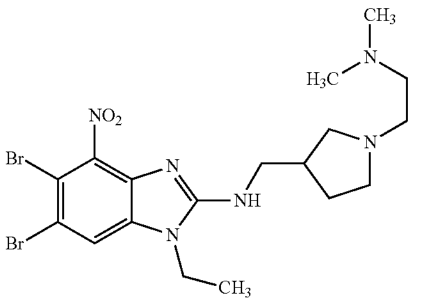 [SMILES: CCn1c(NCC2CCN(CCN(C)C)C2)nc2c([N+](=O)[O-])c(Br)c(Br)cc21] | — | 519 | 2.3 | 2,5,6-tribromo-1-ethyl-4-nitro-1H-1,3-benzodiazole<br>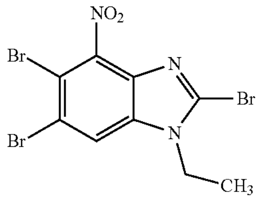<br>Method 3A And {1-[2-(dimethylamino)ethyl]pyrrolidin-3-yl}methanamine |
| 22P | 5,6-dibromo-1-ethyl-4-nitro-N-[3-(pyrrolidin-1-yl)propyl]-1H-1,3-benzodiazol-2-amine<br>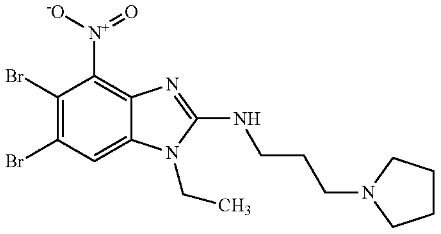 | 1H NMR (600 MHz, DMSO) δ 7.87 (s, 1H), 7.59 (t, J = 5.3 Hz, 1H), 4.07 (q, J = 7.1 Hz, 2H), 3.41 (dd, J = 12.3, 6.8 Hz, 2H), 2.54 (d, J = 12.3 Hz, 6H), 1.81-1.77 (m, 2H), 1.71 (bs, 4H), 1.18 (t, J = 7.1 Hz, 3H). | 475.9 | 2.7 | 2,5,6-tribromo-1-ethyl-4-nitro-1H-1,3-benzodiazole<br>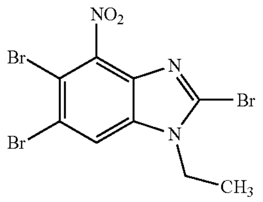<br>Method 3A 3-(pyrrolidin-1-yl)propan-1-amine |
| 22R | 5,6-dibromo-1-ethyl-4-nitro-2-{4{3-(piperazin-1-yl)propyl]piperazin-1-yl}-1H-1,3-benzodiazole<br>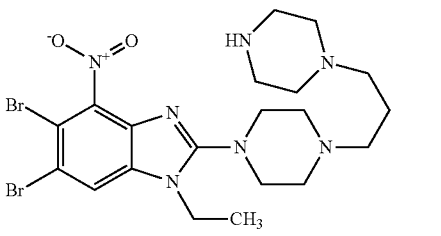 | 1H NMR (600 MHz, DMSO) δ 9.83 (bs, 2H), 8.23 (s, 1H), 4.20 (q, J = 7.1 Hz, 2H), 3.86-3.71 (m, 16H), 3.33-3.26 (m, 4H), 2.29-2.22 (m, 2H), 1.33 (t, J = 7.2 Hz, 3H). | 560 | 2.2 | 2,5,6-tribromo-1-ethyl-4-nitro-1H-1,3-benzodiazole<br>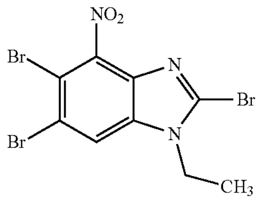<br>Method 3A And1-[3-(piperazin-1-yl)propyl]piperazine |

-continued

| Ex. | Compound | 1HNMR (400 MHz) | m/z | RT | SM |
|---|---|---|---|---|---|
| 22V | 1-N-(5,6-dibromo-1-ethyl-4-nitro-1H-1,3-benzodiazol-2-yl)benzene-1,3-diamine 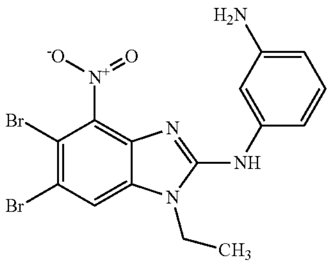 | 1H NMR (600 MHz, DMSO) δ 9.10 (s, 1H), 8.03 (s, 1H), 7.03-6.95 (m, 2H), 6.86 (s, 1H), 6.29 (d, J = 7.4 Hz, 1H), 5.07 (s, 2H), 4.31 (q, J = 7.0 Hz, 2H), 1.24 (t, J = 7.1 Hz, 3H). | 462 | 2.5 | 2,5,6-tribromo-1-ethyl-4-nitro-1H-1,3-benzodiazole 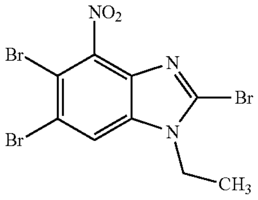 Method 3A And meta-phenylenediamine |
| 22W | 5,6-dibromo-2-(3,3-dimethylpiperazin-1-yl)-1-ethyl-4-nitro-1H-1,3-benzodiazole 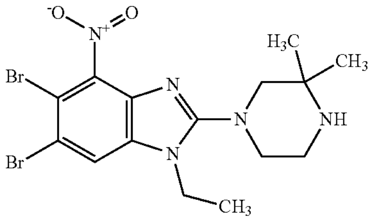 | 1H NMR (600 MHz, DMSO) δ 8.25 (s, 1H), 4.21 (q, J = 7.1 Hz, 2H), 3.46 (d, J = 5.2 Hz, 2H), 3.40-3.25 (m, 6H), 1.39 (s, 6H), 1.32 (t, J = 7.2 Hz, 3H). | 447.9 | 2.5 | 2,5,6-tribromo-1-ethyl-4-nitro-1H-1,3-benzodiazole 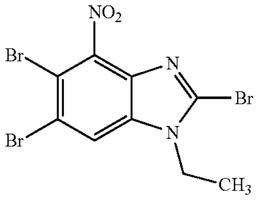 Method 3A And 2,2-dimethylpiperazine |
| 22X | 5,6-dibromo-1-ethyl-2-(3-methylpiperazin-1-yl)-4-nitro-1H-1,3-benzodiazole 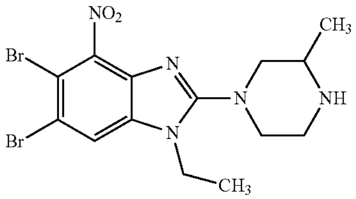 [SMILES: CCn1c(N2CCNC(C)C2)nc2c([N+](=O)[O-])c(Br)c(Br)cc21] | $^{1}$H NMR (600 MHz, DMSO) δ 9.35 (bs, 2H), 8.22 (s, 1H), 4.19 (q, J = 7.3 Hz, 2H), 3.71 (d, J = 13.3 Hz, 2H), 3.46 (ddd, J = 9.9, 6.6, 3.2 Hz, 1H), 3.37 (dd, J = 22.3, 9.7 Hz, 2H), 3.26-3.14 (m, 2H), 1.32 (t, J = 7.2 Hz, 3H), 1.29 (d, J = 6.5 Hz, 3H). | 433.9 | 1.6 | 2,5,6-tribromo-1-ethyl-4-nitro-1H-1,3-benzodiazole 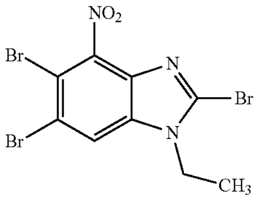 Method 3A And 2-methylpiperazine |
| 22Z | 5,6-dibromo-2-[(3S)-3-methylpiperazin-1-yl]-4-nitro-1-(propan-2-yl)-1H-1,3-benzodiazole 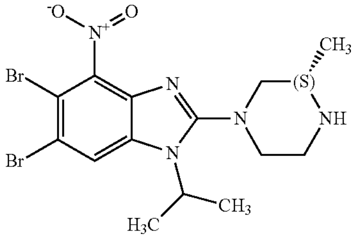 | 1H NMR (600 MHz, DMSO) δ 8.20 (s, 1H), 4.54 (dq, J = 13.7, 6.9 Hz, 1H), 3.30-3.26 (m, 2H), 2.88 (tdd, J = 13.5, 10.0, 7.2 Hz, 4H), 2.58 (dd, J = 11.8, 10.3 Hz, 1H), 1.54 (d, J = 6.9 Hz, 3H), 1.52 (d, J = 6.9 Hz, 3H), 0.99 (d, J = 6.3 Hz, 3H). | 477.9 | 2.8 | 2,5,6-tribromo-1-(2-propyl)-4-nitro-1H-1,3-benzodiazole 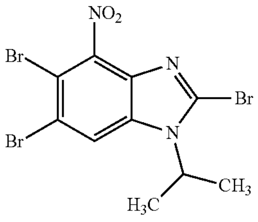 Method 3B and (2S)-2-methylpiperazine |

-continued

| Ex. | Compound | 1HNMR (400 MHz) | m/z | RT | SM |
|---|---|---|---|---|---|
| 22AA | 5,6-dibromo-2-[(3R)-3-methylpiperazin-1-yl]-4-nitro-1-(propan-2-yl)-1H-1,3-benzodiazole 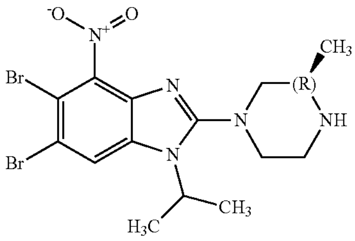 | — | 461.8 | 3 | 2,5,6-tribromo-1-(2-propyl)-4-nitro-1H-1,3-benzodiazole 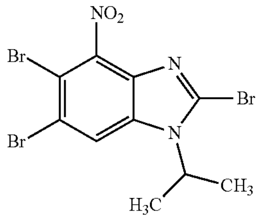 Method 3B And (2R)-2-methylpiperazine |
| 22AB | N-(3-amino-2-methoxypropyl)-5,6-dibromo-4-nitro-1-(propan-2-yl)-1H-1,3-benzodiazol-2-amine 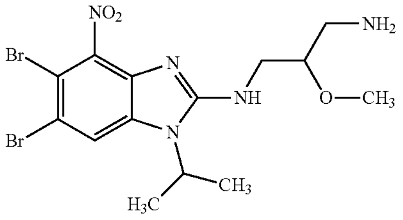 [SMILES: COC(CN)CNc1nc2c([N+](=O)[O-])c(Br)c(Br)cc2n1C(C)C] | — | 465.8 | 2.7 | 2,5,6-tribromo-1-(2-propyl)-4-nitro-1H-1,3-benzodiazole 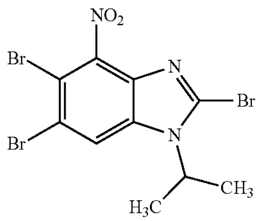 Method 3B And 2-methoxy-1,3-diaminopropane |
| 22AC | 2-[(3-amino-2-methoxypropyl)amino]-5,6-dibromo-1-(propan-2-yl)-1H-1,3-benzodiazole-4-carbonitrile 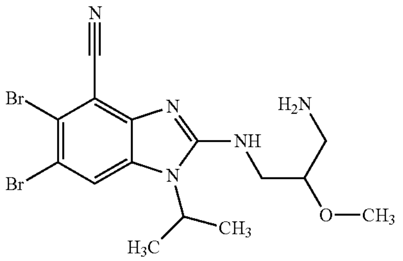 [SMILES: COC(CN)CNc1nc2c(C#N)c(Br)c(Br)cc2n1C(C)C] | — | 445.9 | 2.3 | 2,5,6-tribromo-1-(propan-2-yl)-1H-1,3-benzodiazole-4-carbonitrile 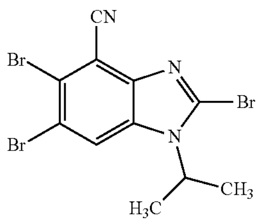 Method 8B And 2-methoxy-1,3-propylenediamine |

-continued

| Ex. | Compound | 1HNMR (400 MHz) | m/z | RT | SM |
|---|---|---|---|---|---|
| 22AD | {4-[5,6-dibromo-4-nitro-1-(propan-2-yl)-1H-1,3-benzodiazol-2-yl]piperazin-2-yl}methanol 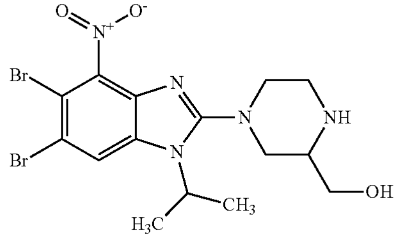 [SMILES: CC(C)n1c(N2CCNC(CO)C2)nc2c([N+](=O)[O-])c(Br)c(Br)cc21] | 1H NMR (600 MHz, DMSO) δ 9.19 (bs, 1H), 8.78 (bs, 1H), 8.30 (s, 1H), 5.52 (bs, 1H), 4.63 (hept, J = 7.0 Hz, 1H), 3.68 (dd, J = 11.7, 4.5 Hz, 1H), 3.61 (dd, J = 11.6, 5.6 Hz, 1H), 3.58-3.51 (m, 2H), 3.51-3.44 (m, 2H), 3.26 (ddd, J = 14.1, 10.0, 4.2 Hz, 2H), 3.20 (dd, J = 13.6, 10.7 Hz, 1H), 1.54 (dd, J = 26.9, 6.9 Hz, 6H). | 477.9 | 2.6 | 2,5,6-tribromo-1-(2-propyl)-4-nitro-1H-1,3-benzodiazole 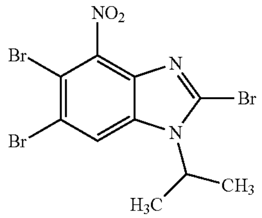 Method 3B And piperazin-2-ylmethanol |
| 22AE | 5,6-dibromo-2-[(1R,4R)-2,5-diazabicyclo[2.2.1]heptan-2-yl]-4-nitro-1-(propan-2-yl)-1H-1,3-benzodiazole 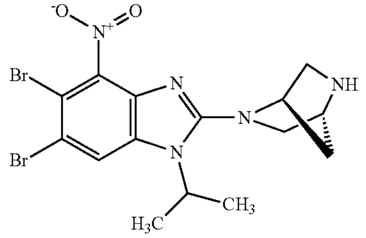 | | | | 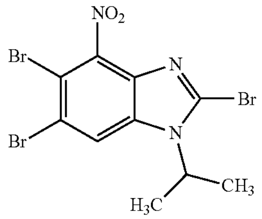 Method 3B And (1R,4R)-2,5-diazabicyclo[2.2.1]heptane |

3.9. Compounds of Example 26

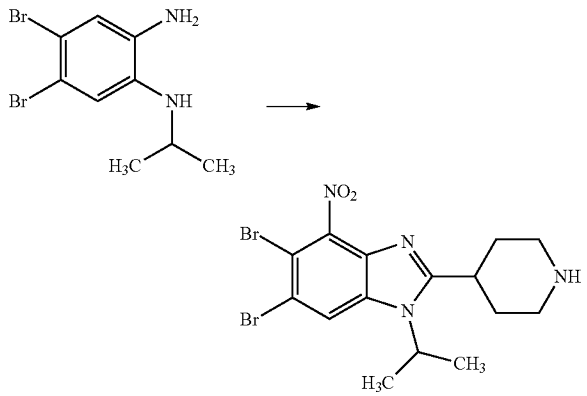

5,6-dibromo-4-nitro-2-(piperidin-4-yl)-1-(propan-2-yl)-1H-1,3-benzodiazole (Example 26A)

4,5-dibromo-1-N-(propan-2-yl)benzene-1,2-diamine (2.8 g, 9.1 mmol) and isonipeconic acid (1.17 g, 9.1 mmol) were taken up in phosphoric acid (17.82 g, 0.18 mol). The resulting mixture was stirred at 180° C. for 3.5 hours. The mixture was allowed to cool to RT and diluted with water to 200 ml. The solution was basified to pH 14.0 using solid NaOH. The resulting precipitate was then filtered off and washed repeatedly with MeOH. The filtrate was concentrated in-vacuo. The product was purified on $Al_2O_3$(basic) using DCM/MeOH/$NH_3$ sat. in MEOH (25:15:1). The obtained product (8.7 mmol, 3.9 g) was dissolved in conc. $H_2SO_4$ (30 ml). Next $KNO_3$ (8.7 mmol, 0.89 g) was added in one portion at 0° C. The resulting mixture was stirred at 0° C. for 3 h and at RT overnight. Then the mixture was poured onto ice. The product was filtered and washed with water. The product was purified on $Al_2O_3$ (basic) using DCM/MeOH/$NH_3$ sat. in MEOH (25:15:1) to afford 5,6-dibromo-4-nitro-2-(piperidin-4-yl)-1-(propan-2-yl)-1H-1,3-benzodiazole (1.9 g). 1H NMR (600 MHz, DMSO) δ 8.74 (bs, 1H), 8.48 (s, 1H), 8.35 (bs, 1H), 4.94 (hept, J=6.8 Hz, 1H), 3.52-3.46 (m, 1H), 3.42-3.37 (m, 2H), 3.08 (bs, 2H), 2.07-1.96 (m, 4H), 1.60 (d, J=6.9 Hz, 6H). m/z 446.8; rt 2.7 min.

The following compounds were prepared by the procedure of Example 26A, using the appropriate starting materials.

| Ex. | Compound | 1HNMR (400 MHz) | m/z | RT | SM |
|---|---|---|---|---|---|
| 26B | Diastereoisomer I of 3-[5,6-dibromo-4-nitro-1-(propan-2-yl)-1H-1,3-benzodiazol-2-yl]cyclohexan-1-amine 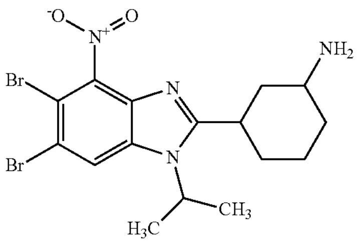 | | | | 3-aminocyclohexane-1-carboxylic acid |
| 26C | Diastereosomer II of 3-[5,6-dibromo-4-nitro-1-(propan-2-yl)-1H-1,3-benzodiazol-2-yl]cyclohexan-1-amine 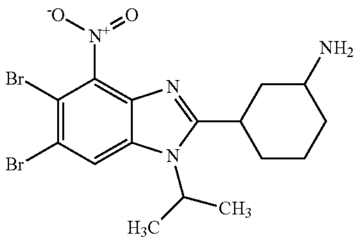 | | | | 3-aminocyclohexane-1-carboxylic acid |
| 26D | 4-[5,6-dibromo-4-nitro-1-(propan-2-yl)-1H-1,3-benzodiazol-2-yl]cyclohexan-1-amine 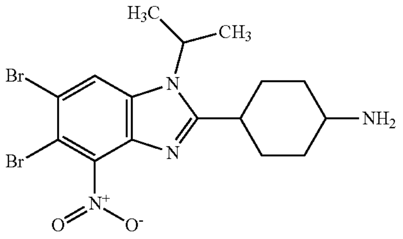 [SMILES: CC(C)n1c(C2CCC(N)CC2)nc2c([N+](=O)[O-])c(Br)c(Br)cc21] | | | | 4-aminocyclohexane-1-carboxylic acid |

3.10. Compounds of Example 27

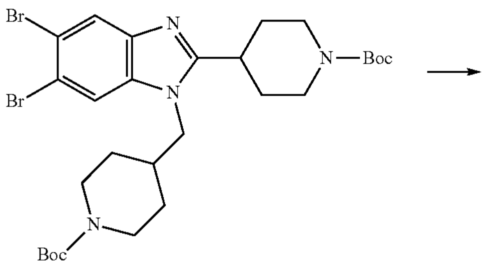

-continued

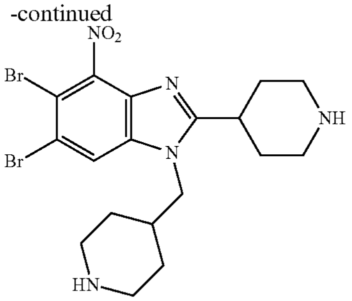

5,6-dibromo-4-nitro-2-(piperidin-4-yl)-1-(piperidin-4-ylmethyl)-1H-1,3-benzodiazole (27A)

tert-butyl 4-[5,6-dibromo-1-({1-[(tert-butoxy)carbonyl]piperidin-4-yl}methyl)-1H-1,3-benzodiazol-2-yl]piperidine-1-carboxylate (Method 16A)(0.04 mmol, 20 mg) was dissolved in concentrated $H_2SO_4$ (1 ml). Then $KNO_3$ (0.07 mmol, 6.6 mg) was added in one portion at 0° C. The resulting mixture was stirred at 0° C. for 3 h and at RT overnight. The mixture was poured onto ice. The product was purified on preparative HPLC to afford compound 5,6-dibromo-4-nitro-2-(piperidin-4-yl)-1-(piperidin-4-ylmethyl)-1H-1,3-benzodiazole trifluoroacetate (10 mg); m/z 502.0; rt 1.9 min.

3.11. Methods in Order to Prepare Compounds According to the Present Invention

3.11.1. Method 1

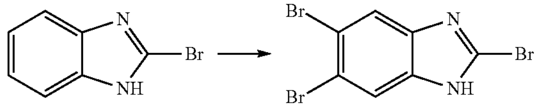 [SMILES: Brc1nc2ccccc2[nH]1 ; Brc1nc2cc(Br)c(Br)cc2[nH]1]

2,5,6-tribromo-1H-1,3-benzodiazole 2-bromo-1H-1,3-benzodiazole (170 mmol, 33.5 g) was suspended in acetonitrile (400 ml). Then NBS (357 mmol, 63.55 g) in acetonitrile (300 ml) was added. The resulting mixture was stirred at RT until the reaction was complete (24 hours) by LC/MS. The product was filtered and washed with acetonitrile. The product was purified on silica gel using EA/hex (1:4) to afford compound 2,5,6-tribromo-1H-1,3-benzodiazole (56 g). 1H NMR (600 MHz, DMSO) δ 7.95 (s, 1H); m/z 356.7; rt 3.0 min.

3.11.2. Method 2A

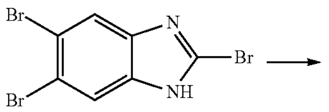

-continued

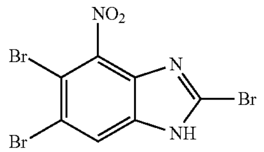

2,5,6-tribromo-4-nitro-1H-1,3-benzodiazole 2,5,6-tribromo-1H-1,3-benzodiazole (Method 1)(1.4 mmol, 500 mg) was dissolved in concentrated $H_2SO_4$ (4 ml). Then $KNO_3$ (1.7 mmol, 171 mg) was added in one portion at 0° C. The resulting mixture was stirred at 0° C. for 3 h and at RT overnight. The mixture was poured onto ice. The product was filtered and washed with water to afford compound 2,5,6-tribromo-4-nitro-1H-1,3-benzodiazole (487 mg). 1H NMR (600 MHz, DMSO) δ 14.33 (s, 1H), 8.22 (s, 1H); m/z 399.7; rt 3.0 min.

The following compound was prepared by the procedure of Method 2A, using the appropriate starting materials:

| Method | Compound | 1HNMR (400 MHz) | m/z | RT | SM |
|---|---|---|---|---|---|
| 2B | 2-bromo-5,6-dichloro-1-ethyl-4-nitro-1,3-benzodiazole 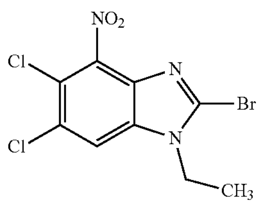 | — | 339.7 | 3.5 | 2-bromo-5,6-dichloro-1-ethyl-1,3-benzodiazole 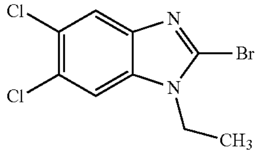 Method 3J |

3.11.3. Method 3A

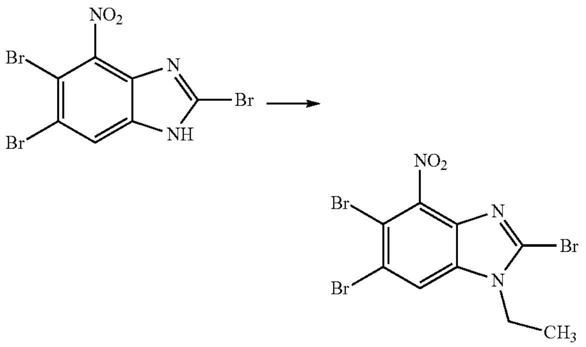

2,5,6-tribromo-1-ethyl-4-nitro-1H-1,3-benzodiazole 2,5,6-tribromo-4-nitro-1H-1,3-benzodiazole (Method 2) (28 mmol, 10 g) was dissolved in acetonitrile (200 ml), and then NaOH (33.8 mmol, 1.35 g) was added. The resulting mixture was stirred at temperature for 0.5 h. Next 2-iodoethane (225 mmol, 35.16 g) was added, and the mixture was heated to 85° C. until the reaction was complete (20 h) by LC/MS. The mixture was allowed to cool to RT and concentrated in-vacuo. The product was taken up into ethyl acetate and washed with water. The organic extract was dried over MgSO4, filtered and concentrated. The product was purified on silica gel using EA/hex (1:1) to afford compound 2,5,6-tribromo-1-ethyl-4-nitro-1H-1,3-benzodiazole (mg). 1H NMR (600 MHz, DMSO) δ 8.58 (s, 1H), 4.36 (q, J=7.2 Hz, 2H), 1.33 (t, J=7.2 Hz, 3H); m/z 427.8; rt 3.5 min.

The following compounds were prepared by the procedure of Method 3A, using the appropriate starting materials:

| Method | Compound | 1HNMR (400 MHz) | m/z | RT | SM |
|---|---|---|---|---|---|
| 3B | 2,5,6-tribromo-4-nitro-1-(propan-2-yl)-1H-1,3-benzodiazole<br>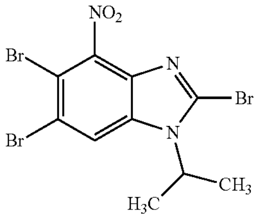 | — | 441.7 | 3.7 | 2,5,6-tribromo-4-nitro-1H-1,3-benzodiazole:<br>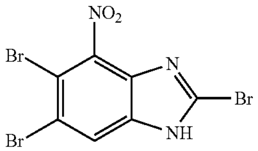<br>Method 2A And Isopropyl Iodide (commercial) |
| 3C | 2,5,6-tribromo-1-(cyclopropylmethyl)-4-nitro-1H-1,3-benzodiazole<br>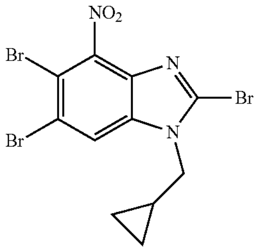 [SMILES: O=[N+]([O-])c1c(Br)c(Br)cc2c1nc(Br)n2CC1CC1] | 1H NMR (600 MHz, DMSO) δ 8.62 (s, 1H), 4.25 (d, J = 7.2 Hz, 2H), 1.35-1.27 (m, 1H), 0.55-0.51 (m, 2H), 0.50-0.48 (m, 2H). | 455.8 | 4.0 | 2,5,6-tribromo-4-nitro-1H-1,3-benzodiazole:<br>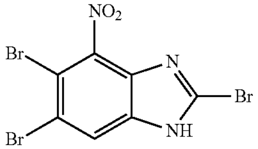<br>Method 2A and Methylcyclopropyl iodide (commercial) |
| 3D | 2,5,6-tribromo-1-(2-methylpropyl)-4-nitro-1H-1,3-benzodiazole<br>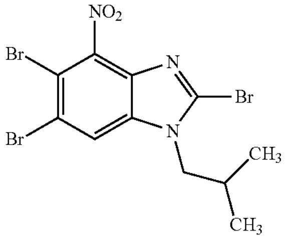 [SMILES: CC(C)Cn1c(Br)nc2c([N+](=O)[O-])c(Br)c(Br)cc21] | $^1$H NMR (600 MHz, DMSO) δ 8.60 (s, 1H), 4.14 (d, J = 7.7 Hz, 2H), 2.24-2.14 (m, 1H), 0.90 (d, J = 6.7 Hz, 6H). | 455.8 | 3.9 | 2,5,6-tribromo-4-nitro-1H-1,3-benzodiazole:<br>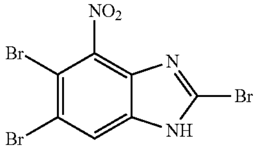<br>Method 2A And Isobutyl Iodide (commercial) |
| 3E | 2,5,6-tribromo-1-(2-methoxyethyl)-4-nitro-1H-1,3-benzodiazole<br>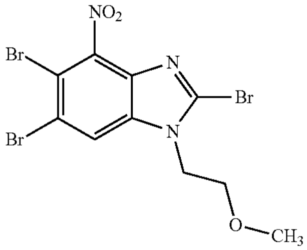 [SMILES: COCCn1c(Br)nc2c([N+](=O)[O-])c(Br)c(Br)cc21] | — | 457.7 | 15.4 | 2,5,6-tribromo-4-nitro-1H-1,3-benzodiazole:<br>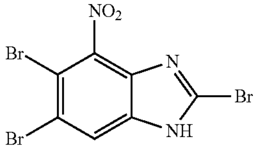<br>Method 2A And 1-Bromo-2-methoxyethane (commercial) |

-continued

| Method | Compound | 1HNMR (400 MHz) | m/z | RT | SM |
|---|---|---|---|---|---|
| 3F | 2,5,6-tribromo-4-nitro-1-propyl-1H-1,3-benzodiazole<br>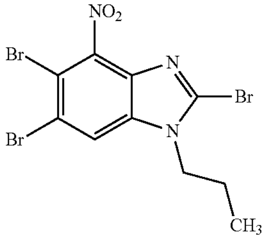 [SMILES: CCCn1c(Br)nc2c([N+](=O)[O-])c(Br)c(Br)cc21] | 1H NMR (600 MHz, DMSO) δ 8.60 (s, 1H), 4.28 (t, J = 7.3 Hz, 2H), 1.81-1.73 (n, 2H), 0.89 (t, J = 7.4 Hz, 3H). | 441.8 | 3.7 | 2,5,6-tribromo-4-nitro-1H-1,3-benzodiazole:<br>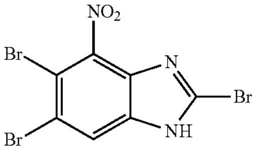<br>Method 2A And 1-Propyl Iodide (commercial) |
| 3G | 2,5,6-tribromo-1-(propan-2-yl)-1H-1,3-benzodiazole<br>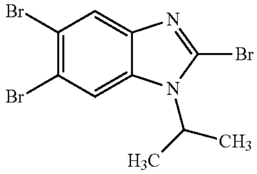 | 1H NMR (600 MHz, DMSO) δ 8.25 (s, 1H), 8.04 (s, 1H), 4.91 (hept, J = 6.9 Hz, 1H), 1.58 (d, J = 7.0 Hz, 6H). | 396.7 | 3.7 | 2,5,6-tribromo-1H-1,3-benzodiazole<br>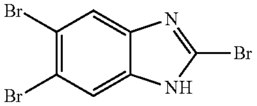<br>Method 1 And isopropyl iodide |
| 3H | 2,5,6-tribromo-1-ethyl-1H-1,3-benzodiazole<br>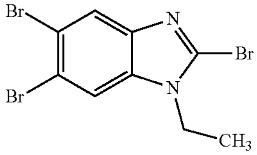 | 1H NMR (600 MHz, DMSO) δ 8.23 (s, 1H), 8.04 (s, 1H), 4.29 (q, J = 7.2 Hz, 2H), 1.30 (t, J = 7.2 Hz, 3H). | 384.7 | 3.4 | 2,5,6-tribromo-1H-1,3-benzodiazole<br>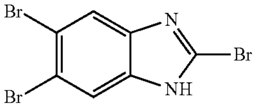<br>Method 1 And ethyl iodide |
| 3J | 2-bromo-5,6-dichloro-1-ethyl-1,3-benzodiazole<br>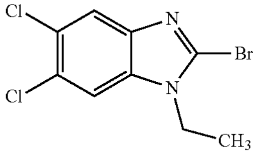 | — | 294.7 | 3.4 | 2-bromo-5,6-dichloro-3H-1,3-benzodiazole<br>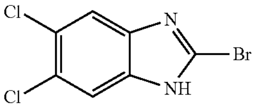<br>Method 14A and ethyl iodide |
| 3K | 2,5,6-tribromo-4-nitro-1-[3-(oxan-2-yloxy)propyl]-1H-1,3-benzodiazole<br>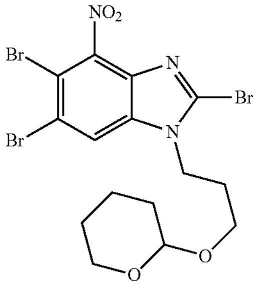 [SMILES: O=[N+]([O-])c1c(Br)c(Br)cc2c1nc(Br)n2CCCOC1CCCCO1] | — | 543.7 | 3.8 | 2,5,6-tribromo-4-nitro-1H-1,3-benzodiazole:<br>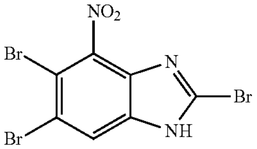<br>Method 2A And 2-(3-bromopropoxy)oxane (commercial) |

-continued

| Method | Compound | 1HNMR (400 MHz) | m/z | RT | SM |
|---|---|---|---|---|---|
| 3L | 2,5,6-tribromo-4-nitro-1-[2-(oxan-2-yloxy)ethyl]-1H-1,3-benzodiazole 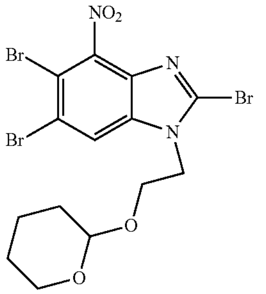 [SMILES: O=[N+]([O-])c1c(Br)c(Br)cc2c1nc(Br)n2CCOC1CCCCO1] | — | 527.7 | 3.7 | 2,5,6-tribromo-4-nitro-1H-1,3-benzodiazole: 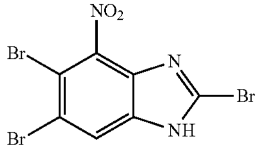 Method 2A And 2-(3-bromoethoxy)oxane (commercial) |

3.11.4. Method 4A

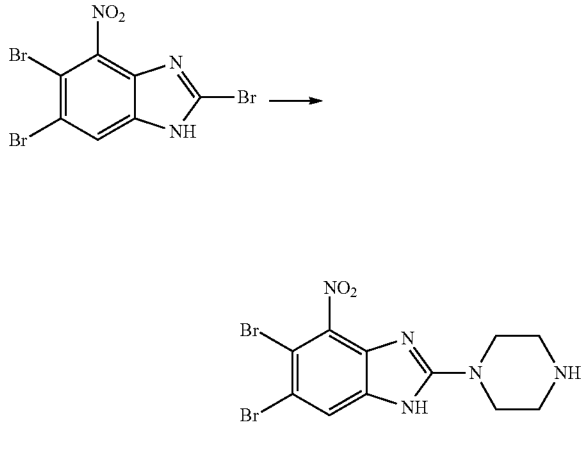

tert-butyl 4-(5,6-dibromo-4-nitro-1H-1,3-benzodiazol-2-yl)piperazine-1-carboxylate 2,5,6-tribromo-4-nitro-1H-1,3-benzodiazole (Method 2A)(17.5 mmol, 7 g) was dissolved in EtOH (30 ml) with N-Boc-piperazine (52.5 mmol, 9.78 g). The resulting mixture was stirred at 120° C. until the reaction was complete (8 h) by LC/MS. The mixture was allowed to cool to RT and concentrated in-vacuo. The product was purified on silica gel using DCM/MeOH (99:1) to afford tert-butyl 4-(5,6-dibromo-4-nitro-1H-1,3-benzodiazol-2-yl)piperazine-1-carboxylate (6 g). m/z 405.8; rt 2.4 min.

The following compounds were prepared by the procedure of Examples 4A, using the appropriate starting materials:

| Method | Compound | 1HNMR (400 MHz) | m/z | RT | SM |
|---|---|---|---|---|---|
| 4B | tert-butyl 4-(5,6-dibromo-1-ethyl-4-nitro-1H-1,3-benzodiazol-2-yl)piperazine-1-carboxylate 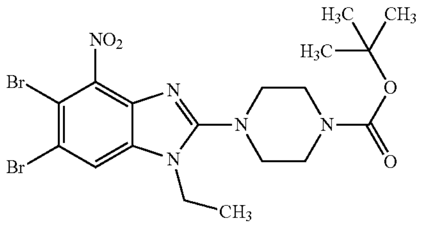 [SMILES: CCn1c(N2CCN(C(=O)OC(C)(C)C)CC2)nc2c([N+](=O)[O-])c(Br)c(Br)cc21] | 1H NMR (600 MHz, DMSO) δ 7.88 (s, 1H), 7.78 (s, 1H), 4.09 (q, J = 7.2 Hz, 2H), 3.55-3.47 (m, 4H), 3.24-3.20 (m, 4H), 1.43 (s, 9H), 1.31 (t, J = 7.2 Hz, 3H). | 533.9 | 3.9 | 2,5,6-tribromo-1-ethyl-4-nitro-1H-1,3-benzodiazole 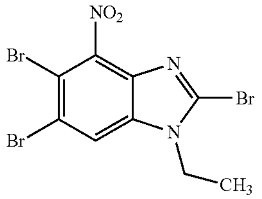 Method 3A and tert-butyl piperazine-1-carboxylate |

-continued

| Method | Compound | 1HNMR (400 MHz) | m/z | RT | SM |
|---|---|---|---|---|---|
| 4C | tert-butyl N-{3-[(5,6-dibromo-4-nitro-1H-1,3-benzodiazol-2-yl)amino]propyl}carbamate 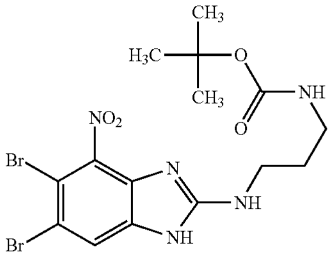 [SMILES: CC(C)(C)OC(=O)NCCCNc1nc2c([N+](=O)[O-])c(Br)c(Br)cc2[nH]1] | — | 494.1 | 3.5 | 2,5,6-tribromo-4-nitro-1H-1,3-benzodiazole 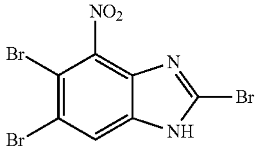 Method 2A and tert-butyl N-(3-aminopropyl)carbamate |
| 4D | tert-butyl N-[1-(5,6-dibromo-1-ethyl-4-nitro-1H-1,3-benzodiazol-2-yl)piperidin-3-yl]carbamate 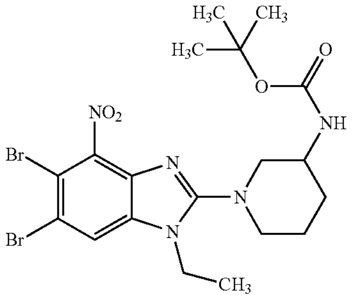 [SMILES: CCn1c(N2CCCC(NC(=O)OC(C)(C)C)C2)nc2c([N+](=O)[O-])c(Br)c(Br)cc21] | — | 548.0 | 3.9 | 2,5,6-tribromo-1-ethyl-4-nitro-1H-1,3-benzodiazole 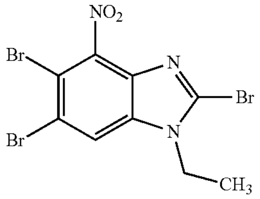 Method 3A and tert-butyl N-(piperidin-3-yl)carbamate |
| 4E | tert-butyl N-{3-[(5,6-dibromo-1-ethyl-4-nitro-1H-1,3-benzodiazol-2-yl)amino]propyl}carbamate 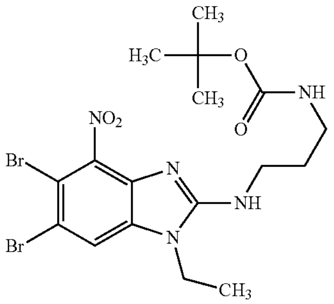 [SMILES: CCn1c(NCCCNC(=O)OC(C)(C)C)nc2c([N+](=O)[O-])c(Br)c(Br)cc21] | — | 522.0 | 3.6 | 2,5,6-tribromo-1-ethyl-4-nitro-1H-1,3-benzodiazole 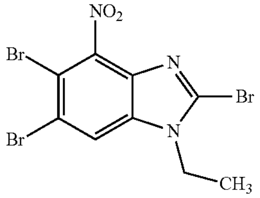 Method 3A And tert-butyl N-(3-aminopropyl)carbamate |

-continued

| Method | Compound | 1HNMR (400 MHz) | m/z | RT | SM |
|---|---|---|---|---|---|
| 4F | tert-butyl 4-(5,6-dibromo-1-ethyl-1H-1,3-benzodiazol-2-yl)piperazine-1-carboxylate 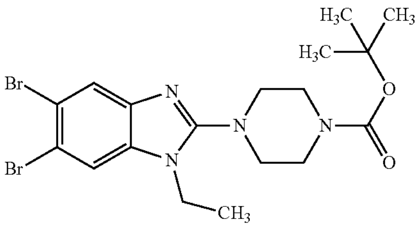 [SMILES: CCn1c(N2CCN(C(=O)OC(C)(C)C)CC2)nc2cc(Br)c(Br)cc21] | | 489.0 | 3.5 | 2,5,6-tribromo-1-ethyl-1H-1,3-benzodiazole (Method 3H) 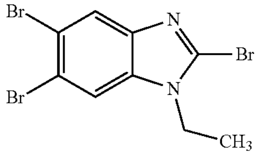 Method 3H And tert-butyl piperazine-1-carboxylate |
| 4G | tert-butyl N-{3-[(5,6-dibromo-1-ethyl-1H-1,3-benzodiazol-2-yl)amino]propyl}carbamate 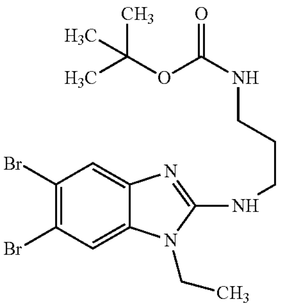 [SMILES: CCn1c(NCCCNC(=O)OC(C)(C)C)nc2cc(Br)c(Br)cc21] | | 476.9 | 2.8 | 2,5,6-tribromo-1-ethyl-1H-1,3-benzodiazole 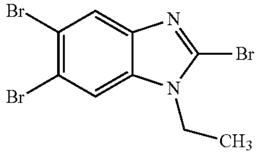 Method 3H And tert-butyl N-(3-aminopropyl)carbamate |
| 4H | tert-butyl (3S)-3-{5,6-dibromo-2-[(3R)-3-{[(tert-butoxy)carbonyl]amino}pyrrolidin-1-yl]-1H-1,3-benzodiazol-1-yl}pyrrolidine-1-carboxylate 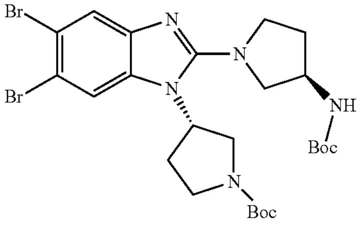 [SMILES: CC(C)(C)OC(=O)N[C@@H]1CCN(c2nc3cc(Br)c(Br)cc3n2[C@H]2CCN(C(=O)OC(C)(C)C)C2)C1] | | 630.1 | 3.2 | tert-butyl (3S)-3-(2,5,6-tribromo-1H-1,3-benzodiazol-1-yl)pyrrolidine-1-carboxylate Method 17A 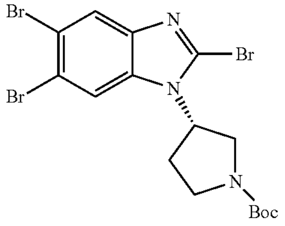 |

3.11.5. Method 5A

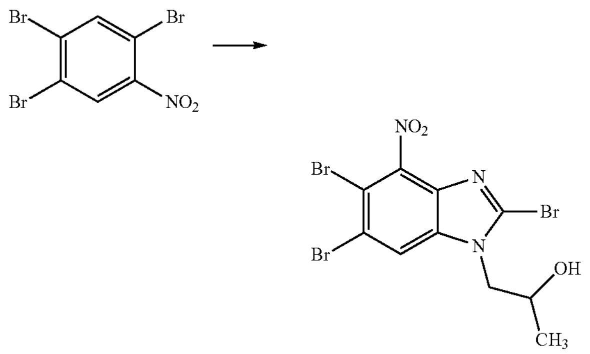

1-(2,5,6-tribromo-4-nitro-1H-1,3-benzodiazol-1-yl) propan-2-ol 1,2,4-tribromo-5-nitrobenzene (10 mmol, 2.5 g) is dissolved in THF (75 ml). Triethylamine (7.6 mmol, 773 mg) and amino-2-propanol (7.6 mmol, 574 mg) were added. The resulting mixture was stirred at 45° C. until the reaction was complete (24 hours) by LC/MS. The mixture was allowed to cool to RT and concentrated in-vacuo. The product was purified on silica gel using EA/hex (1:4). The obtained product (1.5 g, 4 mmol) was suspended in a mixture of EtOH, AcOH and $H_2O$ (2:2:1), then iron filings (17 mmol, 0.947 mg) were added. The mixture was sonicated for 5 hours. The product was purified on silica gel using EA/hex (1:1). The obtained product was suspended in EtOH (30 ml), and $H_2O$ (2 ml) was added. Next potassium ethyl xanthogenate (3.8 mmol, 608 mg) was added in one portion. The resulting mixture was stirred at 85° C. until the reaction was complete (24 hours) by LC/MS. The reaction was cooled down to 60° C., and $H_2O$ (30 ml) was added, followed by addition of $H_2O$/AcOH (2:1). The mixture was allowed to cool to RT, and solid was filtered and washed with $H_2O$. The obtained product (2 mmol, 740 mg) was dissolved in MeOH (20 ml). The reaction mixture was cooled to 0° C. and hydrobromic acid (0.4 ml) was added, then bromine (8 mmol, 1.3 g) was added. The resulting mixture was stirred at RT overnight, then $Na_2SO_4$ was added. Next MeOH was evaporated. The aqueous layers extracted with DCM. The product was purified on silica gel using EA/hex (1:1). The obtained product (1 mmol, 400 mg) was dissolved in concentration $H_2SO_4$ (7 ml). Next $KNO_3$ (1.1 mmol, 118 mg) was added in one portion at 0° C. The resulting mixture was stirred at 0° C. for 3 h and at RT overnight. Then the mixture was poured onto ice. The product was filtered and washed with water. The product was purified on silica gel using DCM/MeOH (95:5) to afford 2,5,6-tribromo-1-(propan-2-ol)-4-nitro-1H-1,3-benzodiazole (200 mg). m/z 457.7; rt 3.3.

The following compounds were prepared by the procedure of Method 5A, using the appropriate starting materials:

| Method | Compound | 1HNMR (400 MHz) | m/z | RT | SM |
|---|---|---|---|---|---|
| 5B | 2,5-dibromo-6-fluoro-1-(propan-2-yl)-1H-1,3-Benzodiazole 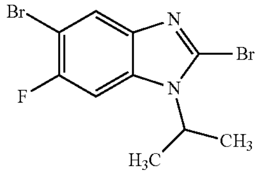 | — | 336.8 | 3.4 | 1-bromo-2,4-difluoro-5-nitrobenzene 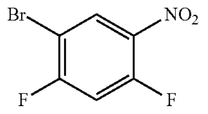 Commercial and isopropyl amine |
| 5C | 2,5,6-tribromo-1-cyclobutyl-4-nitro-1H-1,3-benzodiazole 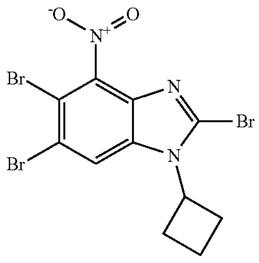 | — | 453.7 | 3.8 | 1,2,4-tribromo-5-nitrobenzene 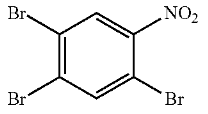 Commercial and cyclobutyl amine |

3.11.6. Method 7A

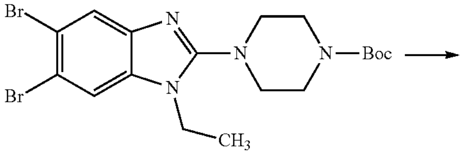

-continued

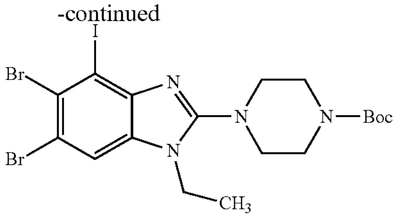

tert-butyl 4-(5,6-dibromo-1-ethyl-4-iodo-1H-1,3-benzodiazol-2-yl)piperazine-1-carboxylate tert-butyl 4-(5,6-dibromo-1-ethyl-1H-1,3-benzodiazol-2-yl)piperazine-1-carboxylate (6 mmol, 3 g) was dissolved in dry THF (20 ml). The resulting mixture was cooled down to −78° C., then magnesium chloro-2,26,6-tetramethylpiperidine lithium chloride complex was added dropwise at this temperature. The resulting mixture was stirred at −78° C. for 2 hours. The mixture was allowed to warm to −20° C. and a1M solution of $I_2$ in THF was added dropwise. The mixture was warmed to RT and stirred for 1.5 h. The reaction mixture was poured onto a mixture of ice/$NH_4Cl$, then sat. $Na_2SO_3$ was added. The aqueous mixture was extracted with ethyl acetate.

The organic extract was dried over MgSO4, filtered and concentrated. The product was purified on silica gel using EA/hex (1:1) to afford tert-butyl 4-(5,6-dibromo-1-ethyl-4-iodo-1H-1,3-benzodiazol-2-yl)piperazine-1-carboxylate (1.5 g). m/z 614.8; rt 4.4 min.

The following compounds were prepared by the procedure of Method 7A, using the appropriate starting materials:

| Method | Compound | 1HNMR (400 MHz) | m/z | RT | SM |
|---|---|---|---|---|---|
| 7B | 2,5,6-tribromo-4-iodo-1-(propan-2-yl)-1H-1,3-benzodiazole 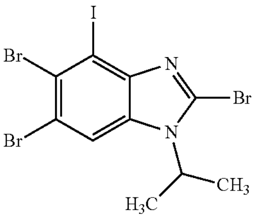 [SMILES: CC(C)n1c(Br)nc2c(I)c(Br)c(Br)cc21] | | 524.6 | 4.0 | 2,5,6-tribromo-1-(propan-2-yl)-1H-1,3-benzodiazole 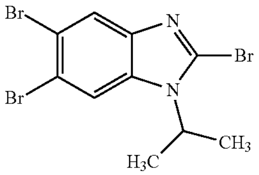 Method 3G |
| 7C | tert-butyl N-{3-[(5,6-dibromo-1-ethyl-4-iodo-1H-1,3-benzodiazol-2-yl)amino]propyl}carbamate 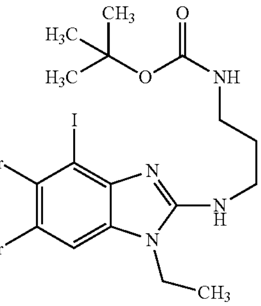 | | 602.9 | 4.3 | tert-butyl N-{3-[(5,6-dibromo-1-ethyl-1H-1,3-benzodiazol-2-yl)amino]propyl}carbamate 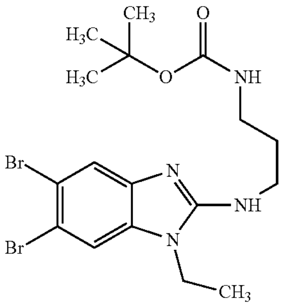 Method 4G |
| 7E | 2,5,6-tribromo-1-ethyl-4-iodo-1,3-benzodiazole 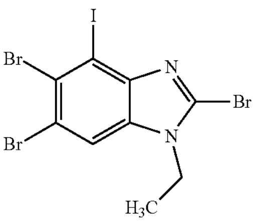 | | 510.6 | 3.6 | 2,5,6-tribromo-1-ethyl-1H-1,3-benzodiazole 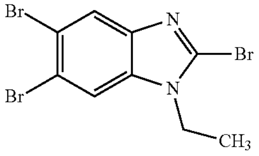 Method 3H |

-continued

| Method | Compound | 1HNMR (400 MHz) | m/z | RT | SM |
|---|---|---|---|---|---|
| 7F | tert-butyl (3S)-3-{5,6-dibromo-2-[(3R)-3-{[(tert-butoxy)carbonyl]amino}pyrrolidin-1-yl]-4-iodo-1H-1,3-benzodiazol-1-yl}pyrrolidine-1-carboxylate<br>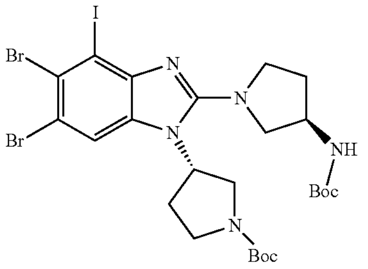 [SMILES: CC(C)(C)OC(=O)N[C@@H]1CCN(c2nc3c(I)c(Br)c(Br)cc3n2[C@H]2CCN(C(=O)OC(C)(C)C)C2)C1] | — | 756 | 4.3 | tert-butyl (3S)-3-{5,6-dibromo-2-[(3R)-3-{[(tert-butoxy)carbonyl]amino}pyrrolidin-1-yl]-1H-1,3-benzodiazol-1-yl}pyrrolidine-1-carboxylate<br>Method 4H<br>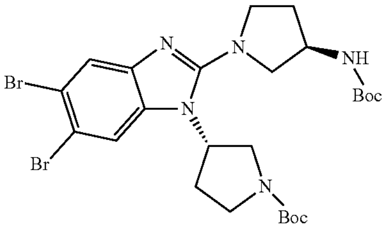 |

3.11.7. Method 8A

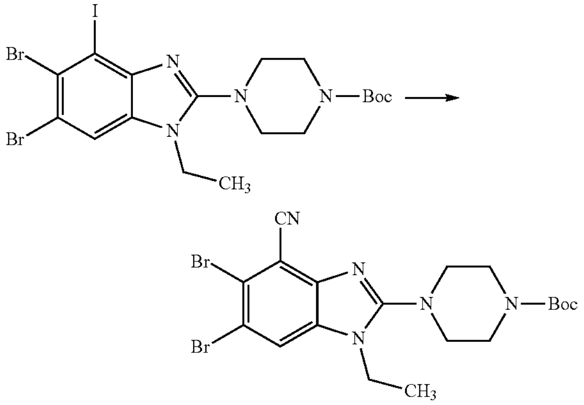

tert-butyl 4-(5,6-dibromo-1-ethyl-4-cyano-1H-1,3-benzodiazol-2-yl)piperazine-1-carboxylate tert-butyl 4-(5,6-dibromo-1-ethyl-4-iodo-1H-1,3-benzodiazol-2-yl)piperazine-1-carboxylate (0.2 mmol, 100 mg) was dissolved in acetonitrile (1.5 ml). Then copper (I) cyanide was added. The reaction was carried out in a microwave at 160° C. for 25 min.

The mixture was concentrated in-vacuo. The product was taken up into ethyl acetate and washed with water. The organic extract was dried over MgSO4, filtered and concentrated. The product was purified on silica gel using EA/hex (1:4) to afford tert-butyl 4-(5,6-dibromo-1-ethyl-4-cyano-1H-1,3-benzodiazol-2-yl)piperazine-1-carboxylate (80 mg). m/z 423.7; rt 3.3 min.

The following compounds were prepared by the procedure of Method 8A, using the appropriate starting materials:

| Method | Compound | 1HNMR (400 MHz) | m/z | RT | SM |
|---|---|---|---|---|---|
| 8B | 2,5,6-tribromo-1-(propan-2-yl)-1H-1,3-benzodiazole-4-carbonitrile<br>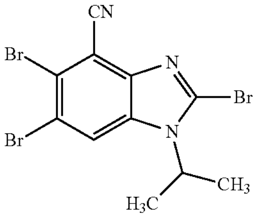 | — | 423.7 | 3.5 | 2,5,6-tribromo-4-iodo-1-(propan-2-yl)-1H-1,3-benzodiazole<br>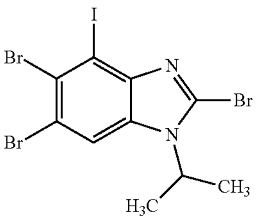<br>Method 7B |

-continued

| Method | Compound | 1HNMR (400 MHz) | m/z | RT | SM |
|---|---|---|---|---|---|
| 8C | 2,5,6-tribromo-1-ethyl-1,3-benzodiazole-4-carbonitrile 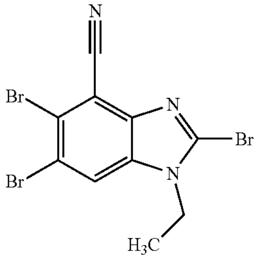 [SMILES: CCn1c(Br)nc2c(C#N)c(Br)c(Br)cc21] | — | 409.7 | 3.2 | 2,5,6-tribromo-1-ethyl-4-iodo-1,3-benzodiazole Method 7E 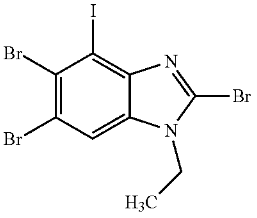 |
| 8D | tert-butyl (3S)-3-{5,6-dibromo-2-[(3R)-3-{[(tert-butoxy)carbonyl]amino} pyrrolidin-1-yl]-4-cyano-1H-1,3-benzodiazol-1-yl}pyrrolidine-1-carboxylate 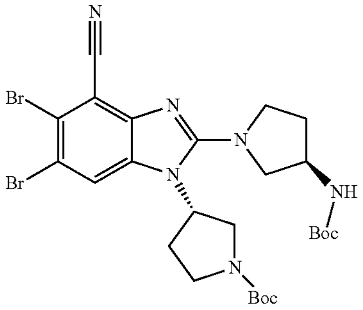 [SMILES: CC(C)(C)OC(=O)N[C@@H]1CCN(c2nc3c(C#N)c(Br)c(Br)cc3n2[C@H]2CCN(C(=O)OC(C)(C)C)C2)C1] | — | 654.9 | 4.3 | tert-butyl (3S)-3-{5,6-dibromo-2-[(3R)-3-{[(tert-butoxy)carbonyl]amino}pyrrolidin-1-yl]-4-iodo-1H-1,3-benzodiazol-1-yl}pyrrolidine-1-carboxylate Method 7F 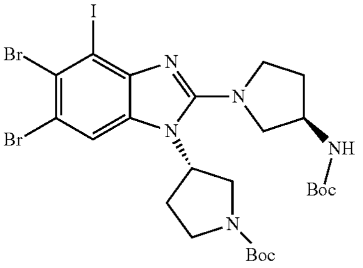 |

3.11.8. Method 13

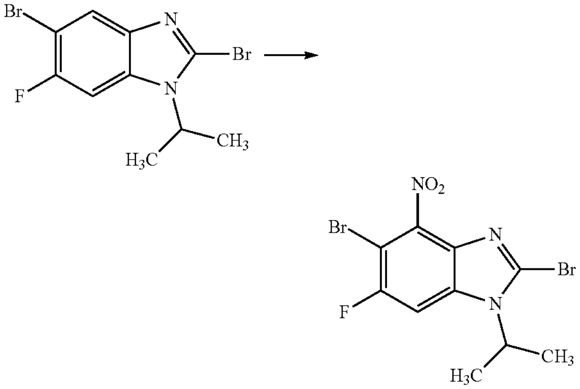

2,5-dibromo-6-fluoro-4-nitro-1-(propan-2-yl)-1H-1,3-benzodiazole 2,5-dibromo-6-fluoro-1-(propan-2-yl)-13.11H-1,3-benzodiazole (Method 5B) (0.15 mmol, 50 mg) was dissolved in TFA (0.5 ml). Then $HNO_3$ (2.9 mmol, 0.12 ml) was added slowly at RT. The resulting mixture was stirred at RT for overnight. The mixture was poured onto ice. The product was filtered and washed with water to afford compound 2,5,6-tribromo-4-nitro-1H-1,3-benzodiazole (487 mg). 1H NMR (600 MHz, DMSO) 14.33 (s, 1H), 8.22 (s, 1H); m/z 381; rt 3.4.

3.11.9. Method 14A

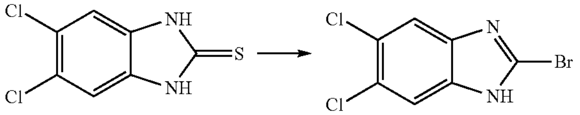 [SMILES: S=c1[nH]c2cc(Cl)c(Cl)cc2[nH]1 ; Clc1cc2nc(Br)[nH]c2cc1Cl]

2-bromo-5,6-dichloro-1H-1,3-benzodiazole 5,6-dichloro-2,3-dihydro-1H-1,3-benzodiazole-2-thione (2 mmol, 438 mg) was dissolved in MeOH (20 ml). The reaction mixture was cooled to 0° C. and hydrobromic acid (0.4 ml) was added, then bromine (8 mmol, 1.3 g) was added. The resulting mixture was stirred at RT overnight, then $Na_2SO_4$ was added. Next MeOH was evaporated. The aqueous layer was extracted with DCM. The product was purified on silica gel using EA/hex (1:1) to afford yellow solid (1 mmol, 260 mg), m/z 266.7; rt 2.8 min.

3.11.10. Method 15A

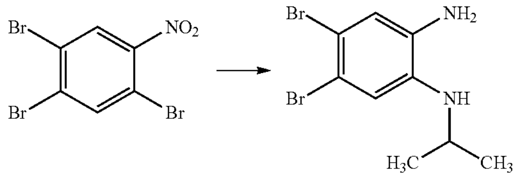

1,2,4-tribromo-5-nitrobenzene (14 mmol, 5 g) was dissolved in i-PrOH (130 ml). Triethylamine (15.3 mmol, 1.55 g) and 2-aminopropane (15.3 mmol, 0.91 g) were added. The resulting mixture was stirred at 90° C. until the reaction was complete (24 hours) by LC/MS. The mixture was allowed to cool to RT and concentrated in-vacuo. The product was purified on silica gel using EA/hex (1:4). The obtained product (3.33 g, 9.85 mol) was suspended in a mixture of EtOH, AcOH and $H_2O$ (2:2:1), then iron filings (49.3 mmol, 2.75 g) were added. The mixture was sonicated for 5 hours. The product was purified on silica gel using EA/hex (1:1). yield (2.8 g) m/z 308, rt. 3.2 min.

3.11.11. Method 16A

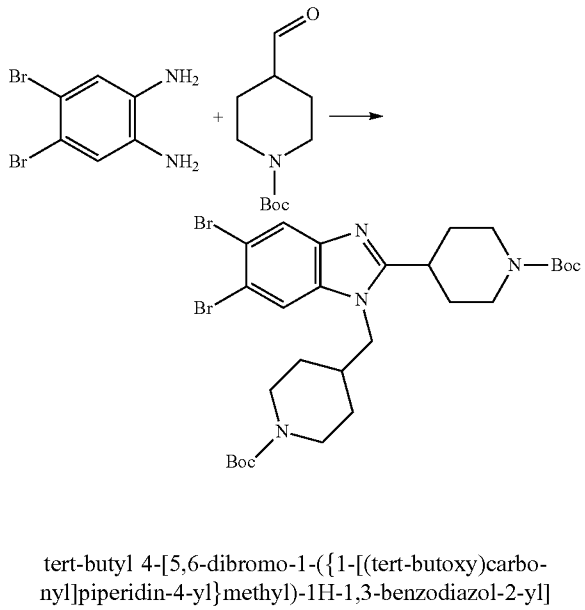

tert-butyl 4-[5,6-dibromo-1-({1-[(tert-butoxy)carbonyl]piperidin-4-yl}methyl)-1H-1,3-benzodiazol-2-yl] piperidine-1-carboxylate (16A)

4,5-dibromobenzene-1,2-diamine (100 mg, 0.38 mmol) and tert-butyl 4-formylpiperidine-1-carboxylate (160 mg, 0.76 mmol) were stirred for 1 hour in 2,2,2trifluoroethanol. Then Solvent was evaporated and product was purified on silica gel using EA/hex (1/1). Yield: 20 mg. m/z 657.1, rt. 4.2 min.

3.11.12. Method 17A

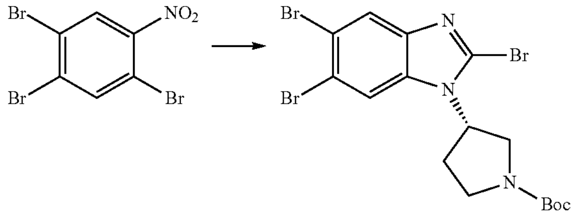 [SMILES: O=[N+]([O-])c1cc(Br)c(Br)cc1Br ; CC(C)(C)OC(=O)N1CC[C@H](n2c(Br)nc3cc(Br)c(Br)cc32)C1]

tert-butyl (3S)-3-(2,5,6-tribromo-1H-1,3-benzodiazol-1-yl)pyrrolidine-1-carboxylate (17A)

1,2,4-tribromo-5-nitrobenzene (4.4 mmol, 1.6 g) is dissolved in THF (75 ml). Triethylamine (7.6 mmol, 773 mg) and tert-butyl (3S)-3-aminopyrrolidine-1-carboxylate (4.4 mmol, 828 mg) were added. The resulting mixture was stirred at 100° C. until the reaction was complete (72 hours) by LC/MS. The mixture was allowed to cool to RT and concentrated in-vacuo. The product was purified on silica gel using EA/hex (1:4). The obtained product (1.86 g, 4 mmol) was suspended in a mixture of EtOH, AcOH and $H_2O$ (2:2:1), then iron filings (17 mmol, 0.947 mg) were added. The mixture was sonicated for 5 hours. The product was purified on silica gel using EA/hex (1:1). The obtained product was suspended in EtOH (30 ml), and $H_2O$ (2 ml) was added. Next potassium ethyl xanthogenate (3.8 mmol, 608 mg) was added in one portion. The resulting mixture was stirred at 85° C. until the reaction was complete (24 hours) by LC/MS. The reaction was cooled down to 60° C., and $H_2O$ (30 ml) was added, followed by addition of $H_2O$/AcOH (2:1). The mixture was allowed to cool to RT, and solid was filtered and washed with $H_2O$. The obtained product (2 mmol, 954 mg) was dissolved in MeOH (20 ml). The reaction mixture was cooled to 0° C. and hydrobromic acid (0.4 ml) was added, then bromine (8 mmol, 1.3 g) was added. The resulting mixture was stirred at RT overnight, then $Na_2SO_4$ was added. Next MeOH was evaporated. The aqueous layers extracted with DCM. The product was purified on silica gel using EA/hex (1:1). Yield 200 mg, m/z: 523.8, rt: 3.2 min.

3.12. Determination of the Inhibitory Activity In Vitro

Compounds of the present invention were tested for their inhibitory activity against Pim-1, Pim-2, Pim-3, Flt3 wt, Flt3 ITD, CDK2/E and DYRK1. The testing of the compounds was carried out using the ADP-Glo™ Kinase Assay from Promega Corporation (Madison, Wis., USA). Percent inhibition at 1 μM concentration was determined for the compounds and the results are shown in Table 1A.

The ADP-Glo™ Kinase Assay is a luminescent ADP detection assay to measure kinase activity by quantifying the amount of ADP produced during a kinase reaction. The kinase assay is performed in kinase assay buffer (5 mM MOPS, pH 7.5, 5 mM $MgCl_2$, 0.4 mM EDTA, 1.5 mM DTT). Test samples initially dissolved in DMSO at 10 mM were diluted with the assay buffer to 1000 nM. A 30 μL volume/well of a mixture of substrates containing ATP (final ATP concentration in each kinase assay was equal to its apparent ATP Km).

Pim-1 (Biocentrum, Kraków, Poland) was used at the concentration of 3 ng/well and the peptide KKRNRTLTV (Lipopharm, Gdańsk, Poland) was used as a substrate at the concentration of 80 μM, the determined Km ATP was 50 μM.

Pim-2 (Biocentrum, Kraków, Poland) was used at the concentration of 120 ng/well and the peptide RSRHSSYPAGT (Lipopharm, Gdańsk, Poland) was used as a substrate at the concentration of 10 μM, the determined Km ATP was 6 μM.

Pim-3 (Biocentrum, Kraków, Poland) was used at the concentration of 80 ng/well and the peptide KKRNRTLTV (Lipopharm, Gdańsk, Poland) was used as a substrate at the concentration of 150 μM, the determined Km ATP was 36.6 μM.

Flt3 wt (Carna Bioscience, Kobe, Japan) was used at the concentration of 75 ng/well and the peptide EAIYAAPFAKKK (Lipopharm, Gdańsk, Poland) was used as a substrate at the concentration of 40 μM, the determined Km ATP was 65 μM.

FLT3-ITD (Human FLT3, C-terminal fragment, amino acids R571-S993; Product No.: 0778-0000-1, Proqinase, Germany) was used at the concentration of 70 ng/well, the peptide EAIYAAPFAKKK (Lipopharm, Gdańsk, Poland) was used as a substrate at the concentration of 250 μM, the determined Km ATP was 70 μM.

CDK2/E (Millipore Billerica, Mass., USA) was used at the concentration of 20 ng/well and the peptide PKTPKKAKKL (Lipopharm, Gdańsk, Poland) was used as a substrate at the concentration of 108 μM, the determined Km ATP was 130 μM.

DYRK1 (Milipore, Billerica, Mass., USA) was used at the concentration of 50 ng/well and the peptide KKISGRLSPIMTEQ (Lipopharm, Gdańsk, Poland) was used as a substrate at the concentration of 36 μM, the determined Km ATP was 35 μM.

The assay was performed in two steps: first, after the kinase reaction, an equal volume of ADP-Glo™ Reagent was added to terminate the kinase reaction and deplete the remaining ATP. Second, the Kinase Detection Reagent was added to simultaneously convert ADP to ATP and allowed the newly synthesized ATP to be measured using a luciferase/luciferin reaction. The luminescent signal generated was proportional to the ADP concentration produced and was correlated with kinase activity. A microplate spectrophotometer (Synergy 2 multi-mode microplate reader [BioTek]) was used for detecting the luminescence. The data was normalized and the percent of inhibition was obtained according to the following equation:

$$\%\ \text{inhibition} = 100\% - \left(\frac{\text{Lum}_{Cpd} \times 100\%}{\text{Lum}_{PC}}\right)$$

% inhibition-percent of inhibition $\text{Lum}_{Cpd}$-value of compound's luminescence (in *RLU*)

$\text{Lum}_{PC}$-value of positive control's luminescence (in *RLU*)

TABLE 1A

In vitro inhibitory activity of compounds of the present invention

| Ex. | Pim-1 % INH (1 μM) | Pim-2 % INH (1 μM) | Pim-3 % INH (1 μM) | Flt3wt % INH (1 μM) | Flt3ITD % INH (1 μM) | CDK2/E % INH (1 μM) | DYRK1A % INH (1 μM) |
|---|---|---|---|---|---|---|---|
| 1A | 81 | 22 | 65 | 26 | 81 | <5 | 66 |
| 1AA | >95 | 53 | >95 | 11 | | <5 | 40 |
| 1AB | >95 | 46 | 87 | <5 | | <5 | |
| 1AC | 94 | 18 | 72 | <5 | | <5 | |
| 1AD | >95 | 52 | >95 | 18 | | 26 | 72 |
| 1AE | 91 | 20 | >95 | <5 | | <5 | 66 |
| 1AF | >95 | 23 | 71 | <5 | | <5 | 47 |
| 1AG | >95 | 51 | 77 | 11 | | 43 | 62 |
| 1AH | >95 | 55 | >95 | 9 | 29 | 6 | 39 |
| 1AI | >95 | 22 | >95 | <5 | | 9 | 13 |
| 1AJ | >95 | 41 | 83 | <5 | | 28 | 37 |
| 1AK | 92 | 17 | >95 | <5 | | 16 | 75 |
| 1AL | >95 | 42 | >95 | <5 | | <5 | 49 |
| 1AM | 85 | | 53 | <5 | | 12 | |
| 1AN | 80 | 39 | 88 | <5 | | <5 | 19 |
| 1AO | 95 | | 59 | 26 | | | 15 |
| 1AP | >95 | 80 | 93 | 56 | | 13 | 70 |
| 1AQ | >95 | 40 | 83 | <5 | | <5 | 22 |
| 1AR | >95 | 30 | 52 | <5 | | <5 | 13 |
| 1AS | >95 | 77 | 93 | 22 | | <5 | 70 |
| 1AT | >95 | 85 | >95 | 45 | | <5 | 45 |
| 1AU | >95 | 52 | 68 | 7 | | <5 | |
| 1AV | >95 | 54 | 91 | 37 | | 12 | 46 |
| 1AW | >95 | 38 | 73 | <5 | | <5 | 37 |
| 1AX | >95 | 77 | 95 | 83 | 96 | | >95 |
| 1AY | >95 | 89 | >95 | 60 | | | 87 |
| 1AZ | >95 | 70 | 94 | 48 | | 38 | 72 |
| 1BA | >95 | 51 | 82 | 15 | | 6 | 52 |
| 1BB | >95 | 12 | 65 | 33 | | 29 | 61 |
| 1BC | 79 | 16 | 46 | <5 | | <5 | 14 |
| 1BD | >95 | 65 | 88 | 28 | | <5 | 53 |
| 1BG | >95 | 82 | >95 | 23 | | <5 | >95 |
| 1BH | 83 | 13 | 60 | <5 | | <5 | 22 |
| 1BI | >95 | 82 | 95 | 27 | | 22 | 79 |
| 1BJ | >95 | 82 | >95 | 31 | | <5 | 54 |
| 1BK | >95 | 63 | 92 | 20 | | <5 | 48 |

TABLE 1A-continued

In vitro inhibitory activity of compounds of the present invention

| Ex. | Pim-1 % INH (1 μM) | Pim-2 % INH (1 μM) | Pim-3 % INH (1 μM) | Flt3wt % INH (1 μM) | Flt3ITD % INH (1 μM) | CDK2/E % INH (1 μM) | DYRK1A % INH (1 μM) |
|---|---|---|---|---|---|---|---|
| 1BL | >95 | 33 | 81 | 54 | | 7 | 75 |
| 1BM | >95 | | 62 | <5 | | <5 | |
| 1BN | >95 | 29 | 77 | <5 | | <5 | 21 |
| 1BS | >95 | 21 | 48 | 39 | | 21 | 66 |
| 1BT | 70 | 16 | 56 | 23 | | 26 | 22 |
| 1BV | >95 | 82 | 91 | 39 | | 11 | 80 |
| 1C | 85 | 28 | 70 | <5 | | <5 | |
| 1CA | 77 | | | | | | 64 |
| 1CD | >95 | 62 | 72 | 5 | | <5 | 19 |
| 1CE | >95 | 53 | 76 | 12 | | <5 | 37 |
| 1CH | 82 | 10 | 32 | 17 | | 9 | 14 |
| 1CI | >95 | 64 | 75 | 19 | | 10 | 57 |
| 1CK | >95 | | | 30 | | 24 | 23 |
| 1CL | 82 | | | | | | 45 |
| 1CM | >95 | | | 26 | | | 95 |
| 1CN | 76 | | | | | | 27 |
| 1CO | >95 | 25 | 69 | 12 | | 27 | 30 |
| 1CP | >95 | | | 32 | | 39 | 44 |
| 1CQ | >95 | | | 17 | | 50 | 28 |
| 1CR | >95 | | | 44 | | | 70 |
| 1CS | >95 | 23 | 56 | 10 | | 9 | 37 |
| 1CT | >95 | 28 | 64 | 7 | | 6 | 22 |
| 1CX | >95 | | | 44 | | | 73 |
| 1CY | >95 | | | <5 | | | |
| 1D | >95 | 41 | 57 | <5 | | 21 | 16 |
| 1DA | 91 | | | | | | 36 |
| 1DC | >95 | | | 52 | | | >95 |
| 1DF | >95 | | | 18 | | | 55 |
| 1DG | >95 | | | | | | 92 |
| 1DJ | 95 | | | | | | >95 |
| 1DK | >95 | | | | | | 25 |
| 1DN | >95 | | | 55 | | | 38 |
| 1DO | 93 | | | | | | |
| 1DP | >95 | | | 57 | | | >95 |
| 1DQ | >95 | 53 | 86 | <5 | | <5 | 38 |
| 1DR | >95 | 59 | 91 | 18 | 50 | 28 | 65 |
| 1DS | >95 | 54 | | 8 | | 47 | 23 |
| 1DT | >95 | | | <5 | | 46 | 34 |
| 1DU | >95 | | | 12 | | 53 | 39 |
| 1DV | >95 | | | <5 | | 50 | 95 |
| 1DW | >95 | | | 8 | | 48 | |
| 1DY | >95 | 18 | 62 | <5 | | 7 | 20 |
| 1DZ | >95 | | | | | | |
| 1EA | >95 | | | | | | |
| 1EB | >95 | | | | | | |
| 1F | 90 | 36 | 83 | 6 | | <5 | 20 |
| 1G | 76 | 34 | 57 | 6 | | <5 | 12 |
| 1H | 58 | 25 | 38 | <5 | | <5 | 9 |
| 1L | >95 | 58 | >95 | 21 | | 32 | 47 |
| 1M | >95 | 44 | 73 | 46 | | <5 | >95 |
| 1N | >95 | 69 | >95 | 55 | | 39 | >95 |
| 1P | >95 | 36 | 77 | 37 | | <5 | 23 |
| 1Q | 86 | 22 | >95 | <5 | | 6 | 11 |
| 1R | >95 | 61 | >95 | 54 | | 25 | >95 |
| 1T | >95 | 81 | >95 | 21 | | 7 | 27 |
| 1U | >95 | 37 | >95 | 9 | | <5 | 35 |
| 1V | >95 | | >95 | <5 | | <5 | 11 |
| 1W | 89 | | 92 | <5 | | <5 | 40 |
| 1X | >95 | 36 | >95 | <5 | | 17 | 16 |
| 1Y | >95 | 25 | 86 | <5 | | 6 | |
| 1Z | 67 | | 92 | <5 | | <5 | |
| 21A | 87 | 42 | 71 | 37 | | 5 | 50 |
| 22A | 65 | | 28 | 8 | | <5 | |
| 22AA | >95 | 36 | 88 | 49 | | 11 | 43 |
| 22AB | >95 | 31 | 76 | <5 | | <5 | 17 |
| 22AC | >95 | 30 | 61 | 7 | | <5 | 16 |
| 22AD | >95 | | | | | | 31 |
| 22AE | 76 | | | | | | 95 |
| 22G | >95 | 47 | 87 | 13 | | 5 | |
| 22H | >95 | | 71 | <5 | | 16 | |
| 22I | >95 | 28 | 84 | <5 | | <5 | 20 |
| 22J | >95 | 31 | 79 | <5 | 5 | <5 | 16 |
| 22K | >95 | 40 | 85 | 23 | | <5 | 28 |
| 22L | 80 | | >95 | <5 | | <5 | 17 |

TABLE 1A-continued

In vitro inhibitory activity of compounds of the present invention

| Ex. | Pim-1 % INH (1 μM) | Pim-2 % INH (1 μM) | Pim-3 % INH (1 μM) | Flt3wt % INH (1 μM) | Flt3ITD % INH (1 μM) | CDK2/E % INH (1 μM) | DYRK1A % INH (1 μM) |
|---|---|---|---|---|---|---|---|
| 22M | 74 | 18 | 29 | <5 | | <5 | |
| 22N | 82 | 23 | 44 | <5 | | <5 | 21 |
| 22W | 80 | | 57 | <5 | | <5 | |
| 22X | 74 | | 56 | <5 | | <5 | 39 |
| 22Z | >95 | 37 | 85 | 73 | | | 63 |
| 26A | >95 | 68 | 90 | 65 | 93 | 36 | >95 |
| 26B | >95 | | | 43 | | 36 | |
| 26C | >95 | | | 55 | | 55 | |
| 26D | >95 | | | 38 | | 36 | |
| 27A | 56 | | | | | | |
| 2A | >95 | 49 | 89 | 66 | 93 | 44 | >95 |
| 2B | 53 | | | <5 | | <5 | 61 |
| 2D | >95 | 53 | >95 | 55 | | 21 | >95 |
| 2E | 79 | 63 | 56 | 25 | | 15 | 72 |
| 2F | >95 | 70 | 89 | 78 | | 15 | >95 |
| 2G | 71 | | 34 | 10 | | <5 | 25 |
| 2H | >95 | 56 | >95 | <5 | | <5 | 62 |
| 2I | >95 | 75 | >95 | 89 | | 60 | >95 |
| 2L | 67 | | | | | | |
| 3A | >95 | | | <5 | | 20 | |
| 3B | >95 | | | | | | 18 |
| 4A | 81 | | | | | | |
| 4B | >95 | | | | | | 51 |
| 8A | 82 | 14 | 92 | 11 | | <5 | 46 |
| 8G | >95 | | | | | | |
| 9A | >95 | 15 | 66 | 76 | | <5 | 77 |
| 9B | 59 | | | | | | 33 |

Based on the activity shown in the in vitro tests, the compounds of the present invention are useful PIM-kinase inhibitors since they inhibit Pim-1 to a high degree (>50% when tested at 1 μM). The compounds according to the present invention also inhibit Pim-2 and Pim-3 to a rather high degree. Some of the compounds inhibit Flt3 wt, whereas others do not show an inhibitory activity against Flt3 wt. The compounds of the present invention fail to substantially inhibit CDK2/E, whereas the compounds of the present invention display a rather strong inhibitory efficacy against DYRK1.

Selected compounds were also tested for their binding properties against FLT3 kinase mutants using suitable in vitro assays (performed according to standard assays at DiscoveRx Corporation). The compounds show strong binding to the main oncogenic mutants of the FLT3 kinase, see Table 1B.

TABLE 1B

Binding activity of compounds 1A and 2A towards FLT wildtype and kinase mutants

| Kd[nM] | 1A | 2A |
|---|---|---|
| FLT3wt | 400 | 130 |
| FLT3(ITD) | 74 | 18 |
| FLT3(D835H) | 120 | 28 |
| FLT3(D835Y) | 46 | 15 |

3.13. Determination of the Growth Inhibitory Activity in Cancer Cell Lines

The following cell lines, were obtained and used in tests as outlined below:

- Human myelomonocytic, biphenotypic leukemia MV4-11 cells (harboring a Flt3-ITD mutation);
- Human Acute Myeloid Leukemia MOLM16 cells;
- Human Acute Myeloid Leukemia MOLM13 cells (harboring a Flt3-ITD mutation);
- Human Myeloid Leukemia KG-1 cells;
- Human erythroleukemia HEL92 cells;
- Human mantle cell lymphoma Jeko-1 cells;
- Human hepatocellular carcinoma HepG2 cells; and
- Human colon adenocarcinoma SW-480 cells.

The assays were carried out according to the following protocol, which is described as an example for the MV4-11 cells:

Ten thousand MV4-11 cells were inoculated into each well of a 96-well microplate (manufactured by Corning Corp.) using Iscove's MDM medium (culture medium) containing 10% fetal calf serum (FCS). The same day, a dimethyl sulfoxide (DMSO) solution of each test compound prepared in a concentration of 10 mmol/L was further diluted with DMSO to the desired concentrations (0.1, 0.5, 1, 2.5, 5 and 10 micromol/L), and the diluted solution was added to each well. The individual wells were further cultured in 5% carbon dioxide at 37° C. for 72 hours. Following this incubation, a standart MTS assay according to the Manufacturer's instructions (CellTiter96® AQueous One Solution Cell Proliferation Assay, Promega) was performed. Briefly, 10 μl MTS (3-(4,5-Dimethyl-2-thiazolyl)-5-(carboxymethoxyphenyl)-2-(4-sulfophenyl)-2H-tetrazolium was added to each well, and culturing was performed in 5% carbon dioxide at 37° C. for 2 hours. After this incubation and using a microplate spectrophotometer (Synergy 2 multi-mode microplate reader (BioTek)), the absorbance of each well was measured at 490 nm. The value for cells not incubated with a test compound was designated as 100%. By comparing these values with the absorbance difference obtained at the well in which each test compound was added, the cell viability (% viability) after treatment with the test compound was calculated. The results are shown in Table 2.

TABLE 2

Inhibitory activity of compounds of the present invention on oncogenic cell growth

| Ex. | MV4-11 ED50 (μM) | HEL92 ED50 (μM) | HepG2 ED50 (μM) | Jeko-1 ED50 (μM) | SW-480 ED50 (μM) | MOLM 16 ED50 (μM) | MOLM 13 ED50 (μM) | KG-1 ED50 (μM) |
|---|---|---|---|---|---|---|---|---|
| 1A | 0.5 | 2.6 | 1.3 | 0.8 | 2.5 | 0.5 | 0.7 | |
| 1AA | 1.3 | 4.6 | 2.1 | 1.8 | 5.5 | | | |
| 1AB | 2.8 | 5.8 | 2.3 | 1.2 | 3.2 | | | |
| 1AC | 1.5 | 5.0 | 1.5 | 0.6 | 2.7 | | | |
| 1AD | 0.5 | 0.5 | 0.6 | 0.4 | 0.7 | | | |
| 1AE | 0.7 | 5.8 | 1.6 | 2.6 | 3.8 | | | |
| 1AF | 1.2 | 8.5 | 1.8 | 2.3 | 5.2 | | | |
| 1AG | 2.0 | 3.2 | 2.0 | 1.4 | 2.7 | | | |
| 1AH | 0.6 | 6.0 | 2.2 | 1.9 | 7.0 | 0.2 | 1.8 | 0.65 |
| 1AI | 1.1 | 3.8 | 1.4 | 3.1 | 4.6 | | | |
| 1AJ | 0.9 | 3.1 | 1.8 | 1.6 | 2.9 | | | |
| 1AK | | | | | 7.5 | | | |
| 1AL | 2.2 | 5.3 | 1.4 | 2.3 | 5.3 | | | |
| 1AM | 2.6 | 8.0 | 2.7 | 2.8 | | | | |
| 1AO | 0.6 | 3.8 | 1.7 | | | | | |
| 1AP | 0.3 | 2.4 | 0.9 | 1.3 | 2.4 | | | |
| 1AQ | 2.5 | 9.6 | 4.9 | | | | | |
| 1AR | 7.8 | | | | | | | |
| 1AS | 0.6 | 5.4 | 1.4 | 1.1 | | | | |
| 1AT | 1.0 | 5.2 | 2.0 | | | | | |
| 1AU | 2.4 | 5.8 | 1.9 | | | | | |
| 1AV | 1.4 | | 4.5 | | | | | |
| 1AW | 4.5 | | 4.2 | | | | | |
| 1AX | 0.1 | 0.1 | 0.1 | >0.1 | | 0.02 | 0.06 | 0.12 |
| 1AY | 0.5 | 1.9 | 1.5 | | | | 0.9 | |
| 1AZ | 1.1 | 2.6 | 2.2 | | | | | |
| 1BA | 1.1 | 6.9 | 1.9 | | | | | |
| 1BB | 0.7 | 5.4 | 2.0 | | | | 3.0 | |
| 1BC | 3.2 | 7.9 | | 3.0 | | | | |
| 1BD | 0.7 | 5.5 | 3.3 | 1.6 | | | 2.1 | |
| 1BF | 2.0 | 7.6 | 2.3 | | | | | |
| 1BG | 1.6 | | 4.0 | | | | | |
| 1BH | 4.6 | | 5.6 | | | | | |
| 1BI | 0.6 | 5.1 | 1.5 | 0.7 | | 0.08 | 3.25 | 0.09 |
| 1BJ | 0.6 | | 4.8 | | | | | |
| 1BK | 0.8 | | 5.2 | | | 0.06 | | |
| 1BL | 0.4 | 2.4 | 1.4 | | | | 1.0 | |
| 1BM | 4.9 | | 4.5 | | | | | |
| 1BN | 1.9 | | 5.1 | | | | | |
| 1BS | 0.9 | 4.6 | 3.6 | | | | | |
| 1BT | 0.5 | 5.7 | 1.2 | | | | | |
| 1BV | 5.1 | 5.3 | 2.9 | | | | | |
| 1C | 3.1 | >10 | 4.1 | | 7.4 | | | |
| 1CA | 2.6 | 9.7 | 1.8 | | | | | |
| 1CD | 2.4 | 5.5 | 5.3 | | | | | |
| 1CE | 2.8 | | 3.2 | | | | | |
| 1CH | 5.0 | 5.7 | 2.2 | | | | | |
| 1CI | 1.6 | 6.1 | 1.4 | | | | | |
| 1CJ | 5.5 | 5.5 | 5.3 | | | | | |
| 1CK | 2.0 | 6.9 | 5.3 | | | | | |
| 1CL | 1.0 | 2.4 | 1.5 | | | | | |
| 1CM | 0.8 | 5.2 | 2.6 | | | | | |
| 1CN | 3.3 | 9.4 | 4.5 | | | | | |
| 1CO | 4.3 | | 3.9 | | | | | |
| 1CP | 0.6 | 5.8 | 1.2 | | | | | |
| 1CQ | 1.7 | 6.0 | 2.0 | | | | | |
| 1CR | 1.1 | 8.7 | 1.9 | | | | | |
| 1CS | 4.8 | | 4.7 | | | | | |
| 1CT | 2.7 | | 6.0 | | | | | |
| 1CX | 1.2 | 4.1 | 3.1 | | | | | |
| 1CY | 2.1 | 8.9 | 2.8 | | | | | |
| 1D | 5.9 | 8.2 | 6.2 | | 6.2 | | | |
| 1DA | 0.5 | 1.1 | 0.9 | | | | | |
| 1DC | 0.2 | 2.0 | 1.0 | | | 0.16 | | |
| 1DF | 2.0 | | 3.7 | | | | | |
| 1DG | 0.2 | 1.8 | 0.4 | | | | | |
| 1DJ | 0.6 | 6.7 | 2.1 | | | | | |
| 1DK | 5.5 | 5.8 | 5.7 | | | | | |
| 1DN | 0.5 | 4.5 | 0.9 | | | | | |
| 1DO | 4.3 | | 2.2 | | | | | |
| 1DP | 0.1 | 0.5 | 0.2 | | | | | |
| 1DQ | 0.9 | 7.6 | 1.4 | 1.6 | | 0.1 | 2.8 | 0.5 |
| 1DR | 1.0 | 6.2 | 1.2 | 1.3 | | 0.1 | 3.9 | 0.14 |
| 1DS | 0.8 | 5.8 | 0.6 | 1.4 | | 0.32 | 9.9 | 0.2 |

TABLE 2-continued

Inhibitory activity of compounds of the present invention on oncogenic cell growth

| Ex. | MV4-11 ED50 (μM) | HEL92 ED50 (μM) | HepG2 ED50 (μM) | Jeko-1 ED50 (μM) | SW-480 ED50 (μM) | MOLM 16 ED50 (μM) | MOLM 13 ED50 (μM) | KG-1 ED50 (μM) |
|---|---|---|---|---|---|---|---|---|
| 1DT | 1.5 | | 1.0 | | | 0.3 | | |
| 1DU | 1.0 | 5.5 | 1.3 | | | 0.9 | | |
| 1DV | 2.1 | | 2.9 | | | 1.5 | | |
| 1DW | 5.1 | | | | | 0.3 | | |
| 1DY | 2.3 | | | 2.8 | | 1.1 | 6.4 | 1.9 |
| 1E | 3.3 | | 6.8 | | 8.1 | | | |
| 1F | 2.3 | 5.0 | 3.3 | | 3.3 | | | |
| 1H | 2.3 | 7.6 | 2.7 | | 3.4 | | | |
| 1I | 5.1 | | 4.3 | | 5.6 | | | |
| 1L | 1.2 | 5.7 | 1.6 | | 3.3 | | | |
| 1M | 0.6 | 2.2 | 1.8 | | 2.1 | | | |
| 1N | 0.6 | 1.4 | 1.7 | | 1.2 | | | |
| 1P | 1.4 | 7.0 | 1.5 | | 2.9 | | | |
| 1Q | 6.9 | 8.2 | 1.1 | 5.4 | 5.3 | | | |
| 1R | 0.6 | 1.5 | 1.1 | 0.5 | 1.4 | | | |
| 1S | 3.0 | >10 | 3.3 | 8.9 | 8.5 | | | |
| 1T | 0.6 | 5.1 | 1.3 | 1.7 | 3.2 | | | |
| 1U | 0.6 | 4.7 | 1.5 | 1.8 | 3.3 | | | |
| 1V | 0.7 | 5.6 | 0.9 | 2.9 | 3.1 | | | |
| 1X | 1.2 | | | 4.3 | | | | |
| 1Y | 1.4 | | | 3.4 | | | | |
| 1Z | 1.7 | | 6.4 | 5.6 | 6.9 | | | |
| 21A | 0.5 | 1.9 | 1.6 | 0.6 | 3.2 | | | |
| 22AA | 0.5 | 1.2 | 1.8 | | | | | |
| 22AB | 3.2 | | 5.1 | | | | | |
| 22AC | 4.1 | | 7.2 | | | | | |
| 22AD | 0.7 | 6.2 | 1.2 | | | | | |
| 22AE | 2.7 | | >10 | | | 2.8 | | |
| 22B | 7.9 | 8.8 | >10 | 3.0 | 6.0 | | | |
| 22G | 4.8 | | | | | | | |
| 22I | 5.4 | | | | | | | |
| 22J | 2.8 | | 4.7 | | | | | |
| 22K | 4.1 | | | | | | | |
| 22L | 1.9 | 3.2 | 1.3 | | 1.2 | | | |
| 22M | 3.7 | 6.5 | 5.0 | | 4.7 | | | |
| 22N | 2.6 | | 4.2 | | | | | |
| 22O | 2.8 | 2.5 | 1.4 | | 1.4 | | | |
| 22P | 2.9 | 5.9 | 2.7 | | 2.5 | | | |
| 22R | 1.1 | 2.9 | 1.2 | | 0.5 | | | |
| 22W | 1.7 | 9.5 | 1.5 | | 4.9 | | | |
| 22X | 0.7 | 8.7 | 2.3 | | 5.0 | | | |
| 22Z | 0.7 | 2.4 | 1.6 | | | | | |
| 26A | 0.2 | 0.9 | 0.6 | 0.3 | | 0.22 | 0.32 | 0.47 |
| 26B | 0.4 | 6.1 | | | | 0.1 | | |
| 26C | 0.1 | 3.0 | | | | 0.2 | | |
| 26D | 0.8 | 9.7 | | | | 1.0 | | |
| 2A | 0.3 | 0.7 | 0.6 | 0.4 | 0.8 | 0.14 | 0.25 | 0.63 |
| 2B | 3.1 | 6.7 | 1.4 | | 5.5 | | | |
| 2C | 2.8 | | 7.0 | 6.2 | | | | |
| 2D | 0.6 | 4.7 | 0.7 | | 0.6 | | | |
| 2E | 5.5 | 5.4 | 0.9 | 1.6 | 1.8 | | | |
| 2F | 0.3 | 2.1 | 1.8 | | | | | |
| 2G | 2.3 | 6.0 | 1.3 | | 3.1 | | | |
| 2H | 2.0 | 6.8 | 1.5 | | 1.4 | | | |
| 2I | 0.2 | 0.8 | 1.3 | | | | | |
| 2L | 6.1 | | | | | 3.1 | | |
| 3A | 2.3 | | 6.3 | | | 1.9 | | |
| 3B | 1.3 | | | | | 1.5 | | |
| 4A | 1.0 | 8.7 | | | | | | |
| 4B | 1.2 | 4.1 | 1.8 | | | | | |
| 8A | 1.3 | 4.8 | 1.7 | 1.4 | 4.7 | | | |
| 9A | 0.3 | | 1.5 | | | | | |
| 9B | 5.9 | | 2.7 | | | 7.29 | | |

If a compound exhibits an ED50<10 μM, the compound is regarded as efficiently inhibiting the cell growth. The assays establish that the compounds according to the present invention are effective in inhibiting oncogenic cell growth in human cancer cell lines as described above.

3.14. Analysis of Pim-Kinase Biomarkers in Response to Cell Treatment with Compounds of the Present Invention The efficacy of compounds 1A and 2A on Pim kinase-inhibition was tested in MV4-11 cells (see above). Cells were treated with each compound at concentrations of 0.25, 0.5, 1, 2.5 and 5 μM for 4 and 24 h. The positive control Ref A (the commercially available inhibitor SGI-1776 [obtained from Selleck Bio]) was used at a concentration of 5 μM. DMSO (Dimethyl sulfoxide) was used as a negative control. The levels of the following classical Pim-1 kinase biomarkers were assessed: c-Myc, phospho-4EBP1 (Ser65, Thr37&46) and phosphorylated S6 (Ser235). The levels of c-myc protein, phosphorylated 4EBP1 and pS6 were down-regulated both after 4 and 24 hours of treatment, in a dose-dependent manner (in the test using compound 2A, pS6 phosphorylation is increasing again at higher concentrations and longer incubation times; this effect is unspecific and due to massive apoptosis, which can be recognized from drastically increased PARP-cleavage). Also, the levels of pro-apoptotic and pro-survival biomarkers were assessed. First, induction of apoptosis, recognizable as an appearance and increased expression of cleaved form of the PARP protein, was observed, both at 4 and 24 hours after compound stimulation at high concentrations. Analysis of Mcl-1, a pro-survival protein, showed dosed-dependent protein down-regulation after 4 and 24 hours. Levels of tubulin were assessed as a reference loading control. Further, the levels of phosphorylated p44/42 (Erk1/2) as Flt3 biomarker were assessed; as can be derived from FIGS. 1 and 2, the levels of phosphoryled p44/42 were also downregulated.

Figure 2:
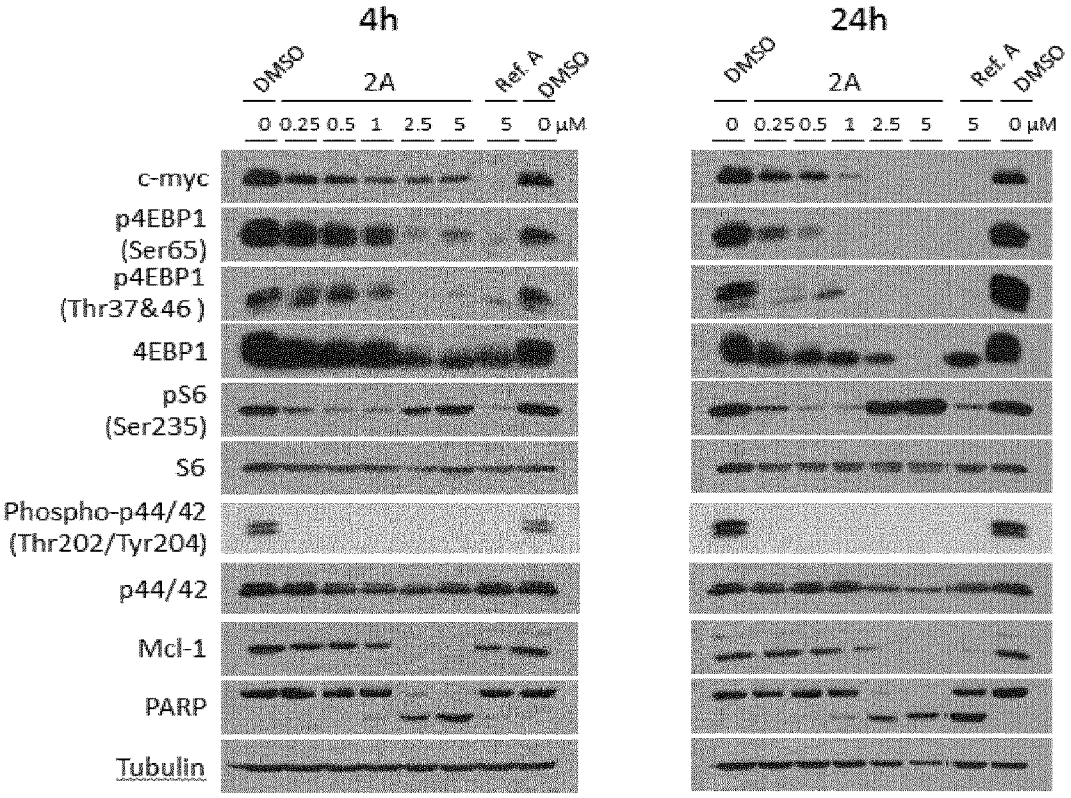
FIG. 2: PIM-kinase biomarkers in MV4-11 cells upon incubation of the cells with compound 2A of the present invention (see example 3.14 for further details).

The results for compound 1A are shown in FIG. 1, whereas the results for compound 2A are shown in FIG. 2.

The efficacy of compound 1BI on Pim kinase-inhibition was tested in MV4-11 cells. The cells were treated with compound 1BI at concentrations of 0.25, 0.5, 1, 2.5 and 5 μM for 4 and 24 h. The positive controls Ref. A (SGI-1776, see above) and Ref. B (the commercially available inhibitor Sunitinib [obtained from Ark Pharm]) were used at 5 μM concentration. DMSO (Dimethyl sulfoxide) was used as a negative control. The levels of the following classical Pim-1 kinase biomarkers were assessed: c-myc, phospho-4EBP1 (Ser65, Thr37&46) and phosphorylated S6 (Ser235/236). The levels of c-myc protein and phosphorylated 4EBP1 (Ser65, Thr37/46 at higher concentrations and 24 h) were down-regulated both after 4 and 24 hours of treatment, in a dose-dependent manner. The levels of phosphorylated S6 were diminished almost completely both after 4 and 24 hours of treatment in all concentrations. The levels of pro-apoptotic and pro-survival biomarkers were also assessed. First, induction of apoptosis, presented as an appearance and increased expression of cleaved form of PARP protein, was observed in the highest concentration at 4 hours after compound stimulation. Analysis of Mcl-1, a pro-survival protein, showed dosed-dependent protein down-regulation after 4 and 24 hours. Levels of tubulin were assessed as a reference loading control. Further, the levels of phosphorylated p44/42 (Erk1/2) as Flt3 biomarker were assessed; as can be derived from FIG. 3, the levels of phosphoryled p44/42 were also downregulated.

Figure 3:
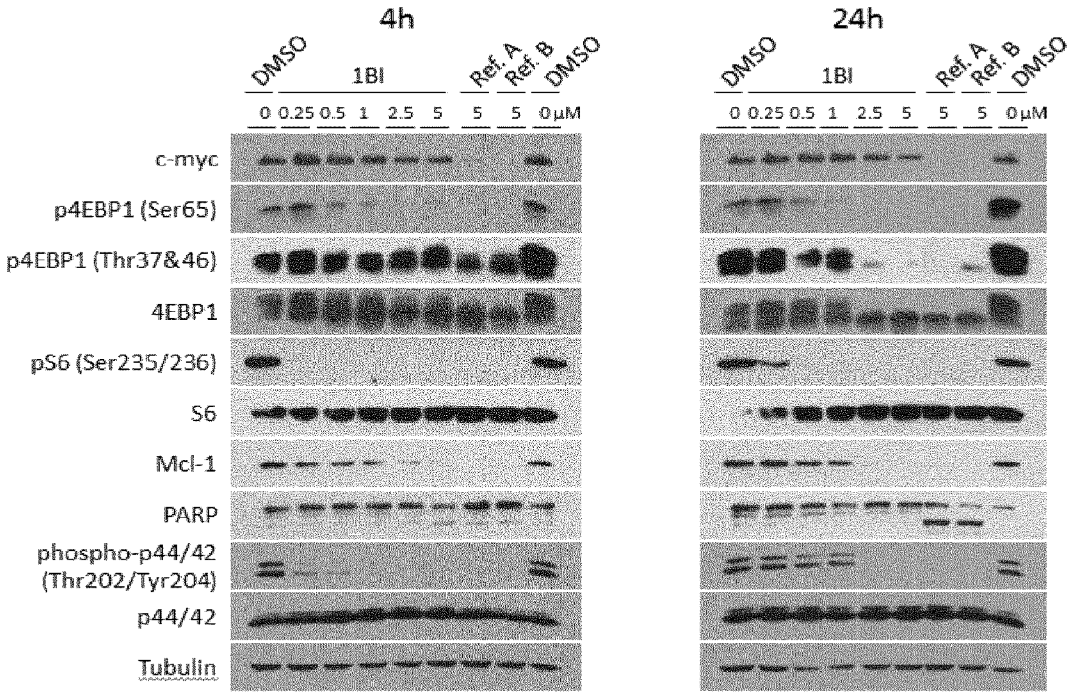
FIG. 3: PIM-kinase biomarkers in MV4-11 cells upon incubation of the cells with compound 1BI of the present invention (see example 3.14 for further details).

The results for compound 1BI are shown in FIG. 3.

The efficacy of compound 1BI on Pim kinase-inhibition was also tested in MOLM16 cells (an acute myeloid leukemia cell line). The cells were treated with compound 1BI at concentrations of 0.1, 0.25, 0.5, 1 and 2.5 μM for 4 and 24 h. The positive controls Ref. A (SGI-1776, see above) and Ref. B (Sunitinib, see above) were used at 5 μM concentration. DMSO (Dimethyl sulfoxide) was used as a negative control. The levels of the following classical Pim-1 kinase biomarkers were assessed: c-myc, phospho-4EBP1 (Scr65, Thr37&46) and phosphorylated S6 (Scr235/236). The levels of c-myc protein and phosphorylated 4EBP1 (Ser65 and Thr37/46) were downregulated both after 4 and 24 hours of treatment, in a dose-dependent manner. The levels of phosphorylated S6 were diminished completely both after 4 and 24 hours of treatment in all concentrations. The levels of a pro-apoptotic biomarker were assessed; induction of apoptosis, presented as an appearance and increased expression of cleaved form of PARP protein, was observed. Levels of tubulin were assessed as a reference loading control.

Figure 4:
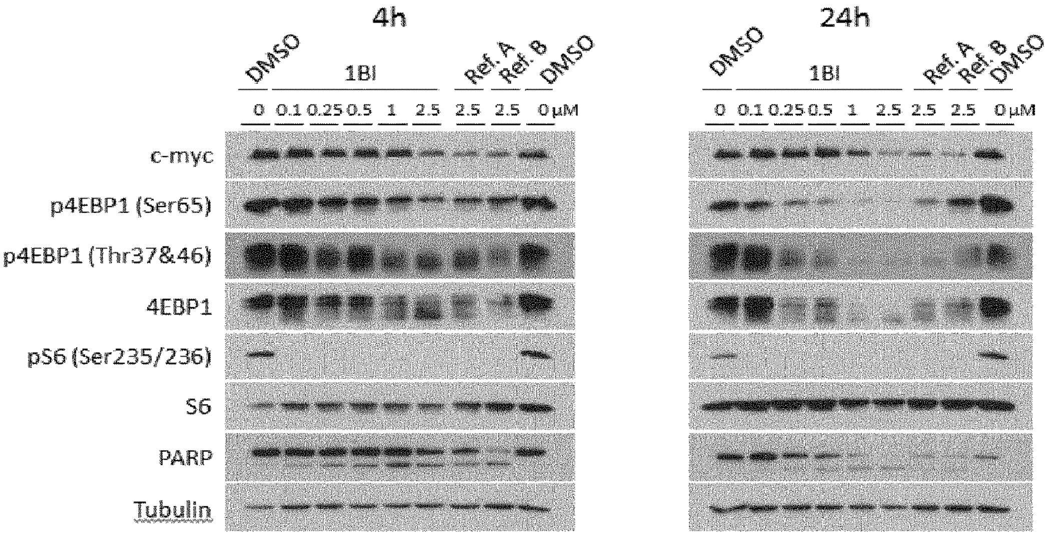
FIG. 4: PIM-kinase biomarkers in MOLM-16 cells upon incubation of the cells with compound 1BI of the present invention (see example 3.14 for further details).

The results for compound 1A in MOLM-16 cells are shown in FIG. 4.

The above analysis clearly establishes that the compounds according to the present invention are capable of inhibiting PIM-kinases in vivo since downstream PIM-kinase targets are clearly affected.

3.15. Determination of In Vivo Activity Against Xenograft Tumors Implanted in Immunosuppressed Animals Several compounds of the present invention have been studied in a xenograft in mice, an in vivo tumor transplantation model used to investigate the factors involved in malignant transformation, invasion and metastasis, as well as to examine response to therapy. For the purpose of acceptance of donor leukemic cells (MV4-11 or MOLM16 cells), immunocompromised mice were used, namely particularly severely compromised immunodeficient mice (NOD/scid, SCID/beige). When tumors developed size of approx. 50-200 $mm^3$, the compounds as indicated below in Tables 3 and 3a were administered orally every day for 2-3 weeks, in once a day (QD) or twice a day (BID) schedule. During the course of the experiment, the mice were monitored and the following two parameters were measured: the tumor growth inhibition (TGI) factor as a measure of therapeutic efficacy and the body weight change (ΔBW) factor as a measure of possible compound toxicity. The results are depicted in Tables 3 and 3a.

TABLE 3

MV4-11 xenograft results.

| Example | TGI [%] | ΔBW [%] | mg/Kg admin. | Dosing | Comment |
|---|---|---|---|---|---|
| 1A | 73 | 5.4 | 75 | BID | |
| 1N | 52 | −6.5 | 150 | QD | |
| 2A | 99 | −4.4 | 150 | QD | discontinued after 8 days due to remissions |
| 1M | 76 | 9.2 | 150 | BID | |
| 2D | 88 | −3.5 | 150 | QD | |
| 1R | 61 | −8 | 150 | QD | |
| 1AH | 74 | 0.6 | 150 | QD | |
| 1AP | 99 | 11.7 | 150 | QD | |
| 1AX | 97 | −2.2 | 100 | QD | |
| 1AZ | 76 | −0.2 | 150 | QD | |
| 1BI | 87 | 3.8 | 150 | QD | |

TGI—tumor growth inhibition, ΔBW—body weight change, QD—once a day, BID—twice a day.

Among the tested compounds, compounds 2A, 1AP and 1AX showed the best anti-cancer activity with TGI exceeding 97%. Compounds 2D and 1BI showed very good TGI above 87%. Compounds 1A, 1M, 1AH and 1AZ led to more than 70% inhibition of tumor growth and may thus be classified as compounds with good efficacy. Compounds 1N and 1R showed moderate TGI reaching up to 70%. All tested compounds did not cause major toxicity as assessed by monitoring of the body weight change. If body weight loss was observed, this loss did not exceed 10% such that all compounds were regarded as being not toxic.

Figure 5:
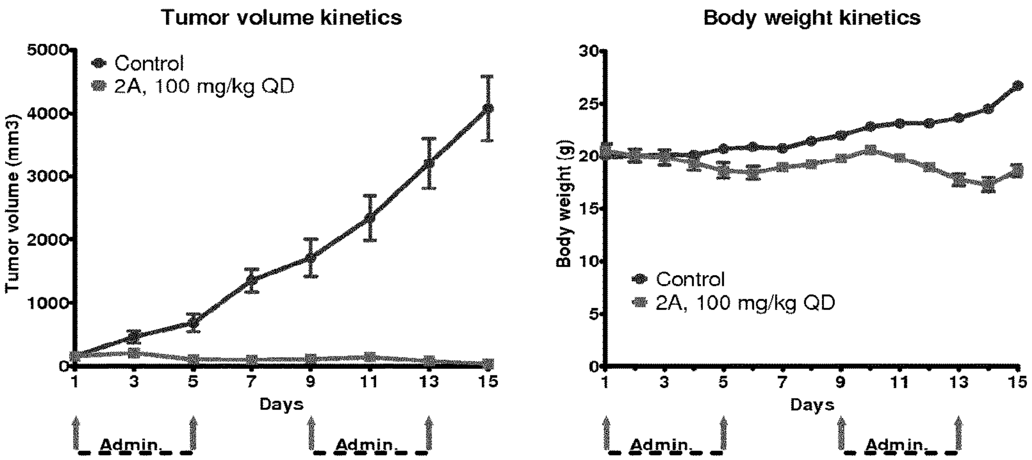
FIG. 5: Tumor volume kinetics and body weight kinetics for MOLM16 xenografts with compound 2A (see example 3.15 for further details).

Additionally, compound 2A, together with other examples was tested in MOLM16 cells xenografted into immunocompromised mice. One of the obtained results is presented below. The treatment with compound 2A resulted in >99% inhibition of the tumour growth as can be derived from Table 3a and FIG. 5.

TABLE 3a

MOLM16 xenograft results.

| Example | TGI (%) | ΔBW (%) | mg/Kg admin. | Dosing | Comment |
|---|---|---|---|---|---|
| 2A | >99 | −8.6 | 100 | QD | |

TGI—tumor growth inhibition, ΔBW—body weight change, QD—once a day.

Figure 6:
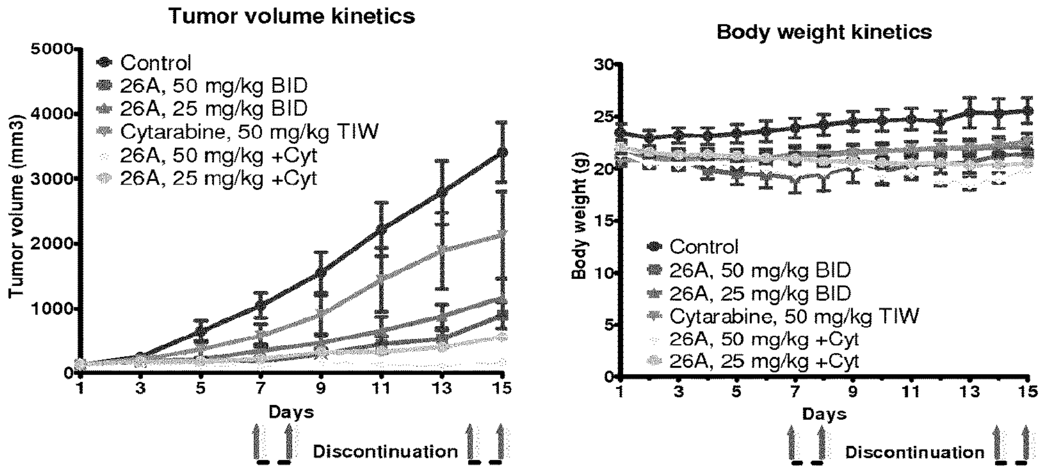
FIG. 6: Tumor volume kinetics and body weight kinetics for MV-4-11 xenografts with compound 26A alone and in combination with Cytarabine (see example 3.15 for further details).

Next, compound 26A was evaluated in a xenograft study of acute myeloid leukemia (MV-4-11), alone or in a combinational treatment with Cytarabine in vivo (Table 3b; FIG. 6). Compound 26A was tested in two doses (50 and 25 mg/kg) and administered twice a day (BID); Cytarabine was administered at dose of 50 mg/kg three times in a week (TIW). During 15 days of compound administration dose-dependent anti-cancer activity of compound 26A (administered alone) was shown. Tumor growth inhibition reached −82% and −77%, respectively. In addition, combinational treatment with Cytarabine showed synergistic effects, similarly dependend on the dose, and resulted in −99% and −89% TGI. Treatment with Cytarabine alone resulted in moderate, −60% inhibition of tumor growth.

TABLE 3b

MV-4-11 xenograft results.

| Compounds | TGI (%) | ΔBW (%) | mg/Kg admin. | Dosing | Comment |
|---|---|---|---|---|---|
| 26A | 87 | −3 | 50 | BID | |
| 26A | 77 | −6 | 25 | BID | |
| Cytarabine | 60 | −2 | 50 | TIW | |
| 26A + Cytarabine | 99 | −4 | 50/50 | BID/TIW | |
| 26A + Cytarabine | 89 | 2 | 50/25 | BID/TIW | |

TGI—tumor growth inhibition, ΔBW—body weight change, BID—twice a day, TIW—three times a week.

3.16. Synergistic and Additive Interactions with Anti-Cancer Agents

In order to determine the efficacy of the compounds of the present invention on cancer cell growth inhibition in combination with commercially available anti-cancer agents, compounds 1A and 26A were added in combination with an anti-cancer agent to cells as indicated in Table 4. The anti-cancer agents are also indicated in Table 4.

The combinations were studied at fixed concentrations, wherein compound 1A or compound 26A were tested at two constant concentrations—one corresponding to ED50 value (for compound 1A in the specified cell line (i.e. for HEL-92: 5.46 μM; U-937: 6.64 μM; MV4-11: 0.50 μM; PC3: 2.91 μM, Mino: 1.7 μM); for compound 26A in MV4-11: 0.1 μM; MOLM-16: 0.4 μM and one below the ED50 value e.g. twice as low (see Table 4), while the therapeutic agents indicated in Table 4 were tested in a range of six increasing concentrations (Table 4). The cells were incubated with the combination of compounds for 72 hours. After this incubation, a cell viability assay was carried out according to the Manufacturer's instructions (CellTiter 96®AQueous Non-Radioactive Cell Proliferation Assay, Promega). The results were expressed as percentage of viable cells upon treatment with the individual drugs or the combination compared to the vehicle (DMSO) treated cells.

Based on these data, combination index (CI) values were determined using CompuSyn Software (ComboSyn Software Incorporated, Paramus, N.J.). In order to indicate the effect of combinations, the following guidelines were implemented: CI value<1 indicates synergism, CI value=1 indicates additive effect and CI value>1 indicates antagonism.

TABLE 4

Combinations study - Examples 1A and 26A.

| Compound | Drug | Concentrations of drug [μM] | Cell line | Effect |
|---|---|---|---|---|
| 1A | Rapamycin | 0.0005; 0.001; 0.0025; 0.005; 0.01; 0.025 | PC3 (Prostate cancer) | Synergistic |
| 1A | Wortmannin | 0.1; 0.25; 0.5; 1.0; 2.5; 5.0 | PC3 (Prostate cancer) | Synergistic |
| 1A | GDC-0941 | 0.01; 0.025; 0.05; 0.1; 0.25; 0.5 | PC3 (Prostate cancer) | Synergistic/ Additive |
| 1A | CP690550 | 0.25; 0.5; 1.0; 2.5; 5.0; 10 | HEL92 (Erythroleukemia) | Synergistic |
| 1A | Cyt387 | 0.25; 0.5; 1.0; 2.5; 5.0; 10 | HEL92 (Erythroleukemia) | Synergistic |
| 1A | Ruxolitinib | 0.25; 0.5; 1.0; 2.5; 5.0; 10 | HEL92 (Erythroleukemia) | Synergistic/ Additive |
| 1A | Obatoclax | 0.05; 0.1; 0.5; 1.0; 2.5; 5.0 | U937 (Histiocytic lymphoma) | Synergistic |

TABLE 4-continued

Combinations study - Examples 1A and 26A.

| Compound | Drug | Concentrations of drug [μM] | Cell line | Effect |
|---|---|---|---|---|
| 1A | ABT737 | 0.1; 0.5; 1.0; 2.5; 5.0; 10 | U937 (Histiocytic lymphoma) | Synergistic |
| 1A | CAL-101 | 0.25; 0.5; 1.0; 2.5; 5.0; 10 | MV4-11 (Acute myeloid leukemia) | Synergistic |
| 1A | CAL-101 | 0.25; 0.5; 1; 2.5; 5; 10 | PC3 (Prostate cancer) | Synergistic |
| 1A | PD0332991 | 0.005; 0.01; 0.025; 0.05; 0.1; 0.25 | Mino (Mantle cell lymphoma) | Synergistic |
| 26A | C | 0.1; 0.25; 0.5; 1.0; 2.5; 5.0 | MV4-11 (Acute myeloid leukemia) | Synergistic |
| 26A | C | 0.01; 0.1; 1.0; 2.5; 5.0; 10.0 | MOLM-16 (Acute myeloid leukemia) | Synergistic |
| 26A | V | 0.01; 0.027; 0.067; 0.0168, 0.42; 1.05 | MV4-11 (Acute myeloid leukemia) | Synergistic |
| 26A | V | 0.022; 0.054; 0.136; 0.34; 0.85; 2.13 | MOLM-16 (Acute myeloid leukemia) | Synergistic |

The above results indicate that the compounds of the present invention act synergistically or additively with established anti-cancer agents or targeted anticancer inhibitors of PI3K/Akt/mTOR or Jak/STAT pathways in inhibiting the cell growth in the tested cancer cell lines (C: Cytarabine; V: Vosaroxin).

3.17. Determination of a Possible Activity on hERG

The hERG (human ether-A-go-go-related gene) channel corresponds to an important anti-target for potential new drugs since its inhibition may lead to sudden death. In order to establish whether the compounds of the present invention act on hERG, the following experiment was carried out.

The in vitro effects of the compounds indicated in Table 5 on the hERG potassium channel current (a surrogate for $I\kappa_r$, the rapidly activating, delayed rectifier cardiac potassium current) expressed in mammalian cells were evaluated at room temperature using the QPatch HT® (Sophion Bioscience A/S, Denmark), an automatic parallel patch clamp system. Each compound indicated in Table 5 was evaluated at 0.1, 1, 3, 10 and 30 μM with each concentration tested in a minimum of two cells (n≥2). The duration of exposure to each compound concentration was 3 minutes. A summary of the results is shown in Table 5. The positive control (E4031) confirmed the sensitivity of the test system to hERG inhibition (98.6% of inhibition at 0.5 μM). Generally, compounds displaying an IC50> about 0.5 μM are regarded as not acting on hERG and thus as safe.

TABLE 5 hERG IC50 determination in automated patch clamp assay.

| Ex. | hERG IC50 [μM] |
|---|---|
| 1A | 1.6 |
| 8A | 0.77 |
| 22L | 0.85 |
| 22R | 1.78 |
| 1M | 0.52 |
| 1N | 1.28 |
| 2A | 3.06 |
| 1P | 1.88 |
| 2C | 2.5 |
| 2D | 1.6 |
| 1X | 20.42 |
| 1Y | 16.91 |
| 1AA | 2.27 |
| 22A | 10.09 |
| 1AB | 8.93 |
| 1AC | 1.86 |
| 1AD | 1.42 |
| 1AE | 0.4 |
| 1AH | 4.99 |
| 1AI | 0.44 |
| 1AL | 2.42 |
| 1AM | 1.46 |
| 1AP | 1.82 |
| 1AQ | 1.86 |
| 1AR | 4.17 |
| 1AS | 5.77 |
| 1AX | 1.23 |
| 1AY | 3.88 |
| 1AZ | 1.88 |
| 22J | 11.91 |
| 1BI | 5.17 |
| 1BD | 4.34 |
| 22AB | 2.02 |
| 1BM | 0.74 |

As can be derived from the results depicted in Table 5, the compounds of the present invention substantially fail to target hERG and can thus be regarded as safe with respect to the risk of sudden death connected to an hERG-inhibition.

3.18. Determination of a Possible Activity on CYP

In general, drugs should preferably not inhibit cytochrome P450 enzymes such that biotransformation is not negatively influenced. Thus, compounds of the present invention were assayed for their activity on such enzymes (CYP).

The assays for cytochrome P450 inhibition facilitate the identification of drug candidates with lower potential for drug-drug interactions (weak enzymes inhibitors). In vitro experiments were conducted to determine whether a drug inhibits a specific CYP enzyme. The experiments comprised the incubation of the drug with probe substrates for the CYP enzymes, wherein the following recombinant cytochrome P450 isoforms were employed: CYP1A2, CYP2C8, CYP2C9, CYP2C19, CYP2D6 and CYP3A4, together with various probe substrates enabling fluorescence detection. The protocol uses a single substrate concentration near the apparent $K_m$ and multiple compound concentrations. An $IC_{50}$ is determined as the point where 50% inhibition of enzyme catalytic activity occurs.

The assay was performed in 96-well microtiter plates. The row designations were A through H and the column designations were 1 through 12. This particular experimental design was to perform an $IC_{50}$ determination in duplicate rows of 12 wells. Each compound (see Table 6 for tested compounds) was added to the wells in column 1 and serially diluted to the wells in column 8. Wells 9 and 10 were control wells which contained no test compound (therefore no inhibition-full signal is detected.) The wells in columns 11 and 12 were blanks, where STOP solution was added prior to the addition of the enzyme/substrate mix to the NADPH regenerating system (the only signal present in these wells is background noise.) The assay was conducted in a final volume of 0.2 ml per well.

The stock solutions of the tested compounds were prepared in DMSO at 10 mM concentration. Stock solutions of all compounds (tested and control) were prepared 500 times the desired concentration in the assay and diluted 500 times with solution buffer A. The following 8 concentrations of the compounds were used for $IC_{50}$ determination: 0.009, 0.027, 0.082, 0.247, 0.741, 2.22, 6.67 and 20 μM. After mixing the compounds with solution containing NADPH-cofactors, the mixed plate was preincubated in a 37° C. incubator for at least 10 minutes; next, the fluorescence of compounds using recommended excitation/emission filters was measured in order to eliminate false results originating from autofluorescence of the compounds. In the following step, the enzyme/substrate mix was added to columns 1 through 10 and the plates were incubated at 37° C. for specific times depending on the CYP tested (incubation times ranged from 30 to 45 minutes). After adding STOP SOLUTION to all wells and respective enzyme/substrate mix to the wells in columns 11 and 12, the plate was scanned with a fluorescent plate scanner. The excitation/emission filters used for the specific assays are described in the GenTest Screening Kit instruction manual. The $IC_{50}$ is calculated via linear interpolation from the fluorescence data, wherein the following classification was used: Strong inhibition: <1.1 μM; Moderate inhibition: 1.1-3.3 μM; Mild inhibition: 3.3-10 μM; Weak inhibition: >10 μM.

TABLE 6

CYP 3A4 screening results

| Ex. | CYP inhibition |
|---|---|
| 1D | Weak |
| 1A | Mild |
| 2A | Mild |
| 1Q | Mild |
| 2H | Mild |
| 1AA | Moderate |
| 1AE | Moderate |
| 1AF | Weak |
| 1AH | Weak |
| 22G | Weak |
| 2I | Mild |
| 1AS | Mild |
| 1AX | Moderate |
| 22I | Weak |
| 22J | Mild |

TABLE 6-continued

CYP 3A4 screening results

| Ex. | CYP inhibition |
|---|---|
| 1BH | Weak |
| 1BI | Moderate |
| 1BK | Weak |
| 1BC | Mild |
| 1BD | Weak |
| 22AB | Mild |
| 1BM | Moderate |
| 26A | Weak |
| 1M | Moderate |
| 2D | Moderate |
| 1AH | Moderate |

The results shown in Table 6 establish that the compounds of the present invention are weak CYP-inhibitors.

Preferred embodiments of the present invention relate to:

1. A compound of formula (I):

(I)

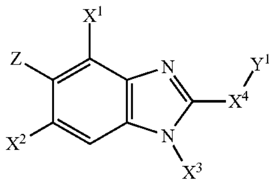

wherein $X^1$ is selected from the group consisting of nitro, cyano, methyl, trifluoromethyl, —C(═O)T, —C(═O)O$T^4$ and —S(═O)$_2$$T^4$;

Z and $X^2$ are each independently selected from the group consisting of F, Cl, Br, I, —$C_{1-3}$alkyl and trifluoromethyl, with the proviso that Z and $X^2$ are not both —$C_{1-3}$alkyl;

$X^3$ is selected from the group consisting of H, —$C_{1-6}$alkyl, —$C_{1-6}$alkenyl, —$C_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —O$T^1$, —N($T^2$)($T^3$), —C(═O)N($T^2$)($T^3$), —C(═O)O$T^1$, —S$T^1$, —S(═O)$_2$$T^1$ and —S(═O)$_2$N($T^2$)($T^3$), and wherein said —$C_{1-6}$alkyl, —$C_{1-6}$alkenyl and —$C_{1-6}$alkynyl is optionally substituted with one or more substituents independently selected from F, —O$T^1$, —N($T^2$)($T^3$), —C(═O)N($T^2$)($T^3$), —C(═O)O$T^1$, —S$T^1$, —S(═O)$_2$$T^1$, —S(═O)$_2$N($T^2$)($T^3$) and a 3- to 6-membered saturated carbocycle or heterocycle, wherein said 3- to 6-membered carbocycle or heterocycle is optionally substituted with one or more substituents independently selected from F, —O$T^1$, —N($T^2$)($T^3$), —C(═O)N($T^2$)($T^3$), —C(═O)O$T^1$, —ST, —S(═O)$_2$$T^1$ and —S(═O)$_2$N($T^2$)($T^3$);

$X^4$ is either absent or selected from —N$R^4$— and —N($R^4$)($CH_2$)—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —N$R^4$— or —N($R^4$)($CH_2$)—, wherein said —$C_{1-6}$alkyl is optionally substituted with one or more substituents independently selected from F, —O$T^1$, —N($T^2$)($T^3$), —C(═O)N($T^2$)($T^3$), —C(═O)OT$^1$, —ST, —S(═O)$_2$T$^1$, —S(═O)$_2$N(T$^2$)(T$^3$) and a 5- to 6-membered saturated heterocycle, and wherein said 4- to 7-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$, —S(═O)$_2$N(T$^2$)(T$^3$), oxo and —C$_{1-3}$alkyl, wherein said —C$_{1-3}$alkyl is optionally substituted with one or more substituents independently selected from —OT$^7$, —N(T$^2$)(T$^3$) and a 6-membered saturated heterocycle;

T$^1$, T$^2$ and T$^3$ are each independently selected from H and —C$_{1-6}$alkyl optionally substituted with one or more substituents independently selected from F, —N(T$^5$)(T$^6$), —OT$^7$, —ST$^7$, cyano, —C(═O)OT$^7$, —C(═O)N(T$^5$)(T$^6$), —OC(═O)N(T$^5$)(T$^6$), —S(═O)$_2$T$^7$, —S(═O)$_2$OT$^8$ and —S(═O)$_2$N(T$^5$)(T$^6$);

T$^4$ is —C$_{1-6}$alkyl optionally substituted with one or more substituents independently selected from F, —N(T$^5$)(T$^6$), —OT$^7$, —ST$^7$, cyano, —C(═O)OT$^7$, —C(═O)N(T$^5$)(T$^6$), —OC(O)N(T$^5$)(T$^6$), —S(═O)$_2$T$^8$, —S(═O)$_2$OT$^7$ and —S(═O)$_2$N(T$^5$)(T$^6$);

T$^5$, T$^6$ and T$^7$ are each independently selected from H and —C$_{1-6}$alkyl optionally substituted with one or more substituents independently selected from F, amino, hydroxyl, thiol and cyano; and T$^8$ is selected from —C$_{1-6}$alkyl optionally substituted with one or more substituents independently selected from F, amino, hydroxyl, thiol and cyano;

or a pharmaceutically acceptable salt thereof.

2. A compound according to 1, wherein Z and X$^2$ are each independently selected from the group consisting of F, Cl, Br, I, and trifluoromethyl.

3. A compound according to 1 or 2, wherein X$^3$ is selected from the group consisting of —C$_{2-6}$alkyl, —C$_{2-6}$alkenyl, —C$_{2-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$ and —S(═O)$_2$N(T$^2$)(T$^3$), and wherein said —C$_{2-6}$alkyl, —C$_{2-6}$alkenyl and —C$_{2-6}$ alkynyl is optionally substituted with one or more substituents independently selected from F, —OT, —N(T$^2$)(T$^3$), —C(═O)N(T$^2$)(T$^3$), —C(═O)OT$^1$, —ST$^1$, —S(═O)$_2$T$^1$, —S(═O)$_2$N(T$^2$)(T$^3$) and a 3- to 6-membered saturated carbocycle or heterocycle, wherein said 3- to 6-membered carbocycle or heterocycle is optionally substituted with one or more substituents independently selected from F, —OT$^1$, —N(T$^2$)(T$^3$), —C(═O)N(T$^2$)(T$^3$), —C(═O)OT, —ST$^1$, —S(═O)$_2$T$^1$ and —S(═O)$_2$N(T$^2$)(T$^3$).

4. A compound according to 1 or 2, wherein X$^3$ is selected from the group consisting of H, —C$_{1-6}$alkyl, —C$_{1-6}$alkenyl, —C$_{1-6}$alkynyl, wherein said —C$_{1-6}$ alkyl, —C$_{1-6}$alkenyl and —C$_{1-6}$alkynyl is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$ and —S(═O)$_2$N(T$^2$)(T$^3$).

5. A compound according to 1 or 2, wherein X$^3$ is selected from the group consisting of —C$_{1-6}$alkyl, —C$_{1-6}$alkenyl, —C$_{1-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$ and —S(═O)$_2$N(T$^2$)(T$^3$), and wherein said —C$_{1-6}$alkyl, —C$_{1-6}$alkenyl and —C$_{1-6}$ alkynyl is substituted with a 3- to 6-membered carbocycle or heterocycle, wherein said 3- to 6-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$ and —S(═O)$_2$N(T$^2$)(T$^3$).

6. A compound according to any one of 1 to 5, wherein X$^4$ is —NR$^4$— and Y$^1$ is selected from the group consisting of H and —C$_{1-6}$alkyl, wherein said —C$_{1-6}$alkyl is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$, —S(═O)$_2$N(T$^2$)(T$^3$).

7. A compound according to any one of 1 to 5, wherein Y$^1$ is a 4- to 7-membered saturated or unsaturated aromatic carbocycle or heterocycle, with the proviso that the point of attachment on said heterocycle is carbon if X$^4$ is —NR$^4$— or —N(R$^4$)(CH$_2$)—, wherein said 4- to 7-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST$^1$, —S(═O)$_2$T$^1$, —S(═O)$_2$N(T$^2$)(T$^3$), oxo and —C$_{1-3}$alkyl, wherein said —C$_{1-3}$alkyl is optionally substituted with one or more substituents independently selected from —OT$^7$, —N(T$^2$)(T$^3$) and a 6-membered saturated heterocycle.

8. A compound according to 7, wherein Y$^1$ is a 4- to 7-membered saturated carbocycle or heterocycle, with the proviso that the point of attachment on said heterocycle is carbon if X$^4$ is —NR$^4$— or —N(R$^4$)(CH$_2$)—, wherein said 4- to 7-membered carbocycle or heterocycle is optionally substituted with one or more substituents independently selected from F, —OT$^1$, —N(T$^2$)(T$^3$), —C(═O)N(T$^2$)(T$^3$), —C(═O)OT$^1$, —ST, —S(═O)$_2$T$^1$, —S(═O)$_2$N(T$^2$)(T$^3$), oxo and —C$_{1-3}$alkyl, wherein said —C$_{1-3}$alkyl is optionally substituted with one or more substituents independently selected from —OT$^7$, —N(T$^2$)(T$^3$) and a 6-membered saturated heterocycle.

9. A compound according to 7 or 8, wherein X$^4$ is absent.

10. A compound according to 1, wherein said compound is selected from the group consisting of:

5,6-dibromo-1-ethyl-4-nitro-2-(piperazin-1-yl)-1H-1,3-benzodiazole;

5,6-dibromo-4-nitro-2-(piperazin-1-yl)-1-(propan-2-yl)-1H-1,3-benzodiazole;

2-[(3R)-3-aminopyrrolidin-1-yl]-5,6-dibromo-1-(propan-2-yl)-1H-1,3-benzodiazole-4-carbonitrile;

2-[(3R)-3-aminopyrrolidin-1-yl]-5,6-dibromo-1-ethyl-1,3-benzodiazole-4-carbonitrile;

5,6-dibromo-2-[(2S)-2-methylpiperazin-1-yl]-4-nitro-1-(propan-2-yl)-1H-1,3-benzodiazole;

trans-1-N-[5,6-dibromo-4-nitro-1-(propan-2-yl)-1H-1,3-benzodiazol-2-yl]cyclohexane-1,4-diamine;

5,6-dibromo-1-cyclopentyl-4-nitro-2-(piperazin-1-yl)-1H-1,3-benzodiazole hydrochloride;

5,6-dibromo-4-nitro-2-(piperazin-1-yl)-1-propyl-1H-1,3-benzodiazole;

5,6-dibromo-1-(2-methylpropyl)-4-nitro-2-(piperazin-1-yl)-1H-1,3-benzodiazole;

5,6-dibromo-1-(cyclopropylmethyl)-4-nitro-2-(piperazin-1-yl)-1H-1,3-benzodiazole;

(3S)-1-(5,6-dibromo-1-ethyl-4-nitro-1H-1,3-benzodiazol-2-yl)piperidin-3-amine;

(3S)-1-[5,6-dibromo-4-nitro-1-(propan-2-yl)-1H-1,3-benzodiazol-2-yl]piperidin-3-amine;

(3S)-1-[5,6-dibromo-4-nitro-1-(propan-2-yl)-1H-1,3-benzodiazol-2-yl]pyrrolidin-3-amine;

(3R)-1-[5,6-dibromo-4-nitro-1-(propan-2-yl)-1H-1,3-benzodiazol-2-yl]pyrrolidin-3-amine;

5,6-dibromo-4-nitro-1-(propan-2-yl)-N-[(3S)-pyrrolidin-3-yl]-1H-1,3-benzodiazol-2-amine hydrochloride;

2-[(3S)-3-aminopiperidin-1-yl]-5,6-dibromo-1-ethyl-1,3-benzodiazole-4-carbonitrile hydrochloride;

5,6-dibromo-4-nitro-N-[(3S)-piperidin-3-yl]-1-(propan-2-yl)-1H-1,3-benzodiazol-2-amine hydrochloride; and 5,6-dibromo-1-(2-methylpropyl)-4-nitro-2-(piperazin-1-yl)-1H-1,3-benzodiazole hydrochloride.

11. A compound according to any one of 1 to 10, wherein the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate.

12. A pharmaceutical composition comprising a compound according to any one of 1 to 11.

13. A pharmaceutical composition according to 12 for use in the treatment of a disease selected from the group consisting of cancer, an autoimmune disease and an inflammatory disease.

14. A pharmaceutical composition according to 12 or 13 for use in the treatment of a disease selected from the group consisting of leukemias including acute lymphoblastic leukemia, acute myelogenous leukemia and chronic lymphocytic leukemia, lymphoma, myeloma, myeloproliferative disorder, allograft rejection, inflammatory bowel disease, multiple sclerosis, psoriasis, rheumatoid arthritis, systemic lupus erythamatosus, Alzheimer disease and Down syndrome.

15. Method for modulating or regulating and preferably inhibiting serine/threonine or tyrosine kinases, preferably selected from the group consisting of PIM1-3, FLT3 and DYRK1A and more preferably selected from the group consisting of PIM1-3 and DYRK1A, wherein said serine/threonine or tyrosine kinases are exposed to at least one compound of formula (I) according to any one of 1 to 11, wherein said method is preferably performed outside the human or animal body.

16. Use of a compound of formula (I) according to any one of 1 to 11 as serine/threonine or tyrosine kinase modulating and preferably inhibiting agent, wherein said kinase is preferably selected from the group consisting of PIM1-3, FLT3 and DYRK1A and more preferably selected from the group consisting of PIM1-3 and DYRK1A.

The invention claimed is:

1. A compound of formula (I):

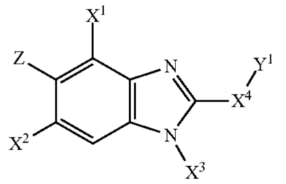

(I)

wherein $X^1$ is selected from the group consisting of nitro, cyano, methyl, trifluoromethyl, —C(═O)$T^1$, —C(═O)O$T^4$ and —S(═O)$_2T^4$;

Z and $X^2$ are each independently selected from the group consisting of F, Cl, Br, and I;

$X^3$ is isopropyl or ethyl;

$X^4$ is either absent or selected from —N$R^4$— and —N($R^4$)($CH_2$)—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —N$R^4$— or —N($R^4$)($CH_2$)—, wherein said —$C_{1-6}$alkyl is optionally substituted with one or more substituents independently selected from —O$T^1$, —N($T^2$)($T^3$), —C(═O)N($T^2$)($T^3$), —C(═O)O$T^1$, —S$T^1$, —S(═O)$_2T^1$, —S(═O)$_2$N($T^2$)($T^3$) and a 5- to 6-membered saturated heterocycle, wherein said 4- to 7-membered carbocycle or heterocycle is selected from the group consisting of cyclobutyl, cyclopentyl, cyclohexyl, cycloheptyl, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane, homopiperazine, phenyl, pyrrole, furan, thiophene, imidazole, pyrazole, oxazole, isoxazole, thiazole, isothiazole, pyrazine, pyrimidine and pyridazine, and wherein said 4- to 7-membered carbocycle or heterocycle is optionally substituted with one or more substituents independently selected from F, —O$T^1$, —N($T^2$)($T^3$), —C(═O)N($T^2$)($T^3$), —C(═O)O$T^1$, —S$T^1$, —S(═O)$_2T^1$, —S(═O)$_2$N($T^2$)($T^3$), oxo and —$C_{1-3}$alkyl, wherein said —$C_{1-3}$ alkyl is optionally substituted with one or more substituents independently selected from —O$T^7$, —N($T^2$)($T^3$) and a 6-membered saturated heterocycle;

$T^1$, $T^2$ and $T^3$ are each independently selected from H and —$C_{1-6}$alkyl optionally substituted with one or more substituents independently selected from F, —N($T^5$)($T^6$), —O$T^7$, —S$T^7$, cyano, —C(═O)O$T^7$, —C(═O)N($T^5$)($T^6$), —OC(═O)N($T^5$)($T^6$), —S(═O)$_2T^7$, —S(═O)$_2$O$T^8$ and —S(═O)$_2$N($T^5$)($T^6$);

$T^4$ is —$C_{1-6}$alkyl optionally substituted with one or more substituents independently selected from F, —N($T^5$)($T^6$), —O$T^7$, —S$T^7$, cyano, —C(═O)O$T^7$, —C(═O)N($T^5$)($T^6$), —OC(═O)N($T^5$)($T^6$), —S(═O)$_2T^8$, —S(═O)$_2$O$T^7$ and —S(═O)$_2$N($T^5$)($T^6$);

$T^5$, $T^6$ and $T^7$ are each independently selected from H and —$C_{1-6}$alkyl optionally substituted with one or more substituents independently selected from F, amino, hydroxyl, thiol and cyano; and $T^8$ is selected from —$C_{1-6}$alkyl optionally substituted with one or more substituents independently selected from F, amino, hydroxyl, thiol and cyano;

or a pharmaceutically acceptable salt thereof.

2. The compound according to claim 1, wherein $X^1$ is selected from the group consisting of nitro, cyano, trifluoromethyl, —C(═O)$T^1$, and —S(═O)$_2T^4$;

or a pharmaceutically acceptable salt thereof.

3. The compound according to claim 1, wherein $Y^1$ is a 4- to 7-membered saturated or unsaturated aromatic carbocycle or heterocycle, with the proviso that the point of attachment on said heterocycle is carbon if $X^4$ is —$NR^4$— or —N($R^4$)($CH_2$)—, wherein said 4- to 7-membered carbocycle or heterocycle is selected from the group consisting of cyclobutyl, cyclopentyl, cyclohexyl, cycloheptyl, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane, homopiperazine, phenyl, pyrrole, furan, thiophene, imidazole, pyrazole, oxazole, isoxazole, thiazole, isothiazole, pyrazine, pyrimidine and pyridazine, and wherein said 4- to 7-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$), oxo and —$C_{1-3}$alkyl, wherein said —$C_{1-3}$alkyl is optionally substituted with one or more substituents independently selected from —$OT^7$, —N($T^2$)($T^3$) and a 6-membered saturated heterocycle;

or a pharmaceutically acceptable salt thereof.

4. The compound according to claim 3, wherein $Y^1$ is a 4- to 7-membered saturated carbocycle or heterocycle, with the proviso that the point of attachment on said heterocycle is carbon if $X^4$ is —$NR^4$— or —N($R^4$)($CH_2$)—, wherein said 4- to 7-membered carbocycle or heterocycle is selected from the group consisting of cyclobutyl, cyclopentyl, cyclohexyl, cycloheptyl, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, thiane, piperazine, morpholine, thiomorpholine, azepane, oxepane, thiepane, and homopiperazine, and wherein said 4- to 7-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$), oxo and —$C_{1-3}$alkyl, wherein said —$C_{1-3}$alkyl is optionally substituted with one or more substituents independently selected from —$OT^7$, —N($T^2$)($T^3$) and a 6-membered saturated heterocycle;

or a pharmaceutically acceptable salt thereof.

5. The compound according to claim 3, wherein $X^4$ is absent;

or a pharmaceutically acceptable salt thereof.

6. The compound according to claim 1, wherein $X^4$ is absent and $Y^1$ is a 6-membered saturated heterocycle, wherein said 6-membered saturated heterocycle is selected from the group consisting of piperidine, tetrahydropyran, thiane, piperazine, morpholine, and thiomorpholine, and wherein said 6-membered heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$), oxo and —$C_{1-3}$alkyl;

or a pharmaceutically acceptable salt thereof.

7. The compound according to claim 1, wherein said compound is selected from the group consisting of:

5,6-dibromo-1-ethyl-4-nitro-2-(piperazin-1-yl)-1H-1,3-benzodiazole;

5,6-dibromo-4-nitro-2-(piperazin-1-yl)-1-(propan-2-yl)-1H-1,3-benzodiazole;

(3 S)-1-(5,6-dibromo-1-ethyl-4-nitro-1H-1,3-benzodiazol-2-yl)piperidin-3-amine;

5,6-dibromo-2-[(2 S)-2-methylpiperazin-1-yl]-4-nitro-1-(propan-2-yl)-1H-1,3-benzodiazole; and 5,6-dibromo-4-nitro-2-(piperidin-4-yl)-1-(propan-2-yl)-1H-1,3-benzodiazole.

8. The compound according to claim 1, wherein the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate.

9. A pharmaceutical composition comprising:

a pharmaceutically effective amount of a compound of formula (I):

(I)

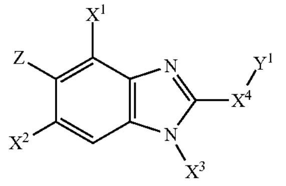

wherein said compound of formula (I) is a pharmaceutically active agent; and wherein said pharmaceutical composition comprises a pharmaceutically acceptable excipient;

wherein $X^1$ is selected from the group consisting of nitro, cyano, methyl, trifluoromethyl, —C(═O)$T^1$, —C(═O)$OT^4$ and —S(═O)$_2T^4$;

Z and $X^2$ are each independently selected from the group consisting of F, Cl, Br, and I;

$X^3$ is selected from the group consisting of —$C_{1-6}$alkyl, —$C_{2-6}$alkenyl, —$C_{2-6}$alkynyl and a 3- to 6-membered saturated carbocycle or heterocycle, with the proviso that the point of attachment on said heterocycle is carbon, wherein said 3- to 6-membered carbocycle or heterocycle is optionally substituted with one or more substituents independently selected from F, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$), and wherein said —$C_{1-6}$alkyl, —$C_{2-6}$alkenyl and —$C_{2-6}$alkynyl is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$, —S(═O)$_2$N($T^2$)($T^3$) and a 3- to 6-membered saturated carbocycle or heterocycle, wherein said 3- to 6-membered carbocycle or heterocycle is optionally substituted with one or more substituents independently selected from F, —$OT^1$, —N($T^2$)($T^3$), —C(═O)N($T^2$)($T^3$), —C(═O)$OT^1$, —$ST^1$, —S(═O)$_2T^1$ and —S(═O)$_2$N($T^2$)($T^3$);

$X^4$ is either absent or selected from —$NR^4$— and —$N(R^4)(CH_2)$—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —$NR^4$— or —$N(R^4)(CH_2)$—, wherein said —$C_{1-6}$alkyl is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$, —$S(=O)_2N(T^2)(T^3)$ and a 5- to 6-membered saturated heterocycle, and wherein said 4- to 7-membered carbocycle or heterocycle is optionally substituted with one or more substituents independently selected from F, —$OT^1$, —$N(T^2)(T^3)$, —$C(=O)N(T^2)(T^3)$, —$C(=O)OT^1$, —$ST^1$, —$S(=O)_2T^1$, —$S(=O)_2N(T^2)(T^3)$, oxo and —$C_{1-3}$alkyl, wherein said —$C_{1-3}$alkyl is optionally substituted with one or more substituents independently selected from —$OT^7$, —$N(T^2)(T^3)$ and a 6-membered saturated heterocycle;

$T^1$, $T^2$ and $T^3$ are each independently selected from H and —$C_{1-6}$alkyl optionally substituted with one or more substituents independently selected from F, —$N(T^5)(T^6)$, —$OT^7$, —$ST^7$, cyano, —$C(=O)OT^7$, —$C(=O)N(T^5)(T^6)$, —$OC(=O)N(T^5)(T^6)$, —$S(=O)_2T^7$, —$S(=O)_2OT^8$ and —$S(=O)_2N(T^5)(T^6)$;

$T^4$ is —$C_{1-6}$alkyl optionally substituted with one or more substituents independently selected from F, —$N(T^5)(T^6)$, —$OT^7$, —ST, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^5$, $T^6$ and $T^7$ are each independently selected from H and —$C_{1-6}$alkyl optionally substituted with one or more substituents independently selected from F, amino, hydroxyl, thiol and cyano; and $T^8$ is selected from —$C_{1-6}$alkyl optionally substituted with one or more substituents independently selected from F, amino, hydroxyl, thiol and cyano;

or a pharmaceutically acceptable salt thereof, wherein said compound is provided in a sterile injectable solution or suspension in a non-toxic parenterally acceptable diluent or solvent, or wherein said compound is provided as an oral dosage form.

10. A method for treating a disease in a subject, comprising administering to said subject a pharmaceutical composition according to claim 9, wherein said disease is selected from the group consisting of prostate cancer, a leukemia, and a lymphoma.

11. The method of claim 10, wherein said disease is prostate cancer.

12. The method of claim 10, wherein said disease is a leukemia selected from the group consisting of acute lymphoblastic leukemia, acute myeloid leukemia, and chronic lymphocytic leukemia.

13. The method of claim 10, wherein said disease is a lymphoma selected from diffuse large B-cell lymphoma.

* * * * *

UNITED STATES PATENT AND TRADEMARK OFFICE

CERTIFICATE OF CORRECTION

PATENT NO. : 10,174,013 B2
APPLICATION NO. : 15/179601
DATED : January 8, 2019
INVENTOR(S) : Czardybon et al.

It is certified that error appears in the above-identified patent and that said Letters Patent is hereby corrected as shown below:

In the Specification

In Column 1, Line 57, "Heamatologica," should read --Haematologica,--.

In Column 4, Lines 53-54, "lamelliopodia" should read --lamellipodia--.

In Column 4, Line 64, "lamelliopodia" should read --lamellipodia--.

In Column 5, Line 66, "neurodegencrative" should read --neurodegenerative--.

In Column 14, Line 59, "benzensulfonate," should read --benzenesulfonate,--.

In Column 17, Lines 62-63, "benzensulfonate," should read --benzenesulfonate,--.

In Column 18, Lines 17-18, "nonsuperimposeable" should read --nonsuperimposable--.

In Column 21, Line 15, "chondromatous hanlartoma," should read --chondromatous hamartoma,--.

In Column 21, Line 30, "osteochronfroma" should read --osteochondroma--.

In Column 22, Line 49, "taupathies" should read --tauopathies--.

In Column 22, Lines 63-64, "myloproliferative" should read --myeloproliferative--.

In Column 68, Ex. 1BT, below the first structure and the title "Method B", "And tert-butyl (3R)-3-aminopyrrolidine-1-carboxylate" should read --And tert-butyl (3R)-3-aminopiperidine-1-carboxylate--.

Signed and Sealed this
Fifteenth Day of October, 2019

Andrei Iancu
*Director of the United States Patent and Trademark Office*

In Column 71, the last structure for Ex. 1CK, should read -- 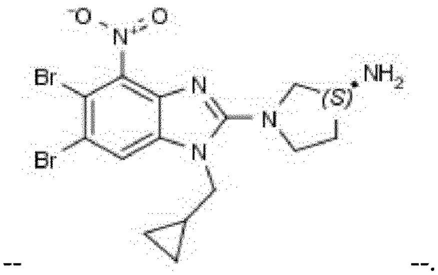 --.

In Column 75, above the last structure for Ex. 1CQ, “diamine hydrochloride hydrochloride” should read --diamine hydrochloride--.

In Column 102, end of Line 35, “(48 uL,” should read --(48 µL,--.

In Column 107, Line 53, “0.65 mmols” should read --0.65 mmol--.

In Columns 111 and 112, in the $^{1}$H NMR spectrum for Ex. 22J, Lines 6-7, “6.8 Hz, (m, 4H)” should read --6.8 Hz, 1H), 3.66 - 3.62 (m, 4H)--.

In Column 123, Line 1 of Ex. 26C, ““Diastereosomer” should read --Diastereoisomer--.

In Columns 129 and 130, Method 3F, Line 8 of the 1H NMR spectrum, “(n, 2H),” should read --(m, 2H),--.

In Column 148, Line 1, “(Milipore,” should read --(Millipore,--.

In Column 157, Line 37, “phosphoryled” should read --phosphorylated--.

In Column 157, Line 64, “phosphoryled” should read --phosphorylated--.

In Column 159, Line 35, “dependend” should read --dependent--.

In Column 167, Lines 33-34, “benzensulfonate,” should read --benzenesulfonate,--.

In the Claims

Claim 7, in Column 170, Lines 7-8, “(3 S)-1-(5,6-dibromo-1 -ethyl-4-nitro-1H-1,3-benzodiazol-2-yl)piperidin-3-amine” should read --(3S)-1-(5,6-dibromo-1-ethyl-4-nitro-1H-1,3-benzodiazol-2-yl)piperidin-3-amine--.

Claim 7, in Column 170, Lines 9-10, “5,6-dibromo-2-[(2 S)-2-methylpiperazin-1-yl]-4-nitro-1-(propan-2-yl)-1H-1,3-benzodiazole” should read --5,6-dibromo-2-[(2S)-2-methylpiperazin-1-yl]-4-nitro-1-(propan-2-yl)-1H-1,3-benzodiazole--.

Claim 8, in Column 170, Lines 21-22, “benzensulfonate,” should read --benzenesulfonate,--.

Claim 9, in Column 172, Line 1, “-ST,” should read -- $-ST^{7}$,--.